United States Patent
Kim et al.

(10) Patent No.: US 8,349,885 B2
(45) Date of Patent: Jan. 8, 2013

(54) INDOLE AND INDAZOLE DERIVATIVES HAVING A CELL-, TISSUE- AND ORGAN-PRESERVING EFFECT

(75) Inventors: Soon Ha Kim, Daejeon (KR); Hyoung Jin Kim, Daejeon (KR); Chul Woong Chung, Daejeon (KR); Heui Sul Park, Daejeon (KR); Hyo Shin Kwak, Daejeon (KR); Sung Ho Kim, Daejeon (KR); Jin Gu Park, Daejeon (KR)

(73) Assignee: LG Life Sciences Ltd., Seoul (KR)

( * ) Notice: Subject to any disclaimer, the term of this patent is extended or adjusted under 35 U.S.C. 154(b) by 0 days.

(21) Appl. No.: 13/534,682

(22) Filed: Jun. 27, 2012

(65) Prior Publication Data

US 2012/0270203 A1    Oct. 25, 2012

Related U.S. Application Data

(62) Division of application No. 12/811,525, filed as application No. PCT/KR2009/000031 on Jan. 5, 2009.

(30) Foreign Application Priority Data

Jan. 4, 2008  (KR) .................. 10-2008-0001477

(51) Int. Cl.
  *A61K 31/416* (2006.01)
  *A61K 31/404* (2006.01)
  *C07D 231/56* (2006.01)
  *C07D 209/10* (2006.01)

(52) U.S. Cl. .......... 514/406; 514/416; 548/362.1; 548/452

(58) Field of Classification Search ........ 514/406, 514/416; 548/362.1, 452
See application file for complete search history.

(56) References Cited

U.S. PATENT DOCUMENTS

| | | | |
|---|---|---|---|
| 4,695,581 A | 9/1987 | Suzuki et al. | |
| 6,897,231 B2 * | 5/2005 | Bhagwat et al. | 514/403 |
| 2008/0096877 A1 * | 4/2008 | Yasuma et al. | 514/228.2 |
| 2009/0247746 A1 * | 10/2009 | Yasuma et al. | 544/105 |

FOREIGN PATENT DOCUMENTS

| | | |
|---|---|---|
| EP | 1 873 144 A1 | 1/2008 |
| WO | WO 95/07276 A1 | 3/1995 |
| WO | WO 2004/018428 A1 | 3/2004 |
| WO | WO 2006/053227 A2 | 5/2006 |
| WO | WO 2006/062982 A2 | 6/2006 |
| WO | WO 2006/112549 A1 | 10/2006 |

OTHER PUBLICATIONS

Abstract for Korean Patent Publication 10-2009-0018593-A (Application No. 10-2008-0080519).
Abstract for Korean Patent Publication No. 10-2009-0018594-A (Application No. 10-2008-0080537).
Degterev, Alexei, et al., "Chemical inhibitor of nonapoptotic cell death with therapeutic potential for ischemic brain injury," Nature Chemical Biology, vol. 1, No. 2, pp. 112-119 & 234, Jul. 2005.
Huang, "Crystal structures of p-methyl-N-(2-phenyl-1H-indol-7-yl)-benzene-sulfonamide, C21H18N2O2S, and p-methoxy-N-(2-phenyl-1H-indol-7-yl)-benzene-sulfonamide, C21H18N2O3S," 2005, Z. Kristallogr., vol. 220, pp. 258-260.
KIPO International Search Report for Appl. No. PCT/KR2009/000031 dated Aug. 3, 2009.
Kreamer, Bill L., et al., "Use of a Low-Speed, Iso-Density Percoll Centrifugation Method to Increase the Viability of Isolated Rat Hepatocyte Preparations," In Vitro Cellular & Developmental Biology, vol. 22, No. 4, pp. 201-211, Apr. 1986.
Natori, Shiho, et al., "The Caspase Inhibitor IDN-6556 Prevents Caspase Activation and Apoptosis in Sinusoidal Endothelial Cells During Liver Preservation Injury," Liver Transplantation, vol. 9, No. 3, pp. 278-284, Mar. 2003.
Seglen, P. O., "Preparation of Rat Liver Cells," Experimental Cell Research vol. 74, pp. 450-454, 1972.
Wahlberg, Jan A., et al., "72-Hour Preservation of the Canine Pancreas," Transplantation, vol. 43, No. 1, pp. 5-8, Jan. 1987.

* cited by examiner

*Primary Examiner* — Golam M M Shameem
*Assistant Examiner* — Karen Cheng
(74) *Attorney, Agent, or Firm* — Birch, Stewart, Kolasch & Birch, LLP

(57) ABSTRACT

The present invention relates to a composition for preserving cells, tissues and organs, comprising as an active ingredient indole and indazole compounds of formula (1), or a pharmaceutically acceptable salt or isomer thereof, which are effective for preventing injury of organs, isolated cell systems or tissues caused by cold storage, transplant operation or post-transplantation reperfusion; a preservation method; and a preparation method of the composition.

20 Claims, 2 Drawing Sheets

INDOLE AND INDAZOLE DERIVATIVES HAVING A CELL-, TISSUE- AND ORGAN-PRESERVING EFFECT

This application is a Divisional of co-pending U.S. application Ser. No. 12/811,525 filed Jul. 2, 2010, which is the National phase of PCT International Application No. PCT/KR2009/000031 filed on Jan. 5, 2009. This application also claims priority to Patent Application No. 10-2008-0001477 filed in the Republic of Korea on Jan. 4, 2008. All of the above applications are hereby expressly incorporated by reference into the present application.

TECHNICAL FIELD

The present invention relates to a composition for preserving cells, tissues or organs of animals comprising an indole or indazole compound of formula (1) or a pharmaceutically acceptable salt or isomer thereof as an effective ingredient, a preservation method by using the same and a method for preparing the same. Specifically, the indole and indazole compounds according to the present invention are effective in protecting cells, tissues and organs of animals to be transplanted and preventing their injury caused during transportation or storage. Furthermore, the indole and indazole compounds according to the present invention protect organs from injury of tissues or organs caused by reperfusion after transplantation.

BACKGROUND ART

Recently, cases of organ transplantation have increased according to the development of surgical operation technique and medicines such as immunosuppressant. A number of patients are in need of transplants but many organs are not kept in a proper condition for use and thus discarded. Thus, it has been reported that there are still many patients awaiting transplant surgeries. It is most preferable that an organ is transplanted to a recipient as soon as it is removed from a donor. However, many transplant surgeries are not done immediately as such. Therefore, the extended time of storage and improved quality of organs to be transplanted by improving storage method remain as urgent technical problems.

In these days, low temperature storage (below 20° C., typically below 4° C.) is utilized to preserve organs, which inhibits metabolism rather than provides appropriate physiological conditions in vivo. A various kind of preserving solutions for such method have been developed and used clinically.

At an early stage, Euro-Collin's solution was used. Recently, UW solution (University of Wisconsin, Wahlberg, J. A., et al., Transplantation, 43, pp. 5-8, 1987) has been developed, which is useful as a preserving solution for liver, intestine and kidney as well as pancreas and capable of preserving liver up to 24 hours experimentally. However, in clinical tests, it is used for a shorter period to protect the patients. Thus, preserving solutions or additional agents capable of maintaining viability of organs for more extended time and providing effective storage of organs are strongly required to be developed.

Indole and indazole compounds according to the present invention have a very suitable structure to medical purpose, and a number of researches on compounds having an indole core structure have been published. For example, their activities to glucokinase (WO2006/112549), usefulness as anticancer drug and cardiovascular angiogenesis inhibitor (WO95/07276) and as antibiotics (WO2004/018428) are representatively known.

DISCLOSURE OF THE INVENTION

The inventors of the present invention carried out intensive and extensive researches to develop compounds which can inhibit necrosis of various animal cells in preserving various tissues, organs or blood and thus can provide an extended preservation period, enhanced protection effect and improved organ function after transplantation. As a result, we have now found out that the indole and indazole derivatives represented by the following formula (1) show remarkable effects as described below. Indole and indazole compounds according to the present invention have been already disclosed and claimed in Korean Patent Application Nos. 10-2007-0082687, 10-2008-0080519 and 10-2008-0080537, which were filed by the present applicant.

Accordingly, the present invention provides a composition for preserving cells, tissues or organs of animals comprising an indole or indazole compound represented by formula (1) or a pharmaceutically acceptable salt or isomer thereof as an effective ingredient, with a pharmaceutically acceptable carrier.

The present invention also provides a preparation method of a composition for preserving cells, tissues or organs of animals, specifically for preventing injury of organs, isolated cell systems or tissues caused by cold storage, transplant operation- or post-transplantation reperfusion, said method comprising a step of mixing a compound represented by formula (1) or a pharmaceutically acceptable salt or isomer thereof as an effective ingredient, together with a pharmaceutically acceptable carrier.

The present invention also provides a method of using the composition according to the present invention comprising a compound represented by formula (1) or a pharmaceutically acceptable salt or isomer thereof as an effective ingredient, for preserving cells, tissues or organs of animals for transplantation.

The composition of the present invention uses an indole or indazole compound represented by the following formula (1), or a pharmaceutically acceptable salt or isomer thereof as an effective ingredient:

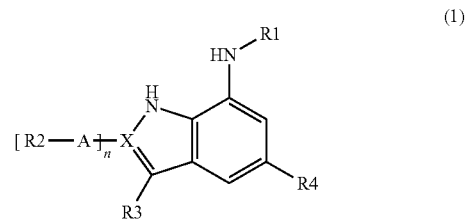

(1)

wherein
X represents C or N,
n is 0 or 1, and n is 1 when X is C and n is 0 when X is N,
A represents a direct bond, $C_3$-$C_8$-cycloalkyl, phenyl, or 5~6-membered heteroaryl or heterocycle, each of which includes 1-3 heteroatoms selected from N, O and S atoms,
R1 represents hydrogen, —C(O)—B—X'—R7 or —(CR5R6)$_m$-B—X'—R7,
m is an integer of 0 to 4,
each of R5 and R6 independently represents hydrogen or $C_1$-$C_5$-alkyl, B represents a direct bond, $C_3$-$C_8$-cycloalkyl optionally containing oxo, or 3~10-membered heterocycle or heteroaryl, each of which includes 1~3 heteroatoms selected from O, S and N atoms, X' represents a direct bond, —C(O)—, —SO$_2$—, —CO$_2$— or —C(O)NR5—, R7 represents hydrogen, $C_1$-$C_6$-alkyl, halogeno-$C_1$-$C_6$-alkyl, halogen, (CR5R6)$_m$-phenyl, (CR5R6)$_m$-hydroxy or (CR5R6)$_m$-heterocycle where the heterocycle optionally contains oxo and is a 3~10-membered ring including 1-3 heteroatoms selected from N, O and S atoms, R2 represents —(CR5R6)$_m$-D-X"—R8, D represents a direct bond or a 3~10-membered heterocycle or heteroaryl, each of which optionally contains oxo and is optionally fused, and includes 1~4 heteroatoms selected from N, O and S atoms, X" represents a direct bond, —C(O)—, —C(O)O—, —NR5C(O)—, —C(O)NR5- or —O—, R8 represents hydrogen, halogen, $C_1$-$C_6$-alkyl, halogeno-$C_1$-$C_6$-alkyl, tri($C_1$-$C_6$-alkyl)silane or hydroxy-$C_1$-$C_6$-alkyl, R3 represents hydrogen, halogen, cyano, nitro, aryl-R9 or (CR5R6)$_m$-D-R9, R9 represents hydrogen, halogen, $C_1$-$C_6$-alkyl, cyano, nitro or $C_1$-$C_6$-alkoxy, R4 represents —(CR5R6)$_m$-Y-D-R10, Y represents a direct bond, —C(O)O— or —O—, and R10 represents hydrogen, nitro, halogen, $C_1$-$C_6$-alkyl, carboxy-$C_1$-$C_6$-alkyl, aryl or —C(O)O—R5, wherein each of said alkyl, alkoxy, aryl, cycloalkyl, heterocycle and heteroaryl may be optionally substituted with one or more substituents selected from the group consisting of hydroxy, halogen, nitrile, amino, $C_1$-$C_6$-alkylamino, di($C_1$-$C_6$-alkyl)amino, $C_1$-$C_6$-alkyl, halogeno-$C_1$-$C_6$-alkyl, $C_1$-$C_6$-alkylsulfonyl, aryl-$C_1$-$C_6$-alkoxy and oxo.

In the definition of the substituents of the compound of the formula (1) according to the present invention, the term "alkyl" means an aliphatic hydrocarbon radical. Alkyl may be a "saturated alkyl" not including alkenyl or alkynyl moiety, or "unsaturated alkyl" including at least one alkenyl or alkynyl moiety. "Alkenyl" means a group having at least one carbon-carbon double bond and "alkynyl" means a group having at least one carbon-carbon triple bond. Alkyl may be a branched or straight chain when used alone or in combination with alkoxy.

Alkyl may have 1~20 carbon atoms unless defined otherwise herein. Alkyl may be a medium-sized alkyl having 1~10 carbon atoms. Alkyl may be a lower alkyl having 1~6 carbon atoms. Typical alkyl groups include, but are not limited to, methyl, ethyl, propyl, isopropyl, n-butyl, isobutyl, t-butyl, pentyl, hexyl, ethenyl, propenyl, butenyl, etc. For example, $C_1$-$C_4$-alkyl has 1~4 carbon atoms in alkyl chain and is selected from the group consisting of methyl, ethyl, propyl, iso-propyl, n-butyl, iso-butyl, sec-butyl and tert-butyl.

The term "alkoxy" means alkyloxy having 1-10 carbon atoms unless defined otherwise herein.

The term "cycloalkyl" means saturated aliphatic 3-10-membered cycle unless defined otherwise herein. Typical cycloalkyl groups include, but are not limited to, cyclopropyl, cyclobutyl, cyclopentyl, cyclohexyl, etc.

"Aryl" includes at least one ring having shared pi electron system, for example, monocyclic or fused-polycyclic groups (i.e., rings sharing adjacent carbon pairs). In other word, the term "aryl" used herein means 4~10-membered, preferably 6~10-membered aromatic monocyclic or multicyclic ring and includes, for example, phenyl and naphtyl.

The term "heteroaryl" means 3~10-membered, preferably 4~8-membered, more preferably 5~6-membered aromatic ring, which includes 1~3 heteroatoms selected from N, O and S atoms and may be fused with benzo or $C_3$-$C_8$ cycloalkyl, unless defined otherwise herein. Examples of monocyclic heteroaryl include, but are not limited to, thiazole, oxazole, thiophene, furan, pyrole, imidazole, isoxazole, isothiazole, pyrazole, triazole, triazine, thiadiazole, tetrazole, oxadiazole, pyridine, pyridazine, pyrimidine, pyrazine and analogs thereof. Examples of bicyclic heteroaryl include, but are not limited to, indole, indoline, benzothiophene, benzofuran, benzimidazole, benzoxazole, benzisoxazole, benzthiazole, benzthiadiazole, benztriazole, quinoline, isoquinoline, purine, furopyridine and analogs thereof.

The term "heterocycle" means 3~10 membered, preferably 4~8-membered, and more preferably 5~6-membered ring which includes 1~3 heteroatoms selected from N, O and S atoms and may be fused with benzo or $C_3$-$C_8$-cycloalkylalkyl, and may be saturated or contain 1 or 2 double bonds. Examples of heterocycle includes, but are not limited to, pyrroline, pyrrolidine, imidazoline, imidazolidine, pyrazoline, pyrazolidine, pyrane, piperidine, morpholine, thiomorpholine, piperazine, hydrofuran, etc.

The other terms and abbreviations used herein can be understood by a person skilled in the art as having conventional definitions unless defined otherwise herein.

Preferable compounds among the compounds of formula I according to the present invention are those wherein X represents C or N, n is 0 or 1, and n is 1 when X is C and n is 0 when X is N, A represents a direct bond, phenyl, or 5~6-membered heteroaryl or heterocycle, each of which includes 1~3 heteroatoms selected from N, O and S atoms, R1 represents hydrogen, —C(O)—B—X'—R7 or —(CR5R6)$_m$-B—X'—R7, m is an integer of 0 to 2, each of R5 and R6 independently represents hydrogen or $C_1$-$C_5$-alkyl, B represents a direct bond, $C_4$-$C_7$-cycloalkyl optionally containing oxo and optionally substituted with halogen, or 4~8-membered heterocycle or heteroaryl, each of which includes 1~3 heteroatoms selected from O, S and N atoms, X' represents a direct bond, —C(O)—, —SO$_2$—, —CO$_2$— or —C(O)NH—, R7 represents hydrogen, $C_1$-$C_6$-alkyl, halogeno-$C_1$-$C_6$-alkyl, halogen, (CR5R6)$_m$-phenyl, (CR5R6)$_m$ hydroxy or (CR5R6)$_m$-heterocycle where the heterocycle optionally contains oxo and is a 4~8-membered ring including 1-3 heteroatoms selected from N, O and S atoms, R2 represents —(CR5R6)$_m$-D-X"—R8, D represents a direct bond or a 4~8-membered heterocycle or heteroaryl, each of which optionally contains oxo and is optionally fused, and includes 1~4 heteroatoms selected from N, O and S atoms, X" represents —C(O)—, —C(O)O—, —NR5C(O)—, —C(O)NR5- or —O—, R8 represents hydrogen, halogen, $C_1$-$C_6$-alkyl, halogeno-$C_1$-$C_6$-alkyl, tri($C_1$-$C_6$-alkyl)silane or hydroxy-$C_1$-$C_6$-alkyl, R3 represents hydrogen, halogen, cyano, nitro, aryl-R9 or (CR5R6)$_m$-D-R9, R9 represents hydrogen, halogen, $C_1$-$C_6$-alkyl, cyano, nitro or $C_1$-$C_6$-alkoxy, R4 represents —(CR5R6)$_m$—Y-D-R10, Y represents a direct bond, —C(O)O— or —O—, and R10 represents hydrogen, nitro, halogen, $C_1$-$C_6$-alkyl, carboxy-$C_1$-$C_6$-alkyl, aryl or —C(O)O—R5.

In the compound of formula (1) according to the present invention, X is C or N and the compound structure for each case may be represented by the following formula (1a) or (1b), respectively.

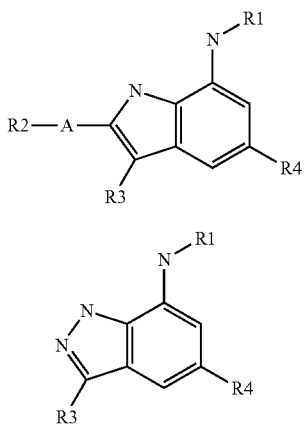

[Formula 1a]

[Formula 1b]

In the compound of formula (1) according to the present invention, the substituent A is more preferably selected from the group consisting of phenyl, pyridine, 1,4-pyrazine, 4,5-dihydro-thiazole, thiazole, 4,5-dihydrooxazole, [1,2,4]oxadiazole and [1,3,4]oxadiazole.

More preferably, the substituent R1 represents —C(O)—B—X'—R7 or —(CHR5)$_m$—B—X'—R7 where m is an integer of 0 to 2; R5 represents $C_1$-$C_3$-alkyl; B represents a direct bond, $C_5$-$C_6$-cycloalkyl optionally containing oxo, or 5~6-membered heterocycle or heteroaryl, each of which includes 1~3 heteroatoms selected from O, S and N atoms; X' represents a direct bond, —C(O)—, —SO$_2$—, —CO$_2$— or —C(O)NH—; and R7 represents hydrogen, $C_1$-$C_3$-alkyl, halogeno-$C_1$-$C_3$-alkyl, halogen, (CH$_2$)$_m$-phenyl, (CH$_2$)$_m$-hydroxy or (CH$_2$)$_m$-heterocycle where the heterocycle optionally contains oxo and is a 5~6-membered ring including 1~3 heteroatoms selected from N, O and S atoms. In the substituent R1, B is most preferably selected from the group consisting of cyclopentyl, cyclohexyl, piperidine, tetrahydropyran, oxocyclohexyl, pyrrolidine, difluorocyclohexyl and tetrahydrofuran; and R7 is most preferably selected from the group consisting of hydrogen, methyl, ethyl, isopropyl, benzyl, hydroxymethyl, (morpholine-4-yl)-ethyl, tetrahydrofuran, 2,2,2-trifluoroethyl, hydroxyethyl, 1,1-dioxothiomorpholine, tetrahydropyran, (tetrahydropyran-4-yl)-methyl and trifluoromethyl.

In the substituent R2, more preferably, D represents a direct bond, or is selected from the group consisting of piperazine, pyrrolidine, morpholine, 1,1-dioxothiomorpholine and oxopiperazine; and R8 is more preferably selected from the group consisting of hydrogen, ethyl, hydroxymethyl, methyl and fluorine.

More preferably, the substituent R3 represents hydrogen; halogen; phenyl optionally substituted with alkoxy; or 6-membered heterocyclylmethyl including 1-3 heteroatoms selected from N, S and O atoms as ring members and optionally containing oxo. R3 is most preferably selected from the group consisting of hydrogen, bromine, phenyl, methoxyphenyl, morpholine-4-yl-methyl, oxopiperazine-4-yl-methyl and 1,1-dioxo-thiomorpholine-4-yl-methyl.

More preferably, the substituent R4 represents —(CH$_2$)$_m$—Y-D-R10 where m is an integer of 0 to 2; Y represents a direct bond, —C(O)O— or —O—; D represents pyridine or 5~6-membered heterocycle including 1~3 heteroatoms selected from N, S and O atoms and optionally containing oxo; and R10 represents hydrogen, halogen, $C_1$-$C_3$-alkyl, —(CH$_2$)—CO$_2$H, aryl or —C(O)O—R5 where R5 represents hydrogen or $C_1$-$C_3$-alkyl. In the substituent R4, D is most preferably selected from the group consisting of 1,1-dioxo-thio-morpholine, oxopiperazine, pyridine, morpholine and 4,5-dihydro-thiazole; and R10 is most preferably selected from the group consisting of hydrogen, fluorine, chlorine, bromine, methyl, ethyl and —(CH$_2$)—CO$_2$H.

The representative compounds of formula (1) according to the present invention include the following compounds:
cyclopentyl-[2-(4,5-dihydro-1,3-thiazol-2-yl)-1H-indole-7-yl]-amine;
[2-(4,5-dihydro-thiazole-2-yl)-1H-indole-7-yl]-(4-methyl-cyclohexyl)-amine;
[2-(4,5-dihydro-thiazole-2-yl)-1H-indole-7-yl]-piperidine-4-yl-amine;
2-5-[7-(tetrahydro-pyran-4-ylamino)-1H-indole-2-yl]-[1,2,4]oxadiazole-3-yl}-ethanol;
[(R)-2-(7-cyclopentylamino-1H-indole-2-yl)-4,5-dihydro-1,3-thiazole-4-yl]-methanol;
cyclopentyl-[2-((R)-4-pyrrolidine-1-ylmethyl-4,5-dihydro-thiazole-2-yl)-1H-indole-7-yl]-amine;
{(R)-2-[7-(tetrahydro-pyran-4-ylamino)-1H-indole-2-yl]-4,5-dihydro-thiazole-4-yl}-methanol;
[(R)-2-(7-cyclopentylamino-5-fluoro-1H-indole-2-yl)-4,5-dihydro-thiazole-4-yl]-methanol;
{(R)-2-[5-fluoro-7-(tetrahydro-pyran-4-ylamino)-1H-indole-2-yl]-4,5-dihydro-thiazole-4-yl}-methanol;
{(R)-2-[5-(pyridine-3-yloxy)-7-(tetrahydro-pyran-4-ylamino)-1H-indole-2-yl]-4,5-dihydro-thiazole-4-yl}-methanol;
[(R)-2-(5-chloro-7-cyclopentylamino-1H-indole-2-yl)-4,5-dihydro-thiazole-4-yl]-acetic acid;
[(R)-2-(5-chloro-7-cyclopentylamino-1H-indole-2-yl)-4,5-dihydro-thiazole-4-yl]-acetic acid ethyl ester;
2-{(R)-2-[5-chloro-7-(tetrahydro-pyran-4-ylamino)-1H-indole-2-yl]-4,5-dihydro-thiazole-4-yl}-ethanol;
1-[4-(2-{(R)-2-[5-chloro-7-(tetrahydro-pyran-4-ylamino)-1H-indole-2-yl]-4,5-dihydro-thiazole-4-yl}-ethyl)-piperazine-1-yl]-2-hydroxy-ethanone;
1-(2-{(R)-2-[5-chloro-7-(tetrahydro-pyran-4-ylamino)-1H-indole-2-yl]-4,5-dihydro-thiazole-4-yl}-ethyl)-pyrrolidine-3-ol;
[(R)-2-(5-bromo-7-cyclopentylamino-1H-indole-2-yl)-4,5-dihydro-thiazole-4-yl]acetic acid;
[(R)-2-(7-cyclopentylamino-5-ethoxy-1H-indole-2-yl)-4,5-dihydro-thiazole-4-yl]-acetic acid;
[(R)-2-(7-cyclopentylamino-5-ethoxy-1H-indole-2-yl)-4,5-dihydro-thiazole-4-yl]-acetic acid;
[2-(7-cyclopentylamino-5-phenoxy-1H-indole-2-yl)-4,5-dihydro-thiazole-4-yl]-acetic acid;
[(R)-2-(7-cyclopentylamino-5-phenoxy-1H-indole-2-yl)-4,5-dihydro-thiazole-4-yl]-acetic acid;
[(S)-2-(7-cyclopentylamino-5-phenoxy-1H-indole-2-yl)-4,5-dihydro-thiazole-4-yl]-acetic acid;
3-[(R)-2-(5-chloro-7-cyclopentylamino-1H-indole-2-yl)-4,5-dihydro-thiazole-4-yl]-proponic acid ethyl ester;
3-[(R)-2-(5-chloro-7-cyclopentylamino-1H-indole-2-yl)-4,5-dihydro-thiazole-4-yl]-proponic acid;
cyclopentyl-(2-pyridine-2-yl-1H-indole-7-yl)-amine;
cyclopentyl-(2-pyrazine-2-yl-1H-indole-7-yl)amine;
(2-pyrazine-2-yl-1H-indole-7-yl)-(tetrahydropyran-4-yl)-amine;
cyclopentyl-(2-thiazole-2-yl-1H-indole-7-yl)-amine;

2-(7-cyclopentylamino-5-methyl-1H-indole-2-yl)-thiazole-4-carboxylic acid ethyl ester;
2-(7-cyclopentylamino-5-methyl-1H-indole-2-yl)-thiazole-4-carboxylic acid;
[2-(7-cyclopentylamino-5-methyl-1H-indole-2-yl)-thiazole-4-yl]-methanol;
[2-(7-cyclopentylamino-5-methyl-1H-indole-2-yl)-thiazole-5-yl]-methanol;
cyclopentyl-(5-methyl-2-[1,3,4]oxadiazole-2-yl-1H-indole-7-yl)-amine;
cyclopentyl-(5-methyl-2-pyridine-2-yl-1H-indole-7-yl)-amine;
(5-methyl-2-pyridine-2-yl-1H-indole-7-yl)-(tetrahydro-pyran-4-yl)-amine;
cyclohexyl-(5-methyl-2-pyridine-2-yl-1H-indole-7-yl)-amine;
1-[4-(5-methyl-2-pyridine-2-yl-1H-indole-7-ylamino)-piperidine-1-yl]-ethanone;
(1-methyl-piperidine-4-yl)-(5-methyl-2-pyridine-2-yl-1H-indole-7-yl)-amine;
4-(5-methyl-2-pyridine-2-yl-1H-indole-7-ylamino)-cyclohexanone;
(1-benzyl-pyrrolidine-3-yl)-(5-methyl-2-pyridine-2-yl-1H-indole-7-yl)-amine;
cyclopentylmethyl-(5-methyl-2-pyridine-2-yl-1H-indole-7-yl)-amine;
N-(5-methyl-2-pyridine-2-yl-1H-indole-7-yl)-benzamide;
cyclopentyl-(5-methyl-2-pyrazine-2-yl-1H-indole-7-yl)-amine;
cyclopentyl-(5-ethoxy-2-pyridine-2-yl-1H-indole-7-yl)-amine;
cyclopentyl-(5-phenoxy-2-pyridine-2-yl-1H-indole-7-yl)-amine;
cyclopentyl-(3,5-dimethyl-2-phenyl-1H-indole-7-yl)-amine;
cyclopentyl-(5-methyl-2-phenyl-1H-indole-7-yl)-amine;
(2-cyclohexyl-5-methyl-1H-indole-7-yl)-cyclopentyl-amine;
cyclopentyl-[5-methyl-2-(6-methyl-pyridine-2-yl)-1H-indole-7-yl]-amine;
(5-methyl-2-phenyl-1H-indole-7-yl)-(tetrahydro-pyran-4-yl)-amine;
(5-methyl-2-phenyl-1H-indole-7-yl)-(1-methyl-piperidine-4-yl)-amine;
1-[4-(5-methyl-2-phenyl-1H-indole-7-ylamino)-piperidine-1-yl]-ethanone;
(5-methyl-2-phenyl-1H-indole-7-yl)-piperidine-4-yl-amine hydrochloride;
2-hydroxy-1-[4-(5-methyl-2-phenyl-1H-indole-7-ylamino)-piperidine-1-yl]-ethanone;
(1-methanesulfonyl-piperidine-4-yl)-(5-methyl-2-phenyl-1H-indole-7-yl)-amine;
4-(5-methyl-2-phenyl-1H-indole-7-ylamino)-cyclohexanecarboxylic acid;
4-(5-methyl-2-phenyl-1H-indole-7-ylamino)-cyclohexanecarboxylic acid (2-morpholine-4-yl-ethyl)-amide;
cyclopentylmethyl-(5-methyl-2-phenyl-1H-indole-7-yl)-amine;
(5-methyl-2-phenyl-1H-indole-7-yl)-(tetrahydro-pyran-4-ylmethyl)-amine;
(5-chloro-2-phenyl-1H-indole-7-yl)-cyclopentyl-amine;
(5-chloro-2-phenyl-1H-indole-7-yl)-(tetrahydro-pyran-4-yl)-amine;
(5-chloro-2-phenyl-1H-indole-7-yl)-(1-methyl-piperidine-4-yl)-amine;
(5-chloro-2-phenyl-1H-indole-7-yl)-cyclohexyl-amine;
(1-benzyl-pyrrolidine-3-yl)-(5-chloro-2-phenyl-1H-indole-7-yl)-amine;
4-(5-chloro-7-cyclopentylamino-1H-indole-2-yl)-benzoic acid methyl ester;
4-(5-chloro-7-cyclopentylamino-1H-indole-2-yl)-benzoic acid;
[4-(5-chloro-7-cyclopentylamino-1H-indole-2-yl)-phenyl]-methanol;
4-(7-cyclopentylamino-5-methyl-1H-indole-2-yl)-benzoic acid methyl ester;
2-(5-chloro-7-cyclopentylamino-1H-indole-2-yl)-benzoic acid methyl ester;
2-(5-chloro-7-cyclopentylamino-1H-indole-2-yl)-benzoic acid;
[2-(5-chloro-7-cyclopentylamino-1H-indole-2-yl)-phenyl]-methanol;
7-cyclopentylamino-2-phenyl-1H-indole-5-carboxylic acid ethyl ester;
7-cyclopentylamino-2-phenyl-1H-indole-5-carboxylic acid;
(7-cyclopentylamino-2-phenyl-1H-indole-5-yl)-methanol;
(7-cyclopentylamino-2-phenyl-1H-indole-5-yl)-acetic acid ethyl ester;
(7-cyclopentylamino-2-phenyl-1H-indole-5-yl)-acetic acid;
2-[(4S)-2-[5-methyl-7-(oxane-4-ylmethylamino)-1H-indole-2-yl]-4,5-dihydro-1,3-thiazole-4-yl]acetic acid;
2-[(4S)-2-[5-chloro-7-(oxane-4-ylmethylamino)-1H-indole-2-yl]-4,5-dihydro-1,3-thiazole-4-yl]acetic acid;
2-[(4S)-2-[7-[(4,4-difluorocyclohexyl)amino]-5-methyl-1H-indole-2-yl]-4,5-dihydro-1,3-thiazole-4-yl]acetic acid;
2-[(4S)-2-[7-(oxane-4-ylamino)-5-phenoxy-1H-indole-2-yl]-4,5-dihydro-1,3-thiazole-4-yl]acetic acid;
2-[(4R)-2-[7-(oxane-4-ylamino)-5-phenoxy-1H-indole-2-yl]-4,5-dihydro-1,3-thiazole-4-yl]acetic acid;
2-[(4R)-2-[7-(oxane-4-ylmethylamino)-5-phenoxy-1H-indole-2-yl]-4,5-dihydro-1,3-thiazole-4-yl]acetic acid;
2-[(4S)-2-[7-(cyclopentylamino)-1H-indole-2-yl]-4,5-dihydro-1,3-thiazole-4-yl]acetic acid;
2-[(4S)-2-[7-[(1-acetylpyrrolidine-3-yl)amino]-5-methyl-1H-indole-2-yl]-4,5-dihydro-1,3-thiazole-4-yl]acetic acid;
2-[(4S)-2-[7-(oxane-4-ylmethylamino)-1H-indole-2-yl]-4,5-dihydro-1,3-thiazole-4-yl]acetic acid;
2-[(4S)-2-[7-(oxane-4-ylamino)-1H-indole-2-yl]-4,5-dihydro-1,3-thiazole-4-yl]acetic acid;
2-[(4S)-2-[7-(oxane-2-ylmethylamino)-1H-indole-2-yl]-4,5-dihydro-1,3-thiazole-4-yl]acetic acid;
2-[(4S)-2-[5-methyl-7-[[1-(3,3,3-trifluoropropanoyl)piperidine-4-yl]amino]-1H-indole-2-yl]-4,5-dihydro-1,3-thiazole-4-yl]acetic acid;
2-[(4R)-2-[7-(cyclopentylamino)-5-methyl-1H-indole-2-yl]-4,5-dihydro-1,3-thiazole-4-yl]acetic acid;
2-[(4R)-2-[5-methyl-7-(oxane-4-ylmethylamino)-1H-indole-2-yl]-4,5-dihydro-1,3-thiazole-4-yl]acetic acid;
4-[2-[(4S)-2-[5-methyl-7-(oxane-4-ylmethylamino)-1H-indole-2-yl]-4,5-dihydro-1,3-thiazole-4-yl]ethyl]piperazine-2-one;
2-[(4S)-4-[2-(1,1-dioxo-1,4-thiazinane-4-yl)ethyl]-4,5-dihydro-1,3-thiazole-2-yl]-5-meth yl-N-(oxane-4-ylmethyl)-1H-indole-7-yl-amine;
N-(4,4-difluorocyclohexyl)-5-methyl-2-[(4S)-4-(2-morpholine-4-ylethyl)-4,5-dihydro-1,3-thiazole-2-yl]-1H-indole-7-yl-amine;
4-[2-[(4S)-2-[7-[(4,4-difluorocyclohexyl)amino]-5-methyl-1H-indole-2-yl]-4,5-dihydro-1,3-thiazole-4-yl]ethyl]piperazine-2-one;

4-[2-[(4S)-2-[7-(oxane-4-ylmethylamino)-5-phenoxy-1H-indole-2-yl]-4,5-dihydro-1,3-thiazole-4-yl]ethyl]piperazine-2-one;
2-[(4S)-4-(2-morpholine-4-ylethyl)-4,5-dihydro-1,3-thiazole-2-yl]-N-(oxane-4-ylmethyl)-5-phenoxy-1H-indole-7-amine;
5-methyl-2-[(4S)-4-(2-morpholine-4-ylethyl)-4,5-dihydro-1,3-thiazole-2-yl]-N-(oxane-4-ylmethyl)-1H-indole-7-amine;
1-[2-[(4S)-2-[5-methyl-7-(oxane-4-ylmethylamino)-1H-indole-2-yl]-4,5-dihydro-1,3-thiazole-4-yl]ethyl]piperidine-4-carboxyamide;
[(2R)-1-[2-[(4S)-2-[5-methyl-7-(oxane-4-ylmethylamino)-1H-indole-2-yl]-4,5-dihydro-1,3-thiazole-4-yl]ethyl]pyrrolidine-2-yl]methanol;
(2S)-1-[2-[(4S)-2-[5-methyl-7-(oxane-4-ylmethylamino)-1H-indole-2-yl]-4,5-dihydro-1,3-thiazole-4-yl]ethyl]pyrrolidine-2-carboxyamide;
4-[2-[(4R)-2-[7-(cyclopentylamino)-5-methyl-1H-indole-2-yl]-4,5-dihydro-1,3-thiazole-4-yl]ethyl]piperazine-2-one;
2-[(4S)-2-[7-(cyclopentylamino)-5-methyl-1H-indole-2-yl]-4,5-dihydro-1,3-oxazole-4-yl]acetic acid;
{(S)-2-[5-methyl-7-(tetrahydropyran-4-ylamino)-1H-indole-2-yl]-4,5-dihydro-oxazole-4-yl}-acetic acid;
2-[(4S)-2-[5-methyl-7-(tetrahydropyran-4-ylamino)-1H-indole-2-yl]-4,5-dihydro-1,3-oxazole-4-yl]ethanol;
{5-methyl-2-[(S)-4-(2-morpholine-4-yl-ethyl)-4,5-dihydro-1,3-oxazole-2-yl]-1H-indole-7-yl}-(tetrahydro-pyran-4-yl)amine;
4-[(5-chloro-2-phenyl-1H-indole-7-yl)amino]-N-ethylpiperidine-1-carboxyamide;
[4-[(5-chloro-2-phenyl-1H-indole-7-yl)amino]piperidine-1-yl]-(oxolan-3-yl)methanone;
2-[7-(oxane-4-ylamino)-2-phenyl-1H-indole-5-yl]acetic acid;
2-[7-(cyclopentylmethylamino)-2-phenyl-1H-indole-5-yl]acetic acid;
5-fluoro-N-(1-methylpiperidine-4-yl)-2-phenyl-1H-indole-7-amine;
2-[4-[(5-fluoro-2-phenyl-1H-indole-7-yl)amine]piperidine-1-yl]ethanone;
5-fluoro-N-[1-(oxane-4-yl)piperidine-4-yl]-2-phenyl-1H-indole-7-amine;
N-[1-(1,1-dioxan-4-yl)piperidine-4-yl]-5-fluoro-2-phenyl-1H-indole-7-amine;
N-(oxane-4-yl)-5-phenoxy-2-phenyl-1H-indole-7-amine;
methyl 2-[(5-fluoro-2-phenyl-1H-indole-7-yl)-amino]acetate;
2-[(5-fluoro-2-phenyl-1H-indole-7-yl)amino]acetic acid;
methyl 2-[(5-chloro-2-phenyl-1H-indole-7-yl)amino]propanoate;
2-[(5-chloro-2-phenyl-1H-indole-7-yl)amino]propanoic acid;
2-[(5-phenoxy-2-phenyl-1H-indole-7-yl)amino]acetic acid;
2-[(5-phenoxy-2-phenyl-1H-indole-7-yl)amino]propanoic acid;
2-[(4S)-2-[7-(oxane-4-ylmethylamino)-2-phenyl-1H-indole-5-yl]-4,5-dihydro-1,3-thiazole-4-yl]acetic acid;
2-[(4S)-2-[7-(cyclopentylamino)-2-phenyl-1H-indole-5-yl]-4,5-dihydro-1,3-thiazole-4-yl]acetic acid;
methyl 2-[4-[5-chloro-7-(oxane-4-ylamino)-1H-indole-2-yl]phenyl]acetate;
methyl 2-[4-[5-chloro-7-(oxane-4-ylmethylamino)-1H-indole-2-yl]phenyl]acetate;
2-[4-[5-chloro-7-(oxane-4-ylamino)-1H-indole-2-yl]phenyl]acetic acid;
5-[(1,1-dioxo-1,4-thiazinane-4-yl)methyl]-N-(oxane-4-yl)-2-phenyl-1H-indole-7-amine;
5-[(1,1-dioxo-1,4-thiazinane-4-yl)methyl]-N-(oxane-4-ylmethyl)-2-phenyl-1H-indole-7-amine;
4-[[7-(oxane-4-ylamino)-2-phenyl-1H-indole-5-yl]methyl]piperazine-2-one;
5-[(1,1-dioxo-1,4-thiazinane-4-yl)methyl]-2-phenyl-N-piperidine-4-yl-1H-indole-7-amine;
[4-[[5-[(1,1-dioxo-1,4-thiazinane-4-yl)methyl]-2-phenyl-1H-indole-7-yl]amino]piperidine-1-yl]-(oxolan-3-yl)methanone;
N-[4-[5-[(1,1-dioxo-1,4-thiazinane-4-yl)methyl]-7-(oxane-4-ylamino)-1H-indole-2-yl]phenyl]acetamide;
N-[4-[7-(dicyclopentylamino)-5-[(1,1-dioxo-1,4-thiazinane-4-yl)methyl]-1H-indole-2-yl]phenyl]acetamide;
N-[4-[5-[(1,1-dioxo-1,4-thiazinane-4-yl)methyl]-7-(oxane-4-ylmethylamino)-1H-indole-2-yl]phenyl]acetamide;
N-cyclopentyl-5-[(1,1-dioxo-1,4-thiazinane-4-yl)methyl]-2-(4-methoxyphenyl)-1H-indole-7-amine;
5-[(1,1-dioxo-1,4-thiazinane-4-yl)methyl]-2-(4-methoxyphenyl)-N-(oxane-4-yl)-1H-indole-7-amine;
5-[(1,1-dioxo-1,4-thiazinane-4-yl)methyl]-N-(3-methoxybutyl)-2-phenyl-1H-indole-7-amine;
5-[(1,1-dioxo-1,4-thiazinane-4-yl)methyl]-2-(3-fluorophenyl)-N-(oxane-4-yl)-1H-indole-7-amine;
N-cyclopentyl-5-[(1,1-dioxo-1,4-thiazinane-4-yl)methyl]-2-(3-fluorophenyl)-1H-indole-7-amine;
3-bromo-5-[(1,1-dioxo-1,4-thiazinane-4-yl)methyl]-N-(oxane-4-yl)-2-phenyl-1H-indole-7-amine;
3-bromo-5-(morpholine-4-ylmethyl)-N-(oxane-4-yl)-2-phenyl-1H-indole-7-amine;
3-bromo-N-cyclopentyl-5-[(1,1-dioxo-1,4-thiazinane-4-yl)methyl]-2-phenyl-1H-indole-7-amine;
3-bromo-5-[(1,1-dioxo-1,4-thiazinane-4-yl)methyl]-N-(oxane-4-yl)-2-phenyl-1H-indole-7-amine;
5-chloro-N-(oxane-4-yl)-3-phenyl-1H-indole-7-amine;
5-chloro-N-cyclopentyl-3-phenyl-1H-indole-7-amine;
5-chloro-N-(oxane-4-ylmethyl)-3-phenyl-1H-indole-7-amine;
5-[(1,1-dioxo-1,4-thiazinane-4-yl)methyl]-N-(oxane-4-yl)-3-phenyl-2-trimethylsilyl-1H-indole-7-amine;
4-[[5-chloro-7-(cyclopentylamino)-2-phenyl-1H-indole-3-yl]methyl]piperazine-2-one;
4-[[5-chloro-7-(oxane-4-ylamino)-2-phenyl-1H-indole-3-yl]methyl]piperazine-2-one;
4-[[5-chloro-7-(oxane-4-ylmethylamino)-2-phenyl-1H-indole-3-yl]methyl]piperazine-2-one;
N-cyclopentyl-3-(4-methoxyphenyl)-1H-indazol-7-amine;
3-(4-methoxyphenyl)-N-(oxane-4-yl)-1H-indazol-7-amine;
3-(4-methoxyphenyl)-N-(oxane-4-ylmethyl)-1H-indazol-7-amine; and
2-(7-cyclopentylamino-2-phenyl-1H-indole-5-yl)-ethanol.

In addition, the terms and abbreviations used herein have their original meanings unless defined otherwise.

The compound of formula (1) according to the present invention may also form pharmaceutically acceptable salts. Such pharmaceutically acceptable salts include acid-addition salts formed by acid to form a non-toxic acid addition salt having pharmaceutically acceptable anion including, for example, inorganic acid such as hydrochloric acid, sulfuric acid, nitric acid, phosphoric acid, hydrobromic acid, hydroiodic acid and the like; organic acid such as tartaric acid, formic acid, citric acid, acetic acid, trichloroacetic acid, trifluoroacetic acid, gluconic acid, benzoic acid, lactic acid, fumaric acid, maleic acid, salicylic acid and the like; sulfonic acid such as methanesulfonic acid, ethanesulfonic acid, benzenesulfonic acid, p-toluenesulfonic acid and the like. In addition, for example, pharmaceutically acceptable carboxylic acid salts include alkali metal salts or alkali earth metal salts formed by lithium, sodium, potassium, calcium, magnesium and the like; amino acid salts of lysine, arginine, guanidine and the like; organic salts such as dicyclohexylamine, N-methyl-D-glucamine, tris(hydroxymethyl)methylamine, diethanolamine, choline, triethylamine and the like. The compound of formula (1) according to the present invention may be converted to its salt by conventional methods.

Meanwhile, the compound according to the present invention can have asymmetric carbon center(s), and so can be present as R or S isomeric forms, racemates, diastereomeric mixtures, and individual diastereomers. The present invention encompasses all of these isomeric forms and mixtures.

The present invention also provides a process for preparing the compound of formula (1). Hereinafter, to help understanding the present invention, the processes for the preparation of the compound of formula (1) are explained based on exemplary reaction schemes. However, it should be construed that a person skilled in the art could prepare the compound of formula (1) according to various methods based on the structure of formula (1), and such methods are included in the scope of the present invention. That is, the compound of formula (1) can be prepared by optionally combining various methods described in the present specification and/or disclosed in prior arts, which are included in the range of the present invention, and so the processes for the preparation of compound of formula (1) are not limited to those explained below.

The compound of formula (1) may be prepared according to the following Reaction Scheme (1) by reducing nitro group of compound (2) to obtain amine compound (3) and then introducing a substituent to the formed amine group. Alternatively, the compound of formula (1) may be prepared according to the following Reaction Schemes (2) to (8) by modifying the substituents R3, R5, R6, R7 of compound (4).

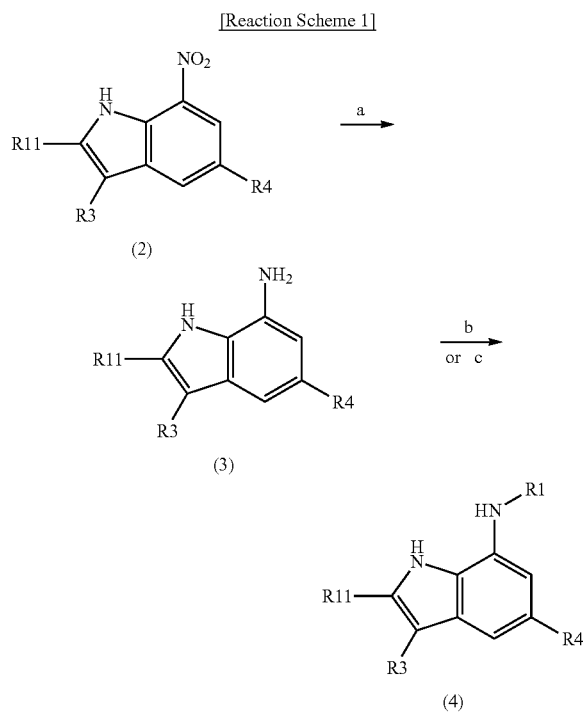

[Reaction Scheme 1]

In the above Reaction Scheme 1, a is Fe, Zn, or $H_2$ (Pd/C);

b is an acylation agent in the form of R7-B—CO—W, wherein R7 and B are the same as defined in formula (1), W is OH or a leaving group such as chloride, bromide, iodide, mixed anhydride and the like;

c is ketone in the form of R7-B=O or aldehyde compound in the form of R7-B—CHO, sodium triacetoxyborohydride ($NaBH(OAc)_3$) or sodium cyanoborohydride($NaBH_3CN$);

R3 is the same as defined in Formula (1);

R11 represents A-R2 or $CO_2$R12, wherein A and R2 are the same as defined in formula (1), R12 represents $C_1$-$C_6$-alkyl;

R4 is the same as defined in formula (1); and

R1 is the same as defined in formula (1).

Compound (2) may be prepared by the methods described in the following Reaction Schemes (2) to (8).

Compound (3) may be prepared by reducing Compound (2). The reduction reaction may be carried out by using an acid catalyst and metal, or a metal catalyst in the presence of hydrogen gas.

In the reduction reaction using an acid catalyst and metal, the acid that can be used is, for example, inorganic acid such as hydrochloric acid, sulfuric acid, nitric acid, phosphoric acid and the like; organo-carbonic acid such as acetic acid, trifluoroacetic acid and the like; or amine acid salt such as ammonium chloride, and preferably hydrochloric acid, acetic acid or ammonium chloride. The use amount of acid is conventionally 0.01-10 equivalents, preferably 0.1-5 equivalents to 1 equivalent of Compound (2). The metal that can be used is, for example, iron, zinc, lithium, sodium, tin (conventionally, tin chloride) and the like, and preferably iron, zinc or tin chloride. The use amount of metal is conventionally 1-20 equivalents, preferably 1-10 equivalents to 1 equivalent of Compound (2). The reaction of metal in the presence of acid catalyst may be carried out in an inert solvent. Such inert solvent is, for example, alkyl alcohol such as methanol, ethanol and the like; ether such as tetrahydrofuran, diethyl ether and the like; or alkyl ester such as ethyl acetate, and preferably methanol, ethanol, tetrahydrofuran or ethyl acetate. The reaction temperature is conventionally −10 to 200° C., preferably 25 to 120° C., and the reaction time is conventionally 10 minutes-60 hours, and preferably 10 minutes-12 hours.

In the reduction reaction in the presence of hydrogen gas, the metal catalyst that can be used is palladium, nickel, platinum, ruthenium, rhodium and the like, and preferably palladium, nickel or the like. The use amount of metal catalyst is conventionally 0.001-2 equivalents, and preferably 0.01-1 equivalent to 1 equivalent of Compound (2). The pressure of hydrogen gas is conventionally 1-10 atms, and preferably 1-3 atms. The reaction may be carried out in an inert solvent, for example, alkyl alcohol such as methanol, ethanol and the like; ether such as tetrahydrofuran, diethyl ether and the like; or alkyl acetate such as methyl acetate, ethyl acetate and the like, and preferably methanol, ethanol or ethyl acetate. The temperature of reaction using metal catalyst is conventionally −10 to 200° C., and preferably 25 to 50° C., and the reaction time is conventionally 10 minutes-60 hours, and preferably 10 minutes-12 hours.

Compound (4) may be prepared though acylation reaction or reductive alkylation reaction of Compound (3).

The acylation reaction to amine group of Compound (3) may be carried out by using an acylation agent in the presence of a base. The base that can be used is an organic base such as triethylamine, diisopropylethylamine, pyridine, N-methylmorpholine and the like. The use amount of base is conventionally 1-10 equivalents, and preferably 1-5 equivalents to 1 equivalent of Compound (3). The use amount of acylation agent is conventionally 1-10 equivalents, and preferably 1-3 equivalents to 1 equivalent of Compound (3). The reaction may be carried out in an inert solvent, for example, ether such as tetrahydrofuran, diethyl ether and the like; or chloroalkane such as dichloromethane, chloroform and the like, and preferably dichloromethane or chloroform. The temperature of reaction is conventionally −10 to 100° C., preferably −10 to 50° C., and reaction time is conventionally 10 minutes-60 hours, preferably 10 minutes-12 hours.

The reductive alkylation to amine group of Compound (3) may be carried out thorough the reaction with aldehyde or ketone with the use of a reducing agent. An acid catalyst may also be used if necessary. The amount of aldehyde or ketone is conventionally 1-10 equivalents, and preferably 1-3 equivalents to 1 equivalent of Compound (3). The reducing agent that can be used is sodium borohydride, sodium cyanoborohydride, sodium triacetoxyborohydride and the like. The use amount of reducing agent is conventionally 1-10 equivalents, and preferably 1-3 equivalents to 1 equivalent of Compound (3). The acid catalyst that can be used is, for example, inorganic acid such as hydrochloric acid, sulfuric acid, nitric acid, phosphoric acid and the like; organo-carbonic acid such as acetic acid, trifluoroacetic acid and the like; or amine acid salt such as ammonium chloride, and preferably hydrochloric acid or acetic acid. The use amount of acid is conventionally 0.1-10 equivalents, and preferably 1-5 equivalents to 1 equivalent of Compound (3). The reaction may be carried out in an inert solvent, for example, ether such as tetrahydrofuran, diethyl ether and the like; or chloroalkane such as dichloromethane, chloroform, dichloroethane and the like, and preferably dichloroethane or chloroform. The temperature of reaction is conventionally −10 to 100° C., preferably −10 to 50° C., and the reaction time is conventionally 10 minutes-60 hours, preferably 10 minutes-12 hours.

Compound (2) according to the present invention may be prepared by the methods concretely exemplified in the following Reaction Schemes (2) to (8).

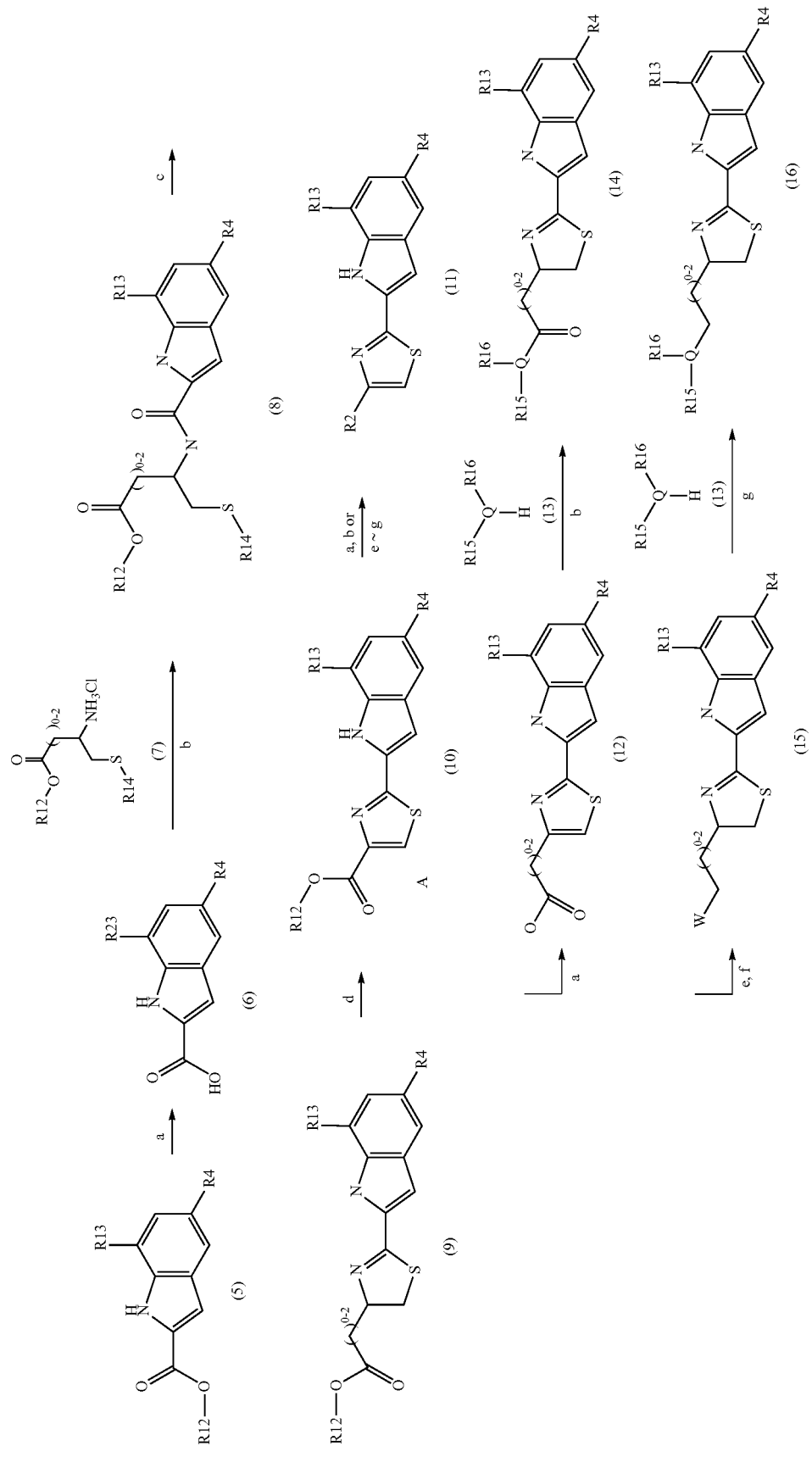

c is PCl$_5$ or Tf$_2$O and Ph$_3$PO;

d is a metal catalyst (e.g., Pd/C, MnO$_2$, etc.) or BrCCl$_3$ or the like;

e is a reducing agent (e.g., NaBH$_4$, LiAlH$_4$);

f is I$_2$ or MSCl;

g is Compound (13);

R2 is the same as defined in formula (1);

R4 is the same as defined in formula (1);

R12 represents C$_1$-C$_6$-alkyl;

R13 represents NO$_2$ or R1;

R14 represents p-MeOBn or Ph$_3$C;

when Q is nitrogen, each of R15 and R16 independently represents H, C$_1$-C$_6$-alkyl, 6 to 12-membered aryl or 5 to 12-membered heteroaryl; or R15 and R16 may be linked with each other to form 3 to 10-membered ring;

when Q is oxygen or sulfur, R15 represents H, C$_1$-C$_6$-alkyl, 6 to 12-membered aryl or 5 to 12-membered heteroaryl, and R16 is not present; and W is a leaving group, for example, halogen such as chloride, bromide, iodide and the like, or sulfonyl such as methanesulfonyl, p-toluenesulfonyl and the like.

Compound (5) may be prepared by the method described in Reaction Scheme (7) or (8).

Compound (6) may be prepared by hydrolysis reaction of Compound (5) by using a base. The base that can be used is lithium hydroxide, sodium hydroxide, potassium hydroxide, metal bicarbonate, metal carbonate and the like. The use amount of base is conventionally 1-10 equivalents, preferably 1-5 equivalents to 1 equivalent of Compound (5). The hydrolysis reaction may be carried out in an inert solvent, for example, alkyl alcohol such as methanol, ethanol and the like; ether such as tetrahydrofuran, diethyl ether and the like. The temperature of reaction is conventionally −10 to 200° C., preferably 25 to 120° C., and reaction time is conventionally 10 minutes-60 hours, preferably 10 minutes-12 hours.

Compound (7) may be prepared by the method described in the following Reaction Scheme (9).

Compound (8) may be prepared by a coupling reaction of carboxylic acid group of Compound (6) and amine group of Compound (7). Known coupling agents that can be used in the coupling reaction include, but not limited thereto, carboimide such as dicyclohexylcarbodiimide (DCC), 1-(3-dimethylaminopropyl)-3-ethylcarbodiimide (EDC) or 1,1'-dicarbonyldiimidazole (CDI) in a mixed form with 1-hydroxy-benzotriazole (HOBT) or 1-hydroxy-7-azabenzotriazole (HOAT), or bis-(2-oxo-3-oxazolidinyl)-phosphinic chloride (BOP—Cl), diphenylphosphoryl azide (DPPA) or N-[dimethylamino-1H-1,2,3-triazole[4,5-b]-pyridin-1-ylmethylene]-N-methylmethaneaminium (HATU). The use amount of coupling agent is conventionally 1-10 equivalents, preferably 1-3 equivalents to 1 equivalent of Compound (6). The use amount of HOBT or HOAT is conventionally 1-10 equivalents, preferably 1-3 equivalents to 1 equivalent of Compound (5). When hydrochloric acid salt of amine is used in the coupling reaction, acid should be removed with a base. The base that can be used for this is an organic base such as triethylamine, diisopropylethylamine and the like. The use amount of base is conventionally 1-10 equivalents, preferably 1-3 equivalents to 1 equivalent of Compound (7). The coupling reaction may be carried out in an inert solvent such as tetrahydrofuran, diethylether, N,N-dimethylformamide, and the like. The temperature of reaction is conventionally −10 to 200° C., preferably 25 to 120° C., and reaction time is conventionally 10 minutes-60 hours, preferably 10 minutes-12 hours.

Compound (9) may be prepared by a cyclization reaction of Compound (8) according to literatures (Journal of Organic Chemistry, 68(24), 2003, 9506-9509; Tetrahedron, 55(34), 1999, 10271-10282, etc.).

When R14 is p-methoxybenzyl (p-MeOBn) group, the cyclization reaction is carried out by using phosphorus pentachloride (PCl$_5$) in dichloromethane solvent. The use amount of PCl$_5$ is conventionally 1-10 equivalents, preferably 1-3 equivalents to 1 equivalent of Compound (8). The temperature of reaction is conventionally −10 to 50° C., preferably 0 to 25° C., and reaction time is conventionally 10 minutes-60 hours, preferably 10 minutes-12 hours.

When R14 is triphenylmethyl (Ph$_3$C) group, the cyclization reaction is carried out by using trifluoromethanesulfonic anhydride (Tf$_2$O) and triphenyl phosphinoxide (Ph$_3$PO) in dichloromethane solvent. The use amount of each of them is conventionally 1-10 equivalents, preferably 1-3 equivalents to 1 equivalent of Compound (8). The temperature of reaction is conventionally −10 to 50° C., preferably 0-25° C., and reaction time is conventionally 10 minutes-60 hours, preferably 10 minutes-12 hours.

Compound (10) may be prepared by using a dehydrogenation agent or a metal catalyst to Compound (9), or by an introduction of a leaving group therein and its subsequent removal by using a base.

The dehydrogenation agent may be sulfur, selenium, various quinones {e.g., 2,3-dichloro-5,6-dicyano-benzoquinone (DDQ)} and the like, and the dehydrogenation metal catalyst may be palladium (conventionally, Pd/C), platinum, nickel (conventionally, NiO$_2$), manganese (conventionally, MnO$_2$) and the like. The use amount of dehydrogenation agent is conventionally 1-20 equivalents, preferably 1-5 equivalents to 1 equivalent of Compound (9). The use amount of dehydrogenation metal catalyst is conventionally 0.001-10 equivalents, preferably 0.1-1 equivalent to 1 equivalent of Compound (9). A solvent that can be used is benzene, toluene, decalin, quinoline and the like. The temperature of reaction is conventionally 25 to 400° C., preferably 25 to 200° C., and reaction time is conventionally 10 minutes-60 hours, preferably 10 minutes-12 hours.

A reagent that can be used in the introduction of leaving group includes cooper (II) bromide (CuBr$_2$), bromotrichloromethane (BrCCl$_3$), N-bromosuccinimide (NBS) and the like. The use amount is conventionally 1-10 equivalents, preferably 1-5 equivalents to 1 equivalent of Compound (9). The base that can be used is, for example, inorganic base such as sodium carbonate, sodium bicarbonate, potassium carbonate and the like; organic base such as triethylamine, pyridine, 1,8-diazabicyclo[5,4,0]undeca-7-ene (DBU) and the like; preferably sodium carbonate or DBU. The use amount of base is conventionally 0-10 equivalents, preferably 0-3 equivalents to 1 equivalent of Compound (9). The solvent that can be used is an inert solvent, for example, ether such as tetrahydrofuran, diethyl ether and the like; chloroalkane such as dichloromethane, dichloroethane, chloroform and the like, and preferably dichloromethane or chloroform. The temperature of reaction is conventionally −10 to 200° C., preferably 0 to 100° C., and the reaction time is conventionally 10 minutes-60 hours, preferably 10 minutes-12 hours.

Compound (11) may be prepared through the hydrolysis reaction, reduction reaction, coupling reaction of amine and acid and substitution reaction of amine, etc. of Compound (10) by using the synthesis method of Compounds (6), (15) and (16).

Compound (12) may be prepared through the hydrolysis reaction of Compound (9) by using the synthesis method of Compound (6).

Compound (14) may be prepared through the coupling reaction of carboxylic acid of Compound (12) and Compound (13) by using the synthesis method of Compound (8).

Compound (15) may be prepared by modifying ester group of Compound (9) to alcohol group and introducing leaving group X.

A reducing agent to be used for reducing ester group to alcohol group is, for example, sodium borohydride, lithium borohydride, borane, lithium aluminum hydride, diisobutylaluminium hydride (DIBAL-H) and the like. The use amount of reducing agent is conventionally 1-10 equivalents, preferably 1-3 equivalents to 1 equivalent of Compound (9). The reaction may be carried out in an inert solvent, for example, alcohol such as methanol, ethanol and the like; ether such as tetrahydrofuran, diethyl ether and the like; and preferably tetrahydrofuran or ether. The reaction temperature is conventionally −78 to 100° C., preferably −10 to 50° C., and the reaction time is conventionally 10 minutes-60 hours, preferably 10 minutes-12 hours.

The method to introduce a leaving group to alcohol group is a halogenation or sulfonylation reaction. The halogenation reaction may be carried out by using a reagent such as iodine, bromine, N-iodosuccinimide (NIS), N-bromosuccinimide (NBS), carbon tetrachloride (CCl$_4$), carbon tetrabromide (CBr$_4$) and the like in the presence of a base such as imidazole, dimethylaminopyridine (DMAP), etc. and phosphine such as triphenylphosphine (Ph$_3$P), tributylphosphine (Bu$_3$P), etc. The use amount of each of the halogenation agent, base and phosphine compound is conventionally 1-10 equivalents, preferably 1-3 equivalents to 1 equivalent of Compound (9). The reaction may be carried out in an inert solvent, for example, ether such as tetrahydrofuran, diethyl ether and the like; dichloromethane; chloroform; acetonitrile and the like. The temperature of reaction is conventionally −10 to 200° C., preferably 0 to 50° C., and the reaction time is conventionally 10 minutes-60 hours, preferably 10 minutes-12 hours.

The sulfonylation reaction may be carried out by using a reagent such as methanesulfonyl chloride, p-toluenesulfonyl chloride and the like in the presence of an organic base such as pyridine, triethylamine and the like. The use amount of each of the sulfonylation agent and base is conventionally 1-10 equivalents, preferably 1-5 equivalents to 1 equivalent of Compound (9). The reaction may be carried out in an inert solvent, for example, ether such as tetrahydrofuran, diethyl ether and the like; chloroalkane such as dichloromethane, dichloroethane, chloroform and the like, and preferably dichloromethane or dichloroethane. The temperature of reaction using metal catalyst is conventionally −10 to 200° C., preferably 0 to 50° C., and the reaction time is conventionally 10 minutes-60 hours, preferably 10 minutes-12 hours.

Compound (16) may be prepared by the coupling reaction of Compound (13) and Compound (15) by using a base. The base that can be used is, for example, inorganic base such as sodium carbonate, potassium carbonate, cesium carbonate and the like; organic base such as triethylamine, diisopropylethylamine, 1,8-diazabicyclo[5,4,0]undeca-7-ene (DBU) and the like, and preferably potassium carbonate, cesium carbonate or DBU. The use amount of base is conventionally 1-10 equivalents, preferably 1-5 equivalents to 1 equivalent of Compound (13). The solvent that can be used is an inert solvent, for example, ether such as tetrahydrofuran, diethyl ether and the like; alkylnitrile such as acetonitrile, propionitrile and the like; amide such as N,N-dimethylformamide, and preferably tetrahydrofuran, acetonitrile or N,N-dimethylformamide. The temperature of reaction is conventionally −10 to 200° C., preferably 25 to 120° C., and the reaction time is conventionally 10 minutes-60 hours, preferably 10 minutes-12 hours.

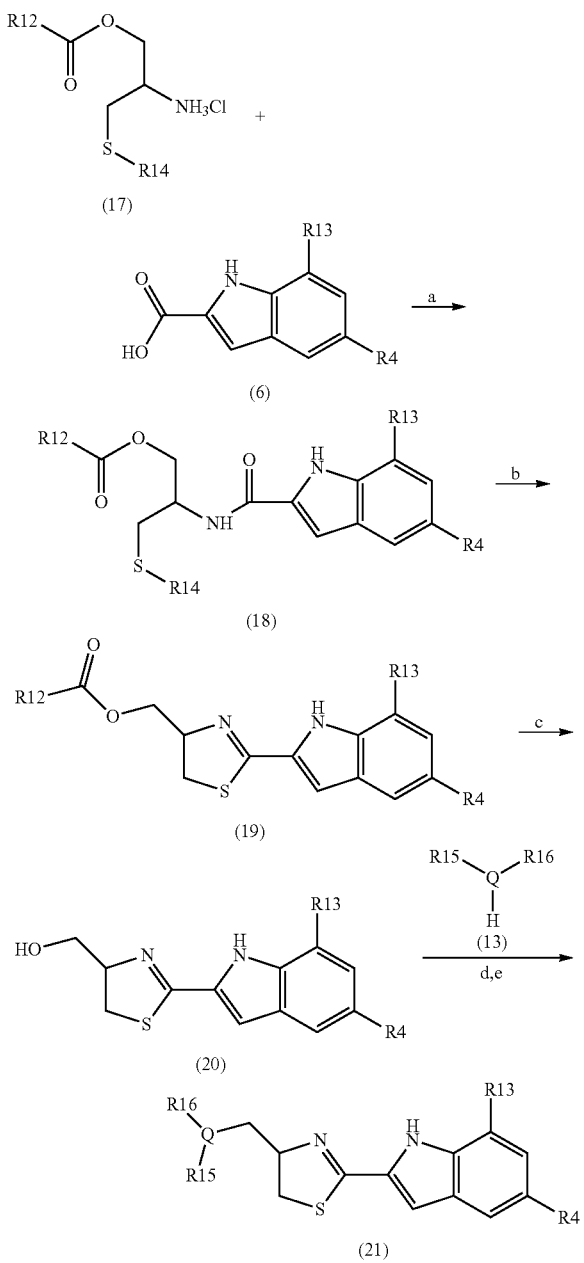

[Reaction Scheme 3]

In the above Reaction Scheme 3,
a is a coupling agent (e.g., EDC, CDI, BOP—Cl);
b is PCl$_5$ or Tf$_2$O and Ph$_3$PO;
c is metal hydroxide (e.g., NaOH, LiOH);
d is I$_2$ or MSCl or the like;
e is Compound (13);
R4 is the same as defined in Reaction Scheme (1);
R12, R13, R14, R15, R16 and Q are the same as defined in Reaction Scheme (2).

Compound (17) may be prepared by the method described in Reaction Scheme (10).

Compound (18) may be prepared by using Compound (6) and Compound (17) according to the synthesis method of Compound (8) in Reaction Scheme (2).

Compound (19) may be prepared by using Compound (18) according to the synthesis method of Compound (9) in Reaction Scheme (2).

Compound (20) may be prepared by using Compound (19) according to the synthesis method of Compound (6) in Reaction Scheme (2).

Compound (21) may be prepared by using Compound (20) according to the synthesis method of Compound (16) in Reaction Scheme (2).

[Reaction Scheme 4]

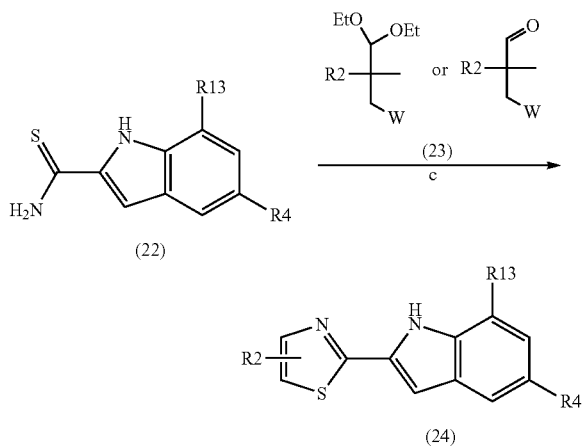

In the above Reaction Scheme (4),
a is $SOCl_2$ or $(COCl)_2$; and aqueous $NH_4OH$ solution;
b is Lawesson's reagent;
c is Compound (23);
R2 is the same as defined in formula (1);
R4 is the same as defined in Reaction Scheme (1);
R13 is the same as defined in Reaction Scheme (2);
W is a leaving group, for example, halogen such as chloride, bromide, iodide and the like, or sulfonyl such as methanesulfonyl, p-toluenesulfonyl.

Compound (22) may be prepared by modifying carboxylic acid of Compound (6) to amide and then converting amide to thioamide with Lawesson's reagent.

The method of modifying carboxylic acid of Compound (6) to amide is carried out through preparing acid chloride by using thionyl chloride ($SOCl_2$) or oxalyl chloride (($COCl)_2$) and then reacting it with ammonia water. The use amount of chlorination agent is conventionally 1-10 equivalents, preferably 1-5 equivalents to 1 equivalent of Compound (6). The use amount of ammonia water is conventionally 1-5 equivalents. The reaction may be carried out in an inert solvent such as dichloromethane, dichloroethane, chloroform and the like. The temperature of reaction is conventionally −10 to 200° C., preferably −10 to 100° C., and reaction time is conventionally 10 minutes-60 hours, preferably 10 minutes-12 hours.

Thioamide group may be prepared by reacting amide with Lawesson's reagent. The use amount of Lawesson's reagent is conventionally 1-10 equivalents, preferably 1-5 equivalents to 1 equivalent of Compound (6). The reaction may be carried out in an inert solvent, for example, ether such as tetrahydrofuran, diethyl ether and the like; chloroalkane such as dichloromethane, dichloroethane, chloroform and the like, aromatic hydrocarbon such as benzene, toluene and the like, and preferably tetrahydrofuran or toluene, etc. The temperature of reaction is conventionally −25 to 200° C., preferably 25 to 150° C., and the reaction time is conventionally 10 minutes-60 hours, preferably 10 minutes-12 hours.

Compound (23) is commercially available or may be prepared by known methods such as that disclosed in WO 1999/02501.

Compound (24) may be prepared by the coupling reaction of Compound (22) and Compound (23), with using a base if necessary. The base that can be used is, for example, inorganic base such as sodium carbonate, potassium carbonate, cesium carbonate and the like; organic base such as diisopropylethylamine, DBU and the like, and preferably potassium carbonate or cesium carbonate. The use amount of base is conventionally 0-10 equivalents, preferably 0-5 equivalents to 1 equivalent of Compound (22). The reaction may be carried out in an inert solvent, for example, ether such as tetrahydrofuran, diethyl ether and the like; alkylnitrile such as acetonitrile, propionitrile and the like; amide such as N,N-dimethylformamide, and preferably tetrahydrofuran or N,N-dimethylformamide. The temperature of reaction is conventionally −10 to 200° C., and the reaction time is conventionally 10 minutes-60 hours, preferably 10 minutes-12 hours.

[Reaction Scheme 5]

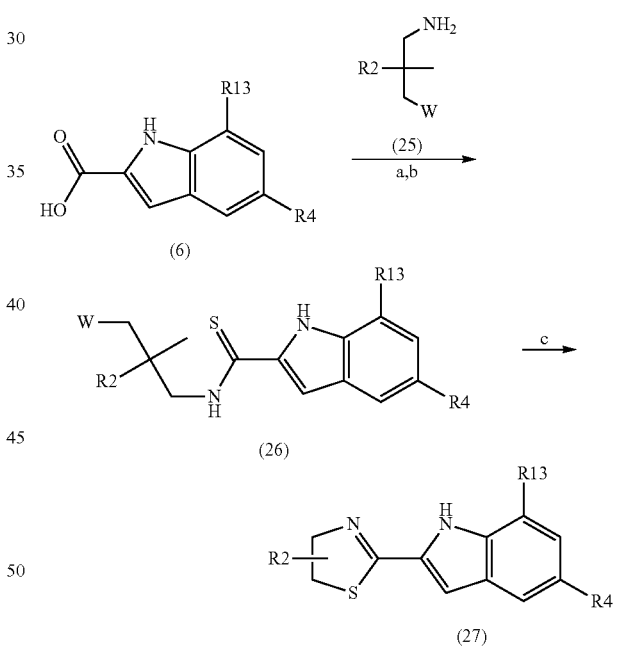

In the above Reaction Scheme 5,
a is amine Compound (25), a coupling agent (e.g., EDC, CDI, BOP—Cl);
b is Lawesson's reagent;
c is a base (e.g., $K_2CO_3$, $Cs_2CO_3$);
R2 is the same as defined in formula (1);
R4 is the same as defined in Reaction Scheme (1);
R13 is the same as defined in Reaction Scheme (2);
W is a leaving group, for example, halogen such as chloride, bromide, iodide and the like, or sulfonyl such as methanesulfonyl, p-toluenesulfonyl and the like.

Compound (25) is commercially available or may be prepared by known methods disclosed in literatures (Tetrahydron Letters, 28(48), 6068-6072, 1987; or Organic Process Research & Development 10(3), 472-480, 2006).

Compound (26) may be prepared by the sequential process of amide synthesis and thioamide synthesis by using Lawesson's reagent. The amide synthesis through coupling of Compound (6) and Compound (25) may be carried out according to the method of preparing amide Compound (8) in Reaction Scheme (2), and the synthesis of thioamide Compound (26) may be carried out according to the method of preparing Compound (22) in Reaction Scheme (4).

Compound (27) may be prepared by the cyclization reaction of Compound (26) by using a base. The base that can be used is potassium carbonate, cesium carbonate, diisopropylethylamine, DBU or the like. The use amount of base is conventionally 1-10 equivalents, preferably 1-5 equivalents to 1 equivalent of Compound (26). The reaction may be carried out in an inert solvent, for example, ether such as tetrahydrofuran, diethyl ether and the like; alkylnitrile such as acetonitrile, propionitrile and the like; amide such as N,N-dimethylformamide, and preferably tetrahydrofuran, acetonitrile or N,N-dimethylformamide. The temperature of reaction is conventionally −10 to 200° C., preferably 25 to 120° C., and the reaction time is conventionally 10 minutes-60 hours, preferably 10 minutes-12 hours.

[Reaction Scheme 6]

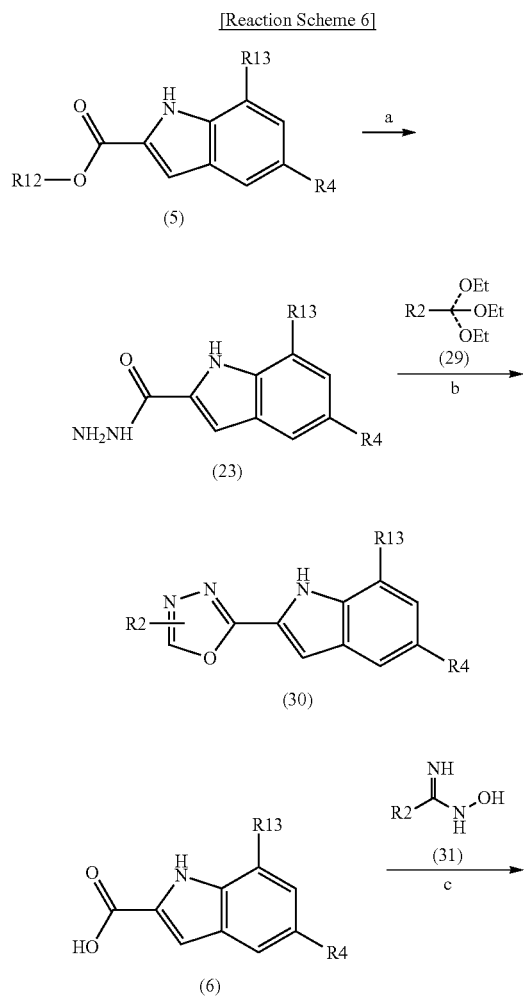

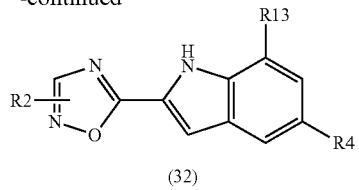

In the above Reaction Scheme 6,
a is $H_2NNH_2$,
b is Compound (29),
c is a coupling agent (e.g. CDI, BOP—Cl) and Compound (31),
R2 is the same as defined in formula (1),
R4 is the same as defined in Reaction Scheme (2), and
R12 and R13 is the same as defined in Reaction Scheme (2).

Compound (28) may be prepared by the reaction of Compound (5) with hydrazine. The use amount of hydrazine is conventionally 1-10 equivalents, preferably 1-5 equivalents to 1 equivalent of Compound (5). The reaction may be carried out in an inert solvent, for example, tetrahydrofuran, methanol, ethanol and the like. The reaction temperature is conventionally −10 to 200° C. and preferably 25 to 120° C. The reaction time is conventionally 10 minutes-60 hours and preferably 10 minutes-12 hours.

As for Compound (29), commercially available one is used.

Compound (30) may be prepared by the coupling reaction of Compound (28) with Compound (29). If necessary, an acid catalyst may be used. The use amount of Compound (29) is conventionally 1-10 equivalents, preferably 1-5 equivalents to 1 equivalent of Compound (28). The acid catalyst that can be used is selected from inorganic acid such as hydrochloric acid, sulfuric acid, nitric acid, phosphoric acid and the like; organic carbonic acid such as acetic acid, trifluoroacetic acid and the like; amine acid salt such as ammonium chloride; and Lewis acid such as aluminium chloride. The use amount of acid is conventionally 0.001-5 equivalents, preferably 0.01-1 equivalent to 1 equivalent of Compound (29). The reaction may be carried out in an inert solvent, for example, ether such as tetrahydrofuran, diethyl ether and the like; aromatic hydrocarbon such as benzene, toluene and the like; saturated hydrocarbon such as cyclohexane, hexane and the like; or amide such as N,N-dimethylamide. The reaction temperature is conventionally −10 to 200° C. and preferably 25 to 120° C. The reaction time is conventionally 10 minutes-60 hours and preferably 10 minutes-12 hours.

Compound (31) is commercially available or may be prepared by the method disclosed in US 2004/0019215.

Compound (32) may be prepared by the coupling reaction of Compound (6) with Compound (31) and subsequent dehydration reaction.

The use amount of coupling agent for the coupling reaction is conventionally 1-10 equivalents, preferably 1-3 equivalents to 1 equivalent of Compound (6). The reaction may be carried out in an inert solvent such as tetrahydrofuran or N,N-dimethyl amide. The reaction temperature is conventionally −10 to 200° C. and preferably 0 to 50° C. The reaction time is conventionally 10 minutes-60 hours and preferably 10 minutes-12 hours.

The dehydration reaction after the coupling reaction may be carried out by optionally using an acid catalyst. It may be carried out by the method for the preparation of Compound (30).

[Reaction scheme 7]

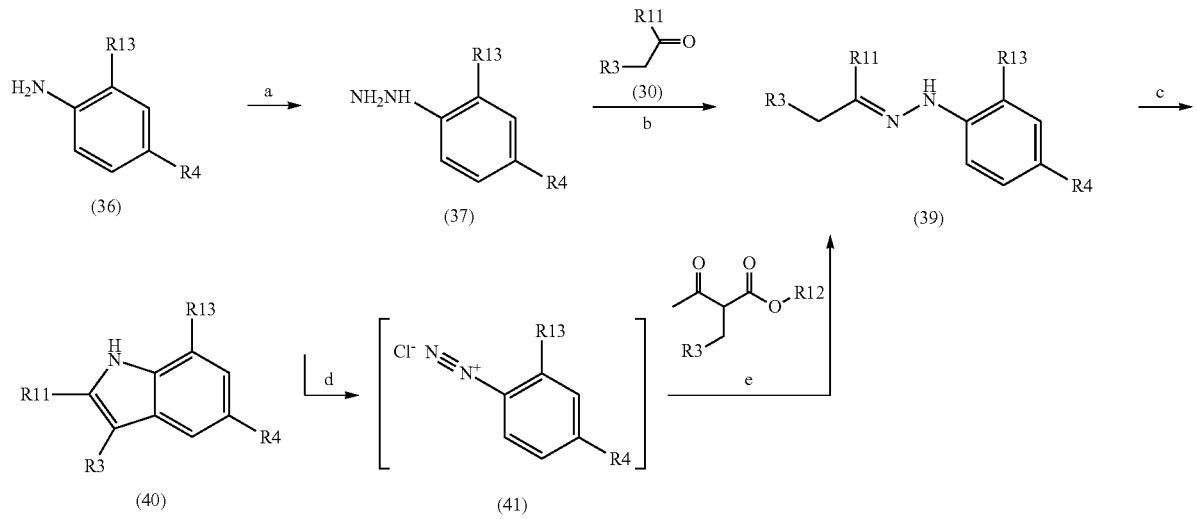

In the above Reaction Scheme (7),
a is sodium nitrate (NaNO$_2$); tin chloride (SnCl$_2$),
b is ketone Compound (38), a base (e.g. NaOAc),
c is an acid (e.g., polyphosphoric acid (PPA)),
d is NaNO$_2$,
e is Compound (42), a base (e.g. NaOH),
R3 is the same as defined in formula (1),
R11, R4 and R12 are the same as defined in Reaction Scheme (1), and
R13 is the same as defined in Reaction Scheme (2).

Compound (36) is commercially available or may be prepared by the methods disclosed in literatures [Heterocycles, 68(11), 285-99, 2006, or Bioorganic & Medicinal Chemistry Letters, 14(19), 903-4906, 2004].

Compound (37) is commercially available or may be prepared by modifying an amine group of Compound (36) to hydrazine group according to the method disclosed in literature [Journal of the America Chemical Society, 198(48), 15374-75, 2006].

Hydrazine compound (37) may be prepared by reacting amine group with NaNO$_2$ in the presence of hydrochloric acid to obtain diazonium salt (42), and without separation, reducing the diazonium salt by using SnCl$_2$. The use amount of NaNO$_2$ is conventionally 1-10 equivalents, preferably 2-5 equivalents to 1 equivalent of Compound (36). The use amount of SnCl$_2$ is conventionally 1-10 equivalents, preferably 2-5 equivalents to 1 equivalent of Compound (36). The reaction may be carried out in aqueous solution of hydrochloric acid with a concentration of 1-12N, preferably 4-8N. The reaction temperature is conventionally −10 to 50° C. The reaction time is conventionally 10 minutes-60 hours and preferably 10 minutes-6 hours.

As for Compound (38), commercially available one is used.

Hydrazone compound (39) may be prepared by the coupling reaction of Compound (37) with ketone Compound (38). If Compound (37) is in a neutral form, a base is not used, but if Compound (37) is in an acid form, a base should be used for making a neutral form. The base that can be used is, for example, metal hydroxide such as sodium hydroxide, lithium hydroxide, etc.; metal carbonate such as sodium bicarbonate, potassium carbonate, etc.; metal acetate such as sodium acetate; or an organic base such as triethylamine, pyridine, etc. The use amount of base is conventionally 1-5 equivalents, preferably 1-2 equivalents to 1 equivalent of Compound (37). The reaction may be carried out in an inert solvent such as tetrahydrofuran, methanol, ethanol, etc. The reaction temperature is conventionally −10 to 100° C., and the reaction time is conventionally 10 minutes-60 hours and preferably 10 minutes-12 hours.

Compound (39) may be prepared by reacting diazonium salt (41) and Compound (42) in the presence of a base according to Japp-Klingemann rearrangement method disclosed in literature [Organic Process Research & Development, 2, 1988, 214-220]. The use amount of hydrochloric acid for the preparation of diazonium salt (41) is conventionally 1-10 equivalents, preferably 2-4 equivalents to 1 equivalent of Compound (36). The base used for the reaction between Compounds (41) and (42) is sodium hydroxide. The use amount of the base is conventionally 1-20 equivalents, preferably 1-10 equivalents to 1 equivalent of Compound (42). Aqueous solution of 50% ethanol may be used as a solvent. The reaction temperature is conventionally −10 to 50° C. The reaction time is conventionally 10 minutes-60 hours and preferably 10 minutes-12 hours.

Compound (40) can be prepared by using an acid catalyst and Compound (39). The acid used in the synthesis is polyphosphoric acid, hydrochloric acid, p-toluenesulfonic acid, sulfuric acid, acetic acid, etc., and preferably poylphosphoric acid.

Polyphosphoric acid may be used alone or in combination with aromatic hydrocarbon such as benzene, toluene, etc. The reaction temperature is conventionally −25 to 150° C. The reaction time is conventionally 5 minutes-60 hours and preferably 5 minutes-12 hours.

Compound (42) is commercially available or may be prepared by the methods disclosed in literatures [WO 2007040289, WO 200601079 or Organic Letters 9(3), 397-400, 2007].

[Reaction Scheme 8]

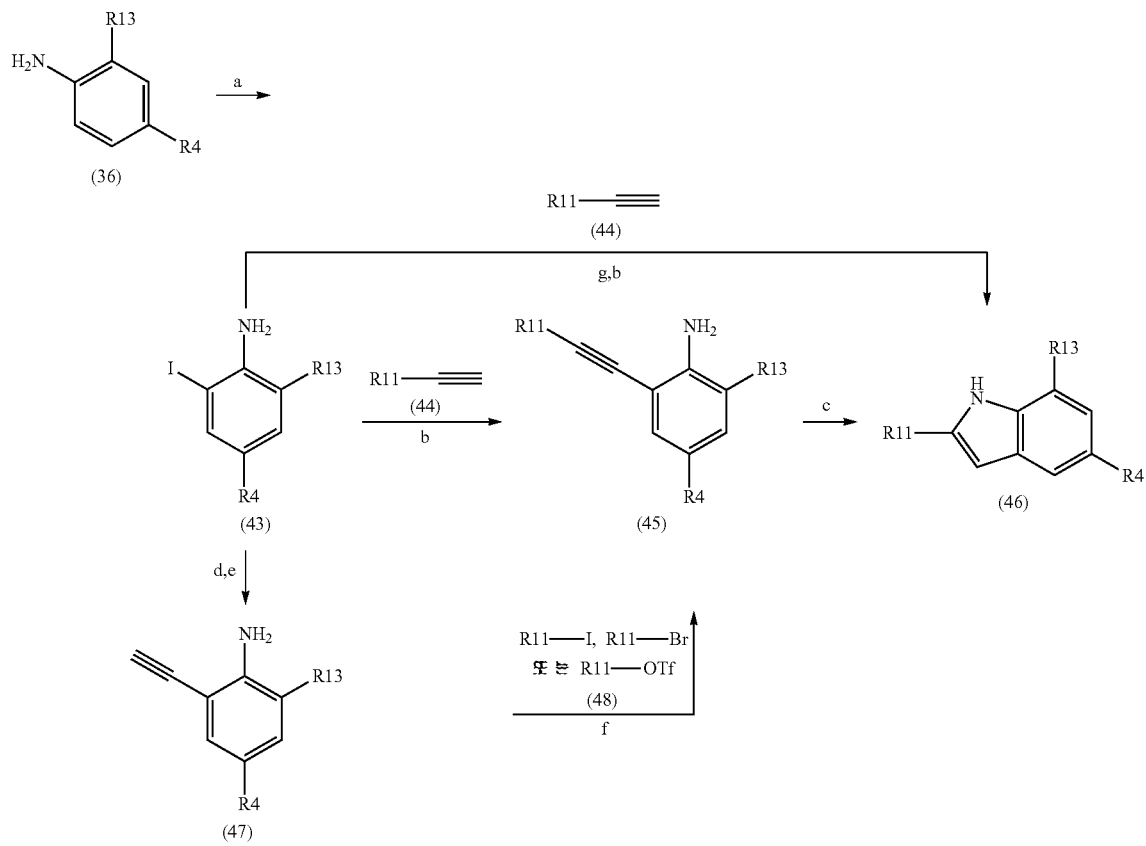

d is trimethylsilylacetylene or 2-methyl-3-butyn-2-ol, Pd, Cu(I), a base (e.g., Et₃N or Et₂NH), e is tetrabutylammonium fluoride (Bu₄NF) or NaOH, f is Compound (48), Pd(II), Cu(I), a base (e.g., Et₃N or Et₂NH), g is trifluoroacetic anhydride((CF₃CO)₂O), R11 and R4 are the same as defined in Reaction Scheme (1), and R13 is the same as defined in Reaction Scheme (2).

Compound (36) is commercially available or may be prepared by the methods disclosed in literatures [Heterocycles, 68(11), 285-99, 2006, or Bioorganic & Medicinal Chemistry Letters, 14(19), 903-4906, 2004].

Compound (43) may be prepared by iodination reaction of Compound (36). The iodination agent for iodination reaction may be selected from iodine, iodine monobromide and iodine monochloride, and silver ion, for example, silver nitrate (AgNO₃), silver carbonate (AgCO₃), silver sulfate (Ag₂SO₄) etc., may be used together. The use amount of iodination agent is conventionally 1-10 equivalents, preferably 1-3 equivalents to 1 equivalent of Compound (36). The use amount of silver ion is conventionally 0-10 equivalents, preferably 0-3 equivalents to 1 equivalent of Compound (36). The reaction may be carried out in an inert solvent, for example, ether such as tetrahydrofuran, diethyl ether, etc.; alkylalcohol such as methanol, ethanol, etc.; alkylnitrile such as acetonitrile, propionitril, etc.; or an organic acid such as acetic acid. The reaction temperature is conventionally −10 to 200° C. and preferably 0 to 50° C. The reaction time is conventionally 10 minutes-60 hours and preferably 10 minutes-12 hours.

Compound (44) is commercially available or may be prepared by the methods disclosed in literatures [Synthesis, 59-61, 2004 or Bioorganic & Medicinal Chemistry Letters, 13, 197-209, 2003] or the synthesis method of Compound (47).

Compound (45) may be prepared by the coupling reaction of iodide group of Compound (43) and acetylene group of Compound (44) according to the method disclosed in literature [Tetrahedron, 59, 2003, 1571-1587].

The coupling reaction may be carried out with the use of Pd (0) or Pd (II) catalyst [e.g., Pd(Ph₃P)₄, PdCl₂(Ph₃P)₂)], Cu(I) catalyst (e.g., CuI) and a base (e.g., triethylamine, diethylamine, etc.). The use amount of Pd catalyst is conventionally 0.001-5 equivalents, preferably 0.01-1 equivalent to 1 equivalent of Compound (43). The use amount of Cu(I) catalyst is conventionally 0.001-5 equivalents, preferably 0.01-1 equivalent to 1 equivalent of Compound (43). The use amount of base is conventionally 1-10 equivalents, preferably 1-5 equivalents to 1 equivalent of Compound (43). The reaction may be carried out in an inert solvent, for example, ether such as tetrahydrofuran, diethyl ether, etc.; aromatic hydrocarbon such as benzene, toluene, etc.; or N,N-dimethylformamide. The reaction temperature is conventionally −10 to 200° C. and preferably 25 to 120° C. The reaction time is conventionally 10 minutes-60 hours and preferably 10 minutes-12 hours.

Compound (46) may be prepared by the cyclization reaction of Compound (45) according to the methods disclosed in literatures [JP 2001/233855; Tetrahedron, 59, 2003, 1571-1587; Tetrahedron Letters, 47(36), 2006, 6485-6388; or Heterocycles, 64, 2004, 475-482, etc.]. The cyclization reaction may be carried out by using a base, Cu (I), Pd (II), etc. The base that can be used is, for example, potassium hydride (KH), potassium t-butoxide (KOBu'), etc., and the use amount of base is conventionally 1-10 equivalents, preferably 1-2 equivalents to 1 equivalent of Compound (45). The use amount of each of Cu (I) and Pd (II) is conventionally 0.001-5 equivalents, preferably 0.01-1 equivalent to 1 equivalent of Compound (45). The reaction may be carried out in an inert solvent, for example, ether such as tetrahydrofuran, diethyl ether, etc.; aromatic hydrocarbon such as benzene, toluene, etc.; alkyl nitrile such as acetonitrile, propionitrile, etc.; N,N-dimethylformamide or N-methyl-pyrrolidinone (NMP). If a base is used, the preferred solvent is NMP. If Cu (I) or Pd (II) is used, the preferred solvent is acetonitrile, toluene, N,N-dimethylformamide, etc. The reaction temperature is conventionally −10 to 200° C. and preferably 0 to 120° C. The reaction time is conventionally 10 minutes-60 hours and preferably 10 minutes-12 hours.

Compound (46) may also be prepared by modifying the amine group of Compound (43) to trifluoroacetamide group and then cyclizing with using Pd (II) according to the method disclosed in literature [Tetrahedron, 60, 2006, 10983-10992].

Compound (47) may be prepared by the coupling reaction of Compound (43) and acetylene in the presence of Pd (II), Cu(I) and a base according to the method disclosed in literature [Journal of Organic Chemistry, 71, 2006, 167-175]. The acetylene used is trimethylsilylacetylene or 2-methyl-3-butyn-2-ol, and the use amount of acetylene is conventionally 1-10 equivalents, preferably 1-3 equivalents to 1 equivalent of Compound (43). The use amount of each of Cu (I) and Pd (II) is conventionally 0.001-5 equivalents, preferably 0.01-1 equivalent to 1 equivalent of Compound (46). The base used is diethylamine, triethylamine, diisopropylethylamine, etc. and the use amount of base is conventionally 1-10 equivalents, preferably 1-5 equivalents to 1 equivalent of Compound (43). The reaction may be carried out in an inert solvent, for example, ether such as tetrahydrofuran, diethyl ether, etc., or aromatic hydrocarbon such as benzene, toluene, etc. The reaction temperature is conventionally −10 to 200° C. and preferably 0 to 120° C. The reaction time is conventionally 10 minutes-60 hours and preferably 10 minutes-12 hours.

Compound (48) is commercially available or may be prepared by the methods disclosed in literatures [Journal of Organic Chemistry, 70, 2005, 6519-6522 or Tetrahedron, 60(48), 2004, 10983-10992].

Compound (7) of the present invention may be prepared by the method specifically illustrated in the following Reaction Scheme (9).

In Reaction Scheme (9), Compounds (50), (52) and (54) correspond to Compound (7).

[Reaction Scheme 9]

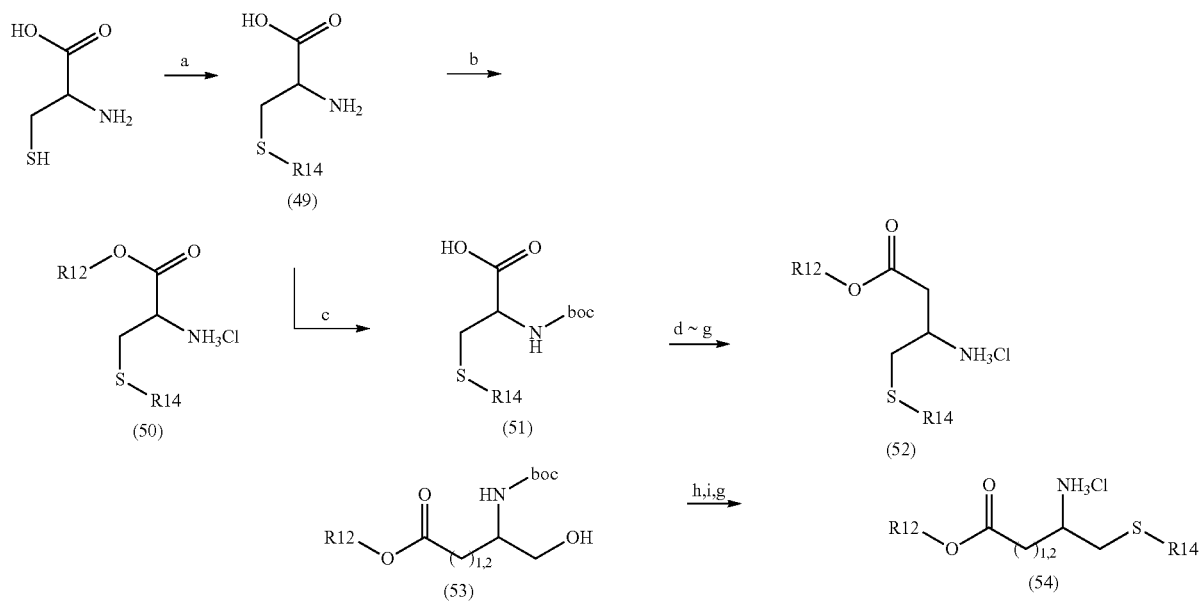

In the above Reaction Scheme (9), a is p-methoxybenzylchloride (PMBCl) or triphenylmethylchloride (TrCl), a base (e.g., NaOH), b is alkylalcohol (e.g., methanol, ethanol), acetylchloride or thionylchloride, c is di-t-butyloxy-dicarbonyl ($Boc_2O$), a base (e.g., NaOH, $K_2CO_3$), d is alkylchloroformate (e.g., EtOCOCl), a base (e.g., N-methylmorpholine), e is diazomethane ($CH_2N_2$), a base (e.g., KOH), f is silver ion (e.g., silver benzoate), g is an acid, h is MsCl, $Et_3N$, i is p-methoxybenzylthiol (PMBSH), NaH, R12 represents $C_1$-$C_6$ alkyl, and R14 represents p-MeOBn or $Ph_3C$.

Compound (49) may be prepared by protecting thiol group of cysteine with p-methoybenzylchloride (PMBCl) or triphenylmethylchloride (TrCl) in the presence of a base.

The use amount of PMBCl or TrCl for the protection of thiol group is conventionally 1-5 equivalents, preferably 1-2 equivalents to 1 equivalent of cysteine. The base used is sodium hydroxide, potassium carbonate, etc., and its use amount is conventionally 1-5 equivalents, preferably 1-2 equivalents to 1 equivalent of cysteine. The reaction may be carried out in an inert solvent such as tetrahydrofuran, methanol, ethanol, water, etc. The reaction temperature is conventionally −10 to 200° C. and preferably 0 to 50° C. The reaction time is conventionally 10 minutes-60 hours and preferably 10 minutes-12 hours.

Compound (51) may be prepared by protecting amine group of Compound (49) with BOC group.

The use amount of Boc$_2$O for the protection of amine group is conventionally 1-5 equivalents, preferably 1-2 equivalents to 1 equivalent of cysteine. The used base is, for example, hydroxide such as sodium hydroxide, lithium hydroxide etc.; carbonate such as sodium carbonate, sodium bicarbonate, potassium carbonate, cesium carbonate, etc.; an organic base such as diisopropylethylamine, triethylamine, etc., and preferably potassium carbonate, triethylamine, etc. The reaction may be carried out in an inert solvent such as tetrahydrofuran, methanol, ethanol, water, etc. The reaction temperature is conventionally −10 to 200° C. and preferably 0 to 50° C. The reaction time is conventionally 10 minutes-60 hours and preferably 10 minutes-12 hours.

Compound (50) may be prepared by the esterification of carboxyl group of Compound (49). The esterification reaction may be carried out with the use of acetylchloride or thionylchloride in an alkylalcohol solvent. The use amount of acetylchloride or thionylchloride is conventionally 1-10 equivalents, preferably 1-5 equivalents to 1 equivalent of Compound (49). The reaction temperature is conventionally −25 to 200° C. and preferably 25 to 100° C. The reaction time is conventionally 10 minutes-60 hours and preferably 10 minutes-12 hours.

Compound (52) may be prepared by the method disclosed in literature [Helvetica Chimica Acta, 87, 2004, 3131-3159].

In the presence of 1-2 equivalents of a base (e.g., N-methylmorpholine (NMM), triethylamine, etc.), 1 equivalent of Compound (51) is reacted with 1-2 equivalents of ethylchloroformate (EtOCOCl) or isobutylchloroformate ($^i$BuOCOCl) in tetrahydrofuran solvent at room temperature to obtain an anhydride compound. The obtained anhydride compound is reacted with 1-5 equivalents of diazomethane and 1-5 equivalents of aqueous potassium hydroxide solution in diethyl ether solvent at 0° C., and then reacted with Ag ion (e.g., silver trifluoroacetate (CF$_3$CO$_2$Ag), silver benzoate, etc.) at room temperature in the absence of light, to prepare an alkyl ester.

The BOC protection group of the prepared compound may be reacted with an acid (e.g., hydrochloric acid, trifluoroacetic acid) in a solvent such as dioxane, tetrahydrofuran or dichloromethane at room temperature for deprotection, and then Compound (52) may be obtained.

Compound (53) may be prepared by the method disclosed in literatures [Synlett, 15, 2005, 2397-2399 or Journal of Organic Chemistry, 66(5), 2001, 1919-1923] with using glutamic acid or aspartic acid as a starting material.

Compound (54) may be prepared by modifying an alcohol group of Compound (53) to a leaving group and then reacting with p-methoxybenzylthiol (PMBSH), as in the method for preparation of Compound (21) in Reaction Scheme (3).

Compound (53) is reacted with 1-5 equivalents of triethylamine and 1-3 equivalents of MSCl in a dichloromethane solvent at 0° C. to obtain a sulfonate compound. The sulfonate compound may be reacted at 25 to 100° C. with PMBSNa solution, which is prepared by adding 2-5 equivalents of NaH and 2-5 equivalents of PMBSH in DMF, to prepare Compound (54).

Compound (17) of the present invention may be prepared by the method specifically illustrated in the following Reaction Scheme (10).

[Reaction Scheme 10]

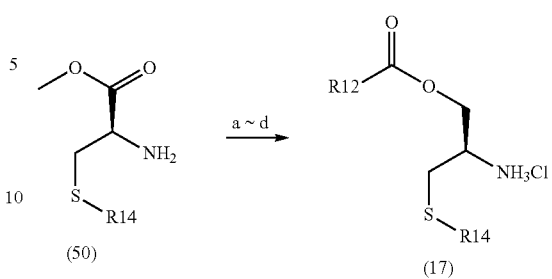

In the above Reaction Scheme (10),
a is Boc$_2$O,
b is a reducing agent (e.g., NaBH$_4$),
c is t-butylcarbonylchloride ($^t$BuCOCl), a base (e.g., Et$_3$N),
d is an acid,
R12 represents C$_1$-C$_6$ alkyl, and
R14 represents p-MeOBn or Ph$_3$C.

Compound (17) may be prepared by subsequently protecting an amine group with BOC group, reducing ester group to an alcohol, protecting the alcohol group with an ester group, and deprotecting the BOC group.

The protection of amine group may be carried out according to the method illustrated in Reaction Scheme (9).

The reduction of ester group may be carried out by reacting with 2-5 equivalents of lithium borohydride for 1-5 hours in tetrahydrofuran solvent at 0° C.

The protection of alcohol group may be carried out by the reacting with t-BuCOCl for 10 minutes-12 hours in the presence of 1-5 equivalents of a base such as triethylamine or pyridine etc., in dichloromethane solvent at 0-25° C.

The deprotection of BOC group may be carried out by dissolving reactants in an inert solvent such as tetrahydrofuran, dioxane, ethyl acetate or dichloromethane and reacting with 1-10 equivalents of hydrochloric acid or acetic acid for 10 minutes-12 hours at 0 to 50° C.

The compounds, which are not specifically explained about preparation thereof in the present specification, are disclosed compounds per se or the compounds that may be prepared according to already-known syntheses or similar syntheses thereof.

The compound of formula (1) prepared by the above methods may be separated or purified from the reaction products by various methods such as recrystallization, ionic electrophoresis, silica gel column chromatography or ion exchange resin chromatography, etc.

As explained in the above, the indole or indazole compounds of the present invention, starting materials or intermediates, etc. for preparation thereof may be prepared by various methods.

Advantageous Effects

The composition of the present invention comprising the above-explained indole or indazole compound of formula (1) as an active component can be used for preserving cells or organs of animals. More specifically, the composition of the present invention can be used for preventing injury of organs, isolated cell systems or tissues caused by cold storage, transplant operation or post-transplantation reperfusion. However, the effects of the composition according to the present invention are not limited to those explained above.

"Cell" as used herein means an animal cell isolated from tissues of human or non-human animals and selected from the group consisting of liver cell, skin cell, mucous membrane cell, Langerhans islet cell, nerve cell, cartilage cell, endothelium cell, epithelial cell, bone cell and muscle cell, or sperm, egg or fertilized egg of livestock or fish. "Organ" is selected from the group consisting of skin, cornea, kidney, heart, liver, pancreas, intestine, nerve, lung, placenta, umbilical cord and blood vessel system.

In addition, the indole or indazole compound according to the present invention can be used by further adding it in a conventional solution for preserving organs. If the indole or indazole compound according to the present invention is added in the conventional solution for preserving organs, the preservation period of the above-mentioned organs for transplantation can be greatly extended and organ damage after transplantation can be effectively prevented or treated.

Furthermore, by adding the indole or indazole compound according to the present invention in conventional cell-culture medium or preservation solutions, liver cells or pancreas cells, etc. of animals can be preserved for a long time even without freezing. Thus, such preserved animal cells can be utilized for applications in cell or tissue engineering to prepare useful materials.

Together with the active ingredient, the "pharmaceutical composition" according to the present invention may comprise a pharmaceutically acceptable carrier, diluent, excipient or combination thereof, if needed. Such a pharmaceutical composition facilitates the administration of the compound into a living organism. There are many administration techniques including oral, injection, aerosol, parenteral and topical administrations, but not limited thereto.

"Carrier" as used herein means a substance which facilitates the incorporation of the compound into cells or tissues. For example, dimethylsulfoxide (DMSO) is a typical carrier which is used to facilitate the introduction of various organic compounds into cells or tissues of living organisms.

"Diluent" as used herein is defined as a substance being diluted in water that dissolves the compound, as well as stabilizing the subject compound in its biologically active form. The salts dissolved in a buffer solution are utilized as diluents in the art. A typical buffer solution is phosphate-buffered saline which mimics the salt form of human solution. Buffer diluents hardly alter biological activities of the compound since the buffer salts can control the pH of solution at low concentration.

"Pharmaceutically acceptable" as used herein means the property that does not impair biological activities and properties of the compound.

The compounds of the present invention can be formulated in various pharmaceutical dosage forms according to the desired purpose. For the preparation of the pharmaceutical composition of the present invention, the active ingredient, specifically the compounds of formula (1), pharmaceutically acceptable salt or isomer thereof, is mixed together with various pharmaceutically acceptable carriers which can be selected according to the formulation to be prepared. For example, according to the desired purpose, the pharmaceutical composition of the present invention can be formulated as injection preparation, oral preparation, etc.

The compounds of the present invention can be formulated by the methods known in the art utilizing known pharmaceutical carriers and excipients, and incorporated into containers of unit dose form or multi-dose form. The form of the preparation can be solutions, suspensions or emulsions in oily or aqueous media, and may contain typical dispersing agents, suspending agents or stabilizers. Further, for example, it can be a form of dry powder which is intended to be reconstructed by dissolving in sterilized, pyrogen-free water prior to use. The compounds of the present invention also can be formulated into suppository forms utilizing typical suppository base such as cocoa butter or other glycerides. As solid dosage forms for oral administration, capsules, tablets, pills, powder and granules can be prepared, and capsules and tablets are especially useful. Preferably, tablets and pills are prepared as enteric coated forms. Solid dosage forms can be prepared by mixing the compound of the present invention together with carriers such as one or more inert diluents such as sucrose, lactose, starch, etc., lubricants such as magnesium stearate, disintegrant, binder, etc.

If needed, the compound of the present invention or the pharmaceutical compositions containing the same can also be administered in combination with other active agents, for example, other materials that can prevent injury of organs, isolated cell systems or tissues caused by cold storage, transplant operation or post-transplantation reperfusion The dosage of the compounds of formula (1) depends on the prescription of a physician, taking into account such factors as body weight and age of the patient, specific nature of the disease and severity of the disease, etc. However, dosage needed for transplanting an organ to an adult is typically from about 1 nM to 100 µM, and generally a concentration of 10 µM or less will be a sufficient dosage but for some patients, higher dosage may be preferable.

"Treatment" as used herein means interrupting or delaying the progress of the disease when applied to the subject showing the onset of disease symptoms and "prevention" means interrupting or delaying the sign of the onset of disease when applied to the subject that does not show but is at risk of the onset of disease symptoms.

The present invention will be more specifically explained by the following preparations and examples. However, it should be understand that they are intended to illustrate the present invention but not in any manner to limit the scope of the present invention. In the following preparations and examples, M means molar concentration, and N means normal concentration.

BEST MODE FOR CARRYING OUT THE INVENTION

Figure 1:
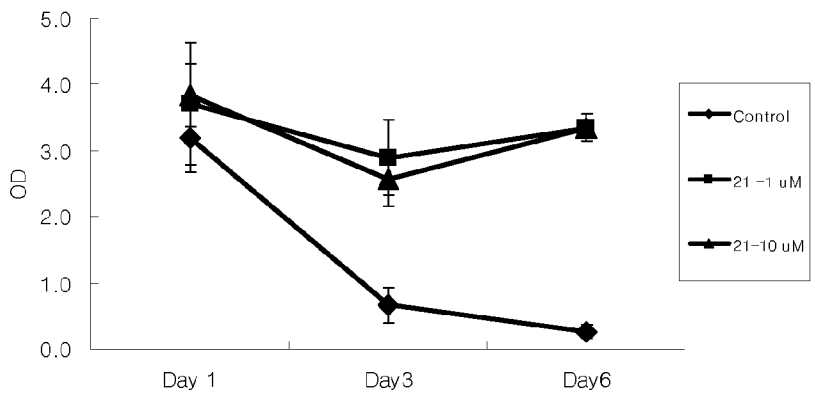
FIG. 1 illustrates a hepatocyte-protecting effect of the compound of Example 21 according to the present invention through the results of experiments using rat primary hepatocytes.

Preparation 1: Synthesis of 2-[(4-fluoro-2-nitro-phenyl-)hydrazono]-propionic acid ethyl ester 4-Fluoro-2-nitroaniline (10 g, 64 mmol) was dissolved in 6N hydrochloric acid (64 ml, 0.27 mol), sodium nitrate (4.4 g, 64 mmol) dissolved in water (50 ml) was slowly added in drops at 0° C., and the mixture was stirred for 30 min at 0° C.~room temperature. At the same time, ethyl 2-methylacetoacetate (9.2 ml, 64 mmol) and sodium hydroxide (19 g, 0.34 mol) were dissolved in 80% ethanol aqueous solution (95 ml) and stirred for 10 min at 0° C. Thus prepared two solutions were mixed and stirred for 8 h at 0° C.~room temperature. To the reaction mixture was added water. The solid not dissolved was collected, washed with water and dried to give the title compound (7.9 g, Yield 46%).

$^1$H-NMR (400 HMz, CDCl$_3$); δ 10.81 (br s, 1H), 8.05 (m, 1H), 7.90 (m, 1H), 7.41 (m, 1H), 4.36 (q, 2H), 2.22 (S, 3H), 1.38 (t, 3H)

Preparation 2: Synthesis of 5-fluoro-7-nitro-1H-indole-2-carboxylic acid ethyl ester The compound obtained in Preparation 1 (8.8 g, 33 mmol) was mixed with polyphosphoric acid (50 ml), and the mixture was stirred for 7 h at 60° C. To the reaction mixture was added water. The solid not dissolved was collected, washed with water and dried to give the title compound (3.4 g, Yield 41%).

$^1$H-NMR (400 HMz, DMSO-d$_6$); δ 11.55 (br s, 1H), 8.16 (m, 1H), 8.10 (m, 1H), 7.42 (s, 1H), 4.40 (q, 2H), 1.36 (t, 3H)

Preparation 3: Synthesis of (4-chloro-2-nitro-phenyl)-hydrazine hydrochloride 4-Chloro-2-nitroaniline (40 g, 0.23 mol) was dissolved in 12N-hydrochloric acid (100 ml). Sodium nitrate (16 g, 0.23 mol) dissolved in water (50 ml) was slowly added in drops at 0° C., and the mixture was stirred for 30 min at 0° C.~room temperature. The temperature was lowered to 0° C., and tin (II) chloride (132 g, 0.70 mol) dissolved in 12N-hydrochloric acid (100 ml) was slowly added in drops. The mixture was stirred for 3 h at 0° C.~room temperature. The resulting yellow solid was filtered, washed with a small amount of 6N—HCl and dried to give the title compound (30 g, Yield, 63%).

$^1$H-NMR (400 HMz, DMSO-d$_6$); δ 9.21 (s, 1H), 7.98 (d, J=2.4 Hz, 1H), 7.66 (d, J=9.6 Hz, 1H), 7.55 (dd, J=2.4, 9.6 Hz, 1H), 4.74 (br s, 2H)

Preparation 4: Synthesis of 2-[(4-chloro-2-nitro-phenyl)-hydrazono]-propionic acid methyl ester The hydrazine (30 g, 0.14 mol) obtained in Preparation 3 and methyl pyruvate (14.4 ml, 0.16 mol) were dissolved in methanol (300 ml), and sodium acetate (14.2 g, 0.17 mol) was added thereto. The mixture was stirred for 8 h at room temperature. The resulting yellow solid was filtered, washed with water and methanol, and dried to give the title compound (30 g, Yield 82%).

$^1$H-NMR (400 HMz, CDCl$_3$); δ 10.88 (s, 1H), 8.21 (d, J=2.4 Hz, 1H), 8.01 (d, J=9.2 Hz, 1H), 7.56 (dd, J=2.4, 9.2 Hz, 1H), 3.96 (5, 3H), 2.23 (s, 3H).

Mass spectrum (ESI, m/z): Calculated for C$_{10}$H$_{10}$C1N$_3$O$_4$: 271.04, Found: 271.66

Preparation 5: Synthesis of 5-chloro-7-nitro-1H-indole-2-carboxylic acid methyl ester To the compound (13 g, 46 mmol) obtained in Preparation 4 was added polyphosphoric acid (100 ml), and the mixture was heated at 100° C. for 4 h. After completion of the reaction, water was added to the reaction mixture. The solid not dissolved was collected, washed with water and dried to give the title compound (6.0 g, Yield 49%).

$^1$H-NMR (400 HMz, CDCl$_3$); δ 10.32 (br s, 1H), 8.29 (d, 1H), 8.03 (d, J=2.4 Hz, 1H), 7.31 (d, J=2.0 Hz, 1H), 4.01 (s, 3H)

Mass spectrum (ESI, m/z): Calculated: 254.01, Found: 254.63

Preparation 6: Synthesis of 5-bromo-7-nitro-1H-indole-2-carboxylic acid methyl ester 4-Bromo-2-nitroaniline (15.6 g, 71.9 mmol) was reacted according to the same procedures as Preparations 3 to 5 to give the title compound (7.2 g, Yield 73%).

$^1$H-NMR (400 HMz, CDCl$_3$); δ 10.33 (br s, 1H), 8.41 (s, 1H), 8.18 (s, 1H), 7.30 (d, J=4.0 Hz, 1H), 4.01 (s, 3H)

Preparation 7: Synthesis of 5-methyl-7-nitro-1H-indole-2-carboxylic acid methyl ester 4-Methyl-2-nitroaniline (40 g, 0.26 mol) was reacted according to the same procedures as Preparations 3 to 5 to give the title compound (20 g, Yield 32%).

$^1$H-NMR (500 HMz, DMSO-d$_6$); δ 11.25 (br s, 1H), 8.08 (3, 1H), 7.96 (s, 1H), 7.32 (s, 1H), 3.87 (s, 3H), 2.44 (s, 3H)

Preparation 8: Synthesis of 4-ethoxy-2-nitro-phenylamine

4-Ethoxyaniline (40 g, 0.29 mol) and triethylamine (61 ml, 0.44 mol) were dissolved in dichloromethane (200 ml). Acetic anhydride (30 ml, 0.32 mmol) was added in drops, and the mixture was stirred for 1 h at 0° C.~room temperature. 1N-hydrochloric acid solution was added thereto, and the resulting mixture was extracted with ethyl acetate, washed with saturated sodium chloride solution and dried over anhydrous magnesium sulfate.

Thus obtained acetamide compound was dissolved in dichloromethane (200 ml), and fuming nitric acid (13 ml, 0.29 mol) was added in drops at 0° C. The resulting mixture was stirred for 1 h at 0° C.~room temperature. Saturated aqueous sodium hydrogen carbonate solution was added, and the mixture was extracted with ethyl acetate, washed with saturated sodium chloride solution and dried over anhydrous magnesium sulfate.

Thus obtained nitrate compound was dissolved in methanol (100 ml) and tetrahydrofuran (100 ml), and 6N-sodium hydride was added in drops. The mixture was stirred for 6 h at room temperature. After completion of the reaction, 6N-hydrochloric acid solution was added to neutralize the reaction mixture to about pH 7. The mixture was extracted with ethyl acetate, washed with saturated sodium chloride solution and dried over anhydrous magnesium sulfate to give the title compound (44 g, Yield 83%).

Preparation 9: Synthesis of 5-ethoxy-7-nitro-1H-indole-2-carboxylic acid methyl ester 4-Ethoxy-2-nitroaniline obtained in Preparation 8 (40 g, 0.22 mol) was reacted according to the same procedures as Preparations 3 to 5 to give the title compound (13 g, Yield 22%).
$^1$H-NMR (400 HMz, DMSO-$d_6$); δ 10.20 (br s, 1H), 7.86 (s, 1H), 7.51 (s, 1H), 7.26 (s, 1H), 4.13 (m, 2H), 3.98 (s, 3H), 1.47 (m, 3H)

Preparation 10: Synthesis of 7-nitro-5-phenoxy-1H-indole-2-carboxylic acid methyl ester 4-Aminophenyl phenyl ether (20 g, 0.11 mol) was reacted according to the same procedures as Preparation 8 and Preparations 3 to 5 in the order to give the title compound (5 g, Yield 15%).
$^1$H-NMR (400 HMz, CDCl$_3$); δ 10.26 (br s, 1H), 8.05 (s, 1H), 7.69 (s, 1H), 7.39 (m, 2H), 7.26 (s, 1H), 7.15 (m, 1H), 7.01 (m, 2H), 4.00 (s, 3H)

Preparation 11: Synthesis of 7-nitro-5-(pyridin-3-yloxy)-1H-indole-2-carboxylic acid ethyl ester (Step 1)
1-Chloro-4-nitrobenzene (40 g, 0.25 mol) and 3-hydroxypyridine (36 g, 0.38 mol) were dissolved in N,N-dimethylformamide (100 ml). Potassium carbonate (52.6 g, 0.38 mol) was added, and the mixture was stirred for 20 h at 100° C. Water was added, and the resulting mixture was extracted with ethyl acetate, washed with saturated sodium chloride solution and dried over anhydrous magnesium sulfate to give 3-(4-nitro-phenoxy)-pyridine.
Thus obtained compound was dissolved using water (100 ml), tetrahydrofuran (100 ml) and methanol (100 ml). Iron dust (103 g, 1.84 mol) and ammonium chloride (99 g, 1.84 mol) were added, and the mixture was stirred using a mechanical stirrer for 3 h at 80° C. After completion of the reaction, the reaction mixture was filtered through celite, washed with methanol and concentrated. The resulting solid was filtered, washed with ether and dried to give 4-(pyridin-3-yloxy)-phenylamine (17 g, Yield 36%).
(Step 2)
4-(Pyridin-3-yloxy)-phenylamine (25 g, 0.13 mol) was reacted according to the same procedures as Preparation 8 and Preparations 3 to 5 in the order to give the title compound (4.2 g, Yield 10%).
$^1$H-NMR (400 HMz, CDCl$_3$); δ 10.32 (br s, 1H), 8.51-8.47 (m, 2H), 8.05 (d, J=2.4 Hz, 1H), 7.73 (d, J=2.0 Hz, 1H), 7.42-7.35 (m, 2H), 7.31 (d, J=2.4 Hz, 1H), 4.48 (q, 2H), 1.47 (t, 3H)

Preparation 12: Synthesis of 5-methyl-7-nitro-2-pyridin-2-yl-1H-indole (4-Methyl-2-nitrophenyl)hydrazine hydrochloride (10 g, 49 mmol) and 2-acetylpyridine (5.5 ml, 49 mmol) were reacted according to the same procedures as Preparations 4 to 5 to give the title compound (2 g, Yield 16%).
$^1$H-NMR (400 HMz, DMSO-$d_6$); δ 10.89 (br s, 1H), 8.70 (d, J=4.4 Hz, 1H), 8.14 (d, J=8.0 Hz, 1H), 7.98-7.92 (m, 3H), 7.42-7.39 (m, 2H), 2.49 (s, 3H)

Preparation 13: Synthesis of 5-methyl-7-nitro-2-pyrazin-2-yl-1H-indole (4-Methyl-2-nitrophenyl)hydrazine hydrochloride (2 g, 9.8 mmol) and 2-acetylpyrazine (1.2 ml, 9.8 mmol) were reacted according to the same procedures as Preparations 4 to 5 to give the title compound (0.3 g, Yield 19%).
$^1$H-NMR (500 HMz, CDCl$_3$); δ 10.64 (br s, 1H), 9.06 (d, J=1.2 Hz, 1H), 8.57 (s, 1H), 8.47 (d, J=2.4 Hz, 1H), 8.00 (s, 1H), 7.76 (s, 1H), 7.12 (d, J=2.4 Hz, 1H), 2.51 (s, 3H)

Preparation 14: Synthesis of 7-nitro-2-pyridin-2-yl-1H-indole

2-Nitrophenylhydrazine hydrochloride (5 g, 26 mmol) and 2-acetylpyridine (2.5 ml, 26 mmol) were reacted according to the same procedures as Preparations 4 to 5 to give the title compound (1 g, Yield 16%).
$^1$H-NMR (400 HMz, DMSO-$d_6$); δ 11.01 (br s, 1H), 8.72 (d, J=4.0 Hz, 1H), 8.15 (m, 3H), 7.93 (m, 1H), 7.49 (s, 1H), 7.42 (m, 1H), 7.30 (m, 1H)

Preparation 15: Synthesis of 7-nitro-2-pyrazin-2-yl-1H-indole

2-Nitrophenylhydrazine hydrochloride (3.1 g, 16 mmol) and 2-acetylpyrazine (2.0 ml, 16 mmol) were reacted according to the same procedures as Preparations 4 to 5 to give the title compound (0.5 g, Yield 13%).
$^1$H-NMR (400 HMz, DMSO-$d_6$); δ 11.24 (br s, 1H), 9.46 (d, J=4.0 Hz, 1H), 8.76 (m, 1H), 8.65 (d, J=4.0 Hz, 1H), 8.20 (dd, J=4.0, 8.0 Hz, 1H), 7.64 (d, J=4.0 Hz, 1H), 7.34 (t, J=8.0 Hz, 1H)

Preparation 16: Synthesis of 5-ethoxy-7-nitro-2-pyridin-2-yl-1H-indole (4-Ethoxy-2-nitrophenyl)hydrazine hydrochloride (5 g, 21 mmol) and 2-acetylpyridine (2.4 ml, 21 mmol) were reacted according to the same procedures as Preparations 4 to 5 to give the title compound (0.5 g, Yield 8%).
$^1$H-NMR (400 HMz, CDCl$_3$); δ 10.97 (br s, 1H), 8.60 (m, 10, 7.79 (m, 1H), 7.73 (m, 1H), 7.61 (d, J=2.8 Hz, 1H), 7.49 (d, J=2.0 Hz, 1H), 7.24 (m, 1H), 7.02 (d, J=2.4 Hz, 1H), 4.03 (q, 2H), 1.45 (t, 3H)

Preparation 17: Synthesis of 7-nitro-5-phenoxy-2-pyridin-2-yl-1H-indole (4-Phenoxy-2-nitrophenyl)hydrazine hydrochloride (10 g, 49 mmol) and 2-acetylpyridine (5.5 ml, 49 mmol) were reacted according to the same procedures as Preparations 4 to 5 to give the title compound (2 g, Yield 16%).
$^1$H-NMR (400 HMz, CDCl$_3$); δ 10.86 (br s, 1H), 8.68 (d, J=4.8 Hz, 1H), 7.92 (d, J=2.0 Hz, 1H), 7.84-7.76 (m, 2H), 7.65 (d, J=2.0 Hz, 1H), 7.36 (m, 3H), 7.28 (m, 1H), 7.13 (m, 1H), 7.06 (d, J=2.0 Hz, 1H), 7.03 (s, 1H), 7.02 (s, 1H)

Preparation 18: Synthesis of 3,5-dimethyl-7-nitro-2-phenyl-1H-indole (4-Methyl-2-nitrophenyl)hydrazine hydrochloride (1.0 g, 4.9 mmol) and 2-propiophenone (0.7 ml, 4.9 mmol) were reacted according to the same procedures as Preparations 4 to 5 to give the title compound (150 mg, Yield 11%).

Preparation 19: Synthesis of 5-methyl-7-nitro-2-phenyl-1H-indole (Step 1)

4-Methyl-2-nitroaniline (20 g, 131.5 mmol) was dissolved in ethanol (300 ml), silver nitrate (27 g, 157.7 mmol) and iodine (40 g, 157.7 mmol) were added, and the mixture was stirred for 8 h at room temperature. After completion of the reaction, the reaction mixture was filtered through celite, washed with ethyl acetate (100 ml) and concentrated. Water was added, and the mixture was extracted with ethyl acetate, washed with saturated sodium chloride solution and dried over anhydrous magnesium sulfate to give 2-iodo-4-methyl-6-nitro-phenylamine (29 g, Yield 69%).

$^1$H-NMR (500 MHz, CDCl$_3$); δ 7.94 (s, 1H), 7.75 (s, 1H), 6.48 (br s, 2H), 2.23 (s, 3H)

(Step 2)

The compound obtained in Step 1 (7 g, 25.2 mmol) and phenylacetylene (3.3 ml, 30, 22 mmol) were dissolved in tetrahydrofuran (100 ml), triethylamine (11 ml, 75.5 mmol), dichloro(bistriphenylphosphine)palladium(II) (1.8 g, 2.52 mmol) and copper(I) iodide (0.48 g, 2.52 mmol) were added, and the mixture was stirred for 8 h at room temperature. After completion of the reaction, water was added. The mixture was extracted with ethyl acetate, washed with saturated sodium chloride solution, dried over anhydrous magnesium sulfate and purified by column chromatography to give 4-methyl-2-nitro-6-phenylethinyl-phenylamine (4.5 g, Yield 71%).

$^1$H-NMR (400 HMz, CDCl$_3$); δ 7.93 (s, 1H), 7.53 (m, 2H), 7.46 (s, 1H), 7.39 (m, 3H), 6.62 (br s, 2H), 2.26 (s, 3H)

(Step 3)

The compound obtained in Step 2 (4.5 g, 17.8 mmol) was dissolved in tetrahydrofuran (120 ml) and N-methyl-pyrrolidinone (30 ml). Potassium t-butoxide (4 g, 35.7 mmol) was added, and the mixture was stirred for 3 h at room temperature. After completion of the reaction, water was added. The mixture was extracted with ethyl acetate, washed with saturated sodium chloride solution, dried over anhydrous magnesium sulfate and purified by column chromatography to give 5-methyl-7-nitro-2-phenyl-1H-indole (1.0 g, Yield 22%).

$^1$H-NMR (400 HMz, CDCl$_3$); δ 11.53 (br s, 1H), 8.02 (d, J=7.6 Hz, 1H), 7.94 (s, 1H), 7.87 (s, 1H), 7.50 (m, 2H), 7.41 (m, 1H), 7.09 (m, J=2.0 Hz, 1H), 2.49 (s, 3H)

Preparation 20: Synthesis of 2-cyclohexyl-5-methyl-7-nitro-1H-indole

6-Iodo-4-methyl-2-nitroaniline (500 mg, 1.8 mmol) and cyclohexylacetylene (0.23 ml, 1.8 mmol) were reacted according to the same procedure as Preparation 19 to give the title compound (290 mg, Yield 62%).

$^1$H-NMR (500 HMz, CDCl$_3$); δ 9.34 (br s, 1H), 7.88 (s, 1H), 7.63 (s, 1H), 6.26 (s, 1H), 2.76 (m, 1H), 2.47 (s, 3H), 2.10 (m, 2H), 1.87 (m, 2H), 1.78 (m, 1H), 1.52-1.42 (m, 4H), 1.31 (m, 1H)

Preparation 21: Synthesis of 5-methyl-2-(6-methyl-pyridin-2-yl)-7-nitro-1H-indole 6-Iodo-4-methyl-2-nitroaniline (500 mg, 1.8 mmol) and 2-ethinyl-6-methylpyridine (210 mg, 1.8 mmol) were reacted according to the same procedure as Preparation 19 to give the title compound (170 mg, Yield 35%).

$^1$H-NMR (500 HMz, CDCl$_3$); δ 10.77 (br s, 1H), 7.98 (s, 1H), 7.73 (s, 1H), 7.64-7.58 (m, 2H), 7.08 (d, J=7.4 Hz, 1H), 6.98 (d, J=2.5 Hz, 1H), 2.62 (s, 3H), 2.50 (s, 3H)

Preparation 22: Synthesis of (R)-3-amino-4-(4-methoxy-benzylsulfanyl)-butyric acid methyl ester hydrochloride (Step 1)

To a mixed solution of diethyl ether (400 ml) and conc. hydrochloric acid (400 ml) was added in drops 4-methoxybenzyl chloride (280 g, 1780 mmol) dissolved in diethyl ether (400 ml) for 2 h, and the mixture was stirred for 1 h. The organic layer was separated and added to a solution which was prepared by dissolving L-cysteine (197 g, 1625 mmol) and 2N aqueous sodium hydroxide solution (980 ml) in ethanol (1890 ml). The mixture was stirred for 2 h at room temperature. After completion of the reaction, the mixture was cooled to 0° C., and neutralized to pH 7 using 3N aqueous hydrochloric acid solution. The resulting solid was filtered and dried to give (R)-2-amino-3-(4-methoxy-benzylsulfanyl)-propionic acid (250 g, 1035 mmol, Yield 64%).

(Step 2)

The compound obtained in Step 1 (30.7 g, 127.3 mmol) was dissolved in tetrahydrofuran (150 ml) and water (150 ml). Potassium carbonate (26.4 g, 190 mmol) and di-t-butyloxy-dicarbonyl (27.7 g, 127.3 mmol) were added, and the mixture was stirred for 2 h at room temperature. After completion of the reaction, the mixture was distilled under reduced pressure to remove tetrahydrofuran. The mixture was cooled to 0° C., and acidified to pH 3 using 3N aqueous hydrochloric acid solution. The resulting solid was washed with water and dried to give (R)-2-t-butoxycarbonylamino-3-(4-methoxy-benzylsulfanyl)-propionic acid (43 g, 126 mmol, Yield 99%).

(Step 3)

The compound obtained in Step 2 (43 g), 1-methylmorpholine (14.5 ml, 132 mmol) and ethyl chloroformate (14.1 ml, 132 mmol) were dissolved in tetrahydrofuran (500 ml), and the mixture was stirred for 1 h at −25° C. At the same time, potassium hydroxide (75 g, 1336 mmol) was dissolved in water (75 ml) and diethylether (750 ml), N-methyl-nitrosourea (26 g, 252 mmol) was added in drops for 2 h at 0° C., and the mixture was stirred for 30 min. Thus prepared two solutions were mixed and stirred for 3 h at −25° C.~room temperature. After completion of the reaction, water was added. The mixture was washed with saturated sodium hydrogen carbonate aqueous solution and saturated ammonium chloride aqueous solution in the order. The organic layer was concentrated to give [(R)-3-diazo-1-(4-methoxy-benzylsulfanylmethyl)-2-oxo-propyl]-carbamic acid t-butyl ester.

$^1$H-NMR (400 HMz, CDCl$_3$); δ 7.25 (d, J=8.8 Hzm 2H), 6.86 (d, J=8.8 Hz, 2H), 5.48 (br s 1H), 5.29 (m, 1H), 4.31 (m, 1H), 3.79 (s, 3H), 3.69 (s, 2H), 2.76 (d, J=6.0 Hz, 2H), 1.45 (s, 9H)

(Step 4)

The compound obtained in Step 3 was dissolved in methanol (1000 ml), silver benzoate (7.1 g, 31.1 mmol) was added, and the mixture was reacted for 1 h under sonication. After completion of the reaction, the mixture was concentrated and purified by column chromatography to give (R)-3-t-butoxycarbonylamino-4-(4-methoxy-benzylsulfanyl)-butyric acid methyl ester (35.2 g, 95.3 mmol, Yield 76%).

$^1$H-NMR (500 HMz, CDCl$_3$); δ 7.24 (d, J=8.6 Hz, 2H), 6.83 (d, J=8.6 Hz, 2H), 5.09 (m, 1H), 4.08 (m, 1H), 3.79 (s, 3H), 3.68 (s, 2H), 3.66 (s, 3H), 2.70-2.52 (m, 4H), 1.44 (s, 9H)

(Step 5)

The compound obtained in Step 4 (35.2 g) was dissolved in dichloromethane (70 ml), 4N hydrochloric acid/1,4-dioxane solution (71 ml) was added, and the mixture was stirred for 2 h at room temperature. After completion of the reaction, the mixture was concentrated. The solid produced by adding dichloromethane (30 ml) and diethylether (150 ml) was filtered and dried to give the title compound (25.5 g, 83.3 mmol, Yield 87%).

$^1$H NMR (400 MHz, DMSO-$d_6$); δ 8.21 (br s, 3H), 7.25 (d, 2H), 6.83 (d, 2H), 3.78 (s, 3H), 3.68 (s, 2H), 3.65 (s, 3H), 3.29 (m, 1H), 2.51-2.48 (m, 2H), 2.35-2.31 (m, 2H)

Preparation 23: Synthesis of (R)-3-amino-4-(4-methoxy-benzylsulfanyl)-butyric acid ethyl ester hydrochloride L-cysteine (50 g, 0.41 mol) was reacted according to the same procedure as Preparation 22 except that ethanol was used instead of methanol in Step 4 of Preparation 22 to give the title compound (5.2 g, Yield 40%).

$^1$H NMR (400 MHz, CDCl$_3$); δ 8.37 (br s, 3H), 7.28 (d, J=8.0 Hz, 2H), 6.87 (d, J=8.0 Hz, 2H), 4.11 (m, 2H), 3.73 (s, 3H), 3.70 (s, 2H), 2.81-2.67 (m, 4H), 1.18 (t, 3H)

Preparation 24: Synthesis of (R)-4-amino-5-(4-methoxy-benzylsulfanyl)-pentanoic acid ethyl ester hydrochloride (Step 1)

(R)-4-t-butoxycarbonylamino-5-hydroxy-pentanoic acid ethyl ester (36 g, 137.8 mmol) which can be obtained by a known method and triethylamine (38.4 ml, 275.5 mol) were dissolved in dichloromethane (200 ml). Methanesulfonylchloride (11.7 ml, 151.5 mmol) was added in drops, and the mixture was stirred for 1 h at 0° C.~room temperature. 1N hydrochloric acid solution was added. The mixture was extracted with ethyl acetate, washed with saturated sodium chloride solution and dried over anhydrous magnesium sulfate to give (R)-4-t-butoxycarbonylamino-5-methanesulfonyloxy-pentanoic acid ethyl ester.

(Step 2)

The compound obtained in Step 1 and sodium hydride (5.5 g, 137.8 mmol) were added in drops to 4-methoxybenzylmercaptan (15.4 ml, 110.2 mmol) dissolved in N,N-dimethylformamide (150 ml) and stirred for 10 min at 0° C. The mixture was stirred for 4 h at 0° C. After completion of the reaction, water was added. The mixture was extracted with ethyl acetate, washed with saturated sodium chloride solution, dried over anhydrous magnesium sulfate and purified by column chromatography to give (R)-4-t-butoxycarbonylamino-5-(4-methoxy-benzylsulfanyl)-pentanoic acid ethyl ester (21.0 g, Yield 38%).

$^1$H-NMR (400 HMz, CDCl$_3$); δ 7.25 (d, J=8.8 Hz, 2H), 6.85 (d, J=8.8 Hz, 2H), 4.56 (m, 1H), 4.12 (m, 2H), 3.79 (s, 3H), 3.69 (s, 2H), 2.53 (m, 2H), 2.33 (t, 2H), 1.93 (m, 1H), 1.70 (m, 1H), 1.44 (s, 9H), 1.25 (t, 3H)

(Step 3)

The compound obtained in Step 2 (11 g, 62.7 mmol) was dissolved in dichloromethane (200 ml), and 4N hydrochloric acid/ethyl acetate solution (20 ml) was added. The mixture was stirred for 2 h at room temperature. After completion of the reaction, the mixture was thoroughly concentrated, and diethylether (150 ml) was added. The resulting solid was filtered and dried to give the title compound (20 g, Yield 96%).

$^1$H NMR (400 MHz, DMSO-$d_6$); δ 8.69 (br s, 3H), 7.29 (d, J=8.0 Hz, 2H), 6.89 (d, J=8.0 Hz, 2H), 4.08 (m, 2H), 3.74 (m, 5H), 3.26 (m, 1H), 2.76-2.63 (m, 2H), 2.49-2.40 (m, 2H), 1.89 (m, 2H), 1.20 (t, 3H)

Preparation 25: Synthesis of (S)-3-amino-4-(4-methoxy-benzylsulfanyl)-butyric acid isopropyl ester hydrochloride The same procedure as Preparation 24 was carried out except that (S)-3-t-butoxycarbonylamino-4-hydroxy-butyric acid isopropyl ester (22.0 g, 84.2 mmol) was used instead of (R)-4-t-butoxycarbonylamino-5-hydroxy-pentanoic acid ethyl ester to give the title compound (21.0 g, Yield 75%).

$^1$H NMR (400 MHz, MeOH-$d_4$); δ 7.31 (d, J=8.8 Hz, 2H), 6.91 (d, J=8.8 Hz, 2H), 5.06 (m, 1H), 3.80 (s, 3H), 3.78 (s, 2H), 3.60 (m, 1H), 2.81-2.63 (m, 4H), 1.28 (dd, 6H)

Preparation 26: Synthesis of (R)-2-amino-3-(4-methoxy-benzylsulfanyl)propionic acid ethyl ester hydrochloride The acid compound obtained in Step 1 of Preparation 22 (20 g, 83 mmol) was dissolved in ethanol (100 ml). Acetyl chloride (12 ml, 166 mmol) was added in drops, and the mixture was stirred for 12 h at 50° C. After completion of the reaction, the mixture was thoroughly concentrated, and diethylether was added thereto. The resulting solid was filtered and dried to give the title compound (16.8 g, Yield 69%).

$^1$NMR (400 MHz, CDCl$_3$); δ 8.85 (br s, 3H), 7.27 (d, J=8.0 Hz, 2H), 6.80 (d, J=8.0 Hz, 2H), 4.47 (m, 1H), 3.78-3.69 (m, 8H), 3.17 (m, 2H)

Preparation 27: Synthesis of (R)-2,2-dimethyl-propionic acid 2-amino-3-(4-methoxy-benzylsulfanyl)-propyl ester (Step 1)

The compound obtained in Step 1 of Preparation 22 (50 g, 207.2 mmol) was dissolved in methanol (300 ml). Acetyl chloride (21 ml, 207.2 mmol) was added in drops, and the mixture was stirred for 12 h at 50° C. After completion of the reaction, the mixture was thoroughly concentrated, and diethylether was added thereto. The resulting solid was filtered and dried to give (R)-2-amino-3-(4-methoxybenzylsulfanyl)-propionic acid methyl ester.

$^1$H NMR (400 MHz, DMSO-$d_6$, HCl salt); δ 8.81 (br s, 3H), 7.29 (d, J=8.4 Hz, 2H), 6.91 (d, J=8.4 Hz, 2H), 4.28 (m, 1H), 3.18 (br s, 8H), 2.95 (m, 2H)

(Step 2)

To the compound obtained in Step 1 were added tetrahydrofuran (200 ml) and water (200 ml) to dissolve. Triethylamine (87 ml, 621.6 mmol) was added, and di-t-butyloxydicarbonyl (43.0 g, 196.8 mmol) dissolved in tetrahydrofuran (100 ml) was added in drops while stirring. The mixture was stirred for 8 h at room temperature. After completion of the reaction, water was added. The mixture was extracted with ethyl acetate, washed with saturated sodium chloride solution and dried over anhydrous magnesium sulfate to give (R)-2-t-butoxycarbonylamino-3-(4-methoxy-benzylsulfanyl)-propionic acid methyl ester.

(Step 3)

The compound obtained in Step 2 was dissolved in tetrahydrofuran (300 ml). Lithium borohydride (9.0 g, 414.4 mmol) was added, and the mixture was stirred for 3 h at 0° C. After completion of the reaction, water was added. The mixture was extracted with ethyl acetate, washed with saturated sodium chloride solution and dried over anhydrous magnesium sulfate to give [(R)-2-hydroxy-1-(4-methoxy-benzylsulfanylmethyl)-ethyl]-carbamic acid t-butyl ester.

¹H NMR (500 MHz, DMSO-d₆); δ 7.24 (d, J=8.6 Hz, 2H), 6.84 (d, J=8.6 Hz, 2H), 4.96 (br s, 1H), 3.78 (s, 3H), 3.76 (br s, 1H), 3.70 (s, 2H), 3.7-3.66 (m, 3H), 2.58 (m, 2H), 1.44 (s, 9H)

(Step 4)

The alcohol compound obtained in Step 3 was dissolved in dichloromethane (300 ml). Triethylamine (58 ml, 414.4 mmol) and trimethylacetylchloride (28 ml, 227.9 mmol) were added, and the mixture was stirred for 6 h at 0° C. After completion of the reaction, water was added. The mixture was extracted with ethyl acetate, washed with saturated sodium chloride solution, dried over anhydrous magnesium sulfate and purified by column chromatography to give 2,2-dimethyl-propionic acid (R)-2-t-butoxycarbonylamino-3-(4-methoxy-benzylsulfanyl)-propyl ester (81.0 g, Yield 95%).

¹H NMR (400 MHz, CDCl₃); δ 7.25 (d, J=8.8 Hz, 2H), 6.85 (d, J=8.8 Hz, 2H), 4.71 (m, 1H), 4.11 (m, 2H), 3.79 (s, 3H), 3.70 (s, 2H), 2.55 (d, J=6.4 Hz, 2H), 1.52 (s, (H, 1.27 (s, 9H)

(Step 5)

The trimethyl acetate compound obtained in Step 4 (81 g, 196 mmol) was dissolved in dichloromethane (300 ml). 4N-hydrochloric acid/1,4-dioxane solution (100 ml) was added, and the mixture was stirred for 8 h at room temperature. After completion of the reaction, the mixture was thoroughly concentrated, and diethylether was added thereto. The resulting solid was filtered and dried to give the title compound (68 g, Yield 95%).

¹H NMR (400 MHz, DMSO-d₆, free form); δ 7.24 (d, J=12.0 Hz, 2H), 6.85 (dd, J=4.0, 8.0 Hz, 2H), 4.04 (m, 1H), 3.95 (m, 1H), 3.80 (s, 3H), 3.68 (s, 2H), 3.10 (m, 1H), 2.60 (m, 1H), 2.36 (m, 1H), 1.18 (s, 9H)

Preparation 28: Synthesis of 2-(4,5-dihydro-thiazol-2-yl)-1H-indole-7-ylamine (Step 1)

Ethyl 7-nitroindole-2-carboxylate (500 mg, 2.14 mmol) was dissolved in a solvent mixture of tetrahydrofuran and water (1:1, 20 ml), and lithium hydroxide hydrate (448 mg, 10.7 mmol) was added. The mixture was stirred for 8 h at room temperature, and 1N-hydrochloric acid solution was added thereto. The mixture was extracted with ethyl acetate. The extract was dried over anhydrous magnesium sulfate and filtered. The filtrate was distilled under reduced pressure to give 7-nitro-1H-indole-2-carboxylic acid.

(Step 2)

The compound obtained in Step 1 and 2-chloroethylamine hydrochloride (371 mg, 3.2 mmol) were dissolved in N,N-dimethylformamide (10 ml). Triethylamine (0.6 ml, 4.3 mmol), EDC (614 mg, 3.2 mmol) and HOBT (433 mg, 3.2 mmol) were added. The mixture was stirred for 8 h at room temperature, and 1N-hydrochloric acid solution was added. The mixture was extracted with ethyl acetate, washed with saturated sodium bicarbonate solution, dried over anhydrous magnesium sulfate and filtered. The filtrate was distilled under reduced pressure to give 7-nitro-1H-indole-2-carboxylic acid (2-chloro-ethyl)-amide.

¹H NMR (400 MHz, CDCl₃); δ 10.51 (br s, 1H), 8.28 (d, J=6.4 Hz, 1H), 8.02 (d, J=6.4 Hz, 1H), 7.27 (t, 1H), 7.03 (s, 1H), 6.62 (br s, 1H), 3.86 (m, 2H), 3.77 (m, 2H)

(Step 3)

The compound obtained in Step 2 was dissolved in dichloroethane (10 ml) and toluene (10 ml), and Lawesson's reagent (1.29 g, 3.2 mmol) was added. The mixture was refluxed for 4 h, and distilled under reduced pressure. Water was added to the residue, and the mixture was extracted with ethyl acetate, dried over anhydrous magnesium sulfate and filtered. The filtrate was distilled under reduced pressure and the concentrate was purified by column chromatography to give the product of cyclization reaction, i.e., the compound 2-(4,5-dihydro-thiazol-2-yl)-7-nitro-1H-indole (100 mg, Yield 22%).

¹H-NMR (400 HMz, CDCl₃); δ 10.49 (br s, 1H), 8.24 (d, J=8.0 Hzm 1H), 7.98 (d, J=7.6 Hz, 1H), 7.23 (t, 1H), 7.02 (s, 1H), 4.47 (t, 2H), 3.51 (t, 2H)

(Step 4)

The thiazoline compound obtained in Step 3 was dissolved in methanol (50 ml). 10% Pd/C was added, and the mixture was stirred for 8 h under hydrogen gas. After completion of the reaction, the mixture was filtered through cellite, distilled under reduced pressure and purified by column chromatography to give the title compound (80 mg, Yield 91%).

¹H-NMR (400 HMz, CDCl₃); δ 9.78 (br s, 7.15 (d, J=8.0 Hz, 1H), 6.95 (t, J=8.0 Hz, 1H), 6.90 (d, J=1.6 Hz, 1H), 6.60 (dd, 1H), 4.44 (dd. 2H), 3.45 (dd, 2H)

Mass spectrum (ESI, adz): Calculated: 217.07, Found: 217.29

EXAMPLE 1

Synthesis of cyclopentyl-[2-(4,5-dihydro-1,3-thiazol-2-yl)-1H-indol-7-yl]-amine

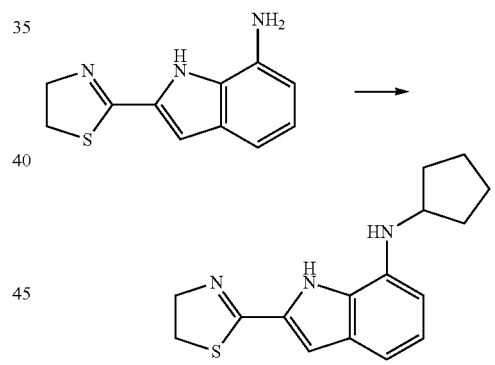

Cyclopentyl-[2-(4,5-dihydro-thiazol-2-yl)-1H-indol-7-yl]-amine

The compound obtained in Preparation 28 (15 mg, 0.07 mmol) was dissolved in 1,2-dichloroethane (10 ml). Cyclopentanone (12 mg, 0.14 mmol) and sodium triacetoxyborohydride (29 mg, 0.14 mmol) were added, and the mixture was stirred for 3 h at room temperature. After completion of the reaction, water was added. The mixture was extracted with ethyl acetate, dried over anhydrous magnesium sulfate and filtered. The filtrate was distilled under reduced pressure and the residue was purified by column chromatography to give the title compound (6.7 mg, Yield 34%).

¹H-NMR (400 HMz, CDCl₃); δ 10.27 (s, 1H), 7.06 (d, J=8.0 Hz, 1H), 7.00 (t, J=7.6 Hz, 1H), 6.92 (s, 1H), 6.52 (d, J=7.2 Hz, 1H), 4.42 (m, 2H), 4.38 (m, ED, 4.35 (m, 2H), 2.00 (m, 2H), 1.64 (m, 4H), 1.46 (m, 2H)

Mass spectrum (ESI, m/z): Calculated: 285.13, Found: 285.41

EXAMPLE 2

Synthesis of [2-(4,5-dihydro-thiazol-2-yl)-1H-indol-7-yl]-(4-methyl-cyclohexyl)-amine

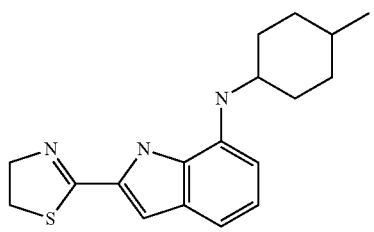

[2-(4,5-Dihydro-thiazol-2-yl)-1H-indol-7-yl]-(4-methyl-cyclohexyl)-amine

The compound obtained in Preparation 28 (19 mg, 0.09 mmol) and 4-methyl-cyclohexanone were reacted according to the same procedure as Example 1 to give the two diastereomers in the amount of 9.1 mg and 7.4 mg (total Yield 60%), respectively.

$^1$H-NMR (400 HMz, CDCl$_3$);

Compound 1: δ 10.26 (s, 1H), 7.05-6.97 (m, 2H), 6.92 (s, 1H), 6.51 (d, J=7.6 Hz, 1H), 4.40 (m, 2H), 3.65 (m, 1H), 3.46 (m, 2H), 1.72 (m, 3H), 1.52 (m, 3H), 1.22 (m, 3H), 0.82 (d, J=8.0 Hz, 3H)

Compound 2: δ 10.24 (s, 1H), 7.05-6.96 (m, 2H), 6.92 (s, 1H), 6.50 (d, J=6.8 Hz, 1H), 4.44 (m, 2H), 3.47 (m, 2H), 3.25 (m, 1H), 2.11 (m, 2H), 1.74 (m, 2H), 1.36 (m, 1H), 1.10 (m, 4H), 0.90 (d, J=6.4 Hz, 1H)

Mass spectrum (ESI, m/z); Calculated: 313.16, Found: 313.47

EXAMPLE 3

Synthesis of [2-(4,5-dihydro-thiazol-2-yl)-1H-indol-7-yl]-piperidin-4-yl-amine

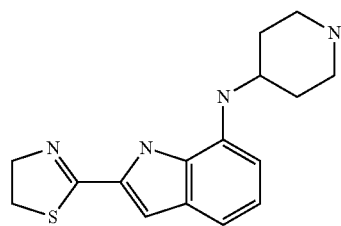

[2-(4,5-Dihydro-thiazol-2-yl)-1H-indol-7-yl]-piperidin-4-yl-amine

To the compound prepared from the compound of Preparation 28 (20 mg, 0.09 mmol) and 1-(t-butylcarbonyl)-4-piperidone according to the same procedure as Example 1 were added dichloromethane and trifluorocarboxylic acid solution (5:1, v/v, 5 ml). The mixture was stirred for 1 h at room temperature and distilled under reduced pressure. Saturated sodium bicarbonate solution was added, and the mixture was extracted with ethyl acetate, dried over anhydrous magnesium sulfate and filtered. The filtrate was distilled under reduced pressure and purified by column chromatography to give the title compound (4.9 mg, Yield 18%).

$^1$H-NMR (400 HMz, CDCl$_3$, McOH-d$_4$); δ 7.39 (s, 1H), 7.07 (d, J=8.0 Hz, 1H), 6.99 (t, J=8.0 Hz, 1H), 6.93 (s, 1H), 6.47 (d, J=7.6 Hz, 1H), 4.41 (m, 2H), 3.77 (m, 1H), 3.48 (m, 4H), 3.11 (m, 2H), 2.29 (m, 2H), 1.87 (m, 2H)

Mass spectrum (ESI, m/z): Calculated: 300.14, Found: 300.43

Preparation 29: Synthesis of 7-(tetrahydro-pyran-4-ylamino)-1H-indole-2-carboxylic acid Ethyl 7-nitroindole-2-carboxylate (2.5 g, 10.7 mmol) was dissolved in methanol (50 ml). 10% Pd/C (200 mg) was added, and the mixture was stirred for 1 h under hydrogen gas. The mixture was filtered though celite, and the filtrate was distilled under reduced pressure. The distillate was dissolved 1,2-dichloroethane (50 ml), and tetrahydro-4H-pyran-4-one (1.3 ml, 12.8 mmol) and sodium triacetoxyborohydride (3.4 g, 16.1 mmol) were added. The mixture was stirred for 8 h at room temperature. After completion of the reaction, water was added. The mixture was extracted with ethyl acetate, dried over anhydrous magnesium sulfate and filtered. The filtrate was distilled under reduced pressure and concentrated. The residue was purified by column chromatography. Thus obtained compound was dissolved in methanol (50 ml) and tetrahydrofuran (50 ml), 1N-sodium hydroxide (43 ml, 42.8 mmol) was added, and the mixture was stirred for 8 h at room temperature. 1N-hydrochloric acid solution was added, and the mixture was extracted with ethyl acetate, dried over anhydrous magnesium sulfate and filtered. The filtrate was distilled under reduced pressure to give the title compound (2.1 g, Yield 76%).

$^1$H-NMR (400 HMz, DMSO-d$_6$); δ 12.37 (br s, 1H), 11.46 (s, 1H), 6.97 (d, J=2.0 Hz, 1H), 6.86 (d, J=1.6 Hz, 1H), 6.85 (s, 1H), 6.37 (m, 1H), 5.73 (br s, 1H), 3.90 (m, 2H), 3.61 (m, Bp, 3.50 (m, 2H), 2.00 (m, 2H), 1.48 (m, 2H)

Mass spectrum (ESI, m/z): Calculated: 260.12, Found: 260.30

Preparation 30: Synthesis of {5-[7-(tetrahydro-pyran-4-ylamino)-1H-indol-2-yl]-[1,2,4]oxadiazol-3-yl}acetic acid ethyl ester The compound obtained in Preparation 29 (300 mg, 1.15 mmol) was dissolved in dimethylformamide (20 ml). Ethyl 3-(hydroxyamino)-3-iminopropionate (202 mg, 1.38 mmol), EDC (265 mg, 1.38 mmol) and HOBT (187 mg, 1.38 mmol) were added thereto. The mixture was stirred for 8 h at room temperature, and saturated sodium bicarbonate solution was added. The mixture was extracted with ethyl acetate, dried over anhydrous magnesium sulfate and filtered. The filtrate was distilled under reduced pressure and concentrated. The residue was purified by column chromatography. Thus obtained compound was dissolved in toluene (20 ml) and dichloroethane (10 ml). The mixture was refluxed for 8 h at 120° C., distilled under reduced pressure and purified by column chromatography to give the title compound (80 mg, Yield 19%).

$^1$H-NMR (500 HMz, CDCl$_3$); δ 9.71 (br s, 1H), 7.35 (d, = 1.8 Hz, 1H), 7.15 (d, J=8.0 Hz, 1H), 7.06 (t, J=8.0 Hz, 1H), 6.61 (d, J=8.0 Hz, 1H), 4.25 (m. 2H), 4.10 (m, 2H), 3.92 (s, 2H), 3.69 (m, 1H), 3.59 (m. 2H), 2.10 (m, 2H), 1.64 (m, 2H), 1.29 (t, 3H)

Mass spectrum (ESI, m/z): Calculated: 370.16, Found: 370.41

EXAMPLE 4

Synthesis of 2-5-[7-(tetrahydro-pyran-4-ylamino)-1H-indol-2-yl]-[1,2,4]oxadiazol-3-yl}-ethanol

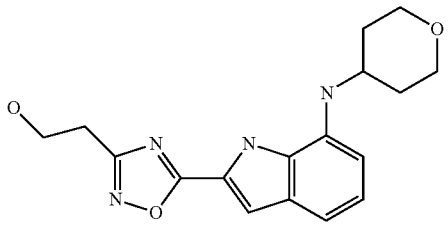

2-{5-[7-(Tetrahydro-pyran-4-ylamino)-1H-indol-2-yl]-[1,2,4]oxadiazol-3-yl}-ethanol The compound obtained in Preparation 30 (20 mg, 0.05 mmol) was dissolved in tetrahydrofuran (2 ml), and lithium borohydride (2.4 mg, 0.10 mmol) was added. The mixture was stirred for 2 h at room temperature, and saturated ammonium chloride solution was added. The mixture was extracted with ethyl acetate. The extract was dried over anhydrous magnesium sulfate and filtered. The filtrate was distilled under reduced pressure and purified by column chromatography to give the title compound (4.7 mg, Yield 27%).

$^1$H-NMR (500 HMz, CDCl$_3$); δ 10.40 (br s, 1H), 7.27 (s, 1H), 7.08 (d, J=8.0 Hz, 1H), 7.04 (t, J=8.0 Hz, 1H), 6.55 (d, J=7.4 Hz, 1H), 4.11 (m, 4H), 3.70 (m, 1H), 3.61 (t, 2H), 3.06 (m, 2H), 2.14 (m, 2H), 1.66 (m, 2H)

Mass spectrum (ESI, m/z): Calculated: 328.15, Found: 328.37

Preparation 31: Synthesis of 2,2-dimethyl-propionic acid (R)-2-(7-amino-1H-indol-2-yl)-4,5-dihydro-thiazol-4-ylmethyl ester (Step 1)

The 7-nitroindole-carboxylic acid compound obtained in Step 1 of Preparation 28 (8.2 g, 22.7 mmol) and the amine compound obtained in Preparation 27 (13.2 g, 27.2 mmol) were dissolved in dimethylformamide (100 ml), and EDC (6.6 g, 25.0 mmol) and HOBT (4.6 g, 25.0 mmol) were added. The mixture was stirred for 8 h at room temperature, and saturated sodium bicarbonate solution was added. The mixture was extracted with ethyl acetate, dried over anhydrous magnesium sulfate and filtered. The filtrate was distilled under reduced pressure and concentrated. The residue was purified by column chromatography to give 2,2-dimethyl-propionic acid (R)-3-(4-methoxy-benzylsulfanyl)-2-[(7-nitro-1H-indole-2-carbonyl)-amino-propyl ester (8.1 g, Yield 71%).

$^1$H-NMR (400 HMz, CDCl$_3$); δ 10.47 (br s, 1H), 8.27 (d, J=8.0 Hz, 1H), 8.01 (d, J=8.0 Hz, 1H), 7.26 (m, 2H), 6.93 (d, J=4.0 Hz, 1H), 6.83 (m, 2H), 6.74 (d, J=8.0 Hz, 1H), 4.56 (m, 1H), 4.44 (m, 1H), 4.24 (m, 1H), 3.74 (m, 5H), 2.77 (m, 1H), 2.62 (m, 1H), 1.18 (s, 9H)

(Step 2)

The compound obtained in Step 1 (1.6 g, 3.2 mmol) was dissolved in dichloromethane (50 ml). Phosphorus pentachloride (1.3 g, 6.4 mmol) was added, and the mixture was stirred for 5 h at room temperature. After completion of the reaction, saturated sodium bicarbonate solution was added. The mixture was extracted with ethyl acetate, dried over anhydrous magnesium sulfate and filtered. The filtrate was distilled under reduced pressure and concentrated. The residue was purified by column chromatography to give 2,2-dimethyl-propionic acid (R)-2-(7-nitro-1H-indol-2-yl)-4,5-dihydro-thiazol-4-ylmethyl ester (0.8 g, Yield 69%).

$^1$H-NMR (400 HMz, CDCl$_3$); δ 10.53 (br s, 1H), 8.26 (d, J=8.0 Hz, 1H), 7.99 (d, J=8.0 Hz, 1H), 7.04 (d, J=2.0 Hz, 1H), 6.90 (d, J=7.6 Hz, 1H), 4.78 (m, 1H), 4.46 (m, 1H), 4.30 (m, 1H), 3.59 (m, 1H), 3.36 (m, 1H), 1.20 (s, 9H)

(Step 3)

The compound obtained in Step 2 (2.7 g, 7.5 mmol) was dissolved in a solvent mixture of tetrahydrofuran, methanol and water (1:1:1, 150 ml). Iron dust (4.2 g, 74.7 mmol) and ammonium chloride (4.0 g, 74.7 mmol) were added, and the mixture was stirred using a mechanical stirrer for 30 min at 60° C. After completion of the reaction, water was added. The mixture was extracted with ethyl acetate, dried over anhydrous magnesium sulfate and filtered. The filtrate was distilled under reduced pressure and purified by column chromatography to give the title compound (2.0 g, Yield 81%).

$^1$H-NMR (400 HMz, CDCl$_3$); δ 9.86 (br s, 1H), 7.30 (d, J=7.6 Hz, 1H), 7.14 (d, J=8.0 Hz, 1H), 6.89 (d, J=2.0 Hz, 1H), 6.61 (dd, J=0.8, 7.2 Hz, 1H), 4.96 (m, 1H), 4.36 (m, 2H), 3.55 (m, 1H), 3.33 (m, 1H), 1.18 (s, 9H)

Preparation 32: Synthesis of 2,2-dimethyl-propionic acid (R)-2-(7-cyclopentyl amino-1H-indol-2-yl)-4,5-dihydro-thiazol-4-ylmethyl ester The compound obtained in Preparation 31 (2.0 g) was reacted according to the same procedure as Example 1 to give the title compound (1.3 g, Yield 54%).

EXAMPLE 5

Synthesis of [(R)-2-(7-cyclopentylamino-1H-indol-2-yl)-4,5-dihydro-1,3-thiazol-4-yl]-methanol

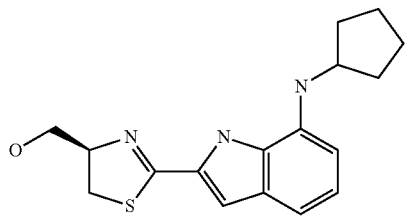

[(R)-2-(7-Cyclopentylamino-1H-indol-2-yl)-4,5-dihydro-thiazol-4-yl]-methanol

The compound obtained in Preparation 32 (1.3 g, 3.3 mmol) was dissolved in tetrahydrofuran (10 ml), methanol (10 ml) and water (10 ml). Lithium hydroxide hydrate (0.4 g, 9.8 mmol) was added. The mixture was stirred for 4 h at room temperature, distilled under reduced pressure and concentrated. 1N hydrochloric acid was added to the residue. The mixture was extracted with ethyl acetate, dried over anhydrous magnesium sulfate and filtered. The filtrate was distilled under reduced pressure and purified by column chromatography to give the title compound (820 mg, Yield 80%).

$^1$H-NMR (500 HMz, CDCl$_3$); δ 11.17-11.08 (m, 1H), 7.09 (m, 1H), 6.99 (t, 1H), 6.96 (s, 1H), 6.52 (m, 1H), 4.72 (m, 1H), 4.04 (m, 1H), 3.75 (m, 1H), 3.65 (m, 1H), 3.51 (m, 1H), 3.40 (m. 1H), 1.90 (m, 2H), 1.60-1.49 (m, 4H), 1.41-1.24 (m, 2H)

Mass spectrum (ESI, m/z): Calculated: 315.14, Found: 315.44

Preparation 33: Synthesis of methanesulfonic acid (R)-2-(7-cyclopentylamino-1H-indol-2-yl)-4,5-dihydro-thiazol-4-ylmethyl ester The compound obtained in Example 5 (820 mg, 2.6 mmol) was dissolved in dichloromethane (50 ml). Methanesulfonyl chloride (0.24 ml, 3.1 mmol) and triethylamine (0.81 ml, 3.1 mmol) were added, which was then stirred for 30 min at 0° C. After completion of the reaction, saturated sodium bicarbonate solution was added. The mixture was extracted with ethyl acetate, dried over anhydrous magnesium sulfate and filtered. The filtrate was distilled under reduced pressure and purified by column chromatography to give the title compound (600 mg, Yield 60%).

EXAMPLE 6

Synthesis of cyclopentyl-[2-((R)-4-pyrrolidin-1-ylmethyl-4,5-dihydro-thiazol-2-yl)-1H-indol-7-yl]-amine

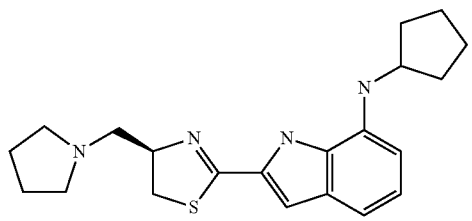

Cyclopentyl-[2-((R)-4-pyrrolidin-1-ylmethyl-4,5-dihydro-thiazol-2-yl)-1H-indol-7-yl]-amine The compound obtained in Preparation 33 (150 mg, 0.38 mmol) was dissolved in N,N-dimethylformamide (5 ml). Pyrrolidine (0.08 ml, 1.1 mmol) was added, and stirred for 4 h at 70° C. After completion of the reaction, water was added. The mixture was extracted with ethyl acetate, dried over anhydrous magnesium sulfate and filtered. The filtrate was distilled under reduced pressure and purified by column chromatography to give the title compound (20 mg, Yield 14%).

$^1$H-NMR (400 HMz, DMSO-d$_6$); δ 11.37 (br s, 1H), 6.83 (m, 1H), 6.75 (d, J=2.0 Hz, 1H), 6.29 (d, J=8.0 Hz, 1H), 5.86 (d, J=8.0 Hz, 1H), 4.80 (m, 1H), 3.87 (m, 1H), 3.52 (m, 1H), 3.43 (m, 1H), 3.33 (m, 2H), 2.78 (m, 2H), 2.61 (m, 2H), 1.99 (m, 2H), 1.72 (m, 6H), 1.60 (m, 4H)

EXAMPLE 7

Synthesis of {(R)-2-[7-(tetrahydro-pyran-4-ylamino)-1H-indol-2-yl]-4,5-dihydro-thiazol-4-yl}-methanol

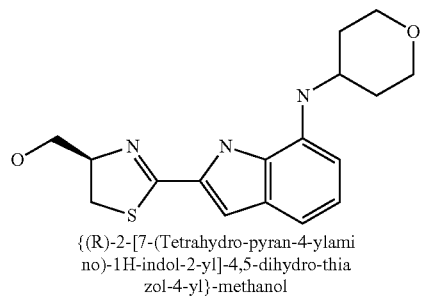 [SMILES: OC[C@@H]1CSC(c2cc3cccc(NC4CCOCC4)c3[nH]2)=N1]

{(R)-2-[7-(Tetrahydro-pyran-4-ylamino)-1H-indol-2-yl]-4,5-dihydro-thiazol-4-yl}-methanol (Step 1)

The compound obtained in Preparation 31 (900 mg, 2.7 mmol) was dissolved in 1,2-dichloroethane (100 ml). Tetrahydro-4H-pyran-4-one (0.8 ml, 8.13 mmol), sodium triacetoxyborohydride (1.72 g, 8.13 mmol) and acetic acid (0.47 ml, 8.13 mmol) were added, and stirred for 48 h at room temperature. After completion of the reaction, the mixture was diluted with dichloromethane, washed with saturated sodium bicarbonate solution, dried over anhydrous magnesium sulfate and filtered. The filtrate was distilled under reduced pressure and purified by column chromatography to give 2,2-dimethylpropionic acid (R)-2-[7-(tetrahydro-pyran-4-ylamino)-1H-indol-2-yl]-4,5-dihydro-thiazol-4-ylmethyl ester.

$^1$H-NMR (400 HMz, CDCl$_3$); δ 10.91 (br s, 1H), 7.01-6.91 (m, 3H), 6.48 (d, J=7.2 Hz, 1H), 4.86 (m, 1H), 4.34 (m, 2H), 4.00 (m, 2H), 3.61 (m, 1H), 3.54 (m, 3H), 3.31 (m, 1H), 2.05 (m, 2H), 1.55 (m, 2H), 1.16 (s, 9H)

(Step 2)

The compound obtained in Step 1 was dissolved in methanol (32 ml), tetrahydrofuran (32 ml) and water (16 ml). 1N sodium hydroxide (7 ml) was added, and stirred for 4 h at room temperature. After completion of the reaction, the mixture was distilled under reduced pressure, extracted with dichloromethane, washed with saturated sodium chloride solution, dried over anhydrous magnesium sulfate and filtered. The filtrate was distilled under reduced pressure and purified by column chromatography to give the title compound (700 mg, Yield 78%).

$^1$H-NMR (500 HMz, CDCl$_3$); δ 11.04-10.95 (m, 1H), 7.11 (m, 1H), 6.99 (t, 1H), 6.96 (s, 1H), 6.52 (m, 1H), 4.74 (m, 1H), 4.02 (m, 1H), 3.92 (m, 2H), 3.68 (m, 1H), 3.46-3.30 (m, 5H), 1.91 (m, 2H), 1.28 (m, 2H)

Mass spectrum (ESI, m/z): Calculated: 331.14, Found: 331.44

EXAMPLE 8

Synthesis of [(R)-2-(7-cyclopentylamino-5-fluoro-1H-indol-2-yl)-4,5-dihydro-thiazol-4-yl]-methanol

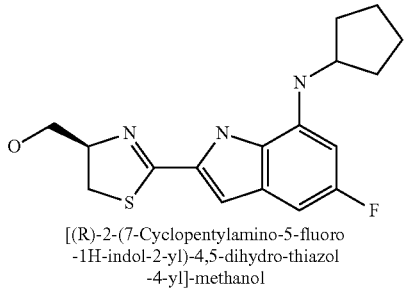 [SMILES: OC[C@@H]1CSC(c2cc3cc(F)cc(NC4CCCC4)c3[nH]2)=N1]

[(R)-2-(7-Cyclopentylamino-5-fluoro
-1H-indol-2-yl)-4,5-dihydro-thiazol
-4-yl]-methanol Ethyl 5-fluoro-7-nitro-1H-indole-2-carboxylate obtained in Preparation 2 (3.0 g, 11.9 mmol) was reacted according to the same procedure as Example 5 to give the title compound (600 mg, Yield 15%).

$^1$H-NMR (400 HMz, CDCl$_3$); δ 10.73 (br s, 1H), 6.91 (s, 1H), 6.72 (m, 1H), 6.33 (m, 1H), 4.78 (m, 1H), 4.12 (m, 1H), 3.97 (br s, 1H), 3.79 (m, 1H), 3.75 (m, 1H), 3.49 (m, 2H), 2.01 (m, 2H), 1.62 (m, 4H), 1.41 (m, 2H)

EXAMPLE 9

Synthesis of {(R)-2-[5-fluoro-7-(tetrahydro-pyran-4-ylamino)-1H-indol-2-yl]-4,5-dihydro-thiazol-4-yl}-methanol

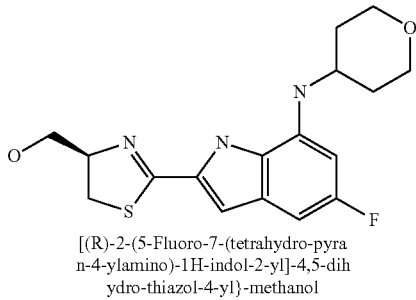 [SMILES: OC[C@@H]1CSC(c2cc3cc(F)cc(NC4CCOCC4)c3[nH]2)=N1]

[(R)-2-(5-Fluoro-7-(tetrahydro-pyra
n-4-ylamino)-1H-indol-2-yl]-4,5-dih
ydro-thiazol-4-yl}-methanol Ethyl 5-fluoro-7-nitro-1H-indole-2-carboxylate obtained in Preparation 2 (3.0 g, 11.9 mmol) was reacted according to the same procedure as Example 7 to give the title compound (750 mg, Yield 18%).

$^1$H-NMR (400 HMz, CDCl$_3$); δ 10.45 (br s, 1H), 6.90 (s, 1H), 6.75 (m, 1H), 6.34 (m, 1H), 4.82 (m, 1H), 4.12 (m, 1H), 4.01 (m, 2H), 3.94 (m, 1H), 3.78 (m, 1H), 3.54-3.43 (m, 5H), 2.03 (m, 2H), 1.50 (m, 2H)

EXAMPLE 10

Synthesis of {(R)-2-[5-(pyridin-3-yloxy)-7-(tetrahydro-pyran-4-ylamino)-1H-indol-2-yl]-4,5-dihydro-thiazol-4-yl}-methanol

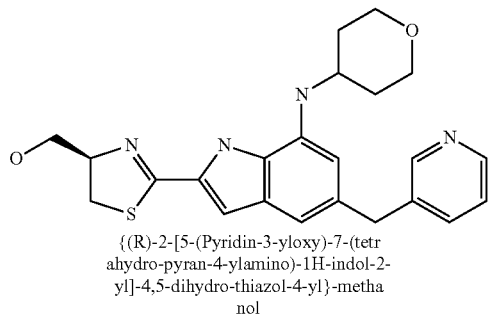 [SMILES: OC[C@@H]1CSC(c2cc3cc(Cc4cccnc4)cc(NC4CCOCC4)c3[nH]2)=N1]

{(R)-2-[5-(Pyridin-3-yloxy)-7-(tetr
ahydro-pyran-4-ylamino)-1H-indol-2-
yl]-4,5-dihydro-thiazol-4-yl}-metha
nol 7-Nitro-5-(pyridin-3-yloxy)-1H-indole-2-carboxylic acid ethyl ester obtained in Preparation 11 (500 mg, 1.5 mmol) was reacted according to the same procedure as Example 7 to give the title compound (40 mg, Yield 6%).

$^1$H-NMR (400 HMz, CDCl$_3$); δ 10.96 (br s, 1H), 8.36 (d, J=2.4 Hz, 1H), 8.26 (m, 1H); 7.27 (m, 1H), 7.19 (m, 1H), 6.83 (s, 1H), 6.63 (d, J=1.6 Hz, 1H), 6.24 (d, J=1.6 Hz, 1H), 4.81 (m, 1H), 4.01-3.94 (m, 3H), 3.75 (m, 1H), 3.47 (s, 3H), 3.48-3.29 (m, 5H), 1.93 (m, 2H), 1.52 (m, 2H)

Preparation 34: Synthesis of 5-chloro-7-nitro-1H-indole-2-carboxylic acid

The compound obtained in Preparation 5 (15.0 g, 59.1 mmol) was dissolved in tetrahydrofuran (300 ml) and methanol (100 ml). Lithium hydroxide (7.43 g, 177 mmol) was dissolved in water (100 ml) and added to the reaction solution, which was then stirred for 3 h at room temperature. After completion of the reaction, tetrahydrofuran and methanol were removed by distillation under reduced pressure. The residue was neutralized to about pH 6 using 3N hydrochloric acid solution. The resulting solid was filtered and dried to give the title compound (13.1 g, Yield 92%).

Preparation 35: Synthesis of [(R)-2-(7-amino-5-chloro-1H-indol-2-yl)-4,5-dihydro-thiazol-4-yl]-acetic acid methyl ester (Step 1)

The compound obtained in Preparation 34 (12.5 g, 52.0 mmol) and the compound obtained in Preparation 22 (19.1 g, 62.4 mmol) were dissolved in N,N-dimethylformamide (200 ml). Triethylamine (8.7 ml, 62.4 mmol), HOBT (14.0 g, 104 mmol) and EDC (16.9 g, 88.4 mmol) were added, and stirred for 4 h at room temperature. After completion of the reaction, the mixture was concentrated. The residue was extracted with ethyl acetate and washed with saturated sodium hydrogen carbonate aqueous solution and saturated ammonium chloride aqueous solution, respectively. The organic layer was concentrated, and the residue was purified by column chromatography to give (R)-3-[(5-chloro-7-nitro-1H-indole-2-carbonyl)-amino]-4-(4-methoxy-benzylsulfanyl)-butyric acid methyl ester (20.2 g, 41.0 mmol, Yield 79%).

$^1$H-NMR (500 HMz, CDCl$_3$); δ 10.47 (br s, 1H), 8.24 (d, J=1.9 Hz, 1H), 7.96 (d, J=1.9 Hz, 1H), 7.24 (d, J=8.6 Hz, 2H), 6.89 (s, 1H), 6.81 (d, J=8.6 Hz, 2H), 4.58 (m, 1H), 3.75 (s, 3H), 3.73 (s, 2H), 3.71 (s, 3H), 2.86 (m, 1H), 2.80 (m, 1H), 2.73 (m, 1H), 2.70 (m, 1H)

(Step 2)

The compound obtained in Step 1 was dissolved in dichloromethane (200 ml). Phosphorus pentachloride (17.1 g, 82 mmol) was added, and stirred for 1 h at room temperature. After completion of the reaction, the mixture was concentrated, and diethylether (200 ml) was added to the residue. The resulting solid was filtered and dried to give [(R)-2-(5-chloro-7-nitro-1H-indol-2-yl)-4,5-dihydro-thiazol-4-yl]-acetic acid methyl ester.

$^1$H-NMR (500 HMz, CDCl$_3$); δ 10.48 (br s, 1H), 8.22 (d, J=1.8 Hz, 1H), 7.94 (d, J=1.8 Hz, 1H), 7.29 (d, J=8.6 Hz, 2H), 6.96 (d, J=2.5 Hz, 1H), 6.89 (d, J=8.6 Hz, 2H), 5.00 (m, 1H), 3.76 (s, 3H), 3.71 (m, 1H), 3.26 (m, 1H), 2.99 (m, 1H), 2.67 (m, 1H)

(Step 3)

The compound obtained in Step 2 was dissolved in tetrahydrofuran (200 ml), methanol (200 ml) and water (200 ml). Iron dust (22.9 g, 410 mmol) and ammonium chloride (21.9 g, 410 mmol) were added, and stirred using a mechanical stirrer for 1 h at 60° C. After completion of the reaction, tetrahydrofuran (300 ml) was added. The mixture was filtered through a cellite, washed with tetrahydrofuran (100 ml), distilled under reduced pressure and concentrated. The residue was extracted with ethyl acetate, washed with saturated sodium chloride solution, dried over anhydrous magnesium sulfate and filtered. The filtrate was distilled under reduced pressure and purified by column chromatography to give the title compound (9.0 g, Yield 68%).

Preparation 36: Synthesis of [(R)-2-(5-chloro-7-cyclopentylamino-1H-indol-2-yl)-4,5-dihydro-thiazol-4-yl]-acetic acid methyl ester The compound obtained in Preparation 35 (4.9 g, 15.1 mmol) was dissolved in dichloroethane (100 ml). Cyclopentanone (2.7 ml, 30.3 mmol), glacial acetic acid (0.86 ml, 15.1 mmol) and sodium triacetoxyborohydride (6.42 g, 30.3 mmol) were added, which was then stirred for 36 h at room temperature. After completion of the reaction, the reaction mixture was washed with saturated sodium hydrogen carbonate solution (200 ml) and concentrated. The residue was purified by column chromatography to give the title compound (5.15 g, Yield 87%).

$^1$H NMR (DMSO-d$_6$, ppm); δ 11.51 (s, 1H), 6.79 (s, 1H), 6.79 (s, 1H), 6.16 (s, 1H), 6.13 (d, 1H), 4.85 (m, 1H), 3.80 (m, 1H), 3.62 (m, 1H), 3.58 (s, 3H), 3.19 (m, 1H), 2.71 (m, 1H), 2.63 (m, 1H), 1.93 (m, 2H), 1.69 (m, 2H), 1.56 (m, 4H)

FAB MS (m/e)=392

EXAMPLE 11

Synthesis of [(R)-2-(5-chloro-7-cyclopentylamino-1H-indol-2-yl)-4,5-dihydro-thiazol-4-yl]-acetic acid

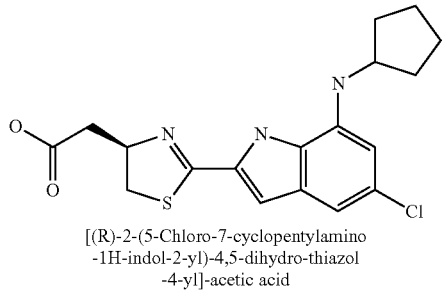 [SMILES: O=C(O)C[C@@H]1CSC(c2cc3cc(Cl)cc(NC4CCCC4)c3[nH]2)=N1]

[(R)-2-(5-Chloro-7-cyclopentylamino
-1H-indol-2-yl)-4,5-dihydro-thiazol
-4-yl]-acetic acid The compound obtained in Preparation 36 (1.5 g, 3.83 mmol) was dissolved in tetrahydrofuran (100 ml) and methanol (50 ml). Lithium hydroxide monohydrate (640 mg, 15.3 mmol) was dissolved in water (50 ml) and added to the reaction solution, which was then stirred for 4 h at room temperature. After completion of the reaction, tetrahydrofuran and methanol were removed by distillation under reduced pressure. 1N hydrochloric acid solution was added. The mixture was extracted with ethyl acetate, washed with saturated sodium chloride solution, dried over anhydrous magnesium sulfate and filtered. The filtrate was distilled under reduced pressure and purified by column chromatography to give the title compound (13.1 g, Yield 92%).

$^1$H NMR (DMSO-d$_6$, ppm); δ 12.51 (br s, 1H), 11.51 (s, 1H), 6.79 (s, 1H), 6.79 (s, 1H), 6.16 (s, 1H), 6.14 (d, 1H), 4.87 (m, 1H), 3.80 (m, 1H), 3.61 (m, 1H), 3.19 (m, 1H), 2.72 (m, 1H), 2.64 (m, 1H), 1.93 (m, 2H), 1.69 (m, 2H), 1.56 (m, 4H)

FAB MS (m/e)=378

EXAMPLE 12

Synthesis of [(R)-2-(5-chloro-7-cyclopentylamino-1H-indol-2-yl)-4,5-dihydro-thiazol-4-yl]-acetic acid ethyl ester

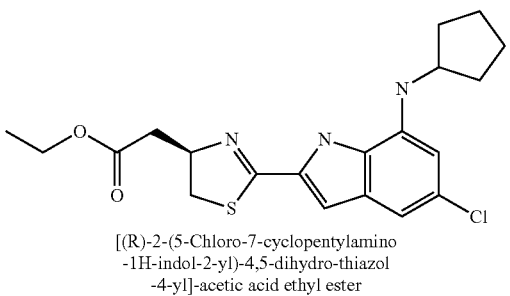 [SMILES: CCOC(=O)C[C@@H]1CSC(c2cc3cc(Cl)cc(NC4CCCC4)c3[nH]2)=N1]

[(R)-2-(5-Chloro-7-cyclopentylamino
-1H-indol-2-yl)-4,5-dihydro-thiazol
-4-yl]-acetic acid ethyl ester The compound obtained in Preparation 5 (5.0 g, 19.7 mmol) and the compound obtained in Preparation 23 (6.3 g, 19.7 mmol) were reacted according to the same procedures as Preparations 34 to 36 to give the title compound (840 mg, Yield 11%).

EXAMPLE 13

Synthesis of 2-{(R)-2-[5-chloro-7-(tetrahydro-pyran-4-ylamino)-1H-indol-2-yl]-4,5-dihydro-thiazol-4-yl}-ethanol

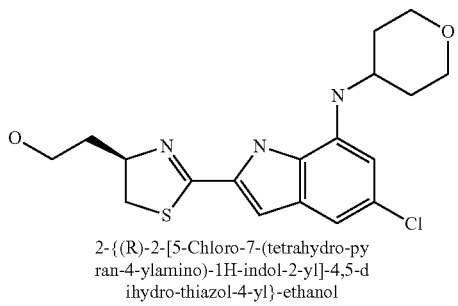 [SMILES: OCC[C@@H]1CSC(c2cc3cc(Cl)cc(NC4CCOCC4)c3[nH]2)=N1]

2-{(R)-2-[5-Chloro-7-(tetrahydro-py
ran-4-ylamino)-1H-indol-2-yl]-4,5-d
ihydro-thiazol-4-yl}-ethanol (Step 1)

The compound obtained in Preparation 35 (4.0 g, 12.4 mmol) was reacted according to the same procedure as Step 1 of Example 7 to give tetrahydropyran-4-ylamine compound (4.1 g, 10.0 mmol, Yield; 81%).

$^1$H NMR (DMSO-d$_6$, ppm); δ 11.52 (1H, s), 6.81 (1H, s), 6.71 (1H, s), 6.28 (1H, s), 6.07 (1H, d), 4.90 (1H, m), 3.86 (2H, m), 3.64 (3H, s), 3.62 (2H, m), 3.44 (2H, t), 2.82-2.71 (2H, m), 1.94 (2H, m), 1.40 (2H, m)

FAB MS (m/e)=408

(Step 2)

The compound obtained in Step 1 (2.5 g, 6.12 mmol) was reacted according to the same procedure as Example 4 to give the title compound (2.19 g, 5.76 mmol, Yield 94%).

$^1$H NMR (DMSO-d$_6$, ppm); δ 11.48 (br s, 1H), 6.81 (s, 1H), 6.68 (s, 1H), 6.28 (s, 1H), 6.05 (d, 1H), 4.66 (q, 1H), 4.54 (t, 1H), 3.87 (m, 2H), 3.61-3.54 (m, 3H), 3.44 (t, 2H), 3.15 (m, 1H), 1.99-1.93 (m, 3H), 1.73 (m, 1H), 1.40 (m, 2H), 1.20 (m, 1H)

FAB MS (m/e)=380

Preparation 37: Synthesis of {5-chloro-2-[(R)-4-(2-iodo-ethyl)-4,5-dihydro-thiazol-2-yl}-1H-indol-7-yl]-(tetrahydro-pyran-4-yl)-amine The compound obtained in Example 13 (3.7 g, 10.2 mmol) was dissolved in tetrahydrofuran (100 ml). Imidazole (2.1 g, 30.6 mmol), triphenylphosphine (4.0 g, 15.3 mmol) and iodine (3.9 g, 15.3 mmol) were added, and stirred for 8 h at 0° C.~room temperature. After completion of the reaction, ethyl acetate (100 ml) was added, and the reaction mixture was washed with water (100 ml×2). The organic layer was concentrated and the residue was purified by column chromatography to give the title compound (2.0 g, 4.07 mmol, Yield 40%).

EXAMPLE 14

Synthesis of 1-[4-(2-{(R)-2-[5-chloro-7-(tetrahydro-pyran-4-ylamino)-1H-indol-2-yl]-4,5-dihydro-thiazol-4-yl}-ethyl)-piperazin-1-yl]-2-hydroxy-ethanone

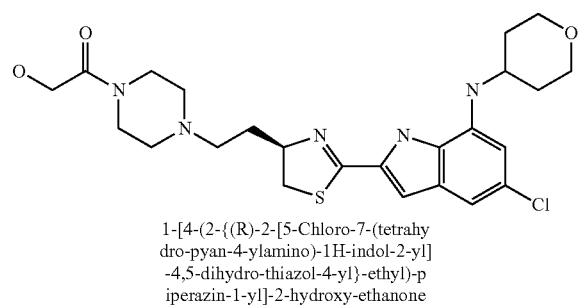 [SMILES: O=C(CO)N1CCN(CC[C@@H]2CSC(c3cc4cc(Cl)cc(NC5CCOCC5)c4[nH]3)=N2)CC1]

1-[4-(2-{(R)-2-[5-Chloro-7-(tetrahydro-pyan-4-ylamino)-1H-indol-2-yl]-4,5-dihydro-thiazol-4-yl}-ethyl)-piperazin-1-yl]-2-hydroxy-ethanone (Step 1)
The compound obtained in Preparation 37 (100 mg, 0.2 mmol) and 1-t-butoxycarbonyl-piperazine (270 mg, 1.4 mmol) were dissolved in N,N-dimethylformamide (20 ml). Potassium carbonate (200 mg, 1.4 mmol) was added, and stirred for 4 h at room temperature. After completion of the reaction, water was added. The mixture was extracted with ethyl acetate, dried over anhydrous magnesium sulfate and filtered. The filtrate was distilled under reduced pressure and concentrated to give 4-(2-{(R)-2-[5-chloro-7-(tetrahydro-pyran-4-ylamino)-1H-indol-2-yl]-4,5-dihydro-thiazol-4-yl}-ethyl)-piperazine-1-carboxylic acid t-butyl ester.

(Step 2)
The compound obtained and concentrated in Step 1 was dissolved in dichloromethane (10 ml). 4N-hydrochloric acid solution (0.5 ml) was added in drops, and stirred for 2 h at room temperature. After completion of the reaction, the reaction mixture was concentrated by distillation under reduced pressure. The concentrate was dissolved in N,N-dimethylformamide (5 ml). Glycolic acid (15.1 mg, 0.2 mmol), triethylamine (28 ul, 0.2 mmol), EDC (45 mg, 0.23 mmol) and HOBT (40 mg, 0.29 mmol) were added, and stirred for 8 h at room temperature. 1N-hydrochloric acid solution was added. The mixture was extracted with ethyl acetate, dried over anhydrous magnesium sulfate and filtered. The filtrate was distilled under reduced pressure and purified by column chromatography to give the title compound (5.1 mg, Yield 5%).

$^1$H-NMR (500 HMz, DMSO-d$_6$); δ 11.48 (br s, 1H), 6.81 (s, 1H), 6.69 (d, J=1.8 Hz, 1H), 6.29 (s, 1H), 6.05 (d, J=7.4 Hz, 1H), 4.62 (m, 1H), 4.49 (t, 1H), 4.04 (m, 2H), 3.87 (m, 2H), 3.56 (m, 1H), 3.45 (m, 4H), 3.29 (m, 4H), 3.16 (m, 1H), 2.36 (m, 4H). 1.96 (m, 3H), 1.80 (m, 1H), 1.40 (m, 2H)

EXAMPLE 15

Synthesis of 1-(2-{(R)-2-[5-chloro-7-(tetrahydro-pyran-4-ylamino)-1H-indol-2-yl]-4,5-dihydro-thiazol-4-yl}-ethyl)-pyrrolidin-3-ol

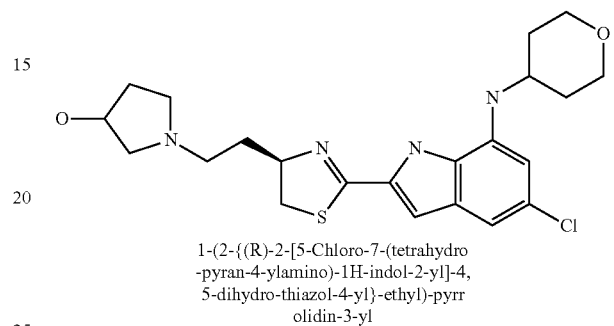

1-(2-{(R)-2-[5-Chloro-7-(tetrahydro-pyran-4-ylamino)-1H-indol-2-yl]-4,5-dihydro-thiazol-4-yl}-ethyl)-pyrrolidin-3-yl The compound obtained in Preparation 37 (100 mg, 0.2 mmol) and 3-pyrrolidinol (0.35 ml, 4.2 mmol) were dissolved in N,N-dimethylformamide (20 ml). Potassium carbonate (580 mg, 4.2 mmol) was added and stirred for 4 h at room temperature. After completion of the reaction, water was added. The reaction mixture was extracted with ethyl acetate, dried over anhydrous magnesium sulfate and filtered. The filtrate was distilled under reduced pressure and concentrated. The residue was purified by column chromatography to give the title compound (2 mg, Yield 2%).

EXAMPLE 16

Synthesis of [(R)-2-(5-bromo-7-cyclopentylamino-1H-indol-2-yl)-4,5-dihydro-thiazol-4-yl]-acetic acid

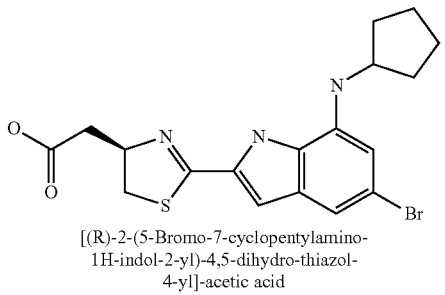 [SMILES: O=C(O)C[C@@H]1CSC(c2cc3cc(Br)cc(NC4CCCC4)c3[nH]2)=N1]

[(R)-2-(5-Bromo-7-cyclopentylamino-1H-indol-2-yl)-4,5-dihydro-thiazol-4-yl]-acetic acid Methyl 5-bromo-7-nitro-1H-indole-2-carboxylate obtained in Preparation 6 (1.1 g, 3.7 mmol) was reacted according to the same procedure as Example 11 to give the title compound (250 mg, Yield 16%).

$^1$H-NMR (400 HMz, CDCl$_3$); δ 12.50 (br s, 1H), 7.10 (sm 1H), 7.06 (s, 1H), 6.56 (s, 1H), 5.31 (m, 1H), 3.89 (m, 2H), 3.40 (m, 1H), 2.99 (m, 1H), 2.83 (m, 1H), 2.08 (m, 2H), 1.86 (m, 2H), 1.66 (m, 4H)

EXAMPLE 17

Synthesis of [(R)-2-(7-cyclopentylamino-5-ethoxy-1H-indol-2-yl)-4,5-dihydro-thiazol-4-yl]-acetic acid

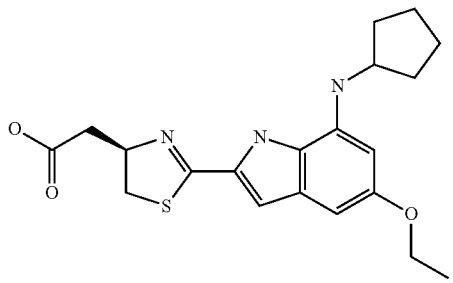

[(R)-2-(7-Cyclopentylamino-5-ethoxy
-1H-indol-2-yl)-4,5-dihydro-thiazol
-4-yl]-acetic acid Methyl 5-ethoxy-7-nitro-1H-indole-2-carboxylate obtained in Preparation 9 (1.5 g, 5.7 mmol) was reacted according to the same procedure as Example 11 to give the title compound (150 mg, Yield 7%).

$^1$H-NMR (400 HMz, DMSO-$d_6$); δ 11.24 (br s, 1H), 6.65 (d, J=2.0 Hz, 1H), 6.26 (d, J=2.0 Hz, 1H), 5.92 (d, J=6.0 Hz, 1H), 5.88 (d, J=2.0 Hz, 1H), 4.89 (m, 1H), 3.94 (q, 2H), 3.81 (m, 1H), 3.65 (m, 1H), 3.20 (m, 1H), 2.74 (m, 1H), 2.62 (m, 1H), 1.94 (m, 2H), 1.72 (m, 2H), 1.61 (m, 4H), 1.31 (t, 3H).

EXAMPLE 18

Synthesis of [(S)-2-(7-cyclopentylamino-5-ethoxy-1H-indol-2-yl)-4,5-dihydro-thiazol-4-yl]-acetic acid

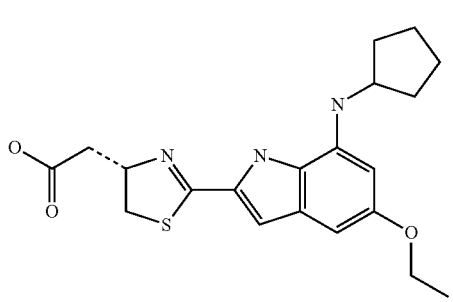

[(S)-2-(7-Cyclopentylamino-5-ethoxy
-1H-indol-2-yl)-4,5-dihydro-thiazol
-4-yl]-acetic acid (Step 1)

D-Cysteine (5.0 g, 31.7 mmol) was used instead of L-cysteine in the procedure of Preparation 22 to give (S)-3-amino-4-(4-methoxy-benzylsulfanyl)-butyric methyl ester (1.2 g, Yield 12%).

(Step 2)

5-Ethoxy-7-nitro-1H-indole-2-carboxylate obtained in Preparation 9 (1.0 g, 3.8 mmol) and the compound obtained in Step 1 were reacted according to the same procedures as Preparation 34 to 36 and Example 11 to give the title compound (27 mg, Yield 2%).

EXAMPLE 19

Synthesis of [2-(7-cyclopentylamino-5-phenoxy-1H-indol-2-yl)-4,5-dihydro-thiazol-4-yl]-acetic acid

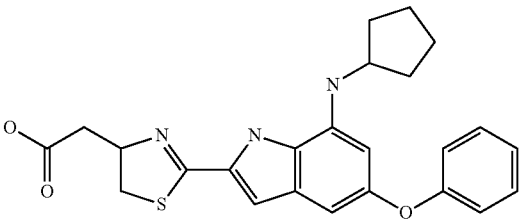

[2-(7-Cyclopentylamino-5-phenoxy-1H
-indol-2-yl)-4,5-dihydro-thiazol-4-
yl]-acetic acid (Step 1)

3-t-Butoxycarbonylamino-4-hydroxy-butyric acid ethyl ester (15.0 g, 60.7 mmol) was used instead of (R)-4-t-butoxycarbonylamino-5-hydroxy-pentanoic acid ethyl ester in the procedure of Preparation 24 to give 3-amino-4-(4-methoxy-benzylsulfanyl)-butyric acid ethyl ester (12.0 g, Yield 61%).

(Step 2)

The compound of Step 1 and 7-nitro-5-phenoxy-1H-indole-2-carboxylic acid methyl ester of Preparation 10 (2.0 g, 6.7 mmol) were reacted according to the same procedures as Preparation 34 to 36 and Example 11 to give the title compound (500 mg, Yield 17%).

EXAMPLE 20

Synthesis of [(R)-2-(7-cyclopentylamino-5-phenoxy-1H-indol-2-yl)-4,5-dihydro-thiazol-4-yl]-acetic acid

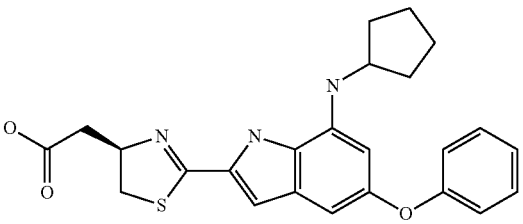

[(R)-2-(7-Cyclopentylamino-5-phenox
y-1H-indol-2-yl)-4,5-dihydro-thiazo
l-4-yl]-acetic acid 7-Nitro-5-phenoxy-1H-indole-2-carboxylic acid methyl ester of Preparation 10 (101.5 g, 264.7 mmol) and (R)-3-amino-4-(4-methoxy-benzylsulfanyl)-butyric acid ethyl ester hydrochloride of Preparation 23 were reacted according to the same procedures as Preparation 34 to 36 and Example 11 to give the title compound (51.0 g, Yield 44%).

$^1$H-NMR (400 HMz, CDCl$_3$); δ 11.92 (br s, 1H), 7.28 (m, 2H), 7.00 (m, 4H), 6.56 (s, 1H), 6.22 (s, 1H), 5.34 (br s, 1H), 3.81 (br s, 1H), 3.70 (m, 1H), 3.22 (d, J=12.0 Hz, 1H), 2.76-2.62 (m, 2H), 1.96 (m, 2H), 1.73 (m, 2H), 1.58 (m, 4H)

EXAMPLE 21

Synthesis of [(S)-2-(7-cyclopentylamino-5-phenoxy-1H-indol-2-yl)-4,5-dihydro-thiazole-4-yl]-acetic acid

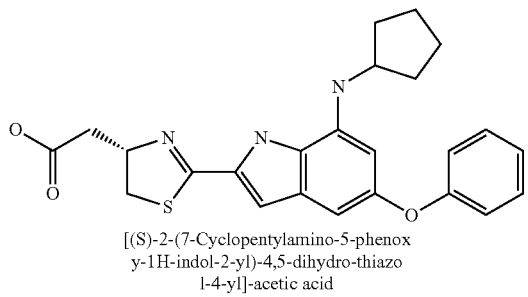 [SMILES: O=C(O)C[C@H]1CSC(c2cc3cc(Oc4ccccc4)cc(NC4CCCC4)c3[nH]2)=N1]

[(S)-2-(7-Cyclopentylamino-5-phenoxy-1H-indol-2-yl)-4,5-dihydro-thiazol-4-yl]-acetic acid 7-Nitro-5-phenoxy-1H-indole-2-carboxylic acid methyl ester of Preparation 10 (55.5 g, 185.9 mmol) and (S)-3-amino-4-(4-methoxy-benzylsulfanyl)-butyric acid isopropyl ester of Preparation 25 were reacted according to the same procedures as Preparation 34 to 36 and Example 11 to give the title compound (21.0 g, Yield 26%).

Preparation 38: Synthesis of 3-[(R)-2-(7-amino-5-chloro-1H-indol-2-yl)-4,5-dihydro-thiazol-4-yl]-propionic acid ethyl ester Acid compound obtained in Preparation 34 (2.0 g, 8.3 mmol) and (R)-4-amino-5-(4-methoxy-benzylsulfanyl)-pentanoic acid ethyl ester hydrochloride obtained in Preparation 24 (3.4 g, 10.2 mmol) were reacted according to the same procedures as Example 35 to give the title compound (0.76 g, Yield 26%).

$^1$H-NMR (400 HMz, CDCl$_3$); δ 10.00 (br s, 1H), 7.08 (s, 1H), 6.80 (s, 1H), 6.57 (s, 1H), 4.71 (m, 1H), 4.07 (m, 2H), 3.88 (br s, 2H), 3.55 (m, 1H), 3.11 (m, 1H), 2.50 (t, 2H), 2.05 (m, 2H), 1.22 (t, 3H)

EXAMPLE 22

Synthesis of 3-[(R)-2-(5-chloro-7-cyclopentylamino-1H-indol-2-yl)-4,5-dihydro-thiazol-4-yl]-propionic acid ethyl ester

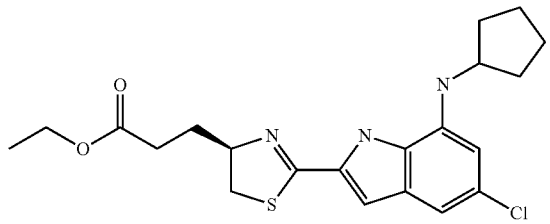

3-[(R)-2-(5-Chloro-7-cyclopentylamino-1H-indol-2-yl)-4,5-dihydro-thiazol-4-yl]-propionic acid ethyl ester The compound obtained in Preparation 38 (760 mg, 2.1 mmol) was reacted according to the same procedures as Example 1 to give the title compound 450 mg (Yield 51%).

EXAMPLE 23

Synthesis of 3-[(R)-2-(5-Chloro-7-cyclopentylamino-1H-indol-2-yl)-4,5-dihydro-thiazol-4-yl]-propionic acid

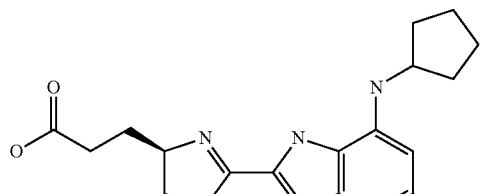

3-[(R)-2-(5-Chloro-7-cyclopentylamino-1H-indol-2-yl)-4,5-dihydro-thiazol-4-yl]-propionic acid The ester compound obtained in Example 22 (500 mg, 1.2 mmol) was reacted according to the same procedures as Example 11 to give the title compound 400 mg (Yield 85%).

$^1$H-NMR (400 HMz, DMSO$_6$, Na salt); δ 11.69 (br s, 1H), 6.82 (d, J=4.0 Hz, 1H), 6.68 (s, 1H), 6.27 (s, 1H), 6.18 (s, 1H), 4.63 (m, 1H), 3.83 (m, 1H), 3.50 (m, 1H), 3.13 (m, 1H), 2.08-1.96 (m, 6H), 1.72 (m, 2H), 1.58 (m, 4H)

Preparation 39: Synthesis of 2-pyridin-2-yl-1H-indol-7-ylamine

The compound obtained in Preparation 14 (1.0 g, 4.2 mmol) was reacted according to the same procedures as Step 3 of Preparation 31 to give the title compound 800 mg (Yield 92%).

EXAMPLE 24

Synthesis of cyclopentyl-(2-pyridin-2-yl-1H-indol-7-yl)amine

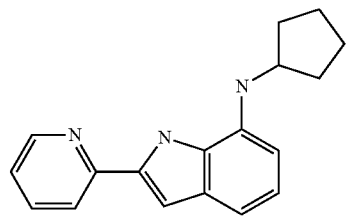

Cyclopentyl-(2-pyridin-2-yl-1H-indol-7-yl)amine

The compound obtained in Preparation 39 (150 mg, 0.7 mmol) was reacted according to the same procedures as Example 1 to give the title compound 55 mg (Yield 28%).

$^1$H-NMR (400 HMz, CDCl$_3$); δ 10.85 (br s, 1H), 8.48 (m, 1H), 7.87 (d, J=8.0 Hz, 1H), 7.74 (m, 1H), 7.12 (m, 1H), 7.08 (d, J=7.6 Hz, 1H), 7.00 (s, 1H), 6.98 (m, 1H), 6.43 (d, J=7.2 Hz, 1H), 3.81 (m, 1H), 1.89 (m, 2H), 1.49 (m, 4H), 1.26 (m, 2H)

Preparation 40: Synthesis of
2-pyrazin-2-yl-1H-indol-7-ylamine

The compound obtained in Preparation 15 (500 mg, 2.1 mmol) was reacted according to the same procedures as Step 3 of Preparation 31 to give the title compound 430 mg (Yield 98%).

EXAMPLE 25

Synthesis of
Cyclopentyl-(2-pyrazin-2-yl-1H-indol-7-yl)amine

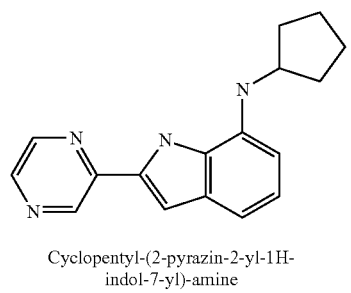 [SMILES: c1cc(NC2CCCC2)c2[nH]c(-c3cnccn3)cc2c1]

Cyclopentyl-(2-pyrazin-2-yl-1H-
indol-7-yl)-amine

The compound obtained in Preparation 40 (80 mg, 0.38 mmol) was reacted according to the same procedures as Example 1 to give the title compound 33 mg (Yield 31%).

$^1$H-NMR (400 HMz, CDCl$_3$); δ 9.72 (br s, 1H), 9.08 (d, J=1.2 Hz, 1H), 8.41 (m, 1H), 8.37 (m, 1H), 7.12 (m, 2H), 7.05 (m, 1H), 6.55 (d, J=7.6 Hz, 1H), 3.94 (m, 1H), 2.04 (m, 2H), 1.70-1.48 (m, 6H)

EXAMPLE 26

Synthesis of (2-pyrazin-2-yl-1H-indol-7-yl)-(tetrahydropyran-4-yl)amine

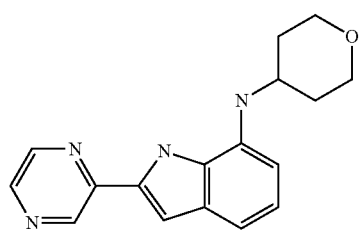

(2-Pyrazin-2-yl-1H-indol-7-yl)-
tetrahydro-pyran-4-yl)-amine

The compound obtained in Preparation 40 (80 mg, 0.38 mmol) was reacted according to the same procedures as Step 1 of Example 7 to give the title compound 35 mg (Yield 31%).

$^1$H-NMR (400 HMz, CDCl$_3$ & MeOH-d$_4$); δ 9.00 (br s, 1H), 8.51 (m, 1H), 8.35 (d, J=2.4 Hz, 1H), 7.13 (s, 1H), 7.10 (d, J=8.0 Hz, 1H), 7.00 (m, 1H), 6.52 (d, J=7.6 Hz, 1H), 4.05 (m, 2H), 3.68 (m, 1H), 3.61 (m, 2H), 2.17 (m, 2H), 1.63 (m, 2H)

Preparation 41: Synthesis of
7-nitro-1H-indol-2-carbothioic acid amide

7-Nitroindol-2-carboxylic acid compound obtained in Step 1 of Preparation 28 (2.0 g, 9.7 mmol) was dissolved in dichloromethane (100 ml). 2 ml (29.1 mmol) of cyonylchloride was added and the mixture was stirred for 1 hour at 60° C. At the end of reaction, the mixture was distilled under reduced pressure to concentrate. The resulting compound was dissolved in 100 ml of tetrahydrofuran and 5.0 g (14.6 mmol) of Lawesson's reagent was added. The mixture was stirred for 3 hours at 80° C. At the end of reaction, the mixture was concentrated. The resulting solids were washed with 100 ml of chloromethane to give the title compound 1.5 g (Yield 71%).

$^1$H-NMR (500 HMz, DMSO-d$_6$); δ 10.92 (br s, 1H), 10.00 (br s, 1H), 9.99 (br s, 1H), 8.22 (m, 2H), 7.50 (d, J=1.9 Hz, 1H), 7.30 (t, 1H)

Preparation 42: Synthesis of
7-nitro-2-thiazol-2-yl-1H-indole 1.1 g (5.0 mmol) of the compound obtained in Preparation 41 was dissolved in 20 ml of ethanol and 1 ml of N,N-dimethylformamide. 3.7 ml (25 mmol) of Bromoacetaldehyde diethylacetal was added and the mixture was stirred for 8 hours at 100° C. At the end of reaction, added water and extracted with ethylacetate. The extract was dried over anhydrous magnesium sulfate and filtered. The filtrate was distilled under reduced pressure to concentrate. The resulting solids were washed with diethyl ether to give the title compound 800 mg (Yield 67%).

Preparation 43: Synthesis of
2-thiazol-2-yl-1H-indol-7-ylamine

The compound obtained in Preparation 42 (800 mg, 3.3 mmol) was reacted according to the same procedures as Step 3 of Preparation 31 to give the title compound 650 mg (Yield 93%).

$^1$H-NMR (500 HMz, DMSO-d$_6$); δ 10.79 (br s, 1H), 9.43 (br s, 1H), 9.29 (br s, 1H), 7.04 (d, J=2.5 Hz, 1H), 6.77-6.71 (m, 2H), 6.33 (m, 1H), 5.50 (br s, 2H)

EXAMPLE 27

Synthesis of Cyclopentyl-(2-thiazol-2-yl-1H-indol-7-yl)-amine

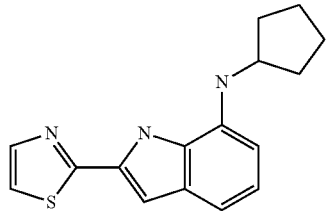

Cyclopentyl-(2-thiazol-2-yl-1H-
indol-7-yl)-amine

The compound obtained in Preparation 43 (30 mg, 3.3 mmol) was reacted according to the same procedures as Example 1 to give the title compound 20 mg (Yield 51%).

¹H-NMR (400 HMz, CDCl₃); δ 9.37 (br s, 1H), 7.36 (br s, 1H), 7.20 (br s, 1H), 7.06-7.00 (m, 2H), 6.86 (d, J=2.0 Hz, 1H), 6.55 (m, 2H), 3.95 (m, 1H), 2.08 (m, 2H), 1.79 (m, 2H), 1.65 (m, 4H)

Preparation 44: Synthesis of 5-methyl-7-nitro-1H-indol-2-carboxylic acid 6.5 g (27.8 mmol) of the compound obtained from Preparation 7 was dissolved in 200 ml of 1:1:1 mixture solution of methanol, tetrahydrofuran and water. 3.5 g (83.3 mmol) of Lithium hydroxide hydrate was added thereto. After stirring for 8 hours at room temperature, 1N—HCl solution was added and the mixture was extracted with ethylacetate. The extract was dried over anhydrous magnesium sulfate and filtered. The filtrate was distilled under reduced pressure to obtain the title compound 5.7 g (Yield 94%).

¹H-NMR (500 HMz, CDCl₃); δ 10.26 (br s, 1H), 8.17 (s, 1H), 7.87 (s, 1H), 7.38 (s, 1H), 2.59 (s, 3H)

Preparation 45: Synthesis of (R)-3-(4-methoxy-benzylsulfanyl)-2-[(5-methyl-7-nitro-1H-indol-2-carbonyl)-amino]-propionic acid ethyl ester The compound obtained in Preparation 44 (3 g, 13.6 mmol) and (R)-2-amino-3-(4-methoxy-benzylsulfanyl)propionic acid ethyl ester hydrochloride obtained in Preparation 26 (5.8 g, 19.1 mmol) was dissolved in 100 ml of dimethylformamide. Triethylamine (1.9 g, 19.1 mmol), EDC (4.4 g, 23.2 mmol) and HOBT (3.7 g, 27.3 mmol) were added thereto. After stirring for 8 hours at room temperature, 1N—HCl solution was added and the mixture was extracted with ethylacetate. The extract was dried over anhydrous magnesium sulfate and filtered. The filtrate was distilled under reduced pressure and purified by column chromatography to obtain the title compound 4.1 g (Yield 64%).

¹H-NMR (400 HMz, CDCl₃); δ 10.06 (br s, 1H), 7.95 (s, 1H), 7.64 (s, 1H), 7.51 (d, J=8.0 Hz, 1H), 7.20 (d, J=8.0 Hz, 1H), 6.87 (s, 1H), 6.86 (d, J=4.0 Hz, 2H), 5.05 (m, 1H), 4.30 (m, 2H), 3.72 (s, 5H), 3.04 (m, 2H), 2.44 (s, 3H), 1.30 (t, 3H)

Preparation 46: Synthesis of (R)-2-(7-amino-5-methyl-1H-indol-2-yl)-4,5-dihydro-thiazole-4-carboxylic acid ethyl ester (Step 1)

The compound obtained in Preparation 45 (4.1 g, 8.7 mmol) of was dissolved in 200 ml of dichloromethane, thereto 3.6 g (17.4 mmol) of Phosphorus pentachloride was added. The mixture was stirred for 4 hours at room temperature. Saturated aqueous sodium bicarbonate solution was added, and the mixture was extracted with ethylacetate. The extract was dried with anhydrous magnesium sulfate, filtered. The filtrate was distilled under reduced pressure to give (R)-2-(5-methyl-7-nitro-1H-indol-2-yl)-4,5-dihydro-thiazol-4-carboxylic acid ethyl ester.

(Step 2)

The compound obtained in Step 1 was dissolved in 300 ml of 1:1:1 mixture of water, tetrahydrofuran and methanol. To the mixture added 4.6 g (86.9 mmol) of ammonium chloride and 4.9 g (86.9 mmol) of iron and stirred for 30 minutes at 60° C. The mixture was filtered through celite and distilled under reduced pressure. To the concentrate added saturated aqueous sodium bicarbonate solution and extracted with ethylacetate. The extract was dried with anhydrous magnesium sulfate, filtered. The filtrate was purified by column chromatography to give the title compound 400 mg (Yield 15%).

Preparation 47: Synthesis of (R)-2-(7-cyclopentylamino-5-methyl-1H-indol-2-yl)-4,5-dihydro-thiazole-4-carboxylic acid ethyl ester The compound obtained in Preparation 46 (4.0 g, 0.91 mmol) was reacted according to the same procedures as Example 1 to give the title compound 590 mg (Yield 12%).

¹H-NMR (400 HMz, CDCl₃); δ 9.74 (br s, 1H), 6.85 (s, 1H), 6.84 (s, 1H), 6.37 (s, 1H), 5.32 (t, 1H), 4.24 (m, 2H), 3.88 (m, 1H), 3.71 (m, 2H), 2.39 (s, 3H), 2.03 (m, 2H), 1.67 (m, 2H), 1.61 (m, 2H), 1.47 (m, 2H)

EXAMPLE 28

Synthesis of 2-(7-cyclopentylamino-5-methyl-1H-indol-2-yl)-thiazole-4-carboxylic acid ethyl ester

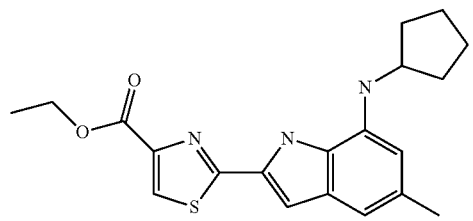

2-(7-Cyclopentylamino-5-methyl-1H-indol-2-yl)-thiazole-4-carboxylic acid ethyl ester The compound obtained in Preparation 47 (560 mg, 1.51 mmol) was dissolved in 20 ml of dichloromethane. Bromotrichloromethane (330 mg, 1.7 mmol) and DBU (250 mg, 1.7 mmol) were added. The mixture was stirred for 2 hours at 0° C. At the end of reaction, added saturated aqueous sodium bicarbonate solution and extracted with ethylacetate. The extract was dried with anhydrous magnesium sulfate, filtered. The filtrate was distilled under reduced pressure and purified by column chromatography to give the title compound 450 mg (Yield 81%).

¹H-NMR (400 HMz, CDCl₃); δ 9.36 (br s, 1H), 8.07 (s, 1H), 6.91 (d, J=4.0 Hz, 1H), 6.84 (s, 1H), 6.37 (s, 1H), 4.37 (q. 2H), 3.95 (m, 1H), 2.40 (s, 3H), 2.03 (m, 2H), 1.75 (m, 2H), 1.65 (m, 2H), 1.55 (m, 2H), 1.33 (t, 3H)

EXAMPLE 29

Synthesis of 2-(7-cyclopentylamino-5-methyl-1H-indol-2-yl)-thiazole-4-carboxylic acid

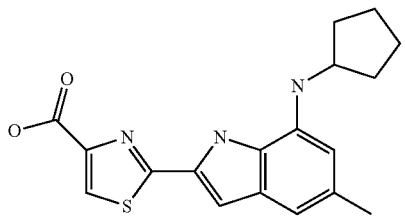

2-(7-Cyclopentylamino-5-methyl-1H-indol-2-yl)-thiazole-4-carboxylic acid

The compound obtained in Example 28 (100 mg, 0.27 mmol) was reacted according to the same procedures as Preparation 44 to give the title compound 70 mg (Yield 76%).

$^1$H-NMR (400 HMz, DMSO-$d_6$, Na salt); δ 13.20 (br s, 1H), 7.89 (s, 1H), 6.81 (s, 1H), 6.65 (br s, 1H), 6.59 (s, 1H), 6.13 (s, 1H), 3.87 (m, 1H), 2.31 (s, 3H), 2.01 (m, 2H), 1.75 (m, 4H), 1.55 (m, 2H)

EXAMPLE 30

Synthesis of [2-(7-cyclopentylamino-5-methyl-1H-indol-2-yl)-thiazole-4-yl]-methanol

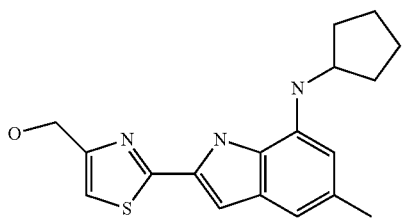

[2-(7-Cyclopentylamino-5-methyl-1H-indol-2-yl)-thiazol-4-yl]-methanol

The compound obtained in Example 28 (300 mg, 0.81 mmol) was reacted according to the same procedures as Example 4 to give the title compound 200 mg (Yield 75%).

$^1$H-NMR (400 HMz, CDCl$_3$); δ 10.42 (br s, 1H), 7.14 (s, 1H), 6.88 (d, J=4.0 Hz, 1H), 6.86 (s, 1H), 4.70 (s, 2H), 3.81 (m, 1H), 2.39 (s, 3H), 1.96 (m, 2H), 1.61 (m, 4H), 1.36 (m, 2H)

Preparation 48: Synthesis of 5-methyl-7-nitro-1H-indole-2-carbothioic acid amido The carboxylic acid compound obtained in Preparation 44 (3.2 g, 1.4 mmol) was reacted according to the same procedures as Preparation 41 to give the title compound 2.4 g (Yield 75%).

$^1$H-NMR (400 HMz, DMSO-$d_6$); δ 10.83 (br s, 1H), 10.00 (br s, 1H), 9.87 (br s, 1H), 8.10 (s, 1H), 8.04 (s, 1H), 7.45 (s, 1H), 2.50 (s, 3H)

Preparation 49: Synthesis of 2-(5-methyl-7-nitro-1H-indol-2-yl)-thiazole-5-carbaldehyde The compound obtained in Preparation 48 (2.5 g, 11.3 mmol) was dissolved in 50 ml of N,N-dimethylformamide. To the solution added 2.56 g (17 mmol) of 2-bromo malonaldehyde and stirred for 6 hours at 100° C. At the end of reaction, the reaction mixture was added to ice water. The resulting solids were collected and dried to give the title compound 2.45 g (Yield 77%).

$^1$H-NMR (400 HMz, DMSO-$d_6$); δ 11.70 (br s, 1H), 10.11 (s, 1H), 8.82 (s, 1H), 8.10 (s, 1H), 8.00 (s, 1H), 7.56 (s, 1H), 2.50 (s, 3H)

Preparation 50: Synthesis of [2-(7-amino-5-methyl-1H-indol-2-yl)-thiazol-5-yl]-methanol The compound obtained in Preparation 49 (1.75 g, 6.1 mmol) was dissolved in 300 ml of 1:1:1 mixture of water, tetrahydrofuran and methanol. To the mixture added 3.26 g (60.9 mmol) of ammonium chloride and 3.4 g (60.9 mmol) of iron and stirred for 30 minutes at 60° C. The mixture was filtered through celite and distilled under reduced pressure. To the concentrate added saturated aqueous sodium bicarbonate solution and extracted with ethylacetate. The extract was dried with anhydrous magnesium sulfate, filtered. The filtrate was distilled under reduced pressure and purified by column chromatography to give the title compound 300 mg (Yield 19%).

$^1$H-NMR (400 HMz, DMSO-$d_6$); δ 11.27 (br s, 1H), 7.69 (s, 1H), 6.76 (d, J=4.0 Hz, 1H), 6.20 (s, 1H), 5.60 (t, 1H), 5.26 (br s, 2H), 4.71 (d, J=8.0 Hz, 2H), 2.23 (s, 3H)

EXAMPLE 31

Synthesis of [2-(7-cyclopentylamino-5-methyl-1H-indol-2-yl)-thiazol-5-yl]-methanol

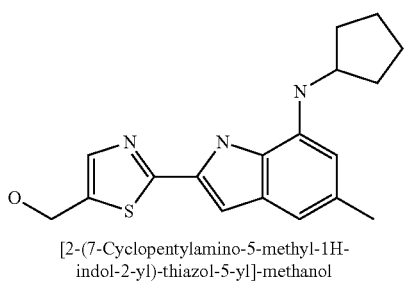 [SMILES: Cc1cc(NC2CCCC2)c2[nH]c(-c3ncc(CO)s3)cc2c1]

[2-(7-Cyclopentylamino-5-methyl-1H-indol-2-yl)-thiazol-5-yl]-methanol

The compound obtained in Preparation 50 (300 mg, 1.16 mmol) was reacted according to the same procedures as Example 1 to give the title compound 380 mg (Yield 100%).

$^1$H-NMR (400 HMz, DMSO-$d_6$); δ 11.39 (br s, 1H), 7.70 (s, 1H), 6.78 (d, J=4.0 Hz, 1H), 6.60 (s, 1H), 6.11 (s, 1H), 5.72 (d, J=8.0 Hz, 1H), 5.62 (t, 1H), 4.72 (d, J=4.0 Hz, 2H), 3.88 (m, 1H), 2.30 (s, 3H), 2.00 (m, 2H), 1.74 (m, 2H), 1.60 (m, 4H)

Preparation 51: Synthesis of 5-methyl-7-nitro-1H-indol-2-carboxylic acid hydrazide The compound obtained in Preparation 7 (5.0 g, 21.3 mmol) of was dissolved in 100 ml of ethanol. 2 ml (40 mmol)

of Hydrazine hydrate was added thereto, and the mixture was stirred for 4 hours at 100° C. At the end of reaction, cooled the solution and solids were precipitated. The solids were collected and washed with dichloromethane to yield the title compound 2.34 g (Yield 47%).

$^1$H-NMR (400 HMz, DMSO-$d_6$); δ 11.08 (br s, 1H), 10.21 (br s, 1H), 8.05 (s, 1H), 7.98 (s, 1H), 7.27 (s, 1H), 4.62 (br s, 2H), 2.48 (s, 3H)

Preparation 52: Synthesis of
5-methyl-7-nitro-2-[1,3,4]oxadiazol-2-yl-1H-indole 2.3 g (9.8 mmol) of the compound obtained in Preparation 51 was combined with 100 ml of triethyl orthoformate and the mixture was stirred for 8 hours at 120° C. At the end of reaction, added water and extracted with ethylacetate. The extract was dried over anhydrous magnesium sulfate, filtered. The filtrate was distilled under reduced pressure to obtain the title compound 600 mg (Yield 25%).

$^1$H-NMR (400 HMz, DMSO-$d_6$); δ 12.12 (br s, 1H), 9.46 (s, 1H), 8.11 (s, 1H), 8.02 (s, 1H), 7.45 (s, 1H), 3.32 (s, 3H)

EXAMPLE 32

Synthesis of cyclopentyl-(5-methyl-2-[1,3,4]oxadiazol-2-yl-1H-indol-7-yl)-amine

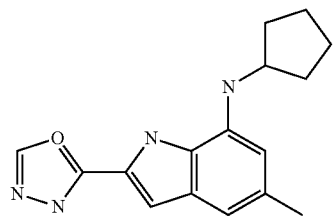

Cyclopentyl-(5-methyl-2-[1,3,4]oxadiazol-
2-yl-1H-indol-7-yl)-amine

The compound obtained in Preparation 52 (300 mg, 1.2 mmol) was reacted according to the same procedures as Preparation 43 and Example 1 to give the title compound 50 mg (Yield 14%).

$^1$H-NMR (400 HMz, CDCl$_3$); δ 9.97 (br s, 1H), 8.43 (s, 1H), 7.10 (d, J=40 Hz, 1H), 6.90 (s, 1H), 6.44 (s, 1H), 4.14 (m, 1H), 3.97 (m, 1H), 2.42 (s, 3H), 2.08 (m, 2H), 1.74 (m, 2H), 1.64 (m, 2H), 1.55 (m, 2H)

Preparation 53: Synthesis of
5-methyl-2-pyridin-2-yl-1H-indol-7-ylamine

The compound obtained in Preparation 12 (300 mg, 1.2 mmol) of was dissolved in 100 ml of 1:1 mixture of methanol and ethylacetate. 10% Pd/C 40 mg was added, and the mixture was stirred for 1 hour under the stream of hydrogen gas. At the end of reaction, the mixture was filtered through celite, and distilled under pressure. The distillate was separated by column chromatography to give the title compound 170 mg (Yield 64%).

$^1$H-NMR (400 HMz, CDCl$_3$); δ 9.67 (br s, 1H), 8.52 (m, 1H), 7.75 (m, 1H), 7.69 (m, 1H), 7.13 (m, 1H), 6.89 (d, J=2.4 Hz, 1H), 6.89 (d, J=2.4 Hz, 1H), 6.60 (d, J=2.0 Hz, 1H), 6.27 (d, J=2.0 Hz, 1H), 4.04 (m, 2H), 1.40 (m, 3H)

EXAMPLE 33

Synthesis of cyclopentyl-(5-methyl-2-pyridin-2-yl-1H-indol-7-yl)-amine

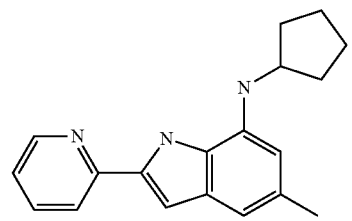

Cyclopentyl-(5-methyl-2-pyridin-2-yl-
1H-indol-7-yl)-amine

The compound obtained in Preparation 53 (50 mg, 0.22 mmol) was reacted according to the same procedures as Example 1 to give the title compound 20 mg (Yield 46%).

$^1$H-NMR (400 HMz, CDCl$_3$); δ 9.73 (br s, 1H), 8.53 (d, J=4.8 Hz, 1H), 7.78 (d, J=8.0 Hz, 1H), 7.70 (m, 1H), 7.13 (m, 1H), 6.91 (d, J=2.0 Hz, 1H), 6.87 (s, 1H), 6.32 (s, 1H), 3.91 (m, 1H), 3.60 (br s, 1H), 2.41 (s, 3H), 2.00 (m, 2H), 1.65 (m, 4H), 1.51 (m, 2H)

EXAMPLE 34

Synthesis of (5-methyl-2-pyridin-2-yl-1H-indol-7-yl)-(tetrahydro-pyran-4-yl)-amine

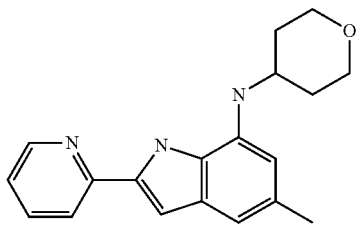

(5-Methyl-2-pyridin-2-yl-1H-indol-7-
yl)-(tetrahydro-pyran-4-yl)-amine

The compound obtained in Preparation 53 (50 mg, 0.22 mmol) was reacted according to the same procedures as Step 1 of Example 7 to give the title compound 25 mg (Yield 36%).

$^1$H-NMR (400 HMz, CDCl$_3$); δ 10.65 (br s, 1H), 8.49 (d, J=4.8 Hz, 1H), 7.81 (d, J=8.0 Hz, 1H) 7.72 (m, 1H), 7.13 (m, 1H), 6.92 (d, J=2.0 Hz, 1H), 6.88 (s, 1H), 6.27 (s, 1H), 3.92 (m, 1H), 3.49 (m, 3H), 2.39 (s, 3H), 1.95 (m, 2H), 1.30 (m, 2H)

EXAMPLE 35

Synthesis of cyclohexyl-(5-methyl-2-pyridin-2-yl-1H-indol-7-yl]-amine

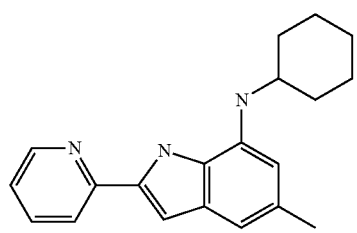

Cyclohexyl-(5-methyl-2-pyridin-2-yl-
1H-indol-7-yl)-amine

The compound obtained in Preparation 53 (50 mg, 0.22 mmol) was reacted to give the title compound 25 mg (Yield 36%), according to the same procedures as Example 1 except that cyclohexanone was used instead of cyclopentanone.

$^1$H-NMR (500 HMz, CDCl$_3$); δ 10.46 (br s, 1H), 8.48 (d, J=4.9 Hz, 1H), 7.79 (d, J=8.0 Hz, 1H), 7.70 (m, 1H), 7.11 (m, 1H), 6.92 (d, J=1.8 Hz, 1H), 6.85 (s, 1H), 3.30 (m, 1H), 2.39 (s, 3H), 1.98 (m, 2H), 1.70 (m, 2H), 1.60 (m, 1H), 1.31 (m, 2H), 1.39 (m, 1H), 0.95 (m, 1H)

EXAMPLE 36

Synthesis of 1-[4-(5-methyl-2-pyridin-2-yl-1H-indol-7-ylamino)-piperidin-1-yl]-ethanone

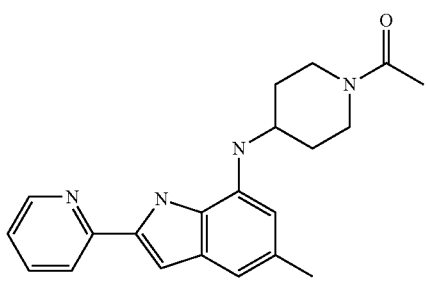

1-[4-(5-Methyl-2-pyridin-2-yl-1H-indol-
7-ylamino)-piperidin-1-yl]-ethanone

The compound obtained in Preparation 53 (30 mg, 0.13 mmol) was reacted to give the title compound 10 mg (Yield 21%), according to the same procedures as Example 1 except that 1-acetyl-4-piperidone was used instead of cyclopentanone.

$^1$H-NMR (500 HMz, CDCl$_3$ & MeOH-d$_4$); δ 8.42 (d, J=4.9 Hz, 1H), 7.71 (d, J=8.0 Hz, 1H), 7.65 (m, 1H), 7.08 (m, 1H), 6.83 (s, 1H), 6.78 (s, 1H), 6.22 (s, 1H), 4.33 (m, 1H), 3.77 (m, 1H), 3.60 (m, 1H), 3.52 (s, 3H), 3.17 (m, 1H), 2.91 (m, 1H), 2.31 (s, 3H), 2.13 (m, 1H), 2.06 (m, 1H), 1.39 (m, 2H)

EXAMPLE 37

Synthesis of (1-methyl-piperidin-4-yl)-(5-methyl-2-pyridin-2-yl-1H-indol-7-yl)-amine

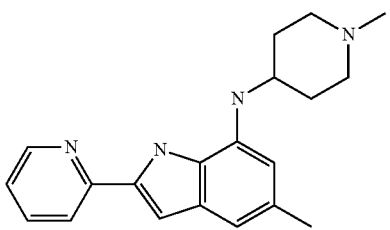

(1-Methyl-piperidin-4-yl)-(5-methyl-
2-pyridin-2-yl-1H-indol-7-yl)-amine

The compound obtained in Preparation 53 (30 mg, 0.13 mmol) was reacted to give the title compound 17 mg (Yield 40%), according to the same procedures as Example 1 except that 1-methyl-4-piperidone was used instead of cyclopentanone.

$^1$H-NMR (400 HMz, CDCl$_3$); δ 10.75 (br s, 1H), 8.45 (d, J=4.8 Hz, 1H), 7.77 (d, J=8.0 Hz, 1H), 7.68 (m, 1H), 7.08 (m, 1H), 6.90 (d, J=2.0 Hz, 1H), 6.85 (s, 1H), 6.24 (s, 1H), 3.30 (m, 1H), 2.73 (m, 2H), 2.38 (s, 3H), 2.24 (s, 3H), 2.08 (m, 2H), 1.97 (m, 2H), 1.33 (m, 2H)

EXAMPLE 38

Synthesis of 4-(5-methyl-2-pyridin-2-yl-1H-indol-7-ylamino)-cyclohexanone

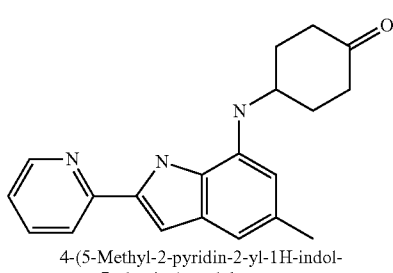

4-(5-Methyl-2-pyridin-2-yl-1H-indol-
7-ylamino)-cyclohexanone

In 10 ml of acetone and 5 ml of water was dissolved the compound obtained by reacting 30 mg (0.13 mmol) of the compound obtained in Preparation 53, according to the same procedures as Example 1 except that 1,4-cyclohexanedione monoethylene acetal was used instead of cyclopentanone. To the solution added 1 ml of 1 N hydrochloride solution, and stirred for 8 hours at 80° C. At the end of reaction, added saturated sodium bicarbonate solution and extracted with ethylacetate. The extract was dried with anhydrous magnesium sulfate, filtered, and distilled under reduced pressure. The distillate was purified by column chromatography to give the title compound 10 mg (Yield 23%).

$^1$H-NMR (400 HMz, CDCl$_3$); δ 10.72 (br s, 1H), 8.48 (d, J=4.4 Hz, 1H), 7.81 (d, J=8.0 Hz, 1H), 7.73 (m, 1H), 7.13 (m, 1H), 6.92 (d, J=2.0 Hz, 1H), 6.91 (s, 1H), 6.32 (s, 1H), 3.78 (m, 1H), 2.41 (s, 3H), 2.35 (m, 4H), 2.20 (m, 2H), 1.52 (m, 2H)

EXAMPLE 39

Synthesis of (1-benzyl-pyrrolidin-3-yl)-(5-methyl-2-pyridin-2-yl-1H-indol-7-yl)-amine

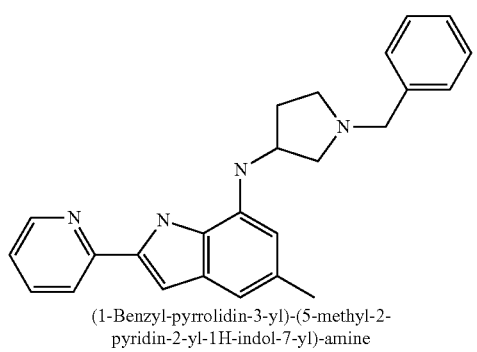 [SMILES: Cc1cc(NC2CCN(Cc3ccccc3)C2)c2[nH]c(-c3ccccn3)cc2c1]

(1-Benzyl-pyrrolidin-3-yl)-(5-methyl-2-pyridin-2-yl-1H-indol-7-yl)-amine

The compound obtained in Preparation 53 (30 mg, 0.13 mmol) was reacted to give the title compound 10 mg (Yield 20%), according to the same procedures as Example 1 except that 1-benzyl-3-pyrrolidone was used instead of cyclopentanone.

$^1$H-NMR (400 HMz, CDCl$_3$); δ 10.72 (br s, 1H), 8.49 (m, 1H), 7.76 (d, J=8.0 Hz, 1H), 7.66 (m, 1H), 7.31-7.21 (m, 5H), 7.08 (m. 1H), 6.89 (d, J=2.0 Hz, 1H), 6.83 (s, 1H), 6.22 (s, 1H), 4.09 (br s, 1H), 3.61 (m, 2H), 2.79 (m, 1H), 2.64 (m, 1H), 2.44 (m, 2H), 2.38 (s, 3H), 2.25 (m, 1H), 1.61 (m, 1H)

EXAMPLE 40

Synthesis of cyclopentylmethyl-(5-methyl-2-pyridin-2-yl-1H-indol-7-yl)-amine

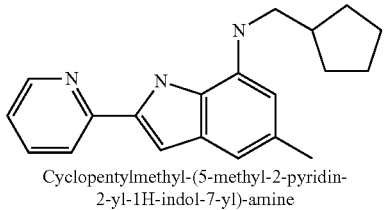 [SMILES: Cc1cc(NCC2CCCC2)c2[nH]c(-c3ccccn3)cc2c1]

Cyclopentylmethyl-(5-methyl-2-pyridin-2-yl-1H-indol-7-yl)-amine

The compound obtained in Preparation 53 (30 mg, 0.13 mmol) was reacted to give the title compound 10 mg (Yield 20%), according to the same procedures as Example 1 except that cyclopentanecarboxaldehyde was used instead of cyclopentanone.

$^1$H-NMR (500 HMz, CDCl$_3$); δ 10.54 (br s, 1H), 8.48 (m, 1H), 7.79 (d, J=8.0 Hz, 1H), 7.71 (m, 1H), 7.12 (m, 1H), 6.93 (d, J=2.5 Hz, 1H), 6.88 (s, 1H), 6.28 (s, 1H), 3.07 (d, J=7.3 Hz, 1H), 2.41 (s, 3H), 2.05 (m, 1H), 1.69~1.51 (m, 6H), 1.19 (m, 2H)

EXAMPLE 41

Synthesis of N-(5-methyl-2-pyridin-2-yl-1H-indole-7-yl)-benzamide

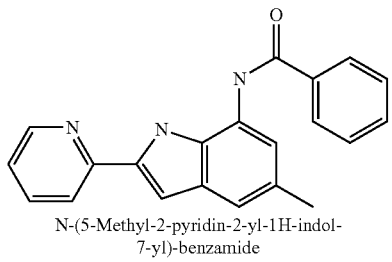 [SMILES: Cc1cc(NC(=O)c2ccccc2)c2[nH]c(-c3ccccn3)cc2c1]

N-(5-Methyl-2-pyridin-2-yl-1H-indol-7-yl)-benzamide

The compound obtained in Preparation 53 (45 mg, 0.20 mmol) was dissolved in chloromethane 10 ml. 0.2 ml of Triethylamine and 0.03 ml (0.22 mmol) of benzoylchloride were added and the mixture was stirred at room temperature for 2 hours. At the end of reaction, added water and extracted with ethylacetate. The extract was dried over anhydrous magnesium sulfate, filtered. The filtrate was distilled under reduced pressure and purified by column chromatography to obtain the title compound 18 mg (Yield 27%).

$^1$H-NMR (500 HMz, CDCl$_3$); δ 10.98 (br s, 1H), 8.61 (s, 1H), 8.50 (d, J=4.9 Hz, 1H), 7.90 (d, J=7.4 Hz, 2H), 7.77 (d, J=8.0 Hz, 1H), 7.69 (m, 1H), 7.50 (m, 1H), 7.43 (m, 2H), 7.31 (s, 1H), 7.26 (s, 1H), 7.14 (m, 1H), 6.95 (d, J=1.8 Hz, 1H), 2.41 (s, 3H)

EXAMPLE 42

Synthesis of cyclopentyl-(5-methyl-2-pyrazin-2-yl-1H-indol-7-yl)amine

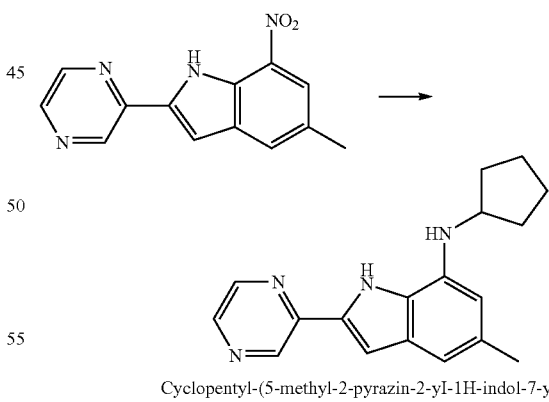

Cyclopentyl-(5-methyl-2-pyrazin-2-yl-1H-indol-7-yl)-amine

The compound obtained in Preparation 13 (100 mg, 0.39 mmol) was reacted according to the same procedures as Preparation 53 and Example 1 to give the title compound 25 mg (Yield 22%).

$^1$H-NMR (400 HMz, CDCl$_3$); δ 9.55 (br s, 1H), 9.06 (s, 1H), 8.41 (d, J=4.0 Hz, 1H), 8.26 (s, 1H), 7.03 (s, 1H), 6.90 (s, 1H), 6.38 (s, 1H), 3.95 (m, 1H), 2.41 (s, 3H), 2.06 (m, 2H), 1.71~1.49 (m, 6H)

EXAMPLE 43

Synthesis of cyclopentyl-(5-ethoxy-2-pyridin-2-yl-1H-indol-7-yl)-amine

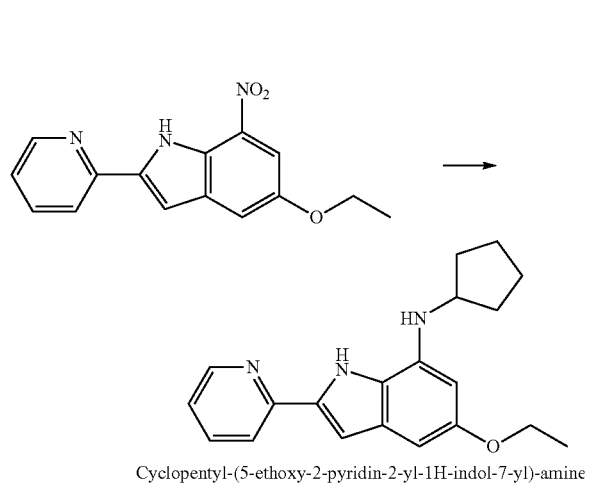 [SMILES: CCOc1cc([N+](=O)[O-])c2[nH]c(-c3ccccn3)cc2c1 ; CCOc1cc(NC2CCCC2)c2[nH]c(-c3ccccn3)cc2c1]

Cyclopentyl-(5-ethoxy-2-pyridin-2-yl-1H-indol-7-yl)-amine

The compound obtained in Preparation 16 (20 mg, 0.07 mmol) was reacted according to the same procedures as Preparation 53 and Example 1 to give the title compound 4.5 mg (Yield 19%).

$^1$H-NMR (400 HMz, CDCl$_3$); δ 9.86 (br s, 1H), 8.56 (d, J=4.8 Hz, 1H), 7.81 (d, J=8.0 Hz, 1H), 7.74 (m, 1H), 7.17 (m, 1H), 6.94 (d, J=2.0 Hz, 1H), 6.54 (d, J=2.0 Hz, 1H), 6.22 (d, J=2.0 Hz, 1H), 4.11 (q, 2H), 3.91 (m, 1H), 2.05 (m, 2H), 1.76~1.63 (m, 4H), 1.54~1.46 (m, 5H)

EXAMPLE 44

Synthesis of cyclopentyl-(5-phenoxy-2-pyridin-2-yl-1H-indole-7-yl)-amine

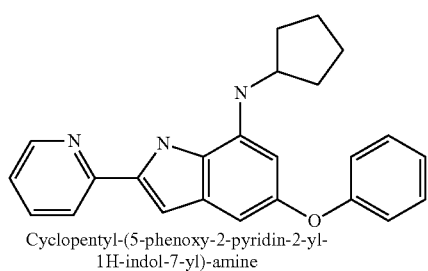 [SMILES: c1ccc(Oc2cc(NC3CCCC3)c3[nH]c(-c4ccccn4)cc3c2)cc1]

Cyclopentyl-(5-phenoxy-2-pyridin-2-yl-1H-indol-7-yl)-amine

The compound obtained in Preparation 17 (250 mg, 0.75 mmol) was reacted according to the same procedures as Preparation 53 and Example 1 to give the title compound 120 mg (Yield 43%).

$^1$H-NMR (400 HMz, CDCl$_3$); δ 10.07 (br s, 1H), 8.55 (d, J=4.0 Hz, 1H), 7.74 (m, 2H), 7.29 (m, 2H), 7.18 (m, 1H), 7.01 (m, 3H), 6.93 (d, J=4.0 Hz, 1H), 6.69 (d, J=4.0 Hz, 1H), 6.27 (s, 1H), 3.81 (m, 1H), 3.70 (br s, 1H), 1.96 (m, 2H), 1.60 (m, 4H), 1.41 (m, 2H)

EXAMPLE 45

Synthesis of cyclopentyl-(3,5-dimethyl-2-phenyl-1H-indole-7-yl)-amine

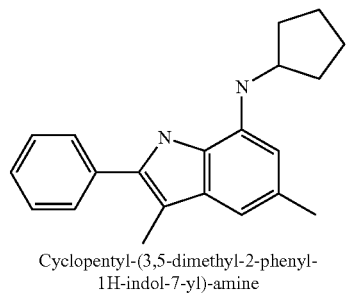 [SMILES: Cc1cc(NC2CCCC2)c2[nH]c(-c3ccccc3)c(C)c2c1]

Cyclopentyl-(3,5-dimethyl-2-phenyl-1H-indol-7-yl)-amine

The compound obtained in Preparation 18 (100 mg, 0.38 mmol) was reacted according to the same procedures as Preparation 53 and Example 1 to give the title compound 35 mg (Yield 31%).

$^1$H-NMR (400 HMz, CDCl$_3$); δ 7.68 (br s, 1H), 7.59 (m, 2H), 7.45 (m, 2H), 7.32 (m, 1H), 6.87 (s, 1H), 6.40 (s, 1H), 3.97 (m, 1H), 2.45 (s, 3H), 2.40 (s, 3H), 2.09 (m, 2H), 1.78~1.56 (m, 4H)

EXAMPLE 46

Synthesis of cyclopentyl-(5-methyl-2-phenyl-1H-indol-7-yl)-amine

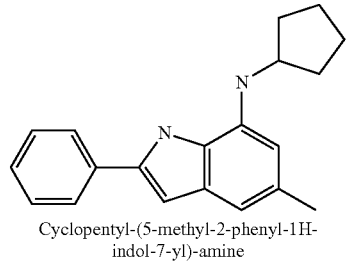 [SMILES: Cc1cc(NC2CCCC2)c2[nH]c(-c3ccccc3)cc2c1]

Cyclopentyl-(5-methyl-2-phenyl-1H-indol-7-yl)-amine

The compound obtained in Preparation 19 (120 mg, 0.48 mmol) was reacted according to the same procedures as Preparation 53 and Example 1 to give the title compound 50 mg (Yield 36%).

$^1$H-NMR (500 HMz, MeOH-d$_4$); δ 7.74 (m, 2H), 7.38 (m, 2H), 7.24 (m, 1H), 6.68 (s, 1H), 6.62 (s, 1H), 6.23 (s, 1H), 3.95 (m, 1H), 2.06 (m, 2H), 1.80 (m, 2H), 1.65 (m, 4H)

EXAMPLE 47

Synthesis of (2-cyclohexyl-5-methyl-1H-indol-7-yl)-cyclopentyl-amine

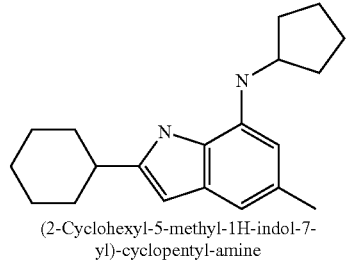 [SMILES: Cc1cc(NC2CCCC2)c2[nH]c(C3CCCCC3)cc2c1]

(2-Cyclohexyl-5-methyl-1H-indol-7-yl)-cyclopentyl-amine

The compound obtained in Preparation 20 (50 mg, 0.19 mmol) was reacted according to the same procedures as Preparation 53 and Example 1 to give the title compound 21 mg (Yield 37%).

$^1$H-NMR (400 HMz, CDCl$_3$); δ 7.80 (br s, 1H), 6.81 (s, 1H), 6.31 (s, 1H), 6.08 (s, 1H), 3.93 (m, 1H), 2.92 (m, 1H), 2.38 (s, 3H), 2.08 (m, 4H), 1.80~1.20 (m, 14H)

EXAMPLE 48

Synthesis of cyclopentyl-[5-methyl-2-(6-methyl-pyridin-2-yl)-1H-indol-7-yl]-amine

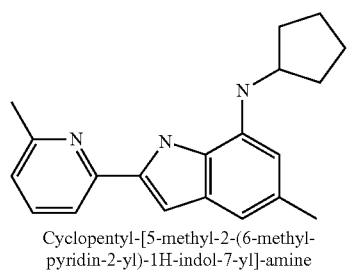 [SMILES: Cc1cc(NC2CCCC2)c2[nH]c(-c3cccc(C)n3)cc2c1]

Cyclopentyl-[5-methyl-2-(6-methyl-pyridin-2-yl)-1H-indol-7-yl]-amine

The compound obtained in Preparation 21 (50 mg, 0.19 mmol) was reacted according to the same procedures as Preparation 53 and Example 1 to give the title compound 35 mg (Yield 40%).

$^1$H-NMR (400 HMz, CDCl$_3$); δ 11.11 (br s, 1H), 7.59 (m, 2H), 6.94 (m, 1H), 6.88 (d, J=2.0 Hz, 1H), 6.82 (s, 1H), 6.19 (s, 1H), 3.73 (m, 1H), 2.37 (s, 3H), 2.31 (s, 3H), 1.80 (m, 2H), 1.43 (m, 4H), 1.14 (m, 2H)

EXAMPLE 49

Synthesis of (5-methyl-2-phenyl-1H-indol-7-yl)-(tetrahydro-pyran-4-yl)-amine

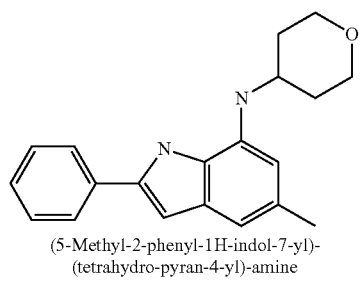 [SMILES: Cc1cc(NC2CCOCC2)c2[nH]c(-c3ccccc3)cc2c1]

(5-Methyl-2-phenyl-1H-indol-7-yl)-(tetrahydro-pyran-4-yl)-amine

The compound obtained in Preparation 19 (70 mg, 0.28 mmol) was reacted to give the title compound 50 mg (Yield 57%), according to the same procedures as Preparation 53 and Example 1 except that tetrahydro-4H-pyran-4-one was used instead of cyclopentanone.

$^1$H-NMR (500 HMz, MeOH-d$_4$); δ 7.74 (m, 2H), 7.39 (m, 2H), 7.24 (m, 1H), 6.71 (s, 1H), 6.63 (s, 1H), 6.28 (s, 1H), 4.01 (m, 1H), 3.68 (m, 1H), 3.58 (m, 2H), 2.32 (s, 3H), 2.12 (m, 2H), 1.56 (m, 2H)

EXAMPLE 50

Synthesis of (5-methyl-2-phenyl-1H-indol-7-yl)-(1-methyl-piperidin-4-yl)-amine

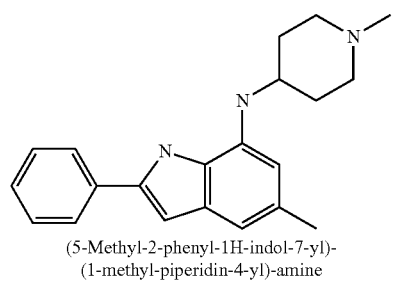 [SMILES: Cc1cc(NC2CCN(C)CC2)c2[nH]c(-c3ccccc3)cc2c1]

(5-Methyl-2-phenyl-1H-indol-7-yl)-(1-methyl-piperidin-4-yl)-amine

The compound obtained in Preparation 19 (70 mg, 0.28 mmol) was reacted to give the title compound 24 mg (Yield 29%), according to the same procedures as Preparation 53 and Example 1 except that 1-methyl-4-piperidone was used instead of cyclopentanone.

$^1$H-NMR (500 HMz, MeOH-d$_4$); δ 7.73 (m, 2H), 7.38 (m, 2H), 7.24 (m, 1H), 6.70 (s, 1H), 6.63 (s, 1H), 6.24 (s, 1H), 3.47 (m, 1H), 2.96 (m, 2H), 2.34 (s, 3H), 2.32 (s, 3H), 2.26 (m, 2H), 2.17 (m, 2H), 1.59 (m, 2H)

EXAMPLE 51

Synthesis of 1-[4-(5-methyl-2-phenyl-1H-indol-7-ylamino)-piperidin-1-yl]-ethanone

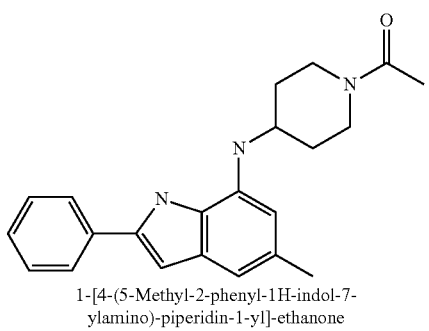 [SMILES: CC(=O)N1CCC(Nc2cc(C)cc3cc(-c4ccccc4)[nH]c23)CC1]

1-[4-(5-Methyl-2-phenyl-1H-indol-7-ylamino)-piperidin-1-yl]-ethanone

The compound obtained in Preparation 19 (96 mg, 0.38 mmol) was reacted to give the title compound 18 mg (Yield 13%), according to the same procedures as Preparation 53 and Example 1 except that 1-acetyl-4-piperidone was used instead of cyclopentanone.

$^1$H-NMR (500 HMz, DMSO-d$_6$); δ 10.77 (brs, 1H), 7.74 (m, 2H), 7.42 (m, 2H), 7.26 (m, 1H), 6.66 (d, J=1.85 Hz, 1H), 6.56 (s, 1H), 6.14 (s, 1H), 5.22 (d, J=7.95, 1H), 4.28 (m, 1H), 3.82 (m, 1H), 3.62 (m, 1H), 3.13 (m, 1H), 2.83 (m, 1H), 2.26 (s, 3H), 2.05 (m, 2H), 2.00 (s, 3H), 1.31 (m, 2H)

EXAMPLE 52

Synthesis of (5-methyl-2-phenyl-1H-indol-7-yl)-piperidin-4-yl)-amine HCl

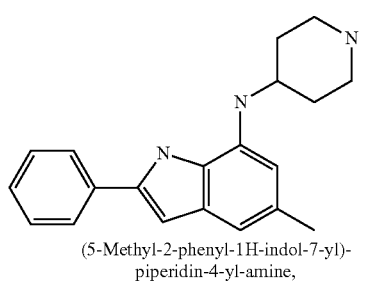

(5-Methyl-2-phenyl-1H-indol-7-yl)-piperidin-4-yl-amine,

The compound obtained in Preparation 19 (140 mg, 0.56 mmol) was reacted to give the title compound 50 mg (Yield 21%), according to the same procedures as Preparation 53 and Example 3 except that 1-acetyl-4-piperidone was used instead of cyclopentanone.

EXAMPLE 53

Synthesis of 2-hydroxy-1-[4-(5-methyl-2-phenyl-1H-indol-7-ylamino)-piperidin-1-yl]-ethanone

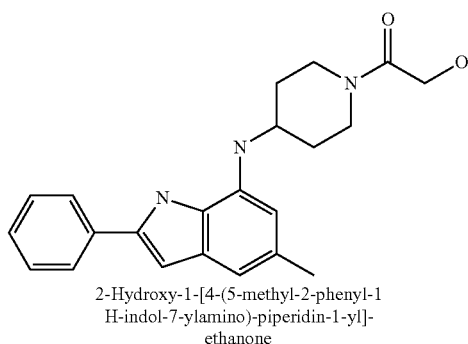 [SMILES: Cc1cc(NC2CCN(C(=O)CO)CC2)c2[nH]c(-c3ccccc3)cc2c1]

2-Hydroxy-1-[4-(5-methyl-2-phenyl-1 H-indol-7-ylamino)-piperidin-1-yl]-ethanone

The compound obtained in Example 52 (50 mg, 0.13 mmol) was dissolved in N,N-dimethylformamide 3 ml. Glycolic acid (15 mg, 0.20 mmol), triethylamine (0.06 ml, 0.43 mmol), EDC (38 mg, 0.20 mmol) and HOBT (27 mg, 0.20 mmol) were added, and the mixture was stirred at room temperature for 8 hours. To the reaction mixture added 1N HCl solution and extracted with ethylacetate. The extract was dried over anhydrous magnesium sulfate, filtered. The filtrate was distilled under reduced pressure and purified by column chromatography to obtain the title compound 20 mg (Yield 43%).

$^1$H-NMR (500 HMz, MeOH-d$_4$); δ 7.72 (m, 2H), 7.38 (m, 2H), 7.23 (m, 1H), 6.71 (2, 1H), 6.63 (s, 1H), 6.30 (s, 1H), 4.40 (m, 1H), 4.23 (m, 2H), 3.74 (m, 2H), 3.24 (m, 1H), 3.02 (m, 1H), 2.33 (s, 3H), 2.19 (m, 2H), 1.45 (m, 2H)

EXAMPLE 54

Synthesis of (1-methanesulfonyl-piperidin-4-yl)-(5-methyl-2-phenyl-1H-indol-7-yl)-amine

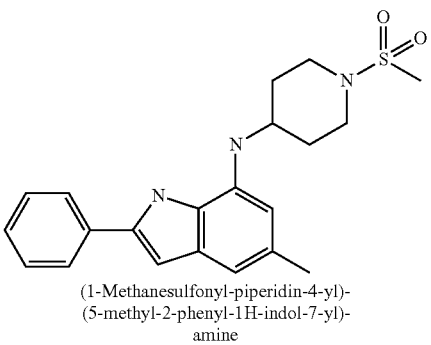 [SMILES: Cc1cc(NC2CCN(S(C)(=O)=O)CC2)c2[nH]c(-c3ccccc3)cc2c1]

(1-Methanesulfonyl-piperidin-4-yl)-(5-methyl-2-phenyl-1H-indol-7-yl)-amine

The compound obtained in Example 52 was dissolved in dichloromethane 10 ml, and triethylamine (0.02 ml, 0.14 mmol), methanesulfonylchloride (10 mg, 0.09 mmol) were added. The mixture was stirred at 0° C. for 1 hour. To the reaction mixture added 1N HCl solution and extracted with ethylacetate. The extract was dried over anhydrous magnesium sulfate, filtered. The filtrate was distilled under reduced pressure and purified by column chromatography to obtain the title compound 18 mg (Yield 67%).

$^1$H-NMR (500 HMz, DMSO-d$_6$); δ 10.79 (brs, 1H), 7.74 (m, 2H), 7.42 (m, 2H), 7.26 (m, 1H), 6.66 (s, 1H), 6.57 (s, 1H), 6.11 (s, 1H), 5.27 (m, 1H), 3.57 (m, 2H), 3.13 (m, 1H), 2.93 (m, 1H), 2.87 (s, 3H), 2.25 (s, 3H), 2.14 (m, 2H), 1.46 (m, 2H)

Preparation 54: Synthesis of 4-(5-methyl-2-phenyl-1H-indol-7-ylamino)-cyclohexane carboxylic acid ethyl ester The compound obtained in Preparation 19 (200 mg, 0.90 mmol) was reacted to give the title compound 170 mg (Yield 50%), according to the same procedures as Preparation 53 and Example 1 except that 4-oxo-cyclohexanecarboxylic acid ethyl ester was used instead of cyclopentanone.

EXAMPLE 55

Synthesis of 4-(5-methyl-2-phenyl-1H-indol-7-ylamino)-cyclohexane carboxylic acid

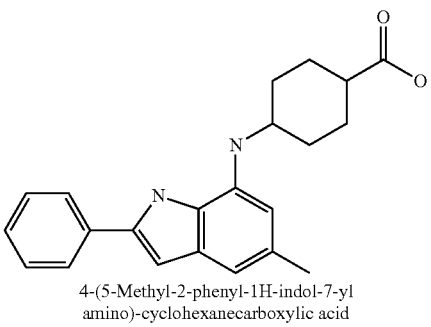 [SMILES: Cc1cc(NC2CCC(C(=O)O)CC2)c2[nH]c(-c3ccccc3)cc2c1]

4-(5-Methyl-2-phenyl-1H-indol-7-yl amino)-cyclohexanecarboxylic acid

The compound obtained in Preparation 54 (170 mg, 0.45 mmol) was dissolved in the 5:1 mixture of tetrahydrofuran and methanol. 6N sodium Hydroxide 0.4 ml was added and the mixture was stirred at room temperature for 8 hours. At the end of reaction, the reaction mixture was distilled under reduced pressure, diluted with 1N-hydrochloric acid solution and extracted with ethylacetate. The extract was dried over anhydrous magnesium sulfate, filtered. The filtrate was distilled under reduced pressure and purified by column chromatography to obtain the title compound 120 mg (Yield 77%).

$^1$H-NMR (500 HMz, DMSO-d$_6$); δ 10.81 (brs, 1H), 7.74 (m, 2H), 7.42 (m, 2H), 7.25 (m, 1H), 6.64 (d, J=2.45 Hz, 1H), 6.53 (s, 1H), 6.05 (s, 1H), 5.17 (m, 1H), 3.50 (m, 2H), 2.24 (s, 3H), 1.95 (m, 1H), 1.81 (m, 2H), 1.64 (m, 2H), 1.57 (m, 2H)

EXAMPLE 56

Synthesis of 4-(5-methyl-2-phenyl-1H-indol-7-ylamino)-cyclohexane carboxylic acid (2-morpholin-4-yl-ethyl)-amide

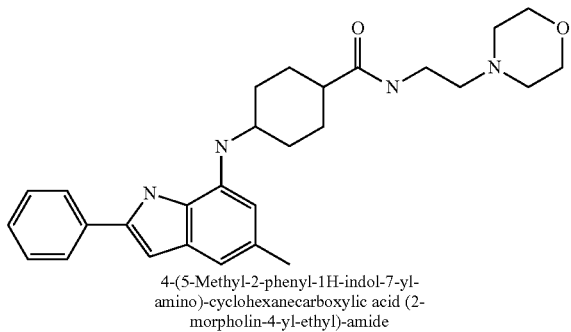 [SMILES: Cc1cc(NC2CCC(C(=O)NCCN3CCOCC3)CC2)c2[nH]c(-c3ccccc3)cc2c1]

4-(5-Methyl-2-phenyl-1H-indol-7-yl-amino)-cyclohexanecarboxylic acid (2-morpholin-4-yl-ethyl)-amide The compound obtained in Example 55 (30 mg, 0.09 mmol) was dissolved in N,N-dimethyl formamide 5 ml. 2-Morpholine-4-yl-ethylamine (22 mg, 0.17 mmol), EDC (25 mg, 0.19 mmol) and HOBT (18 mg, 0.19 mmol) were added. The mixture was stirred for 8 hours at room temperature. Saturated 1N aqueous sodium chloride solution was added, and the mixture was extracted with ethyl acetate. The extract was dried over anhydrous magnesium sulfate, filtered. The filtrate was distilled under reduced pressure and purified by column chromatography to give the title compound 40 mg (Yield 100%).

$^1$H-NMR (500 HMz, DMSO-d$_6$); δ 10.91 (brs, 1H), 7.75 (m, 2H), 7.65 (m, 1H), 7.41 (m, 2H), 7.26 (m, 1H), 6.64 (s, 1H), 6.53 (s, 1H), 6.02 (s, 1H), 5.20 (m, 1H), 3.57 (m, 2H), 3.51 (m, 5H), 3.14 (m, 2H), 2.29 (m, 4H), 2.24 (s, 3H), 1.87 (m, 2H), 1.78 (m, 2H), 1.68 (m, 2H), 1.53 (m, 2H)

EXAMPLE 57

Synthesis of cyclopentylmethyl-(5-methyl-2-phenyl-1H-indol-7-yl)-amine

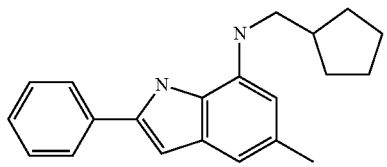 [SMILES: Cc1cc(NCC2CCCC2)c2[nH]c(-c3ccccc3)cc2c1]

The compound obtained from Preparation 19 (70 mg, 0.28 mmol) was reacted according to the same procedures as Preparation 53 and Example 1 except that cyclopentanecarbaldehyde was used instead of cyclopentanone to give the title compound 36 mg (Yield 40%).

$^1$H-NMR (500 HMz, MeOH-d$_4$); δ 7.73 (m, 2H), 7.37 (m, 2H), 7.22 (m, 1H), 6.68 (2, 1H), 6.62 (s, 1H), 6.18 (s, 1H), 3.14 (d, J=7.35 Hz, 2H), 2.32 (s, 3H), 2.30 (m, 1H), 1.91 (m, 2H), 1.69 (m, 2H), 1.59 (m, 2H), 1.36 (m, 2H)

EXAMPLE 58

Synthesis of (5-methyl-2-phenyl-1H-indol-7-yl)-(tetrahydro-pyran-4-ylmethyl)-amine

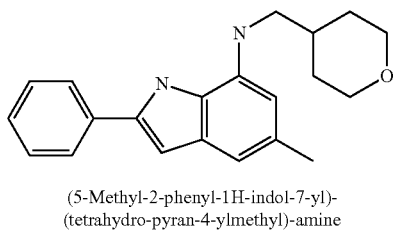 [SMILES: Cc1cc(NCC2CCOCC2)c2[nH]c(-c3ccccc3)cc2c1]

(5-Methyl-2-phenyl-1H-indol-7-yl)-(tetrahydro-pyran-4-ylmethyl)-amine

The compound obtained from Preparation 19 (70 mg, 0.28 mmol) was reacted according to the same procedures as Preparation 53 and Example 1 except that tetrahydro-pyran-4-carbaldehyde was used instead of cyclopentanone to give the title compound 19 mg (Yield 21%).

$^1$H-NMR (500 HMz, MeOH-d$_4$); δ 7.73 (m, 2H), 7.38 (m, 2H), 7.23 (m, 1H), 6.68 (2, 1H), 6.63 (s, 1H), 6.19 (s, 1H), 3.97 (m, 2H), 3.44 (m, 2H), 3.16 (m, 2H), 2.32 (s, 3H), 1.99 (m, 1H), 1.83 (m, 2H), 1.40 (m, 2H)

Preparation 55: Synthesis of 5-Chloro-7-nitro-2-phenyl-1H-indole

4-Chloro-2-nitroaniline (1.0 g, 3.67 mmol) was reacted instead of 4-methyl-2-nitroaniline in Preparation 19 to give the title compound 750 mg (Yield 75%).

EXAMPLE 59

Synthesis of (5-chloro-2-phenyl-1H-indol-7-yl)-cyclopentyl-amine

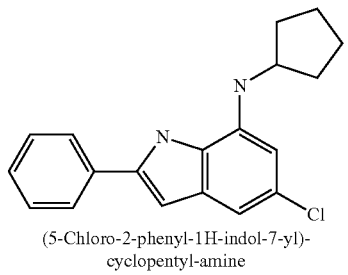 [SMILES: Clc1cc(NC2CCCC2)c2[nH]c(-c3ccccc3)cc2c1]

(5-Chloro-2-phenyl-1H-indol-7-yl)-cyclopentyl-amine

5-Chloro-7-nitro-2-phenyl-1H-indole (225 mg, 0.83 mmol) was reacted instead of 5-methyl-7-nitro-2-phenyl-1H-indole in Preparation 46 to give the title compound 230 mg (Yield 89%).

$^1$H-NMR (500 HMz, DMSO-d$_6$); δ 11.04 (brs, 1H), 7.75 (m, 2H), 7.45 (m, 2H), 7.30 (m, 1H), 6.76 (d, J=1.8 Hz, 1H), 6.72 (d, J=2.45 Hz, 1H), 6.14 (d, J=1.8 Hz, 1H), 3.84 (m, 1H), 2.00 (m, 2H), 1.71 (m, 2H), 1.60 (m, 2H), 1.52 (m, 2H)

EXAMPLE 60

Synthesis of (5-chloro-2-phenyl-1H-indol-7-yl)-(tetrahydro-pyran-4-yl)-amine

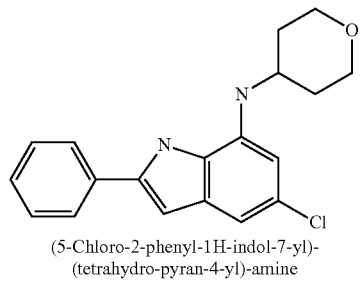 [SMILES: Clc1cc(NC2CCOCC2)c2[nH]c(-c3ccccc3)cc2c1]

(5-Chloro-2-phenyl-1H-indol-7-yl)-
(tetrahydro-pyran-4-yl)-amine

5-Chloro-7-nitro-2-phenyl-1H-indole (337 mg, 1.23 mmol) was reacted instead of 5-methyl-7-nitro-2-phenyl-1H-indole in Preparation 49 to give the title compound 200 mg (Yield 50%).

$^1$H-NMR (500 HMz, DMSO-d$_6$); δ 11.09 (brs, 1H), 7.74 (m, 2H), 7.43 (m, 2H), 7.29 (m, 1H), 6.77 (s, 1H), 6.72 (s, 1H), 6.24 (s, 1H), 5.60 (m, 1H), 4.28 (m, 1H), 3.86 (m, 2H), 3.43 (m, 2H), 1.96 (m, 2H), 1.41 (m, 2H)

EXAMPLE 61

Synthesis of (5-chloro-2-phenyl-1H-indol-7-yl)-(1-methyl-piperidin-4-yl)-amine

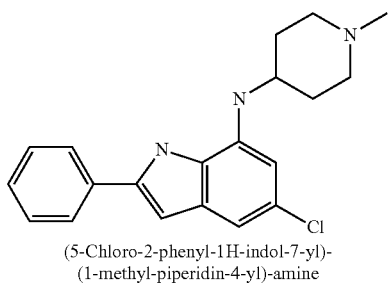 [SMILES: CN1CCC(Nc2cc(Cl)cc3cc(-c4ccccc4)[nH]c23)CC1]

(5-Chloro-2-phenyl-1H-indol-7-yl)-
(1-methyl-piperidin-4-yl)-amine

5-Chloro-7-nitro-2-phenyl-1H-indole (337 mg, 1.23 mmol) was reacted instead of 5-methyl-7-nitro-2-phenyl-1H-indole in Preparation 50 to give the title compound 288 mg (Yield 69%).

$^1$H-NMR (500 HMz, DMSO-d$_6$); δ 11.06 (brs, 1H), 9.57 (brs, 1H), 7.75 (m, 2H), 7.45 (m, 2H), 7.31 (m, 1H), 6.80 (s, 1H), 6.74 (s, 1H), 6.29 (s, 1H), 3.66 (m, 1H), 3.49 (m, 2H), 3.11 (m, 2H), 2.78 (s, 3H), 2.23 (m, 2H), 1.61 (m, 2H)

EXAMPLE 62

Synthesis of (5-chloro-2-phenyl-1H-indol-7-yl)-cyclohexyl-amine

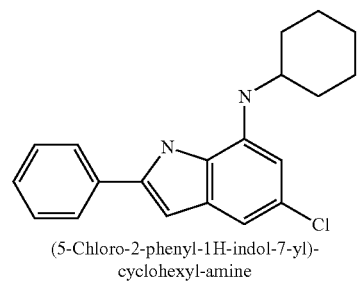 [SMILES: Clc1cc(NC2CCCCC2)c2[nH]c(-c3ccccc3)cc2c1]

(5-Chloro-2-phenyl-1H-indol-7-yl)-
cyclohexyl-amine

The compound obtained from Preparation 55 (170 mg, 0.62 mmol) was reacted to give the title compound 98 mg (Yield 49%), according to the same procedures as Preparation 53 and Example 1 except that cyclohexanone was used instead of cyclopentanone.

$^1$H-NMR (500 HMz, CDCl$_3$); δ 8.18 (brs, 1H), 7.65 (m, 2H), 7.44 (m, 5H), 7.31 (m, 2H), 7.03 (s, 1H), 6.70 (s, 1H), 6.47 (d, 1H), 3.38 (m, 1H), 2.16 (m, 2H), 1.81 (m, 2H), 1.71 (m, 1H), 1.42 (m, 2H), 1.24 (m, 4H)

EXAMPLE 63

Synthesis of (1-benzyl-pyrrolidin-3-yl)-(5-chloro-2-phenyl-1H-indol-7-yl)-amine

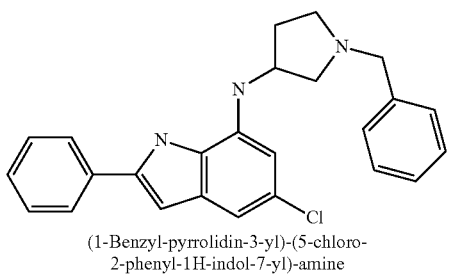 [SMILES: Clc1cc(NC2CCN(Cc3ccccc3)C2)c2[nH]c(-c3ccccc3)cc2c1]

(1-Benzyl-pyrrolidin-3-yl)-(5-chloro-
2-phenyl-1H-indol-7-yl)-amine

The compound obtained from Preparation 55 (225 mg, 0.83 mmol) was reacted to give the title compound 50 mg (Yield 15%), according to the same procedures as Preparation 53 and Example 1 except that 1-benzyl-pyrrolidine-3-one was used instead of cyclopentanone.

$^1$H-NMR (500 HMz, CDCl$_3$); δ 10.33 (brs, 1H), 7.83 (m, 2H), 7.47 (m, 5H), 7.41 (m: 2H), 7.28 (m, 1H), 7.00 (d, J=1.85 Hz, 1H), 6.69 (d, J=1.85 Hz, 1H), 6.19 (d, J=1.8, 1H), 4.49 (m, 1H), 4.36 (d, J=12.8 Hz, 2H), 4.09 (d, J=12.8 Hz, 2H), 3.82 (m, 1H), 3.59 (m, 1H), 3.18 (m, 1H), 3.11 (m, 1H), 2.41 (m, 2H)

Preparation 56: Synthesis of 4-ethynyl-benzoic acid methyl ester (Step 1)

20.60 g (78.61 mmol) of 4-Iodobenzoic acid methyl ester and 9.26 g (94.33 mmol) of ethynyl trimethylsilane were dissolved in 200 ml of tetrahydrofuran, and thereto 23.86 g (235.83 mmol) of triethylamine, 1.65 g (2.36 mmol) of dichloro(bistriphenylphosphine)palladium(II) and 0.45 g (2.36 mmol) of copper(I) iodide were added. The mixture was stirred at room temperature for 8 hours. At the end of reaction, added water and extracted with ethylacetate. The extract was washed with saturated sodium chloride solution, dried over anhydrous magnesium sulfate, and separated by column chromatography to obtain trimethylsilylethynylbenzoic acid methyl ester 18.30 g (Yield 100%).

(Step 2)

The compound obtained in Step 1 (18.30 g, 78.61 mmol) was dissolved in 300 ml of the 2:1 mixture of methanol and dichloromethane, and 5.44 g (39.3 mmol) of potassium carbonate was added. The mixture was stirred at room temperature for 1 hour. At the end of reaction, the reaction mixture was diluted with water and extracted with ethylacetate. The extract was washed with saturated sodium chloride solution, dried over anhydrous magnesium sulfate, and separated by column chromatography to obtain the title compound 11.90 g (Yield 95%).

Preparation 57: Synthesis of 4-(5-Chloro-2-nitro-1H-indol-2-yl)-benzoic acid methyl ester (Step 1)

2-Iodo-4-chloro-6-nitro-phenylamine (10.0 g, 33.50 mmol) of was dissolved in 200 ml of tetrahydrofuran, and 3.97 g (50.25 mmol) of pyridine and 7.74 g (36.85 mmol) of trifluoroacetic anhydride were added. The mixture was stirred for 9 hours at 0° C.~room temperature. At the end of reaction, the reaction mixture was diluted with water and extracted with ethylacetate. The extract was washed with saturated sodium chloride solution, dried over anhydrous magnesium sulfate, and separated by column chromatography to obtain trifluoroacetamide 12.3 g (Yield 85%).

(Step 2)

The compound obtained in Step 1 (12.3 g, 31.18 mmol) and 6.0 g (37.42 mmol) of 4-ethynylbenzoic acid methyl ester were dissolved in 200 ml of N,N-dimethylformamide. 9.47 g (93.54 mmol) of Triethylamine and 11.51 g (31.18 mmol) of tetrabutylammoniumiodide, 1.09 g (1.56 mmol) of dichloro(bistriphenylphosphine)palladium(II) and 0.30 g (1.56 mmol) of copper(I) iodide were added. The mixture was stirred at 80° C. for 8 hours. At the end of reaction, the reaction mixture was diluted with water and extracted with ethylacetate. The extract was washed with saturated sodium chloride solution, dried over anhydrous magnesium sulfate, and separated by column chromatography to obtain the title compound 7.6 g (Yield 81%).

EXAMPLE 64

Synthesis of 4-(5-chloro-7-cyclopentylamino-1H-indol-2-yl)-benzoic acid methyl ester

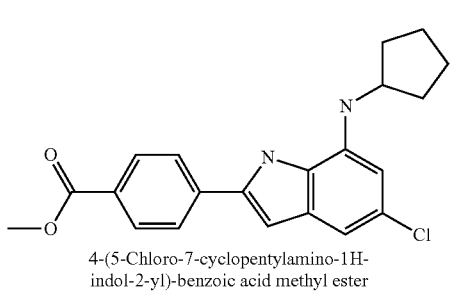 [SMILES: COC(=O)c1ccc(-c2cc3cc(Cl)cc(NC4CCCC4)c3[nH]2)cc1]

4-(5-Chloro-7-cyclopentylamino-1H-indol-2-yl)-benzoic acid methyl ester

The compound obtained in Preparation 57 (7.60 g, 22.98 mmol) was reacted instead of 5-methyl-7-nitro-2-phenyl-1H-indole in Preparation 46 to give the title compound 1.25 g (Yield 15%).

$^1$H-NMR (400 HMz, DMSO-$d_6$); δ 11.25 (brs, 1H), 8.07 (d, J=8 Hz, 2H), 7.94 (d, J=8 Hz, 2H), 6.95 (s, 1H), 6.84 (s, 1H), 6.22 (s, 1H), 5.77 (d, J=8 Hz, 1H), 3.89 (s, 3H), 3.88 (m, 1H), 2.05 (m, 2H), 1.75 (m, 2H), 1.65 (m, 2H), 1.63 (m, 2H)

EXAMPLE 65

Synthesis of 4-(5-chloro-7-cyclopentylamino-1H-indol-2-yl)-benzoic acid

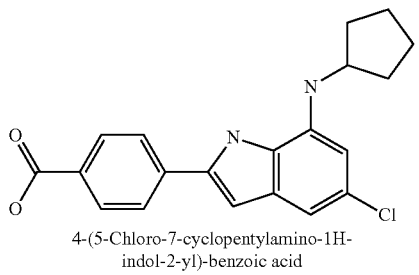 [SMILES: O=C(O)c1ccc(-c2cc3cc(Cl)cc(NC4CCCC4)c3[nH]2)cc1]

4-(5-Chloro-7-cyclopentylamino-1H-indol-2-yl)-benzoic acid

The compound obtained in Example 64 (300 mg, 0.81 mmol) was dissolved in 15 ml of tetrahydrofuran, 5 ml of water and 5 ml of methanol. 100 mg (2.44 mmol) of Lithium hydroxide monohydrate was added. The mixture was stirred at room temperature for 21 hours. At the end of reaction, tetrahydrofurane and methanol were removed by distillation under reduced pressure. To the distillate 1N HCl solution was added the mixture was extracted with ethylacetate. The extract was washed with saturated sodium chloride solution, dried over anhydrous magnesium sulfate, filtered. The filtrate was distilled under reduced pressure, and separated by column chromatography to obtain the title compound 20 mg (Yield 7%).

$^1$H-NMR (400 HMz, DMSO-$d_6$); δ 11.59 (brs, 1H), 8.01 (m, 4H), 6.94 (d, J=12 Hz, 2H), 6.31 (s, 1H), 3.91 (m, 1H), 2.01 (m, 2H), 1.77 (m, 2H), 1.62 (m, 4H)

EXAMPLE 66

Synthesis of [4-(5-chloro-7-cyclopentylamino-1H-indol-2-yl)-phenyl]-methanol

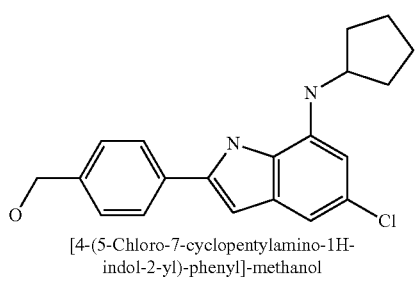 [SMILES: OCc1ccc(-c2cc3cc(Cl)cc(NC4CCCC4)c3[nH]2)cc1]

[4-(5-Chloro-7-cyclopentylamino-1H-indol-2-yl)-phenyl]-methanol

The compound obtained in Example 64 (760 mg, 2.06 mmol) was dissolved in 30 ml of tetrahydrofuran and 2M-lithiumborohydride solution in tetrahydrofuran (2.06 ml, 4.12 mmol) was added. The mixture was at 80° C. for 3 hours. Saturated ammoniumchloride solution was added and the mixture was extracted with ethyl acetate. The extract was dried over anhydrous magnesium sulfate, filtered. The filtrate was distilled under reduced pressure, and purified by column chromatography to obtain the title compound 60 mg (Yield 9%).

$^1$H-NMR (400 HMz, DMSO-$d_6$); δ 11.04 (brs, 1H), 7.75 (d, J=8 Hz, 2H), 7.42 (d, J=8 Hz, 2H), 6.78 (s, 1H), 6.73 (s, 1H), 6.17 (s, 1H), 5.71 (d, J=3 Hz, 1H), 5.23 (t, 1H), 4.54 (d, J=4 Hz, 1H), 4.02 (m, 1H), 2.02 (m, 2H), 1.75 (m, 2H), 1.63 (m, 2H), 1.55 (m, 2H)

EXAMPLE 67

Synthesis of 4-(7-cyclopentylamino-5-methyl-1H-indol-2-yl)-benzoic acid methyl ester

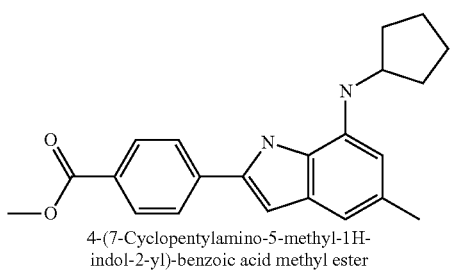 [SMILES: COC(=O)c1ccc(-c2cc3cc(C)cc(NC4CCCC4)c3[nH]2)cc1]

4-(7-Cyclopentylamino-5-methyl-1H-indol-2-yl)-benzoic acid methyl ester

2-Iodo-4-methyl-6-nitro-phenylamine (500 mg, 1.80 mmol) was reacted instead of 2-iodo-4-chloro-6-nitro-phenylamine according to the same procedures as Preparation 57 and Example 64 to give the title compound 30 mg (Yield 3%).

Preparation 58: Synthesis of 2-(5-chloro-7-nitro-1H-indol-2-yl)-benzoic acid methyl ester 2-Ethynyl-benzoic acid methyl ester (6.0 g 37.42 mmol) was reacted instead of 4-Ethynyl-benzoic acid methyl ester in Preparation 57 to give the title compound 1.8 g (Yield 15%).

$^1$H-NMR (400 HMz, CDCl$_3$), δ 10.88 (brs, 1H), 8.15 (s, 1H), 7.94 (d, 2H), 7.70 (s, 1H), 7.64 (s, 1H), 7.54 (s, 1H), 6.76 (s, 1H), 3.88 (s, 3H)

EXAMPLE 68

Synthesis of 2-(5-chloro-7-cyclopentylamino-1H-indol-2-yl)-benzoic acid methyl ester

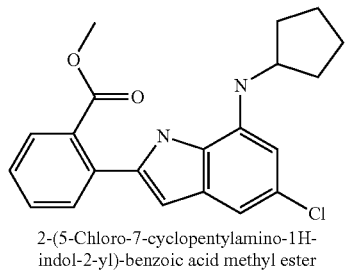 [SMILES: COC(=O)c1ccccc1-c1cc2cc(Cl)cc(NC3CCCC3)c2[nH]1]

2-(5-Chloro-7-cyclopentylamino-1H-indol-2-yl)-benzoic acid methyl ester

The compounds obtained in Preparation 58 (1.80 g, 5.44 mmol) was reacted instead of 5-methyl-7-nitro-2-phenyl-1H-indole in Example 46 to give the title compound 800 mg (Yield 40%).

$^1$H-NMR (400 HMz, CDCl$_3$); δ 9.81 (brs, 1H), 7.71 (d, J=4 Hz, 1H), 7.59 (d, J=4 Hz, 1H), 7.43 (t, 1H), 7.30 (t, 1H), 6.97 (s, 1H), 6.50 (d, J=2 Hz, 1H), 6.36 (d, J=2 Hz, 1H), 3.89 (s, 3H), 3.86 (m, 1H), 2.12 (m, 2H), 1.77 (m, 2H), 1.67 (m, 2H), 1.60 (m, 2H)

EXAMPLE 69

Synthesis of 2-(5-chloro-7-cyclopentylamino-1H-indol-2-yl)-benzoic acid

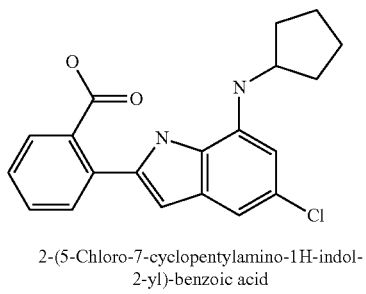 [SMILES: O=C(O)c1ccccc1-c1cc2cc(Cl)cc(NC3CCCC3)c2[nH]1]

2-(5-Chloro-7-cyclopentylamino-1H-indol-2-yl)-benzoic acid

The compound obtained in Example 68 (300 mg, 0.81 mmol) was reacted according to the same procedures as Example 65 to give the title compound 120 mg (Yield 42%).

$^1$H-NMR (400 HMz, DMSO-d$_6$); δ 11.57 (brs, 1H), 7.71 (m, 2H), 7.61 (m, 2H), 7.50 (m, 1H), 7.07 (s, 1H), 6.53 (s, 1H), 6.48 (s, 1H), 3.97 (m, 1H), 2.00 (m, 2H), 1.76 (m, 2H), 1.67 (m, 4H)

EXAMPLE 70

Synthesis of [2-(5-chloro-7-cyclopentylamino-1H-indol-2-yl)-phenyl]-methanol

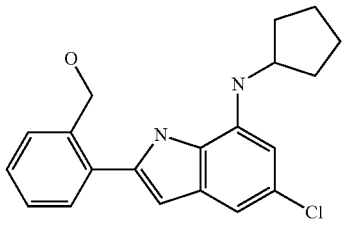

[2-(5-Chloro-7-cyclopentylamino-1H-indol-2-yl)-phenyl]-methanol

The compound obtained in Example 68 (300 mg, 0.81 mmol) was reacted according to the same procedures as Example 66 to give the title compound 150 mg (Yield 54%).

$^1$H-NMR (400 HMz, CDCl$_3$); δ 11.37 (brs, 1H), 7.69 (d, J=8 Hz, 1H), 7.47 (m, 2H), 7.42 (m, 2H), 7.21 (s, 1H), 6.69 (s, 1H), 4.78 (s, 2H), 3.97 (m, 1H), 1.96 (m, 4H), 1.86 (m, 2H), 1.56 (m, 2H)

Preparation 59: Synthesis of 7-nitro-2-phenyl-1H-indol-5-carboxylic acid ethyl ester 4-Amino-3-nitro-benzoic acid ester (3.0 g, 8.9 mmol) was reacted instead of 4-methyl-2-nitroaniline in Preparation 19 to give the title compound 1.6 g (Yield 58%).

¹H-NMR (500 HMz, CDCl₃); δ 10.23 (brs, 1H), 8.82 (s, 1H), 8.65 (s, 1H), 7.74 (m, 2H), 7.52 (m, 2H), 7.44 (m, 1H), 7.02 (s, 1H), 4.45 (q, 2H), 1.45 (t, 3H)

EXAMPLE 71

Synthesis of 7-cyclopenthylamino-2-phenyl-1H-indole-5-carboxylic acid ethyl ester

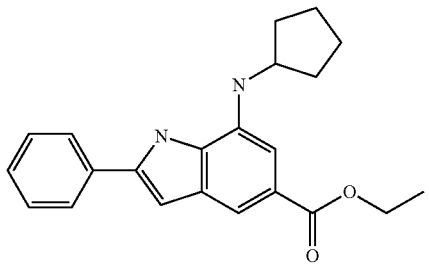

7-Cyclopentylamino-2-phenyl-1H-indole-5-carboxylic acid ethyl ester

The compound obtained in Preparation 59 (600 mg, 1.9 mmol) was reacted instead of 5-methyl-7-nitro-2-phenyl-1H-indole in Example 46 to give the title compound 100 mg (Yield 15%).

¹H-NMR (400 HMz, CDCl₃); δ 9.47 (brs, 1H), 7.90 (s, 1H), 7.67 (m, 2H), 7.34 (m, 2H), 7.24 (m, 1H), 7.18 (s, 1H), 6.83 (s, 1H), 4.41 (q, 2H), 3.87 (m, 1H), 1.95 (m, 2H), 1.62 (m, 2H), 1.49 (m, 4H), 1.39 (t, 3H)

EXAMPLE 72

Synthesis of 7-cyclopenthylamino-2-phenyl-1H-indole-5-carboxylic acid

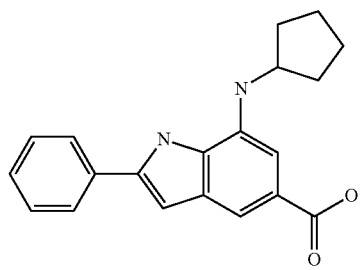

7-Cyclopentylamino-2-phenyl-1H-indole-5-carboxylic acid

The compound obtained in Example 71 (350 mg, 1.0 mmol) was reacted according to the same procedures as Example 65 to give the title compound 300 mg (Yield 94%).

¹H-NMR (400 HMz, MeOH-d₄); δ 7.88 (s, 1H), 7.75 (m, 2H), 7.42 (m, 2H), 7.30 (m, 1H), 7.16 (s, 1H), 6.85 (s, 1H), 4.03 (m, 1H), 2.13 (m, 2H), 1.77 (m, 2H), 1.66 (m, 4H)

EXAMPLE 73

Synthesis of (7-cyclopenthylamino-2-phenyl-1H-indol-5-yl)-methanol

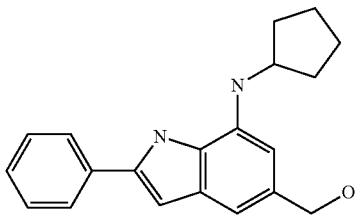

(7-Cyclopentylamino-2-phenyl-1H-indol-5-yl)-methanol

The compound obtained in Example 71 (60 mg, 0.17 mmol) was reacted according to the same procedures as Example 66 to give the title compound 21 mg (Yield 40%).

¹H-NMR (400 HMz, MeOH-d₄); δ 7.88 (s, 1H), 7.75 (m, 2H), 7.42 (m, 2H), 7.30 (m, 1H), 7.16 (s, 1H), 6.85 (s, 1H), 4.03 (m, 1H), 2.13 (m, 2H), 1.77 (m, 2H), 1.66 (m, 4H)

Preparation 60: Synthesis of (7-nitro-2-phenyl-1H-indol-5-yl)-acetic acid ethyl ester (4-Amino-3-nitro-phenyl)acetic acid ethyl ester (4.8 g, 13.7 mmol) was reacted instead of 4-methyl-2-nitroaniline in Preparation 19 to give the title compound 3.0 g (Yield 68%).

¹H-NMR (500 HMz, CDCl₃); δ 10.03 (brs, 1H), 8.05 (s, 1H), 8.00 (s, 1H), 7.72 (m, 2H), 7.49 (m, 2H), 7.49 (m, 1H), 7.39 (m, 1H), 6.87 (s, 1H), 4.19 (q, 2H), 2.04 (s, 2H), 1.26 (t, 3H)

EXAMPLE 74

Synthesis of (7-cyclopenthylamino-2-phenyl-1H-indol-5-yl)-acetic acid ethyl ester

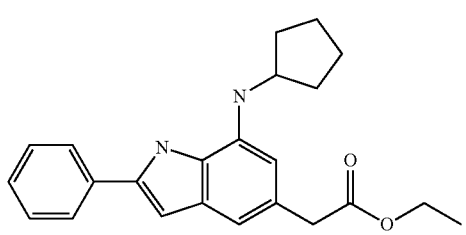

(7-Cyclopentylamino-2-phenyl-1H-indol-5-yl)-acetic acid ethyl ester

The compound obtained in Preparation 60 (3.0 g, 9.2 mmol) was reacted instead of 5-methyl-7-nitro-2-phenyl-1H-indole in Example 46 to give the title compound 2.0 g (Yield 60%).

¹H-NMR (400 HMz, CDCl₃); δ 8.12 (brs, 1H), 7.67 (m, 2H), 7.42 (m, 2H), 7.30 (m, 1H), 6.99 (s, 1H), 6.74 (s, 1H), 6.46 (s, 1H), 4.16 (q, 2H), 3.93 (m, 1H), 3.66 (s, 2H), 2.10 (m, 2H), 1.77 (m, 2H), 1.66 (m, 2H), 1.59 (t, 3H), 1.26 (t, 3H)

EXAMPLE 75

Synthesis of (7-cyclopenthylamino-2-phenyl-1H-indol-5-yl)-acetic acid

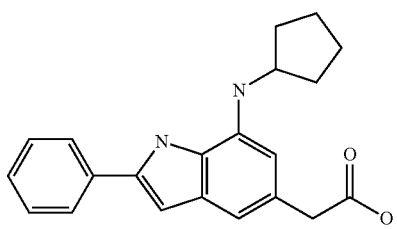

(7-Cyclopentylamino-2-phenyl-1H-indol-5-yl)-acetic acid

The compound obtained in Preparation 74 (90 mg, 0.25 mmol) was reacted according to the same procedures as Example 65 to give the title compound 65 mg (Yield 78%).

$^1$H-NMR (400 HMz, CDCl$_3$+MeOH-d$_4$); δ 11.31 (s, 1H), 7.81 (m, 2H), 7.37 (m, 2H), 7.25 (m, 1H), 7.05 (s, 1H), 6.65 (s, 1H), 3.89 (m, 1H), 1.88 (m, 7H), 1.41 (m, 3H)

EXAMPLE 76

Synthesis of 2-(7-cyclopenthylamino-2-phenyl-1H-indol-5-yl)-ethanol

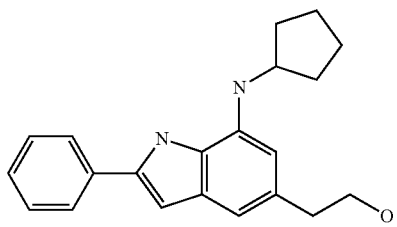

2-(7-Cyclopentylamino-2-phenyl-1H-indol-5-yl)-ethanol

The compound obtained in Preparation 74 (50 mg, 0.14 mmol) was reacted according to the same procedures as Example 66 to give the title compound 40 mg (Yield 89%).

$^1$H-NMR (400 HMz, CDCl$_3$+MeOH-d$_4$); δ 7.71 (m, 2H), 7.40 (m, 2H), 7.28 (m, 1H), 6.89 (s, 1H), 6.72 (s, 1H), 6.32 (s, 1H), 3.97 (m, 1H), 3.87 (m, 2H), 3.43 (m, 1H), 2.91 (m, 2H), 2.09 (m, 2H), 1.77 (m, 2H), 1.62 (m, 4H)

EXAMPLE 77~90

The nitro indole compounds produced in Preparations 5, 7 and 10, the compounds produced in Preparations 23 and 25, and the commercially available ketone compounds were reacted according to the procedures as Preparation 34, 35, 36 and Example 11 in the order to give the following exemplary compounds.

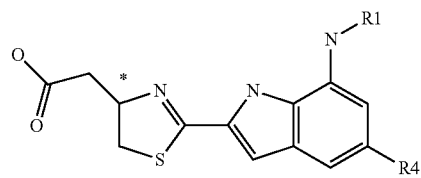

| Example | * | R1 | R4 | $^1$H NMR data |
|---|---|---|---|---|
| 77 | S | (tetrahydropyran-4-yl)methyl | methyl | (400 MHz, CDCl$_3$); δ 11.92 (br s, 1H), 6.98 (s, 1H), 6.77 (s, 1H), 6.22 (s, 1H), 6.29 (br s, 1H), 3.96 (m, 2H), 3.70 (m, 1H), 3.37 (m, 2H), 3.18 (m, 1H), 3.08 (m, 2H), 2.72 (m, 1H), 2.56 (m, 1H), 2.37 (s, 3H), 1.91 (m, 1H), 1.75 (m, 2H), 1.41 (m, 2H) |
| 78 | S | (tetrahydropyran-4-yl)methyl | chloro | (500 MHz, DMSO-d$_6$); δ 11.52 (br s, 1H), 6.80 (s, 1H), 6.69 (s, 1H), 6.16 (s, 1H), 6.12 (m, 1H), 4.94 (m, 1H), 3.81 (m, 1H), 3.63 (m, 1H), 3.45 (m, 1H), 3.38 (m, 3H), 3.14 (m, 1H), 2.85 (m, 1H), 1.93 (m, 2H), 1.68 (m, 2H), 1.48 (m, 10H) |
| 79 | S | 4,4-difluorocyclohexyl | methyl | (400 MHz, CDCl$_3$); δ 11.94 (brs, 1H), 7.00 (s, 1H), 6.78 (s, 1H), 6.26 (s, 1H), 5.35 (m, 1H), 3.71 (m, 1H), 3.63 (m, 1H), 3.22 (m, 1H), 2.75 (m, 1H), 2.62 (m, 1H), 2.37 (s, 3H), 2.25 (m, 1H), 2.09-1.73 (m, 7H) |
| 80 | S | tetrahydropyran-4-yl | OPh | (400 MHz, CDCl$_3$); δ 11.95 (brs, 1H), 7.28 (m, 2H), 7.06-6.96 (m, 4H), 6.58 (s, 1H), 6.24 (s, 1H), 5.33 (m, 1H), 3.98 (m, 2H), 3.75 (m, 1H), 3.58-3.47 (m, 3H), 3.23 (d, 1H), 2.78-2.62 (m, 2H), 2.04 (m, 2H), 1.58 (m, 2H) |

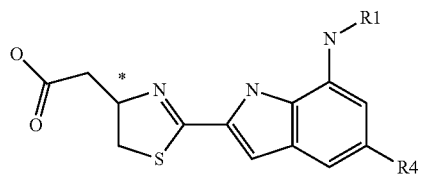

| Example | * | R1 | R4 | ¹H NMR data |
|---|---|---|---|---|
| 81 | R | tetrahydropyran-4-yl | OPh | (400 MHz, CDCl₃); δ 11.98 (br s, 1H), 7.28 (m, 2H), 7.00 (m, 4H), 6.58 (s, 1H), 6.22 (s, 1H), 5.34 (m, 1H), 3.98 (m, 2H), 3.70 (m, 1H), 3.50 (m, 3H), 3.21 (m, 2H), 2.74 (m, 1H), 2.66 (m, 1H), 2.05 (m, 2H), 1.58 (m, 2H) |
| 82 | R | (tetrahydropyran-4-yl)methyl | H | (400 MHz, CDCl₃); δ 11.96 (brs, 1H), 7.30 (m, 2H), 7.03 (m, 4H), 6.60 (s, 1H), 6.20 (s, 1H), 5.36 (m, 1H), 3.93 (m, 1H), 3.73 (m, 1H), 3.35 (m, 2H), 3.23 (m, 1H), 3.06 (m, 2H), 2.72 (m, 1H), 2.62 (m, 1H), 1.92 (m, 1H), 1.73 (m, 2H), 1.40 (m, 2H) |
| 83 | S | Cyclopentyl | H | (400 MHz, CDCl₃); δ 11.74 (brs, 1H), 7.06 (s, 1H), 6.99 (m, 2H), 6.45 (s, 1H), 5.48 (m, 1H), 3.90 (m, 1H), 3.71 (m, 1H), 3.23 (m, 1H), 2.75 (m, 1H), 2.67 (m, 1H), 2.04 (m, 2H), 1.75 (m, 2H), 1.61-1.48 (m, 4H) |
| 84 | S | 1-acetyl-pyrrolidin-3-yl | H | (400 MHz, CDCl₃); δ 10.13 (brs, 1H), 6.93 (s, 1H), 6.82 (s, 1H), 6.38 (s, 1H), 5.09 (m, 1H), 4.16 (m, 1H), 3.67 (m, 2H), 3.52 (m, 2H), 3.38 (m, 1H), 3.25 (m, 1H), 2.91 (m, 1H), 2.66 (m, 1H), 2.48 (s, 3H), 2.23 (m, 1H), 2.00 (m, 1H). |
| 85 | S | (tetrahydropyran-4-yl)methyl | H | (400 MHz, CDCl₃); δ 11.89 (brs, 1H), 7.13 (s, 1H), 7.04 (m, 2H), 6.44 (m, 1H), 5.39 (m, 1H), 3.98 (m, 2H), 3.77 (m, 1H), 3.41 (m, 2H), 3.25 (m, 1H), 3.13 (m, 2H), 2.78 (m, 1H), 2.64 (m, 1H), 2.00 (m, 1H), 1.79 (m, 2H), 1.44 (m, 2H). |
| 86 | S | tetrahydrofuran-3-yl | H | (400 MHz, CDCl₃); δ 11.87 (brs, 1H), 7.15 (s, 1H), 7.03 (m, 2H), 6.50 (m, 1H), 5.39 (m, 1H), 4.06 (m, 2H), 3.80-3.62 (m, 2H), 3.57 (m, 2H), 3.29 (m, 1H), 2.83 (m, 1H), 2.69 (m, 1H), 2.11 (m, 2H), 1.64 (m, 2H) |
| 87 | S | (tetrahydropyran-2-yl)methyl | H | (400 MHz, CDCl₃); δ 11.68 (brs, 1H), 7.06-6.98 (m, 3H), 6.45 (s, 1H), 5.32 (m, 1H), 3.96 (m, 1H), 3.77-3.61 (m, 2H), 3.43 (m, 1H), 3.28-3.21 (m, 3H), 2.80 (m, 1H), 2.65 (m, 1H), 1.83 (m, 1H), 1.71 (m, 1H), 1.62-1.42 (m, 4H) |
| 88 | S | 1-trifluromethyl-carbony-piperidin-4-yl | methyl | (400 MHz, CDCl₃); δ 11.94 (brs, 1H), 6.93 (s, 1H), 6.78 (s, 1H), 6.25 (s, 1H), 5.33 (m, 1H), 4.13 (m, 1H), 3.76-3.68 (m, 5H), 3.47-3.41 (m, 3H), 2.74-2.63 (m, 2H), 2.36 (s, 3H), 2.04 (m, 2H), 1.56 (m, 2H) |
| 89 | R | Cyclopentyl | (400 MHz, CDCl₃); δ 10.52 (br s, 1H), 7.04 (d, 1H), 6.97 (t, 1H), 6.92 (d, 1H), 6.49 (d, 1H), 5.20 (m, 1H), 3.83 (m, 2H), 3.64 (m, 1H), 3.39 (m, 1H), 3.31 (m, 1H), 3.17 (m, 1H), 3.01 (m, 1H), 1.97 (m, 4H), 1.73 (m, 4H), 1.60 (m, 6H), 1.46 (m, 2H), 1.34 (m, 2H) |
| 90 | R | (tetrahydropyran-4-yl)methyl | methyl | (400 MHz, CDCl₃); δ 11.54 (brs, 1H), 7.11 (s, 1H), 6.80 (s, 1H), 6.22 (s, 1H), 5.29 (m, 1H), 3.92 (m, 2H), 3.68 (m, 1H), 3.35 (m, 2H), 3.21-3.04 (m, 3H), 2.84-2.52 (m, 2H), 2.32 (s, 3H), 1.90 (m, 1H), 1.74 (m, 2H), 1.35 (m, 2H) |

EXAMPLE 91~101

The esters obtained during the process of Example 21, 77, 79, 89 and 78 were reduced according to the procedures as Example 4 and then reacted according to the procedures as Preparation 37 and Example 15 to give the following exemplary compounds.

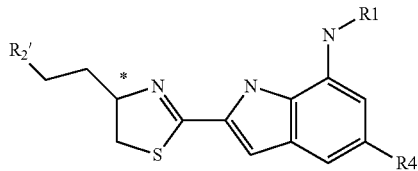

| Example | R2' | * | R1 | R4 | NMR |
|---|---|---|---|---|---|
| 91 | 2-oxopiperazin-4-yl | S | (tetrahydropyran-4-yl)methyl | methyl | (500 MHz, CDCl$_3$); δ 11.03 (s, 1H), 8.20 (br s, 1H), 6.82 (s, 1H), 6.79 (s, 1H), 6.31 (s, 1H), 4.71 (br s, 2H), 4.24 (m, 1H), 3.91 (m, 2H), 3.80-3.51 (m, 4H), 3.31 (m, 2H), 3.20 (m, 1H), 3.14 (d, 2H), 2.95 (m, 2H), 2.70 (m, 1H), 2.41 (m, 1H), 2.40 (s, 3H), 2.20 (m, 1H), 2.00 (m, 1H), 1.81 (d, 2H), 1.40 (m, 2H) |
| 92 | 1,1-dioxothiomorpholin-4-yl | S | (tetrahydropyran-4-yl)methyl | methyl | (500 MHz, CDCl$_3$); δ 9.47 (br s, 1H), 6.88 (s, 1H), 6.47 (s, 1H), 6.39 (s, 1H), 5.87 (br s, 1H), 4.12-4.00 (m, 2H), 3.85 (br s, 4H), 3.66 (m, 1H), 3.58 (t, 2H), 3.08 (br s, 4H), 2.95 (m, 1H), 2.85-2.70 (m, 3H), 2.41 (s, 3H), 2.10 (m, 2H), 1.96 (m, 2H), 1.60 (m, 2H) |
| 93 | morpholin-4-yl | S | 4,4-difluorocyclohexyl | methyl | (400 MHz, CDCl$_3$); δ 9.67 (brs, 1H), 6.87 (s, 1H), 6.82 (s, 1H), 6.34 (s, 1H), 4.71 (m, 1H), 3.65 (m, 6H), 3.55 (dd, J = 8 Hz, 1H), 3.51 (m, 1H), 3.15 (dd, J = 8 Hz, 1H), 2.52-2.29 (m, 9H), 2.15-2.04 (m, 4H), 1.96-1.90 (m, 2H), 1.58-1.51 (m, 2H) |
| 94 | 2-oxopiperazin-4-yl | S | 4,4-difluorocyclohexyl | methyl | (400 MHz, CDCl$_3$); δ 10.14 (brs, 1H), 6.82 (s, 1H), 6.80 (s, 1H), 6.31 (s, 1H), 4.65 (m, 1H), 3.54 (m, 1H), 3.53 (dd, J = 8 Hz, 1H), 3.39 (m, 2H), 3.30 (m, 1H), 3.22-3.08 (m, 4H), 2.78-2.65 (m, 4H), 2.38 (s, 3H), 2.28-2.04 (m, 4H), 1.96-1.86 (m, 2H), 1.73 (m, 2H) |
| 95 | 2-oxopiperazin-4-yl | S | (tetrahydropyran-4-yl)methyl | OPh | (400 MHz, CDCl$_3$); δ 10.70 (brs, 1H), 7.20 (m, 2H), 7.01 (m, 3H), 6.85 (m, 1H), 6.80 (d, 1H), 6.60 (m, 1H), 6.20 (m, 1H), 5.03 (m, 1H), 4.70 (m, 1H), 3.78 (m, 2H), 3.55 (m, 1H), 3.48~3.30 (m, 6H), 3.15-3.10 (m, 4H), 2.81 (m, 1H), 2.71 (m, 3H), 1.94 (m, 3H), 1.72 (m, 2H), 1.42 (m, 2H) |
| 96 | morpholin-4-yl | S | (tetrahydropyran-4-yl)methyl | OPh | (400 MHz, CDCl$_3$); δ 10.19 (brs, 1H), 7.29 (m, 2H), 7.02 (m, 3H), 6.84 (s, 1H), 6.65 (s, 1H), 6.26 (s, 1H), 4.77 (m, 1H), 3.94 (m, 2H), 3.83 (m, 1H), 3.63~3.55 (m, 6H), 3.36 (m, 2H), 3.19 (m, 1H), 3.04 (m, 2H), 2.46 (m, 2H), 2.34 (m, 4H), 2.01 (m, 1H), 1.84 (m, 2H), 1.59 (m, 2H), 1.28 (m, 2H) |
| 97 | morpholin-4-yl | S | (tetrahydropyran-4-yl)methyl | methyl | (500 MHz, CDCl$_3$); δ 11.13 (s, 1H), 6.82 (d, 2H), 6.24 (s, 1H), 4.81-4.78 (m, 1H), 3.88-3.81 (m, 2H), 3.60-3.46 (m, 5H), 3.35-3.30 (m, 2H), 3.19-3.17 (m, 1H), 3.01 (br, 2H), 2.38-2.26 (m, 7H), 2.14 (s, 2H), 1.91-1.88 (m, 1H), 1.75-1.71 (m, 2H), 1.53-1.47 (m, 2H), 1.28-1.16 (m, 2H) |
| 98 | 1-carbamoyl-piperazin-4-yl | S | (tetrahydropyran-4-yl)methyl | methyl | (400 MHz, CDCl$_3$); δ 11.22 (s, 1H), 7.16 (s, 1H), 6.60 (d, 2H), 6.07 (s, 1H), 5.72 (s, 2H), 4.58 (m, 1H), 3.87-3.85 (m, 2H), 3.57-3.50 (m, 2H), 3.28 (m, 2H), 3.16-3.11 (m, 2H), 3.01-3.00 (m, 2H), 2.87 (m, 2H), 2.40-2.35 (m, 1H), 2.24 (s, 3H), 2.02-1.94 (m, 2H), 1.88-1.81 (m, 2H), 1.75-1.72 (m, 2H), 1.65-1.63 (m, 2H), 1.56-1.50 (m, 2H), 1.28-1.21 (m, 2H) |
| 99 | 2-hydroxymethyl-pyrrolidin-1-yl | S | (tetrahydropyran-4-yl)methyl | methyl | (400 MHz, CDCl$_3$); δ 10.25 (s, 1H), 6.76 (s, 1H), 6.74 (s, 1H), 6.23 (s, 1H), 4.67-4.58 (m, 2H), 4.16-4.09 (m, 1H), 4.00-3.94 (m, 2H), 3.73-3.68 (m, 1H), 3.50-3.36 (m, 2H), 3.11 (d, 2H), 2.99-2.94 (m, 2H), 2.32 (s, 3H), 2.15-2.07 (m, 2H), 2.02-1.92 (m, 3H), 1.76-1.73 (m, 2H), 1.42-1.36 (m, 2H), 1.14-1.08 (m, 2H), 0.86-0.81 (m, 2H), 0.73-0.68 (m, 2H) |

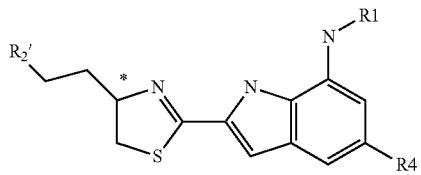

| Example | R2' | * | R1 | R4 | NMR |
|---|---|---|---|---|---|
| 100 | 2-carbamoyl-pyrrolidin-1-yl | S | (tetrahydropyran-4-yl)methyl | methyl | (400 MHz, CDCl$_3$); δ 11.31 (s, 1H), 8.18 (br, 1H), 7.24 (d, 1H), 6.83 (s, 1H), 6.75 (s, 1H), 6.22 (s, 1H), 5.50 (br, 1H), 4.71-4.64 (m, 1H), 4.07-3.99 (m, 2H), 3.57-3.38 (m, 3H), 3.28-3.25 (m, 1H), 3.19-3.06 (m, 4H), 2.88-2.81 (m, 1H), 2.75-2.70 (m, 1H), 2.49-2.41 (m, 1H), 2.39 (s, 3H) 2.25-2.12 (m, 1H), 2.08-2.04(m, 1H), 1.99-1.95 (m, 2H), 1.83-1.80 (m, 4H), 1.53-1.40 (m, 2H) |
| 101 | 2-oxopiperazin-4-yl | R | Cyclopentyl | methy | (400 MHz, CDCl$_3$); δ 10.28 (brs, 1H), 6.83 (s, 1H), 6.68 (s, 1H), 6.33 (s, 1H), 4.73 (m, 1H), 3.91 (m, 1H), 3.55 (m, 1H), 3.48-3.10 (m, 3H), 2.68-2.58 (m, 4H), 2.40 (s, 3H), 2.19-1.98 (m, 3H), 1.93 (m, 1H), 1.78-1.58 (m, 8H) |

Preparation 61: Synthesis of [(S)-2-(5-methyl-7-nitro-1H-indol-2-yl)-4,5-dihydro-oxazol-4-yl]-acetic acid isopropyl ester (Step 1)
5-Methyl-7-nitro-1H-indole-2-carboxylic acid methyl ester obtained in Preparation 7 was hydrolyzed using LiOH according to the same procedures as Step 1 of Preparation 28 to give 5-methyl-7-nitro-1H-indole-2-carboxylic acid.

(Step 2)
(S)-3-t-Butoxycarbonylamino-4-hydroxybutyric acid-isopropyl ester used in Preparation 25 was deprotected according to the same procedures as Step 3 of Preparation 24 to give (S)-3-amino-4-hydroxy-butyric acid isopropyl ester.

(Step 3)
The compounds obtained in Step 1 and 2 were reacted according to the same procedures as Step 2 of Preparation 28 to give (S)-4-hydroxy-3-[(5-methyl-7-nitro-1H-indole-2-carbonyl)-amino]-butyric acid isopropyl ester.

(Step 4)
The compound obtained in Step 3 and methanesulfonyl chloride were reacted according to the same procedures as Preparation 33 to give (S)-4-methansulfonyloxy-3-[(5-methyl-7-nitro-1H-indole-2-carbonyl)-amino]-butyric acid isopropyl ester.

(Step 5)
The compound obtained in Step 4 (890 mg, 2 mmol) was added to THF (10 mL), K$_2$CO$_3$ (330 mg, 10 mmol) was added. The mixture was stirred at 80° C. for 2 hours. Water was added to quench the reaction. The mixture was extracted with EtOAc, dried over MgSO$_4$, and solvent was removed under reduced pressure. The residue was purified by column chromatography (eluent: EtOAc/n-Hex/DMC=1/4/1) to give the title compound (445 mg, Yield 61%).

EXAMPLE 102

Synthesis of [(S)-2-(7-cyclopentylamino-5-methyl-1H-indol-2-yl)-4,5-dihydro-oxazol-4-yl]-acetic acid

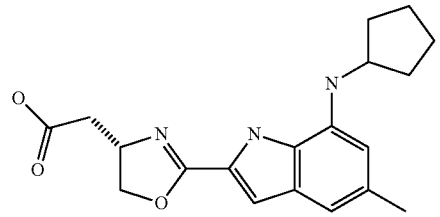

[(S)-2-(7-Cyclopentylamino-5-methyl-1H-indol-2-yl)-4,5-dihydro-oxazol-4-yl]-acetic acid The procedures of Step 3 of Preparation 31, Preparation 36 and Step 1 of Preparation 28 were conducted in the order using the compound obtained in Preparation 61 and cyclopentanone to give the title compound.

$^1$H-NMR (400 MHz, CDCl$_3$/MeOH-d$_4$); δ, 6.97 (s, 1H), 6.79 (s, 1H), 6.33 (s, 1H), 4.86 (m, 1H), 4.62 (dd, 1H), 4.35 (dd, 1H), 3.95 (m, 1H), 2.94 (dd, 1H), 2.67 (dd, 1H), 2.39 (s, 3H), 2.07 (m, 2H), 1.78 (m, 2H), 1.65 (m, 4H)

EXAMPLE 103

Synthesis of [(S)-2-[5-methyl-7-(tetrahydropyran-4-ylamino)-1H-indol-2-yl]-4,5-dihydro-oxazol-4-yl]-acetic acid

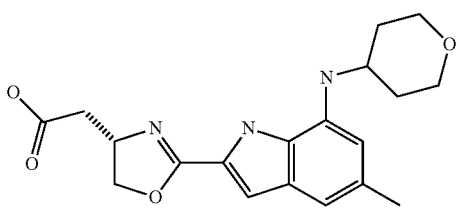

{(S)-2-[5-Methyl-7-(tetrahydro-pyran-4-ylamino)-1H-indol-2-yl]-4,5-dihydro-oxazol-4-yl}-acetic acid Tetrahydropyran-4-one was used instead of cyclopentanone in Example 102 to give the title compound.

$^1$H-NMR (400 MHz, CDCl$_3$/MeOH-d$_4$); δ 6.94 (s, 1H), 6.81 (s, 1H), 6.32 (s, 1H), 4.87 (m, 1H), 4.59 (dd, 1H), 4.34 (dd, 1H), 4.02 (d, 1H), 3.68-3.58 (m, 3H), 2.92 (dd, 1H), 2.68 (dd, 1H), 2.38 (s, 3H), 2.13 (d, 2H), 1.57 (m, 2H)

EXAMPLE 104

Synthesis of {(S)-2-[5-methyl-7-(tetrahydropyran-4-ylamino)-1H-indol-2-yl]-4,5-dihydro-oxazol-4-yl}-ethanol

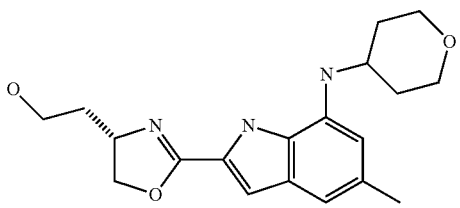

2-{(S)-2-[5-Methyl-7-(tetrahydro-pyran-4-ylamino)-1H-indol-2-yl]-4,5-dihydro-oxazol-4-yl}-ethanol The compound obtained in Example 103 was reduced to give the title compound according to the same method as Example 66.

$^1$H-NMR (400 MHz, CDCl$_3$); δ 10.11 (br s, 1H), 6.91 (s, 1H), 6.86 (s, 1H), 6.34 (s, 1H), 4.60 (t, 1H), 4.48 (m, 1H), 4.10-3.93 (m, 5H), 3.63~3.52 (m, 3H), 2.39 (s, 3H), 2.07 (d, 2H), 1.94 (m, 2H), 1.58 (m, 2H)

EXAMPLE 105

Synthesis of {5-methyl-2-[(S)-4-(2-morpholin-4-yl-ethyl)-4,5-dihydro-oxazol-2-yl]-1H-indol-7-yl}-(tetrahydro-pyran-4-yl)amine

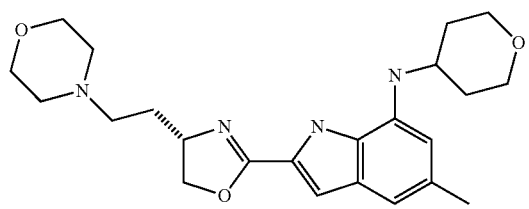

{5-Methyl-2-[(S)-4-(2-morpholin-4-yl-ethyl)-4,5-dihydro-oxazol-2-yl]-1H-indol-7-yl)-(tetrahydro-pyran-4-yl)-amine The compound obtained in Example 104 and morpholine were reacted according to the procedures as Preparation 33 and Example 15 in the order to give the title compound.

$^1$H-NMR (400 HMz, CDCl$_3$); δ 10.11 (br s, 1H), 6.91 (s, 1H), 6.86 (s, 1H), 6.34 (s, 1H), 4.60 (t, 1H), 4.48 (m, 1H), 4.10-3.93 (m, 5H), 3.63-3.52 (m, 3H), 2.39 (s, 3H), 2.07 (d, 2H), 1.94 (m, 2H), 1.58 (m, 2H)

EXAMPLE 106~125

The following exemplary compounds were prepared analogous to Preparation 19, Step 3 of Preparation 35 and Preparation 36.

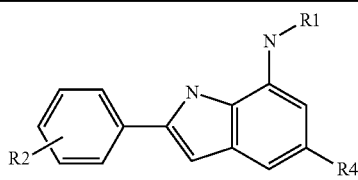

| Example | R2 | R1 | R4 | $^1$H NMR |
|---|---|---|---|---|
| 106 | H | 1-ethylcarbamoyl-piperidin-4-yl | Cl | (500 MHz, DMSO-d$_6$); δ 11.03 (s, 1H), 7.76 (d, J = 7.3 Hz, 2H), 7.44 (t, J = 7.3 Hz, 2H), 7.30 (t, J = 7.3 Hz, 1H), 6.76 (d, J = 1.85 Hz, 1H), 6.72 (d, J = 1.85 Hz, 1H), 6.47 (t, 1H), 6.25 (d, J = 1.85 Hz, 1H), 5.57 (m, 1H), 3.90 (m, 2H), 3.58 (m, 1H), 3.02 (q, 2H), 2.87 (m, 2H), 1.96 (m, 2H), 1.26 (m, 2H), 0.99 (t, 3H) |

-continued

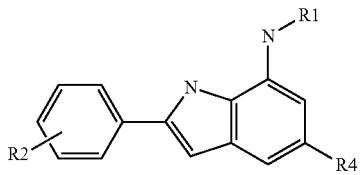

| Example | R2 | R1 | R4 | ¹H NMR |
|---|---|---|---|---|
| 107 | H | 1-(tetrahydrofuran-3-yl)carbonyl-pyrrolidin-3-yl | H | (500 MHz, DMSO-$d_6$); δ 11.04 (brs, 1H), 7.75 (m, 2H), 7.44 (m, 2H), 7.30 (m, 1H), 6.78 (s, 1H), 6.73 (s, 1H), 6.29 (s, 1H), 5.59 (d, 1H), 4.30 (d, 1H), 3.96 (d, 1H), 3.86 (m, 1H), 3.72~3.60 (m, 5H), 2.85 (m, 1H), 2.20 (m, 4H), 1.29 (m, 2H). |
| 108 | H | tetrahydropyran-4-yl | —$CH_2$—$CO_2H$ | (400 MHz, DMSO-$d_6$, Na salt); δ 10.88 (br s, 1H), 7.81 (d, J = 8 Hz, 2H), 7.43 (m, 2H), 7.28 (m, 1H), 6.67 (s, 1H), 6.62 (s, 1H), 6.29 (s, 1H), 5.23 (m, 1H), 3.92 (d, J = 8 Hz, 2H), 3.67 (m, 1H), 3.47 (m, 2H), 3.14 (s, 2H), 2.06 (m, 2H), 1.48 (m, 2H) |
| 109 | H | Cyclopentyl methyl | —$CH_2$—$CO_2H$ | (400 MHz, DMSO-d6, Na salt); δ 10.97 (br s, 1H), 7.80 (d, J = 8 Hz, 2H), 7.43 (t, 2H), 7.26 (t, 1H), 6.67 (s, 1H), 6.62 (s, 1H), 6.20 (s, 1H), 5.33 (br s, 1H), 3.16 (s, 2H), 3.04 (m, 2H), 2.27 (m, 1H), 1.86 (m, 2H), 1.60 (m, 4H), 1.33 (m, 2H) |
| 110 | H | 1-methyl-piperidin-4-yl | F | (400 MHz, DMSO-$d_6$); δ 7.87 (d, 2H), 7.45 (t, 2H), 7.31 (m, 1H), 6.76 (s, 1H), 6.51 (s, 1H), 6.14 (s, 1H), 3.65 (br s, 1H), 3.41 (br s, 2H), 2.99 (br s, 2H), 2.69 (br s, 1H), 2.17 (br s, 2H), 1.79 (br s, 2H) |
| 111 | H | 1-hydroxyethyl-piperidin-4-yl | F | (400 MHz, DMSO-$d_6$); δ 7.78 (d, 2H), 7.45 (t, 2H), 7.30 (t, 1H), 6.75 (s, 1H), 6.46 (d, 1H), 6.07 (d, 1H), 3.37 (t, 1H), 3.36 (t, 1H), 2.90 (d, 2H), 2.45 (t, 2H), 2.20 (t, 2H), 2.03 (t, 2H), 1.09 (t, 2H) |
| 112 | H | 1-(tetrahydropyran-4-yl-piperidin-4-yl | F | (400 MHz, $CDCl_3$); δ 7.78 (br s, 2H), 7.36 (br s, 2H), 7.26 (br s, 1H), 6.71 (s, 1H), 6.68 (d, 1H), 6.12 (s, 1H), 3.90 (br s, 2H), 3.46 (br s, 1H), 3.20 (br s, 2H), 3.09 (br s, 2H), 2.61 (br s, 1H), 2.45 (br s, 2H), 2.23 (d, 2H), 1.87 (br sm 2H), 1.61 (br s, 2H), 1.58 (br s, 2H) |
| 113 | H | 1-(1,2-dioxo-thianocyclohexyl-4-yl) piperidin-4-yl | F | (400 MHz, $CDCl_3$); δ 7.66 (d, 2H), 7.44 (t, 2H), 7.33 (t, 1H), 6.74 (d, 1H), 6.72 (d, 1H), 6.26 (d, 1H), 3.39 (m, 1H), 3.22 (m, 2H), 2.92 (m, 4H), 2.57 (t, 1H), 2.33 (m, 4H), 2.28 (m, 4H), 1.53 (m, 2H) |
| 114 | H | Tetrahydropyran-4-yl | OPh | (400 MHz, $CDCl_3$); δ 8.12 (brs, 1H), 7.68 (m, 2H), 7.44 (m, 2H), 7.34~7.25 (m, 3H), 7.01 (m, 3H), 6.74 (m, 2H), 6.35 (d, 1H), 4.03 (m, 2H), 3.63~3.49 (m, 4H), 2.12 (m, 2H), 1.58 (m, 2H) |
| 115 | H | $MeO_2C$—$CH_2$— | F | (400 MHz, $CDCl_3$); δ 7.56 (d, 2H), 7.41 (t, 2H), 7.34 (t, 1H), 6.80 (d, 1H), 6.71 (s, 1H), 6.19 (d, 1H), 4.09 (s, 2H), 3.85 (s, 3H) |
| 116 | H | $HO_2C$—$CH_2$— | F | (400 MHz, DMSO-$d_6$); δ 7.91 (d, 2H), 7.41 (t, 2H), 7.26 (t, 1H), 6.73 (s, 1H), 6.41 (d, 1H), 5.78 (d, 1H), 6.17 (br s, 1H), 3.48 (s, 2H) |
| 117 | H | $MeO_2C$—CH(Me)— | Cl | (400 MHz, $CDCl_3$); δ 8.62 (br s, 1H), 7.55 (d, J = 8 Hz, 2H), 7.38 (t, 2H), 7.30 (t, 1H), 7.00 (s, 1H), 6.60 (s, 1H), 6.31 (s, 1H), 4.47 (br s, 1H), 4.27 (m, 1H), 1.58 (d, J = 8 Hz, 3H) |
| 118 | H | $HO_2C$—CH(Me)— | Cl | (400 MHz, DMSO-$d_6$, Na salt); δ 12.09 (br s, 1H), 7.91 (d, J = 8 Hz, 2H), 7.42 (t, 2H), 7.27 (t, 1H), 6.72 (d, J = 8 Hz, 1H), 6.21 (d, J = 8 Hz, 1H), 6.08 (s, 1H), 3.67 (t, 1H), 1.34 (d, J-8 Hz, 3H) |

-continued

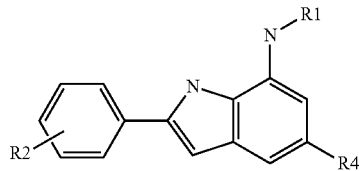

| Example | R2 | R1 | R4 | ¹H NMR |
|---|---|---|---|---|
| 119 | H | HO$_2$C—CH$_2$— | OPh | (500 MHz, MeOH-d4); δ 7.76 (d, J = 7.3 Hz, 2H), 7.39 (t, J = 7.3 Hz, 2H), 7.25 (m, 3H), 6.96 (t, J = 7.3 Hz, 1H), 6.90 (d, J = 7.3 Hz, 2H), 6.68 (m, 1H), 6.53 (d, J = 1.85 Hz, 1H), 6.00 (d, J = 1.85 Hz, 1H), 3.96 (s, 2H) |
| 120 | H | HO$_2$C—CH(Me)— | OPh | (500 MHz, MeOH-d4); δ 7.76 (d, J = 7.3 Hz, 2H), 7.39 (t, J = 7.3 hz, 2H), 7.25 (m, 3H), 6.96 (t, J = 7.3 Hz, 1H), 6.90 (d, J = 7.3 Hz, 2H), 6.68 (m, 1H), 6.53 (d, J = 1.85 Hz, 1H), 6.00 (d, J = 1.85 Hz, 1H), 3.96 (s, 2H) |
| 121 | H | (tetrahydropyran-4-yl)methyl | ![thiazoline-acetate] | (400 MHz, DMSO-d$_6$); δ 11.79 (m, 1H), 7.91 (m, 2H), 7.51 (m, 2H), 7.39 (m, 2H), 7.01 (m, 1H), 6.80 (m, 1H), 4.96 (m, 1H), 3.93 (m, 2H), 3.33 (m, 3H), 3.15 (m, 2H), 2.87 (m, 2H), 2.75 (m, 1H), 1.95 (m, 1H), 1.79 (m, 2H), 1.36 (m, 2H) |
| 122 | H | cyclopentyl | ![thiazoline-acetate] | (400 MHz, DMSO-d$_6$); δ 11.81 (s, 1H), 7.92 (m, 2H), 7.60 (m, 2H), 7.50 (m, 2H), 7.34 (m, 1H), 6.83 (m, 1H), 4.99 (m, 1H), 3.95 (m, 1H), 3.70 (m, 2H), 2.87 (m, 1H), 2.71 (m, 1H), 2.08 (m, 2H), 1.77 (m, 2H), 1.64 (m, 4H) |
| 123 | 4-MeO$_2$C—CH$_2$— | Tetrahydropyran-4-yl | Cl | (400 MHz, CDCl$_3$); δ 8.74 (br s, 1H), 7.53 (d, J = 8 hz, 2H), 7.35 (d, J = 8 Hz, 2H), 7.05 (s, 1H), 6.46 (s, 1H), 6.44 (s, 1H), 3.94 (d, 2H), 3.75 (m, 1H), 3.72 (s, 3H), 3.67 (s, 2H), 3.61 (m, 2H), 2.13 (d, j + 8 Hz, 2H), 1.58 (m, 2H) |
| 124 | 4-MeO$_2$C—CH$_2$— | (tetrahydropyran-4-yl)methyl | Cl | (400 MHz, CDCl$_3$); δ 8.40 (br s, 1H), 7.70 (d, J = 8 Hz, 2H), 7.32 (d, J = 8 Hz, 2H), 7.05 (s, 1H), 6.67 (s, 1H), 6.43 (s, 1H), 3.95 (d, 2H), 3.73 (s, 3H), 3.67 (S, 2h), 3.44 (T, 2h), 3.16 (D, j = 8 Hz, 2H), 1.98 (m, 1H), 1.79 (d, J = 12 Hz, 2H), 1.42 (m, 2H) |
| 125 | 4-HO$_2$C—CH$_2$— | Tetrahydropyran-4-yl | Cl | (400 MHz, DMSO-d$_6$, Na salt); δ 12.53 (s, 1H), 7.70 (d, J = 8 Hz, 2H), 7.30 (d, J = 8 Hz, 2H), 6.72 (s, 1H), 6.60 (s, 2H), 6.19 (s, 1H), 3.90 (d, J = 12 Hz, 2H), 3.60 (m, 1H), 3.48 (m, 2H), 3.35 (s, 2H), 1.96 (d, J = 12 Hz, 2H), 1.59 (m, 2H) |

Preparation 62: Synthesis of 5-(1,1-dioxo-thiomorpolin-4-ylmethyl)-2-phenyl-1H-indol-7-yl amine (Step 1)

7-Nitro-2-phenyl-1H-indole-5-carboxylic acid ethyl ester obtained in Preparation 59 was reacted according to the same procedures as Preparation 66 to give (7-nitro-2-phenyl-1H-indole-5-yl)-methanol.

(Step 2)

The compound obtained in Step 1, iodine and 1,1-dioxo-thiomorpholine were reacted according to the same procedures as Preparation 37 and Example 15 in the order to give 5-(1,1-dioxo-thiomorpholin-4-ylmethyl)-7-nitro-2-phenyl-1H-indole.

(Step 3)
The compound obtained in Step 2 and iron dust were reacted according to the same procedures as Step 3 of Preparation 35, to give the title compound.

EXAMPLE 126

Synthesis of [5-(1,1-dioxo-thiomorpolin-4-ylmethyl)-2-phenyl-1H-indol-7-yl]-(tetrahydropyran-4-yl)-amine

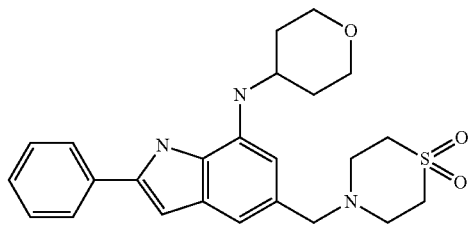

[5-(1,1-Dioxo-1lambda*6*-thiomorphalin-4-ylmethyl)-2-phenyl-1H-indol-7-yl]-(tetrahydro-pyran-4yl)-amine The compound obtained in Preparation 62 and tetrahydropyran-4-one were reacted according to the same procedures as Preparation 36 to give the title compound.

$^1$H-NMR (500 MHz, CDCl$_3$); δ 8.38 (br s, 1H), 7.69 (d, J=7.3 Hz, 1H), 7.44 (t, J=7.3 Hz, 2H), 7.32 (t, J=7.3 Hz, 1H), 7.00 (s, 1H), 6.75 (d, J=1.85 Hz, 1H), 6.47 (d, J=1.85 Hz, 1H), 4.07 (m, 2H), 3.65 (m, 3H), 3.57 (m, 2H), 3.02 (m, 8H), 2.12 (m, 2H), 1.61 (m, 2H)

EXAMPLE 127-138

The indole compound prepared by the method disclosed in Preparations 59, the commercially available amine compounds and carbonyl compounds were reacted according to the same procedures as Preparation 62 and Example 126 in the order to give following exemplary compounds in the table.

| Example | R2 | R1 | R4' | $^1$H-NMR |
|---|---|---|---|---|
| 127 | H | (tetrahydropyran-4-yl)methyl | 1,1-dioxo-thiomorpholin-4-yl | (500 MHz, CDCl$_3$); δ 8.54 (br s, 1H), 7.67 (d, J = 7.3 Hz, 1H), 7.43 (t, J = 7.3 Hz, 2H), 7.32 (t, J = 7.3 Hz, 1H, 6.98 (s, 1H), 6.75 (d, J = 1.85 Hz, 1H), 6.42 (d, J = 1.85 Hz, 1H), 4.07 (m, 2H), 3.67 (s, 2H), 3.46 (m, 2H), 3.19 (m, 2H), 3.04 (m, 8H), 1.97 (m, 1H), 1.80 (m, 2H), 1.50 (m, 2H) |
| 128 | H | (tetrahydropyran-4-yl)methyl | 1,1-dioxo-thiomorpholin-4-yl | (400 MHz, DMSO-d$_6$); δ 7.78 (d, 2H), 7.45 (t, 2H), 7.30 (t, 1H), 6.75 (s, 1H), 6.46 (d, 1H), 6.07 (d, 1H), 3.37 (t, 2H), 3.36 (t, 1H), 2.90 (d, 2H), 2.45 (t, 2H), 2.20 (t, 2H), 2.03 (t, 2H), 1.09 (t, 2H) |
| 129 | H | Tetrahydropyran-4-yl | 2-oxo-piperazin-4-yl | (400 MHz, DMSO-d$_6$); δ 11.04 (s, 1H), 7.82 (d, 2H), 7.50 (t, 2H), 7.34 (t, 1H), 6.89 (s, 1H), 6.83 (s, 1H), 6.39 (s, 1H), 3.74 (m, 1H), 3.61 (br s, 4H), 3.41 (m, 2H), 3.29 (br s, 4H), 3.18 (s, 2H), 3.12 (m, 2H), 2.24 (d, 2H), 1.66 (m, 2H) |
| 130 | H | 1-(tetrahydrofuran-3-yl)carbonyl-piperidin-4-yl | 1,1-dioxo-thiomorpholin-4-yl | (500 MHz, DMSO-d$_6$); δ 10.87 (s, 1H), 7.75 (d, 2H), 7.43 (t, 2H), 7.27 (t, 1H), 6.72 (s, 2H), 6.29 (s, 1H), 5.30 (d, 1H), 4.27 (d, 1H), 3.95 (d, 1H), 3.86 (m, 1H), 3.68 (m, 4H), 3.59 (s, 2H), 3.37 (m, 1H), 3.27 (m, 1H), 3.06 (m, 4H), 2.92 (m, 1H), 2.84 (m, 4H), 2.02 (m, 4H), 1.29 (m, 2H) |
| 131 | 4-AcNH— | Tetrahydropyran-4-yl | 1,1-dioxo-thiomorpholin-4-yl | (400 MHz, MeOH-d$_4$/CDCl$_3$); δ 9.28 (s, 1H), 7.55 (d, J = 4 hz, 2H), 7.47 (d, J = 4 Hz, 2H), 7.37 (s, 1H), 6.94 (s, 1H), 6.63 (s, 1H), 6.42 (s, 1H), 4.10 (m, 2H), 3.58~3.69 (m, 5H), 3.02 (m, 8H), 2.17 (s, 3H), 2.12 (m, 2H), 1.58 (m, 3H) |
| 132 | 4-AcNH— | Cyclopentyl | 1,1-dioxo-thiomorpholin-4-yl | (400 MHz, MeOH-d$_4$/CDCl$_3$); δ 9.08 (s, 1H), 7.48 (d, J = 8 Hz, 2H), 7.39 (dd, J1 = 8 Hz, J2 = 4 Hz, 2H), 6.89 (s, 1H), 6.60 (d, J = 4 |

-continued

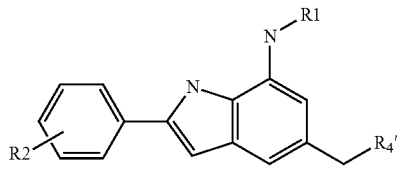

| Example | R2 | R1 | R4' | ¹H-NMR |
|---|---|---|---|---|
| 133 | 4-AcNH— | (tetrahydropyran-4-yl)methyl | 1,1-dioxo-thiomorpholin-4-yl | Hz, 1H), 3.96 (m, 1H), 3.67 (s, 2H), 3.00 (m, 8H), 2.18 (s, 3H), 2.06 (m, 2H), 1.26~1.77 (m, 6H)<br>(400 MHz, MeOH-d₄/CDCl₃); δ 8.95 (s, 1H), 7.57 (d, J = 4 Hz, 2H), 7.49 (d, J = 4 Hz, 2H), 7.33 (s, 1H), 7.00 (s, 1H), 6.65 (s, 1H), 6.40 (s, 1H), 4.02 (m, 4H), 3.74 (s, 2H), 3.42 (t, 2H), 3.17 (d, J = 4 Hz, 2H), 3.02 (m, 8H), 2.21 (s, 3H), 1.97 (m, 1H), 1.78 (m, 2H), 1.47 (m, 2H) |
| 134 | 4-MeO— | Cyclopentyl | 1,1-dioxo-thiomorpholin-4-yl | (400 MHz, DMSO-d₆); δ 10.85 (s, 1H), 7.73 (d, 2H), 7.05 (d, 2H), 6.71 (s, 1H), 6.61 (d, 1H), 6.24 (s, 1H), 5.40 (d, 1H), 3.90 (m, 1H), 3.82 (s, 3H), 3.64 (s, 1H), 3.10 (m, 4H), 2.89 (m, 4H), 2.05 (m, 2H), 1.77 (m, 2H), 1.64 (m, 2H), 1.58 (m, 2H) |
| 135 | 4-MeO— | Tetrahydropyran-4-yl | 1,1-dioxo-thiomorpholin-4-yl | (500 MHz, DMSO-d₆); δ 10.79 (s, 1H), 7.67 (d, 2H), 7.01 (d, 2H), 6.68 (s, 1H), 6.57 (s, 1H), 6.24 (s, 1H), 5.26 (d, 1H), 3.90 (m, 2H), 3.77 (s, 3H), 3.61 (m, 1H), 3.58 (s, 2H), 3.46 (t, 2H), 3.33 (m, 1H), 3.04 (m, 4H), 2.83 (m, 4H), 2.01 (d, 2H), 10.42 (m, 2H) |
| 136 | 4-MeO— | isopentyl | 1,1-dioxo-thiomorpholin-4-yl | (400 MHz, CDCl₃); δ 8.33 (s, 1H), 7.67 (d, 2H), 7.43 (t, 2H), 7.31 (t, 1H), 6.98 (s, 1H), 6.75 (s, 1H), 6.47 (s, 1H), 3.68 (s, 1H), 3.28 (t, 2H), 3.03 (m, 8H), 2.63 (s, 1H), 1.82 (m, 1H), 1.65 (m, 2H), 1.00 (d, 6H) |
| 137 | 3-F— | Tetrahydropyran-4-yl | 1,1-dioxo-thiomorpholin-4-yl | (400 MHz, CDCl₃); δ 8.31 (s, 1H), 7.46 (m, 3H), 7.07 (m, 2H), 6.82 (d, 1H), 6.55 (s, 1H), 4.12 (m, 2H), 3.72 (m, 3H), 3.64 (t, 2H), 3.07 (m, 8H), 2.18 (d, 2H), 1.66 (m, 2H) |
| 138 | 3-F— | Cyclopentyl | 1,1-dioxo-thiomorpholin-4-yl | (400 MHz, CDCl₃); δ 8.46 (s, 1H), 7.50 (d, 1H), 7.42 (m, 2H), 7.06 (t, 1H), 7.02 (s, 1H), 6.80 (d, 1H), 6.54 (s, 1H), 4.03 (m, 1H), 3.72 (s, 2H), 3.07 (m, 8H), 2.16 (m, 2H), 1.85 (m, 2H), 1.74 (m, 2H), 1.67 (m, 2H) |

Preparation 63: Synthesis of 3-bromo-5-(1,1-dioxo-thiomorpholin-4-yl)methyl-7-nitro-2-phenyl-1H-indole (Step 1)

5-Methyl-7-nitro-2-phenyl-1H-indole obtained during the process of Example 46 and (BOC)₂O were reacted according to the same procedures as Preparation 23 to give 1-BOC-5-methyl-7-nitro-2-phenyl-indole.

(Step 2)

1-BOC-5-methyl-7-nitro-2-phenyl-indole (3.5 g, 10 mmol) obtained in Step 1 was dissolved in carbon tetrachloride (30 mL), and thereto N-bromosuccinimide (NBS, 2.3 g, 13 mmol) and benzoyl peroxide (100 mg) were added. The mixture was refluxed under stirring for 4 hours at 80° C. And then the mixture was filtered to remove solids, the filtrate was diluted with water and extracted with DCM. The solvent was removed under reduced pressure. The residue was purified by column chromatography to give 1-BOC-3-bromo-5-bromomethyl-7-nitro-2-phenyl-indole (2.3 g, 46%).

(Step 3)

1-BOC-3-bromo-5-bromomethyl-7-nitro-2-phenyl-indole (1.0 g, 2 mmol) obtained in Step 2 was dissolved in DCM (10 mL), and thereto Et3N (560 uL, 4 mmol) and 1,1-dioxo-thiomorpholine (300 mg, 3 mmol) were added. The mixture was stirred for 12 hours at room temperature. At the end of the reaction, added saturated aqueous NH₄Cl solution, extracted with DCM. After drying the extract, the solvent was removed under reduced pressure and the residue was purified by column chromatography to give 1-BOC-3-bromo-5-(1,1-dioxo-thiomorpholine-4-yl)methyl-7-nitro-2-phenyl-1H-indole (825 mg, 78%).

(Step 4)

1-BOC-3-bromo-5-(1,1-dioxo-thiomorpholine-4-yl)methyl-7-nitro-2-phenyl-1H-indole obtained in Step 3 (825 mg, 1.6 mmol) was dissolved in diethylether (5 mL), and then HCl (4M dioxane solution, 5 mL). The reaction solution was stirred for 2 hours at room temperature. At the end of the reaction, removed solvent under reduced pressure and dried to obtain 3-bromo-5-(1,1-dioxo-thiomorpholine-4-yl)methyl-7-nitro-2-phenyl-1H-indole, which was used in the next step without further purification.

Preparation 64: Synthesis of 4-[(3-bromo-7-nitro-2-phenyl-1H-indol-5-yl)methyl]-morpholine 1-BOC-3-bromo-5-bromomethyl-7-nitro-2-phenyl-indole obtained in Step 2 of Preparation 63 and morpholine were reacted to give the title compound, according to the same procedures as Step 3 and 4 of Preparation 63.

EXAMPLE 139

Synthesis of 3-bromo-5-(1,1-dioxo-thiomorpholin-4-ylmethyl)-2-phenyl-1H-indol-7-yl]-(tetrahydropyran-4-yl)-amine

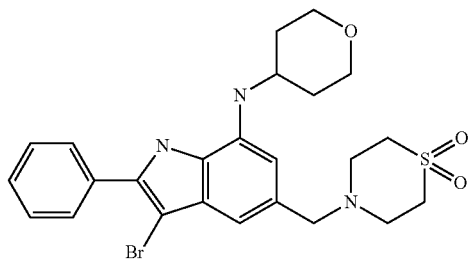

[3-Bromo-5-(1,1-dioxo-1lambda*6*-thiomorpholin-4-ylmethyl)-2-phenyl-1H-indol-7-yl]-(tetrahydro-pyran-4-yl)-amine The compound obtained in Preparation 63 and tetrahydropyran-4-one were reacted according to the same procedures as Step 3 of Preparation 35 and Preparation 36 to give the title compound.

$^1$H-NMR (400 MHz, CDCl$_3$); δ 8.08 (br s, 1H), 7.61 (d, J=8 Hz, 2H), 7.44 (t, 2H), 7.37 (s, 1H), 7.29 (m, 2H), 6.52 (s, 1H), 4.04 (dd, 2H), 3.44 (t, 2H), 3.19 (d, J=4 Hz, 2H), 1.97 (m, 1H), 1.79 (d, J=12 Hz, 2H), 1.41 (m, 2H)

EXAMPLE 140

Synthesis of [3-bromo-(5-morpholin-4-yl)methyl-2-phenyl-1H-indol-7-yl]-(tetrahydropyran-4-yl)-amine

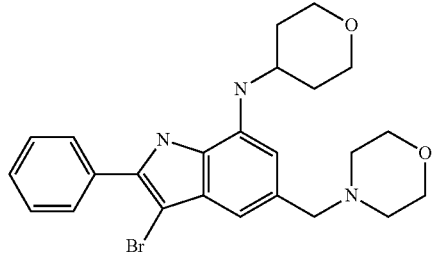

(3-Bromo-5-morpholin-4-ylmethyl-2-phenyl-1H-indol-7-yl)-(tetrahydro-pyran-4-yl)-amine The compound obtained in Preparation 64 and tetrahydropyran-4-one were reacted according to the same procedures as Step 3 of Preparation 35 and Preparation 36 to give the title compound.

$^1$H NMR (500 MHz, DMSO-d$_6$): δ 8.13 (brs, 1H), 7.81 (m, 2H), 7.49 (m, 2H), 7.40 (m, 1H), 7.02 (s, 1H), 6.45 (s, 1H), 4.40 (m, 2H), 3.72 (m, 4H), 3.67 (m, 1H), 3.6~3.53 (m, 4H), 2.48 (m, 4H), 2.10 (m, 2H), 1.56 (m, 4H)

EXAMPLE 141

Synthesis of [3-bromo-5-(1,1-dioxo-thiomorpholin-4-yl methyl)-2-phenyl-1H-indol-7-yl]-cyclopentyl-amine

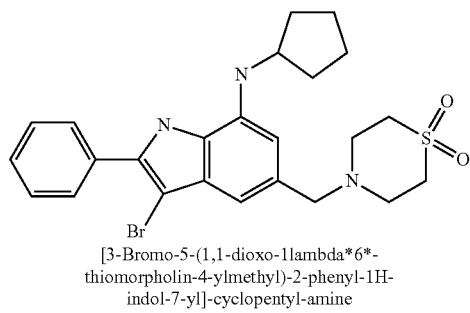 [SMILES: O=S1(=O)CCN(Cc2cc(NC3CCCC3)c3[nH]c(-c4ccccc4)c(Br)c3c2)CC1]

[3-Bromo-5-(1,1-dioxo-1lambda*6*-thiomorpholin-4-ylmethyl)-2-phenyl-1H-indol-7-yl]-cyclopentyl-amine The compound obtained in Preparation 63 and cyclopentanone were reacted according to the same procedures as Step 3 of Preparation 35 and Preparation 36 to give the title compound.

$^1$H-NMR (500 MHz, CDCl$_3$); δ 8.29 (br s, 1H), 7.82 (d, J=7.3 Hz, 1H), 7.49 (t, J=7.3 Hz, 2H), 7.39 (t, J=7.3 Hz, 1H), 6.93 (s, 1H), 6.53 (d, J=1.85 Hz, 1H), 3.95 (m, 1H), 3.70 (s, 2H), 3.02 (m, 8H), 2.10 (m, 2H), 1.77 (m, 2H), 1.68 (m, 2H), 1.56 (m, 2H)

EXAMPLE 142

Synthesis of [3-bromo-5-(1,1-dioxo-thiomorpholin-4-ylmethyl)-2-phenyl-1H-indol-7-yl]-(tetrahydro-pyran-4-ylmethyl)-amine

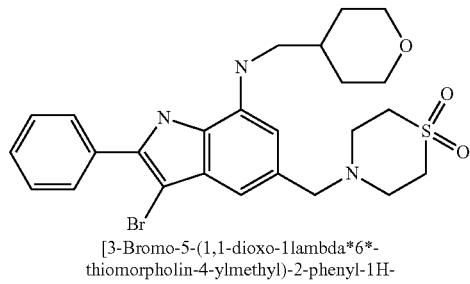

[3-Bromo-5-(1,1-dioxo-1lambda*6*-thiomorpholin-4-ylmethyl)-2-phenyl-1H-indol-7-yl]-(tetrahydro-pyran-4-ylmethyl)-amine The compound obtained in Preparation 63 and tetrahydropyran-4-carboxyaldehyde were reacted according to the same procedures as Step 3 of Preparation 35 and Preparation 36 to give the title compound.

$^1$H-NMR (500 MHz, CDCl$_3$); δ 8.20 (br s, 1H), 7.80 (d, J=7.3 Hz, 1H), 7.49 (t, J=7.3 Hz, 2H), 7.40 (t, J=7.3 Hz, 1H), 6.97 (s, 1H), 6.50 (d, J=1.85 Hz, 1H), 4.03 (m, 2H), 3.71 (s, 2H), 3.42 (m, 2H), 3.18 (m, 2H), 3.03 (m, 8H), 1.94 (m, 1H), 1.78 (m, 2H), 1.47 (m, 2H)

Preparation 65: Synthesis of 5-chloro-3-phenyl-7-nitro-1H-indole (Step 1)

Commercially available 4-chloro-2-nitro-phenylamine (17.4 g, 131.5 mmol) was dissolved in ethanol (300 mL), and thereto silver nitrate (27 g, 157.7 mmol) and iodine (40 g, 157.7 mmol) were added. The mixture was stirred for 8 hours at room temperature. At the end of reaction, the mixture was filtered using celite and washed with 100 ml of ethylacetate and concentrated. To the concentrate, added water and extracted with ethylacetate. The organic layer was washed with saturated sodium chloride solution and dried over anhydrous magnesium sulfate to give 2-amino-5-chloro-3-nitro-phenyliodide (27.4 g, Yield 69%).

$^1$H-NMR (500 MHz, CDCl$_3$); δ 7.94 (s, 1H), 7.75 (s, 1H), 6.48 (br s, 2H), 2.23 (s, 3H)

(Step 2)

2-Amino-5-chloro-3-nitro-phenyliodide (1.5 g, 4.90 mmol) obtained in Step 1 and 1-phenyl-2-trimethylsilylacetylene (4.3 g, 24.50 mmol) were dissolved in DMF (50 mL), and thereto palladium acetate (0.11 g, 0.5 mmol), lithium chloride (0.21 g, 4.90 mmol) and triethylamine (2.48 g, 24.50 mmol) were added. The mixture was heated under stirring for 3 hours at 100° C. At the end of reaction, added water and extracted with ethylacetate. The extract was washed with saturated sodium chloride solution, dried over anhydrous magnesium sulfate and filtered. The solvent was removed under reduced pressure and the residue was separated by column chromatography to give 5-chloro-7-nitro-3-phenyl-2-trimethylsilyl-1H-indole (1.05 g, Yield 87%).

$^1$H-NMR (400 HMz, CDCl$_3$); δ 9.78 (br s, 1H), 8.15 (s, 1H), 7.78 (s, 1H), 7.38~7.48 (m, 5H), 0.26 (s, 9H)

(Step 3)

5-Chloro-7-nitro-3-phenyl-2-trimethylsilyl-1H-indole (1.5 g, 4.35 mmol) obtained in Step 2 was dissolved in tetrahydrofurane (30 mL), and 1 M tetrabutylammoniumfluoride solution (5.2 mL, 5.2 mmol) was added in drops at 0° C. At the end of reaction, the resulting mixture was diluted with water and extracted with ethylacetate. The extract was washed with saturated sodium chloride solution, dried over anhydrous magnesium sulfate and filtered. The solvent was removed under reduced pressure and the residue was separated using column chromatography to give 5-chloro-3-phenyl-7-nitro-1H-indole (1.2 g, Yield 100%).

$^1$H-NMR (400 HMz, CDCl$_3$); δ 10.03 (br s, 1H), 8.24 (d, J=8 Hz, 2H), 7.62 (m, 3H), 7.55 (m, 2H), 7.43 (m, 1H)

EXAMPLE 143

Synthesis of (5-chloro-3-phenyl-1H-indol-7-yl)-(tetrahydro-pyran-4-yl)-amine

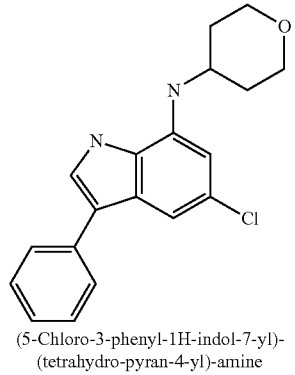 [SMILES: Clc1cc(NC2CCOCC2)c2[nH]cc(-c3ccccc3)c2c1]

(5-Chloro-3-phenyl-1H-indol-7-yl)-
(tetrahydro-pyran-4-yl)-amine

5-Chloro-3-phenyl-7-nitro-1H-indole obtained in Preparation 65 and tetrahydropyran-4-one were reacted according to the same procedures as Step 3 of Preparation 35 and Preparation 36 to give the title compound.

$^1$H-NMR (400 MHz, CDCl$_3$); δ 8.10 (br s, 1H), 7.61 (d, J=8 Hz, 2H), 7.43 (t, 2H), 7.38 (s, 1H), 7.31 (m, 2H), 6.56 (s, 1H), 4.05 (m, 2H), 3.65 (m, 1H), 3.62 (t, 2H), 2.15 (d, J=12 Hz, 2H), 1.62 (m, 5H)

EXAMPLE 144

Synthesis of (5-chloro-3-phenyl-1H-indol-7-yl)-(cyclopentyl)-amine

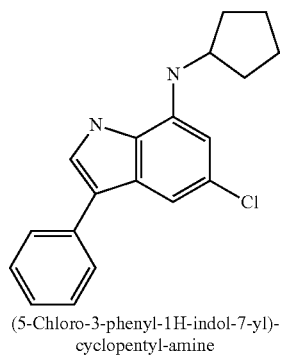 [SMILES: Clc1cc(NC2CCCC2)c2[nH]cc(-c3ccccc3)c2c1]

(5-Chloro-3-phenyl-1H-indol-7-yl)-
cyclopentyl-amine

5-Chloro-3-phenyl-7-nitro-1H-indole obtained in Preparation 65 and cyclopentanone were reacted according to the same procedures as Step 3 of Preparation 35 and Preparation 36 to give the title compound.

$^1$H-NMR (400 MHz, CDCl$_3$); δ 8.06 (br s, 1H), 7.58 (d, J=8 Hz, 2H), 7.39 (t, 2H), 7.33 (s, 1H), 7.26 (m, 1H), 7.17 (s, 1H), 6.51 (s, 1H), 3.91 (m, 1H), 2.08 (m, 2H), 1.74 (m, 2H), 1.66 (m, 2H), 0.54 (m, 2H)

EXAMPLE 145

Synthesis of (5-chloro-3-phenyl-1H-indol-7-yl)-(tetrahydropyran-4-ylmethyl)-amine

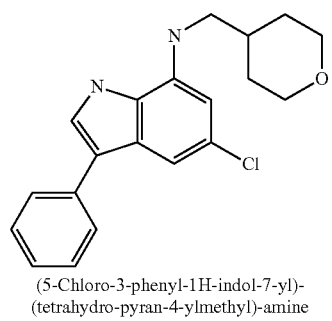 [SMILES: Clc1cc(NCC2CCOCC2)c2[nH]cc(-c3ccccc3)c2c1]

(5-Chloro-3-phenyl-1H-indol-7-yl)-
(tetrahydro-pyran-4-ylmethyl)-amine

5-Chloro-3-phenyl-7-nitro-1H-indole obtained in Preparation 65 and tetrahydropyran-4-carboxylaldehyde were reacted according to the same procedures as Step 3 of Preparation 35 and Preparation 36 to give the title compound.

$^1$H-NMR (400 MHz, CDCl$_3$); δ 8.08 (br s, 1H), 7.61 (d, J=8 Hz, 2H), 7.44 (t, 2H), 7.37 (s, 1H), 7.29 (m, 2H), 6.52 (s, 1H), 4.04 (dd, 2H), 3.44 (t, 2H), 3.19 (d, J=4 Hz, 2H), 1.97 (m, 1H), 1.79 (d, J-12 Hz, 2H), 1.41 (m, 2H)

EXAMPLE 146

Synthesis of [5-(1,1-dioxo-thiomorpholin-4-ylmethyl)-3-phenyl-2-trimethylsilanyl-1H-indol-7-yl]-(tetrahydropyran-4-yl)-amine

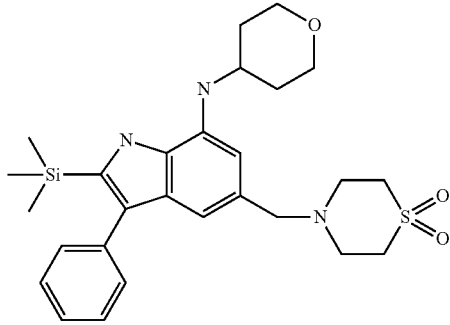

[5-(1,1-Dioxo-1lambda*6*-thiomorpholin-4-ylmethyl)-3-phenyl-2-trimethylsilanyl-1H-indol-7-yl]-(tetrahydro-pyran-4-yl)-amine (Step 1)
4-Amino-3-nitro-benzoic acid ethyl ester and trimethylphenylethynyl-silane were reacted according to the same procedures as Preparation 19 to give 7-nitro-3-phenyl-2-trimethylsilanyl-1H-indole-5-carboxylic acid ethyl ester.

(Step 2)
The compound obtained in Step 1, tetrahydropyran-4-one and 1, 1-dioxo-thiomorpholine were reacted according to Preparation 62 and 36 in the order to give the title compound.
$^1$H-NMR (400 MHz, CDCl$_3$); δ 8.00 (br s, 1H), 7.43 (m, 4H), 7.36 (m, 1H), 6.92 (s, 1H), 6.55 (s, 1H), 4.08 (d, J=12 Hz, 2H), 3.67 (m, 1H), 3.66 (s, 2H), 3.60 (t, 2H), 3.01 (d, 8H), 2.13 (d, J=12 Hz, 2H), 1.64 (m, 2H), Preparation 66: Synthesis of 5-chloro-7-nitro-3-(2-oxo-piperazin-4-yl)methyl-2-phenyl-1H-indole (Step 1)
7-nitro-5-chloro-2-phenyl-1H-indole (1.0 g, 3.67 mmol) obtained in the process of Example 59 was dissolved in dichloromethane (20 mL), and thereto phosphoryloxychloride (0.84 g, 5.50 mmol) and DMF (0.80 g, 11.01 mmol) were added in drops at 0° C. The mixture was stirred at room temperature for 6 hours. At the end of reaction, added saturated aqueous sodium hydrogen carbonate solution to quench the reaction, and extracted with ethylacetate. The extract was washed with saturated sodium chloride solution, dried over anhydrous magnesium sulfate and filtered. The solvent was removed under reduced pressure and the residue was separated by column chromatography to give 5-chloro-3-formyl-7-nitro-2-phenyl-1H-indole (0.5 g, Yield 45%).
$^1$H-NMR (400 HMz, DMSO-d$_6$); δ 9.89 (s, 1H), 8.46 (s, 1H), 7.93 (s, 1H), 7.81 (d, J=9.2 Hz, 2H), 7.53 (m, 3H)

(Step 2)
5-Chloro-3-formyl-7-nitro-2-phenyl-1H-indole (0.5 g, 1.66 mmol) obtained in Step 1 was dissolved in dichloromethane (20 mL), and thereto acetic acid (0.10 g, 1.66 mmol), 2-oxopiperazine (0.3 g, 3.32 mmol) and sodium triacetoxy borohydride (0.71 g, 3.32 mmol) were added in drops. The mixture was stirred at room temperature for 4 hours. At the end of reaction, the mixture was diluted with water, and extracted with dichloromethane. The extract was washed with saturated sodium chloride solution, dried over anhydrous magnesium sulfate and filtered. The solvent was removed under reduced pressure and the residue was separated by column chromatography to give 5-chloro-7-nitro-3-(2-oxo-piperazin-4-yl)methyl-2-phenyl-1H-indole (0.55 g, Yield 86%).
$^1$H-NMR (400 HMzs, DMSO-d$_6$); δ 9.89 (s, 1H), 8.46 (s, 1H), 7.93 (s, 1H), 7.81 (d, J=9.2 Hz, 2H), 7.53 (m, 3H)

EXAMPLE 147

Synthesis of 4-(5-chloro-7-cyclopentylamino-2-phenyl-1H-indol-3-ylmethyl)-piperazin-2-one

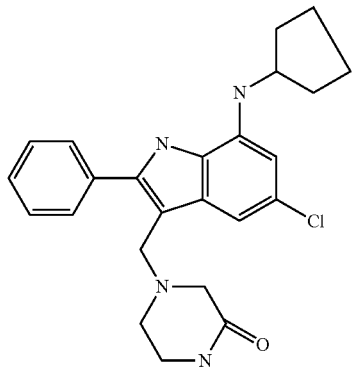

4-(5-Chloro-7-cyclopentylamino-2-phenyl-1H-indol-3-ylmethyl)-piperazin-2-one

The compound obtained in Preparation 66 and cyclopentanone were reacted according to the same procedures as Step 3 of Preparation 35 and Preparation 36 to give the title compounds.
$^1$H-NMR (400 MHz, DMSO-d$_6$); δ 11.07 (s, 1H), 7.82 (d, J=8 Hz, 2H), 7.71 (s, 1H), 7.53 (t, 2H), 7.40 (t, 1H), 6.94 (s, 1H), 6.20 (s, 1H), 5.70 (d, J=8 Hz, 1H), 3.88 (m, 1H), 3.61 (s, 2H), 3.31 (s, 2H), 2.96 (s, 2H), 2.59 (m, 2H), 2.03 (m, 2H), 1.74 (m, 2H), 1.64 (m, 2H), 1.54 (m, 2H)

EXAMPLE 148

Synthesis of 4-[5-chloro-2-phenyl-7-(tetrahydropyran-4-ylamino)-1H-indol-3-ylmethyl]-piperazin-2-one

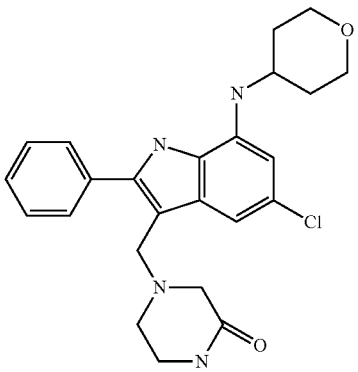

4-[5-Chloro-2-phenyl-7-(tetrahydropyran-4-ylamino)-1H-indol-3-ylmethyl]-piperazin-2-one The compound obtained in Preparation 66 and tetrahydropyran-4-one were reacted according to the same procedures as Step 3 of Preparation 35 and Preparation 36 to give the title compounds.

¹H-NMR (400 MHz, DMSO-d₆); δ 11.09 (s, 1H), 7.83 (d, J=8 Hz, 2H), 7.70 (s, 1H), 7.54 (t, 2H), 7.40 (t, 1H), 6.96 (s, 1H), 6.31 (s, 1H), 5.64 (d, J=8 Hz, 1H), 3.90 (d, J=12 Hz, 2H), 3.62 (m, 1H), 3.61 (s, 3H), 3.50 (m, 2H), 3.31 (s, 2H), 2.96 (s, 2H), 2.59 (s, 2H), 2.00 (d, J=12 Hz, 2H), 1.46 (m, 2H)

EXAMPLE 149

Synthesis of 4-{5-chloro-2-phenyl-7-[(tetrahydropyran-4-ylmethyl)-amino]-1H-indol-3-ylmethyl}-piperazin-2-one

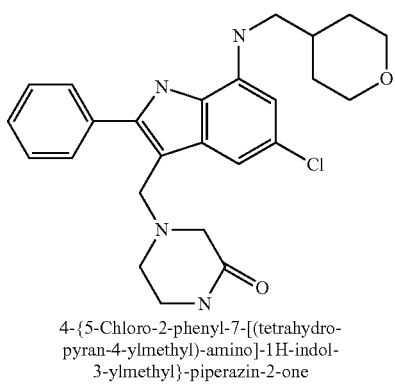 [SMILES: O=C1CN(Cc2c(-c3ccccc3)[nH]c3c(NCC4CCOCC4)cc(Cl)cc23)CCN1]

4-{5-Chloro-2-phenyl-7-[(tetrahydropyran-4-ylmethyl)-amino]-1H-indol-3-ylmethyl}-piperazin-2-one The compound obtained in Preparation 66 and tetrahydropyran-4-carboxyaldehyde were reacted according to the same procedures as Step 3 of Preparation 35 and Preparation 36 to give the title compounds.

¹H-NMR (400 MHz, DMSO-d₆); δ 11.12 (s, 1H), 7.83 (d, J=8 Hz, 2H), 7.71 (s, 1H), 7.54 (t, 2H), 7.40 (t, 1H), 6.96 (s, 1H), 6.21 (s, 1H), 5.73 (m, 1H), 3.91 (d, J=12 Hz, 2H), 3.89 (s, 2H), 3.36 (m, 2H), 3.31 (s, 2H), 3.10 (m, 2H), 2.96 (s, 2H), 2.59 (m, 2H), 1.90 (m, 1H), 1.74 (d, J=12 Hz, 2H), 1.34 (m, 2H)

Preparation 67: Synthesis of 3-(4-methoxy-phenyl-1-yl)-7-nitro-1H-indazole (Step 1)

7-Nitroindazole (1.60 g, 9.80 mmol) was dissolved in DMF (100 mL), and thereto potassium hydroxide (2.20 g, 39.20 mmol) and iodine (4.98 g, 19.61 mmol) were added in drops. The mixture was stirred for 2 hours, and diluted with 10% sodium bisulfite solution. The resulting solid was collected and dried to give 3-iodo-7-nitro-1H-indazole (2.50 g, Yield 88%).

¹H-NMR (400 HMz, CDCl₃); δ 11.49 (br s, 1H), 8.45 (d, J=8 Hz, 7.94 (d, J=8 Hz, 1H), 7.41 (t, 1H)

(Step 2)

3-Iodo-7-nitro-1H-indazole (2.50 g, 8.65 mmol) obtained in Step 1 was dissolved in acetone (50 mL), and thereto potassium hydroxide (0.73 g, 12.97 mmol) and 4-methoxybenzylchloride (1.63 g, 10.38 mmol) were added in drops at 0° C. The mixture was stirred for 2 hours. At the end of reaction, the mixture was diluted with water, and extracted with ethylacetate. The extract was washed with saturated sodium chloride solution, dried over anhydrous magnesium sulfate and filtered. The solvent was removed under reduced pressure and the residue was separated by column chromatography to give 3-iodo-7-nitro-1-(4-methoxybenzyl)-1H-indazole (3.2 g, Yield 91%).

¹H-NMR (400 HMz, CDCl₃); δ 8.08 (d, J=8 Hz, 1H), 7.83 (d, J=8 Hz, 1H), 7.28 (m, 1H), 6.97 (d, J=8 Hz, 1H), 6.75 (d, J=8 Hz, 1H), 5.83 (s, 2H), 3.72 (s, 3H)

(Step 3)

3-Iodo-7-nitro-1-(4-methoxybenzyl)-1H-indazole (1.50 g, 3.67 mmol) obtained in Step 2 was dissolved in dimethoxyethane (20 mL), and thereto sodium carbonate (1.17 g, 11.01 mmol), 4-methoxyphenylboronic acid (0.84 g, 5.50 mmol) and tetrakis(triphenylphosphine)palladium (0) (0.43 g, 0.37 mmol) were added in drops. The mixture was refluxed under stirring for 2 hours. After cooling the solution, the reaction mixture was diluted with water, and extracted with ethylacetate. The extract was washed with saturated sodium chloride solution, dried over anhydrous magnesium sulfate and filtered. The solvent was removed under reduced pressure and the residue was dissolved in trifluoroacetic acid (20 mL) and the resulting solution was refluxed under stirring for 5 hours and then the solvent was removed under reduced pressure. The resulting residue was diluted with water and extracted with ethylacetate. The extract was washed with saturated sodium chloride solution, dried over anhydrous magnesium sulfate and filtered. The solvent was removed under reduced pressure and the residue was separated by column chromatography to give 3-(4-methoxy-phenyl-1-yl)-7-nitro-1H-indazole (0.85 g, Yield 86%).

¹H-NMR (400 HMz, CDCl₃); δ 11.33 (br s, 1H), 8.39 (t, 2H), 7.90 (d, J=8 Hz, 2H), 7.36 (t, 1H), 7.08 (d, J=8 Hz, 2H), 3.91 (s, 3H)

EXAMPLE 150

Synthesis of cyclopentyl-[3-(4-methoxyphenyl)-1H-indazol-7-yl]-amine

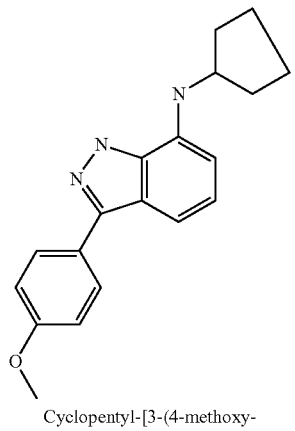

Cyclopentyl-[3-(4-methoxy-phenyl)-1H-indazol-7-yl]-amine

The compound obtained in Preparation 67 and cyclopentanone were reacted according to the same procedures as Step 3 of Preparation 35 and Preparation 36 to give the title compounds.

¹H-NMR (400 MHz, CDCl₃); δ 7.83 (d, J=12 Hz, 2H), 7.31 (d, J=8 Hz, 1H), 7.10 (t, 1H), 7.00 (dd, 2H), 6.53 (d, J=8 Hz, 1H), 3.91 (m, 1H), 3.86 (s, 1H), 2.03 (m, 2H), 1.69 (m, 2H), 1.59 (m, 2H), 1.25 (m, 2H)

EXAMPLE 151

Synthesis of [3-(4-methoxyphenyl)-1H-indazol-7-yl]-(tetrahydropyran-4-yl)-amine

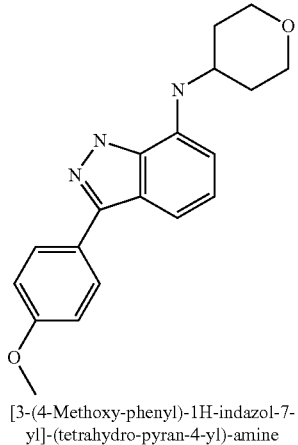 [SMILES: COc1ccc(-c2n[nH]c3c(NC4CCOCC4)cccc23)cc1]

[3-(4-Methoxy-phenyl)-1H-indazol-7-yl]-(tetrahydro-pyran-4-yl)-amine

The compound obtained in Preparation 67 and tetrahydropyran-4-one were reacted according to the same procedures as Step 3 of Preparation 35 and Preparation 36 to give the title compounds.

¹H-NMR (400 MHz, CDCl₃); δ 7.78 (d, J=12 Hz, 2H), 7.24 (d, J=8 Hz, 1H), 7.06 (t, 1H), 6.98 (d, J=8 Hz, 2H), 6.45 (d, J=8 Hz, 1H), 3.93 (m, 2H), 3.86 (s, 1H), 3.46 (t, 2H), 3.44 (m, 1H), 1.92 (d, J=12 Hz, 2H), 1.39 (m, 2H)

EXAMPLE 152

Synthesis of [3-(4-methoxyphenyl)-1H-indazol-7-yl]-(tetrahydropyran-4-ylmethyl)-amine

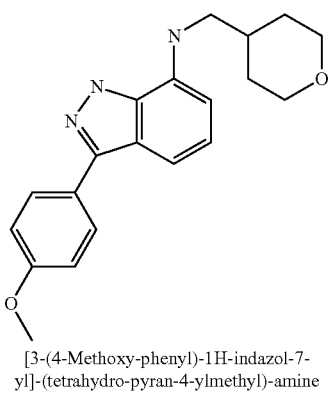 [SMILES: COc1ccc(-c2n[nH]c3c(NCC4CCOCC4)cccc23)cc1]

[3-(4-Methoxy-phenyl)-1H-indazol-7-yl]-(tetrahydro-pyran-4-ylmethyl)-amine

The compound obtained in Preparation 67 and tetrahydropyran-4-carboxyaldehyde were reacted according to the same procedures as Step 3 of Preparation 35 and Preparation 36 to give the title compounds.

¹H-NMR (400 MHz, CDCl₃); δ 7.78 (d, J=8 Hz, 2H), 7.29 (d, J=8 Hz, 1H), 7.07 (t, 1H), 6.97 (d, J=8 Hz, 2H), 6.45 (d, J=8 Hz, 1H), 3.89 (m, 2H), 3.86 (s, 1H), 3.24 (t, 2H), 3.04 (d, J=8 Hz, 2H), 1.73 (m, 1H), 1.57 (d, J=12 Hz, 2H), 1.30 (m, 2H)

EXPERIMENTAL EXAMPLES

Hereinafter, the effects provided by the present invention will be explained through the following experimental examples. However, the effects of the present invention are not limited to those exemplified by the following experimental examples.

Experimental Example 1

Hepatocyte-Protecting Effect

If cells are isolated from in vivo environment and their culture or preservation in vitro is begun, it would act as a stress to cells, and the apoptosis mechanism would begin to work. For preservation of organs or tissues, it is necessary to protect them from such a primary stress.

In order to verify this, primary hepatocytes isolated from rats were treated with the compounds of the working examples to observe how well the compounds can protect them from a primary stress. Primary hepatocytes were isolated using the Seglen PO method (Experimental Cell Research 74 (1972) pp. 450-454). Briefly, hepatocytes were isolated according to the two-step collagenase perfusion method and then centrifuged using percoll gradient (Kreamer BL etc., In Vitro Cellular & Developmental Biology 22 (1986) pp. 201-211) at low speed (500 rpm) for 10 minutes to remove dead cells. Viability of hepatocytes was maintained at 90% or more. Cells were suspended in HepatoZYME media (Gibco BRL) and counted. $1.5 \times 10^4$ cells of 100 μl were put into a 96-well plate (BD biocoat) coated with collagen and attached to the bottom for 3-4 hours. Then, as shown in FIG. 1, a caspase inhibitor, IDN6556 (Liver Transplantation (2003) 9: pp. 278-284), and the compound of Example 21 were treated at a concentration of 1 or 10 μM. After 24, 72 or 144 hours, cell viability was measured to evaluate a hepatocyte-protecting effect.

Cell viability was measured by the optical density at 440 nm according to the WST-1 method (MK-400, Takeda). As shown in FIG. 1, viability declined rapidly in the control group which had been treated with only DMSO. In contrast, IDN6556 maintained viability after 72 hours up to about 50%, compared with viability after 24 hours, and the compound of Example 21 maintained viability after 144 hours up to 80% or more, compared with viability after 24 hours.

Experimental Example 2

Cell-Protecting Effect Against Cold Shock

In order to reproduce a condition for preservation prior to organ transplantation, primary cultured hepatocytes were prepared according to Experimental Example 1 and treated with the compounds of the working examples at 9 different concentrations that had been prepared by 3-fold serial dilution method using a starting concentration of 25 μM. The mixture was cultured at 37° C. for 1 hour, stored at 4° C. for 22 hours, and then transferred into an incubator at 37° C. and cultured therein. Cell viability was measured by the optical density at 440 nm according to the WST-1 method (MK-400, Takeda), and $IC_{50}$ (unit: μM) was obtained using prism software (see Table 1).

TABLE 1

| Example | ($IC_{50}$, μM) |
|---|---|
| 5 | <0.12 |
| 7 | <0.4 |
| 16 | 3.56 |
| 17 | <0.12 |
| 21 | <0.12 |
| 22 | 0.97 |
| 24 | <0.12 |
| 29 | 1.46 |
| 30 | <0.12 |
| 32 | <0.12 |
| 38 | <0.12 |
| 40 | <0.12 |
| 47 | <0.12 |
| 51 | 0.26 |
| 56 | 0.20 |
| 58 | <0.12 |
| 75 | <0.12 |
| 76 | <0.12 |
| 77 | 0.710 |
| 83 | 0.729 |
| 89 | 0.543 |
| 90 | 1.02 |
| 91 | 5.750 |
| 106 | 0.750 |
| 120 | 0.821 |
| 121 | 0.419 |
| 126 | 0.248 |
| 127 | 0.668 |
| 132 | 2.874 |
| 133 | 0.571 |
| 134 | 0.437 |
| 135 | 0.39 |
| 136 | 0.585 |
| 137 | 0.158 |
| 138 | 0.216 |
| 142 | 0.300 |
| 146 | 0.603 |

Figure 2:
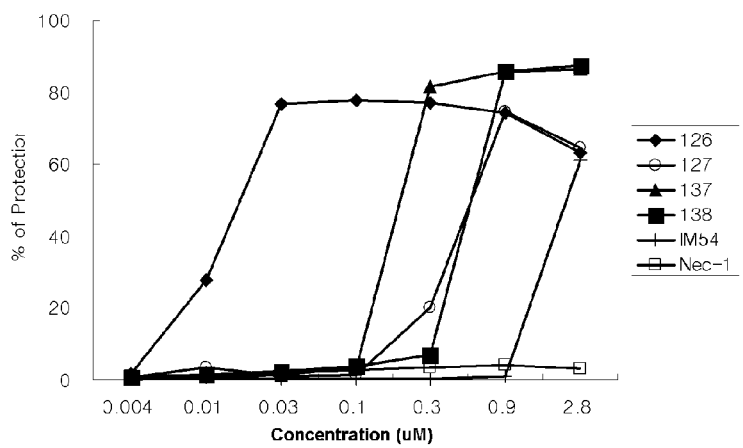
FIG. 2 illustrates a recovery capacity of the compounds of Examples 126, 127, 137 and 138 according to the present invention in lung cell LB-HEL at 37° C. with the passage of time after cold shock for 24 hours, compared with the control drugs, IM54 and nec-1.

The same results as above were also obtained in other types of cells such as human embryonic lung cell line (LB-HEL) as well as hepatocytes (see FIG. 2 and Table 2). More specifically, LB-HEL cells were plated at $1.5 \times 10^6$ cells/well using DMEM medium (Gibco BRL) and treated with DMSO, nec-1, IM-54 or the compounds of Examples 126, 127, 137 and 138 at indicated concentrations. After storage at 4° C. for 24 hours, the mixture was transferred into an incubator at 37° C. and cultured therein. In order to verify recovery capacity at 37° C., cell viability after 24 hours post-transfer was measured by the optical density at 440 nm according to the WST-1 method (MK-400, Takeda) and compared with cell viability prior to cold shock (FIG. 2). The compounds of Examples 126, 127, 137 and 138 exhibited a protecting effect against cold shock. However, neither nec-1, which inhibits necropoptosis (Nat Chem. Biol. (2005) 1:112-119), nor IDN6556, which inhibits apoptosis (pan-caspase inhibitor), exhibited a significant protecting effect.

These results support the fact that the compounds of the present invention exhibit a remarkable effect in preventing and protecting injury caused by cold shock and re-warming that necessarily occurs during organ transplantation or cell preservation.

TABLE 2

| Example | ($IC_{50}$, μM) |
|---|---|
| 77 | 2.600 |
| 78 | 3.420 |
| 79 | 3.299 |
| 83 | 3.664 |
| 84 | 7.108 |
| 91 | 0.664 |
| 92 | 2.123 |
| 93 | 0.530 |
| 94 | 0.200 |
| 95 | <0.1 |
| 96 | <0.1 |
| 97 | <0.1 |
| 98 | <0.1 |
| 99 | 0.097 |
| 100 | 0.532 |
| 101 | 0.345 |
| 109 | <0.1 |
| 110 | <0.1 |
| 111 | <0.1 |
| 112 | 0.043 |
| 113 | 0.294 |
| 114 | 0.580 |
| 116 | 1.180 |
| 118 | 0.400 |
| 119 | 0.418 |
| 120 | 4.145 |
| 121 | 0.462 |
| 122 | 0.240 |
| 123 | 0.130 |
| 124 | 0.400 |
| 126 | <0.1 |
| 127 | 0.042 |
| 128 | 0.056 |
| 134 | 0.664 |
| 135 | 0.344 |
| 136 | 0.775 |
| 139 | <0.1 |
| 140 | <0.1 |
| 141 | <0.1 |
| 142 | <0.1 |
| 143 | <0.1 |
| 144 | <0.1 |
| 145 | <0.1 |
| 146 | 0.823 |
| 147 | 1.076 |
| 148 | 2.349 |
| 149 | 1.451 |
| 150 | 0.21 |
| 151 | 0.384 |
| 152 | 0.59 |
| 138 | 0.473 |
| 137 | 0.071 |

Experimental Example 3

Protecting Effect Against Cold Preservation Injury in Rat-Isolated Perfusion Liver Model In order to verify an organ preservation effect, rat-isolated perfusion liver model was used to evaluate a protecting effect of the compounds of the working examples against cold preservation injury. A white rat was anesthetized by intraperitoneal injection of sodium pentobarbital (50 mg/kg) and administered with heparin (500 U/kg) by intravenous injection to prevent blood coagulation. After incising the abdominal median line, in order to measure bile output, polyethylene tube-10 was inserted into the bile duct, and the coronary vein was tied. Polyethylene tube-190 was inserted into the hepatic portal vein, and a perfusate, Krebs-Henseleit bicarbonate buffer (KHBB) (at pH 7.4 at 37° C.) was perfused at a rate of 4 mL/min/g. In order to prevent liver expansion caused by the perfusate, the inferior vena cava was opened, and then the liver was isolated from the surrounding tissues. During the perfusion, a mixed gas ($O_2$ 95% and $CO_2$ 5%) was continuously injected to KHBB to supply oxygen. The isolated liver was perfused with KHBB for 5 minutes for stabilization, and then 10 mL of histidine-tryptophan-ketoglutarate (HTK) (at 4° C.) was flushed to remove KHBB. The control group and the test groups were preserved at 4° C.: the former in 60 mL of HTK solution and the latter in 60 mL of HTK solution to which the compound of Example 126 at a concentration of 30 µM was added.

Figure 3:
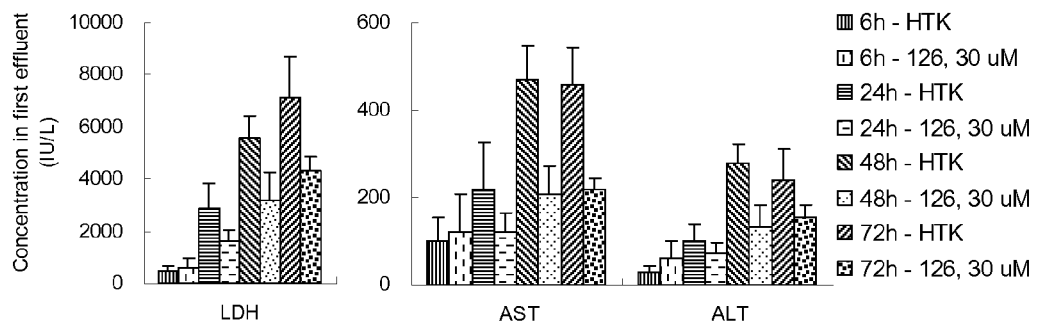
FIG. 3 illustrates a protecting effect of the compound of Example 126 according to the present invention against cold preservation injury in rat-isolated perfusion liver model, compared with the conventional preservation solution, HTK solution, through the measurement of LDH, AST and ALT activity.

In order to observe a preservation effect of the test substances depending on the cold preservation period, the isolated liver was preserved in cold storage condition (4° C.) for 6, 24, 48 and 72 hours, and 10 mL of HTK (4° C.) was flushed into the hepatic portal vein. Perfusate released at that moment was collected and measured for liver damage markers, Lactate Dehydrogenase (LDH), Aspartate Aminotransferase (AST) and Alanine Aminotransferase (ALT) activity (FIG. 3). LDH, ALT and AST activity in the perfusate was measured according to the standard absorption analysis method using a biochemical automatic analyzer, Hitachi 7150.

Experimental Example 4

Protecting Effect Against Cold Ischemia/Warm Reperfusion Injury in Rat-Isolated Perfusion Liver Model In order to verify a protecting effect against ischemia and reperfusion injury that necessarily occurs during organ transplantation, the rat-isolated perfusion liver model of Experimental Example 3 was used to evaluate the protecting effect of the compounds of the working examples. As in Experimental Example 3, the isolated liver was perfused with KHBB for 5 minutes for stabilization, and then 10 mL of histidine-tryptophan-ketoglutarate (HTK) (at 4° C.) was flushed to remove KHBB. The control group and the treatment group were preserved at 4° C.: the former in 60 mL of HTK solution and the latter in 60 mL of HTK solution to which the compound of Example 126 at a concentration of 30 µM was added. After 24 hours post-cold preservation, the isolated liver was connected to a liver perfusion apparatus that maintains 37° C., and then KHBB (at pH 7.4 at 37° C.) was reperfused through the hepatic portal vein at a rate of 4 mL/min/g for 80 minutes. For the IPRL group without cold preservation, the isolated liver was not stored in HTK but immediately perfused with KHBB for 2 hours.

Figure 4:
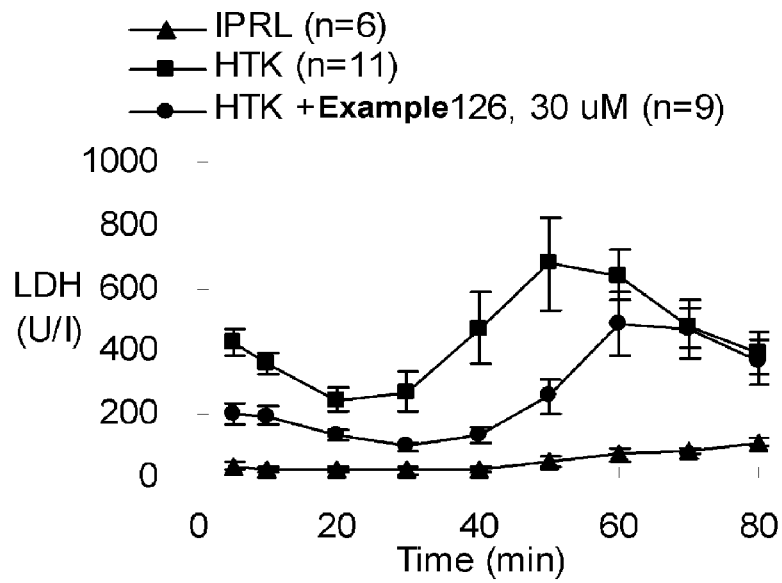
FIG. 4 illustrates a protecting effect of the compound of Example 126 according to the present invention against cold ischemia and warm reperfusion injury in rat-isolated perfusion liver model, compared with the conventional preservation solution, HTK solution, through the measurement of LDH activity.
Figure 5:
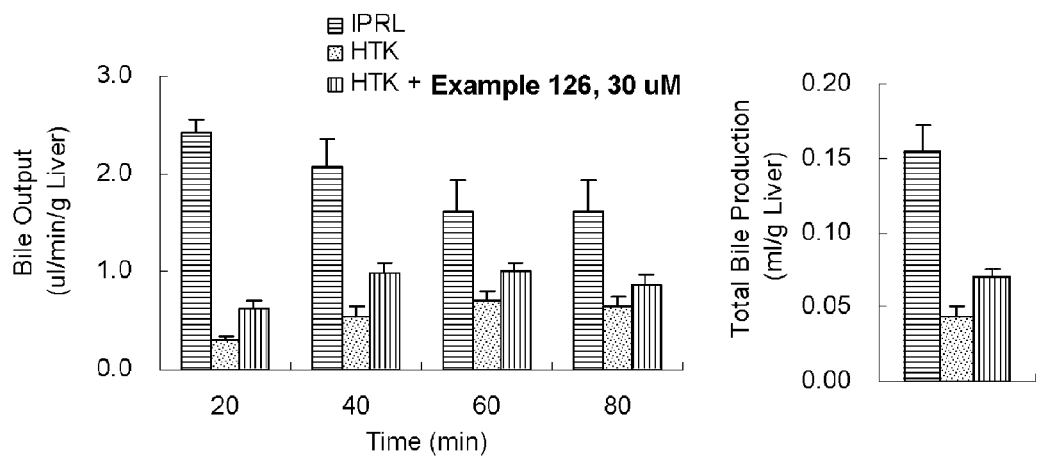
FIG. 5 illustrates a protecting effect of the compound of Example 126 according to the present invention against cold ischemia/warm reperfusion injury in rat-isolated perfusion

In order to observe a protecting effect against ischemia and reperfusion injury, bile output and perfusate's LDH activity were measured. KHBB perfusate released from liver at 5, 10, 20, 30, 40, 50, 60, 70 and 80 minutes after reperfusion was collected, and LDH activity in the perfusate was measured using a biochemical automatic analyzer, Hitachi 7150 (FIG. 4). Bile secreted through the polyethylene tube which had been inserted into the bile duct at 0~20, 20~40, 40~60 and 60~80 minutes after reperfusion was collected, and bile output was measured (FIG. 5).

The results of measurement of activity of LDH that was released through perfusate by reperfusion after 24-hour cold preservation of the isolated liver are as follows. LDH activity in the perfusate of the IPRL group without cold preservation was about 20~110 U/L for 80 minutes of reperfusion, which is the lowest LDH activity during reperfusion. However, LDH activity in the perfusate of the HTK group with cold preservation in HTK solution for 24 hours was about 250~680 U/L level for 80 minutes of reperfusion, which means that LDH activity was outstandingly increased, compared with the IPRL group during the time of reperfusion. In contrast, the treatment group with 30 µM of a test drug, the compound of Example 126, inhibited LDH activity in the perfusate by 50~70% until 50 minutes of reperfusion, compared with the HTK group, and significantly inhibited liver cell damage caused by cold preservation and reperfusion (FIG. 4).

In the IPRL group without cold preservation, bile was secreted at a rate of 1.61~2.40 µl/min/g at 0~20, 20~40, 40~60 and 60~80 minutes of perfusion, and thus the total amount of bile output was 0.154±0.017 ml/g liver for 80 minutes of reperfusion. However, the total amount of bile output of the HTK group with cold preservation for 24 hours was 0.044±0.006 ml/g liver, which means that bile output was substantially decreased by 70% or more, compared with the IPRL group. The total amount of bile output of the treatment group with 30 µM of the compound of Example 126 was 0.070±0.006 ml/g liver, which means that the compound significantly inhibited decline of bile output caused by cold preservation and reperfusion (FIG. 5).

INDUSTRIAL APPLICABILITY

If the results herein are put together, it could be understood that the compounds of the present invention can prevent necrocytosis of organs caused by reperfusion after cold storage and inhibit a decline of their function. Thus, the compounds of the present invention are considered to exhibit a remarkable effect as a preservative in the organ transplantation process.

The invention claimed is:

1. A method for preserving cells, tissues or organs using a composition comprising a compound of the following formula (1) or a pharmaceutically acceptable salt or stereoisomer thereof

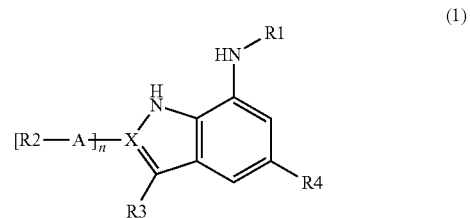

wherein

X represents C or N, n is 0 or 1, and n is 1 when X is C and n is 0 when X is N, A represents a direct bond, $C_3$-$C_8$-cycloalkyl, phenyl, or 5~6-membered heteroaryl or heterocycle, each of which includes 1~3 heteroatoms selected from N, O and S atoms, R1 represents hydrogen, —C(O)—B—X'—R7 or —(CR5R6)$_m$-B—X'—R7, m is an integer of 0 to 4, each of R5 and R6 independently represents hydrogen or $C_1$-$C_5$-alkyl, B represents a direct bond, $C_3$-$C_8$-cycloalkyl optionally containing oxo, or 3~10-membered heterocycle or heteroaryl, each of which includes 1~3 heteroatoms selected from O, S and N atoms, X' represents a direct bond, —C(O)—, —$SO_2$—, —$CO_2$— or —C(O)NR5—, R7 represents hydrogen, $C_1$-$C_6$-alkyl, halogeno-$C_1$-$C_6$-alkyl, halogen, (CR5R6)$_m$-phenyl, (CR5R6)$_m$-hydroxy or (CR5R6)$_m$-heterocycle where the heterocycle optionally contains oxo and is a 3~10-membered ring including 1-3 heteroatoms selected from N, O and S atoms, R2 represents —(CR5R6)$_m$-D-X"—R8, D represents a direct bond or a 3~10-membered heterocycle or heteroaryl, each of which optionally contains oxo and is optionally fused, and includes 1~4 heteroatoms selected from N, O and S atoms, X" represents a direct bond, —C(O)—, —C(O)O—, —NR5C(O)—, —C(O)NR5- or —O—, R8 represents hydrogen, halogen, $C_1$-$C_6$-alkyl, halogeno-$C_1$-$C_6$-alkyl, tri($C_1$-$C_6$-alkyl)silane or hydroxy-$C_1$-$C_6$-alkyl, R3 represents hydrogen, halogen, cyano, nitro, aryl-R9 or (CR5R6)$_m$-D-R9, R9 represents hydrogen, halogen, $C_1$-$C_6$-alkyl, cyano, nitro or $C_1$-$C_6$-alkoxy, R4 represents —(CR5R6)$_m$-Y-D-R10, Y represents a direct bond, —C(O)O— or —O—, and R10 represents hydrogen, nitro, halogen, $C_1$-$C_6$-alkyl, carboxy-$C_1$-$C_6$-alkyl, aryl or —C(O)O—R5, wherein each of said alkyl, alkoxy, aryl, cycloalkyl, heterocycle and heteroaryl is optionally substituted with one or more substituents selected from the group consisting of hydroxy, halogen, nitrile, amino, $C_1$-$C_6$-alkylamino, di($C_1$-$C_6$-alkyl)amino, $C_1$-$C_6$-alkyl, halogeno-$C_1$-$C_6$-alkyl, $C_1$-$C_6$-alkylsulfonyl, aryl-$C_1$-$C_6$-alkoxy and oxo.

2. The method according to claim 1, wherein

X represents C or N, n is 0 or 1, and n is 1 when X is C and n is 0 when X is N, A represents a direct bond, phenyl, or 5~6-membered heteroaryl or heterocycle, each of which includes 1~3 heteroatoms selected from N, O and S atoms, R1 represents hydrogen, —C(O)—B—X'—R7 or —(CR5R6)$_m$-B—X'—R7, m is an integer of 0 to 2, each of R5 and R6 independently represents hydrogen or $C_1$-$C_5$-alkyl, B represents a direct bond, $C_4$-$C_2$-cycloalkyl optionally containing oxo, or 4~8-membered heterocycle or heteroaryl, each of which includes 1~3 heteroatoms selected from O, S and N atoms, X' represents a direct bond, —C(O)—, —SO$_2$—, —CO$_2$— or —C(O)NH—, R7 represents hydrogen, $C_1$-$C_6$-alkyl, halogeno-$C_1$-$C_6$-alkyl, halogen, (CR5R6)$_m$-phenyl, (CR5R6)$_m$-hydroxy or (CR5R6)$_m$-heterocycle where the heterocycle optionally contains oxo and is a 4~8-membered ring including 1~3 heteroatoms selected from N, O and S atoms, R2 represents —(CR5R6)$_m$-D-X"—R8, D represents a direct bond or a 4~8-membered heterocycle or heteroaryl, each of which optionally contains oxo and is optionally fused, and includes 1~4 heteroatoms selected from N, O and S atoms, X" represents —C(O)—, —C(O)O—, —NR5C(O)—, —C(O)NR5- or —O—, R8 represents hydrogen, halogen, $C_1$-$C_6$-alkyl, halogeno-$C_1$-$C_6$-alkyl, tri($C_1$-$C_6$-alkyl)silane or hydroxy-$C_1$-$C_6$-alkyl, R3 represents hydrogen, halogen, cyano, nitro, aryl-R9 or (CR5R6)$_m$-D-R9, R9 represents hydrogen, halogen, $C_1$-$C_6$-alkyl, cyano, nitro or $C_1$-$C_6$-alkoxy, R4 represents —(CR5R6)$_m$-Y-D-R10, Y represents a direct bond, —C(O)O— or —O—, and R10 represents hydrogen, nitro, halogen, $C_1$-$C_6$-alkyl, carboxy-$C_1$-$C_6$-alkyl, aryl or —C(O)O—R5.

3. The method according to claim 2, wherein the compound of the formula (1) has an indole structure of the following formula (1a) or an indazole structure of the following formula (1b):

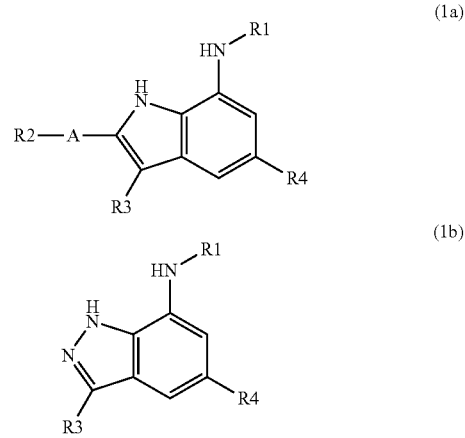

4. The method according to claim 2, wherein A is selected from the group consisting of phenyl, pyridine, 1,4-pyrazine, 4,5-dihydro-thiazole, thiazole, 4,5-dihydrooxazole, [1,2,4]oxadiazole and [1,3,4]oxadiazole.

5. The method according to claim 2, wherein R1 represents —C(O)—B—X'—R7 or —(CHR5)$_m$-B—X'—R7 where m is an integer of 0 to 2; R5 represents $C_1$-$C_3$-alkyl; B represents a direct bond, $C_5$-$C_6$-cycloalkyl optionally containing oxo, or 5~6-membered heterocycle or heteroaryl, each of which includes 1-3 heteroatoms selected from O, S and N atoms; X' represents a direct bond, —C(O)—, —SO$_2$—, —CO$_2$— or —C(O)NH—; and R7 represents hydrogen, $C_1$-$C_3$-alkyl, halogeno-$C_1$-$C_3$-alkyl, halogen, (CH$_2$)$_m$-phenyl, (CH$_2$)$_m$-hydroxy or (CH$_2$)$_m$-heterocycle where the heterocycle optionally contains oxo and is a 5~6-membered ring including 1~3 heteroatoms selected from N, O and S atoms.

6. The method according to claim 5, wherein B is selected from the group consisting of cyclopentyl, cyclohexyl, piperidine, tetrahydropyran, oxocyclohexyl, pyrrolidine, difluorocyclohexyl and tetrahydrofuran.

7. The method according to claim 5, wherein R7 is selected from the group consisting of hydrogen, methyl, ethyl, isopropyl, benzyl, hydroxymethyl, (morpholine-4-yl)-ethyl, tetrahydrofuran, 2,2,2-trifluoroethyl, hydroxyethyl, 1,1-dioxothiomorpholine, tetrahydropyran, (tetrahydropyran-4-yl)-methyl and trifluoromethyl.

8. The method according to claim 2, wherein D represents a direct bond, or is selected from the group consisting of piperazine, pyrrolidine, morpholine, 1,1-dioxothiomorpholine and oxopiperazine.

9. The method according to claim 2, wherein R8 is selected from the group consisting of hydrogen, ethyl, hydroxymethyl, methyl and fluorine.

10. The method according to claim 2, wherein R3 represents hydrogen; halogen; phenyl optionally substituted with alkoxy; or 6-membered heterocyclylmethyl including 1~3 heteroatoms selected from N, S and O atoms as ring members and optionally containing oxo.

11. The method according to claim 10, wherein R3 is selected from the group consisting of hydrogen, bromine, phenyl, methoxy-phenyl, morpholine-4-yl-methyl, oxopiperazine-4-yl-methyl and 1,1-dioxo-thiomorpholine-4-yl-methyl.

12. The method according to claim 2, wherein R4 represents —(CH$_2$)$_m$—Y-D-R10 where m is an integer of 0 to 2; Y represents a direct bond, —C(O)O— or —O—; D represents pyridine or 5~6-membered heterocycle including 1~3 heteroatoms selected from N, S and O atoms and optionally containing oxo; and R10 represents hydrogen, halogen, C$_1$-C$_3$-alkyl, —(CH$_2$)—CO$_2$H, aryl or —C(O)O—R5.

13. The method according to claim 12, wherein D is selected from the group consisting of 1,1-dioxo-thio-morpholine, oxopiperazine, pyridine, morpholine and 4,5-dihydro-thiazole.

14. The method according to claim 12, wherein R10 is selected from the group consisting of hydrogen, fluorine, chlorine, bromine, methyl, ethyl and —(CH$_2$)—CO$_2$H.

15. The method according to claim 2, wherein the compound is selected from the group consisting of:
cyclopentyl-[2-(4,5-dihydro-1,3-thiazole-2-yl)-1H-indole-7-yl]-amine;
[2-(4,5-dihydro-thiazole-2-yl)-1H-indole-7-yl]-(4-methyl-cyclohexyl)-amine;
[2-(4,5-dihydro-thiazole-2-yl)-1H-indole-7-yl]-piperidine-4-yl-amine;
2-5-[7-(tetrahydro-pyran-4-ylamino)-1H-indole-2-yl]-[1,2,4]oxadiazole-3-yl}-ethanol;
[(R)-2-(7-cyclopentylamino-1H-indole-2-yl)-4,5-dihydro-1,3-thiazole-4-yl]-methanol;
cyclopentyl-[2-((R)-4-pyrrolidine-1-ylmethyl-4,5-dihydro-thiazole-2-yl)-1H-indole-7-yl]-amine;
{(R)-2-[7-(tetrahydro-pyran-4-ylamino)-1H-indole-2-yl]-4,5-dihydro-thiazole-4-yl}-methanol;
[(R)-2-(7-cyclopentylamino-5-fluoro-1H-indole-2-yl)-4,5-dihydro-thiazole-4-yl]-methanol;
{(R)-2-[5-fluoro-7-(tetrahydro-pyran-4-ylamino)-1H-indole-2-yl]-4,5-dihydro-thiazole-4-yl}-methanol;
{(R)-2-[5-(pyridine-3-yloxy)-7-(tetrahydro-pyran-4-ylamino)-1H-indole-2-yl]-4,5-dihydro-thiazole-4-yl}-methanol;
[(R)-2-(5-chloro-7-cyclopentylamino-1H-indole-2-yl)-4,5-dihydro-thiazole-4-yl]-acetic acid;
[(R)-2-(5-chloro-7-cyclopentylamino-1H-indole-2-yl)-4,5-dihydro-thiazole-4-yl]acetic acid ethyl ester;
2-{(R)-2-[5-chloro-7-(tetrahydro-pyran-4-ylamino)-1H-indole-2-yl]-4,5-dihydro-thiazole-4-yl}-ethanol;
1-[4-(2-{(R)-2-[5-chloro-7-(tetrahydro-pyran-4-ylamino)-1H-indole-2-yl]-4,5-dihydro-thiazole-4-yl}-ethyl)piperazine-1-yl]-2-hydroxy-ethanone;
1-(2-{(R)-2-[5-chloro-7-(tetrahydro-pyran-4-ylamino)-1H-indole-2-yl]-4,5-dihydro-thiazole-4-yl}-ethyl)-pyrrolidine-3-ol;
[(R)-2-(5-bromo-7-cyclopentylamino-1H-indole-2-yl)-4,5-dihydro-thiazole-4-yl]-acetic acid;
[(R)-2-(7-cyclopentylamino-5-ethoxy-1H-indole-2-yl)-4,5-dihydro-thiazole-4-yl]-acetic acid;
[(S)-2-(7-cyclopentylamino-5-ethoxy-1H-indole-2-yl)-4,5-dihydro-thiazole-4-yl]-acetic acid;
[2-(7-cyclopentylamino-5-phenoxy-1H-indole-2-yl)-4,5-dihydro-thiazole-4-yl]-acetic acid;
[(R)-2-(7-cyclopentylamino-5-phenoxy-1H-indole-2-yl)-4,5-dihydro-thiazole-4-yl]-acetic acid;
[(S)-2-(7-cyclopentylamino-5-phenoxy-1H-indole-2-yl)-4,5-dihydro-thiazole-4-yl]-acetic acid;
3-[(R)-2-(5-chloro-7-cyclopentylamino-1H-indole-2-yl)-4,5-dihydro-thiazole-4-yl]-propionic acid ethyl ester;
3-[(R)-2-(5-chloro-7-cyclopentylamino-1H-indole-2-yl)-4,5-dihydro-thiazole-4-yl]-propionic acid;
cyclopentyl-(2-pyridine-2-yl-1H-indole-7-yl)-amine;
cyclopentyl-(2-pyrazine-2-yl-1H-indole-7-yl)amine;
(2-pyrazine-2-yl-1H-indole-7-yl)-(tetrahydropyran-4-yl)-amine;
cyclopentyl-(2-thiazole-2-yl-1H-indole-7-yl)-amine;
2-(7-cyclopentylamino-5-methyl-1H-indole-2-yl)-thiazole-4-carboxylic acid ethyl ester;
2-(7-cyclopentylamino-5-methyl-1H-indole-2-yl)-thiazole-4-carboxylic acid;
[2-(7-cyclopentylamino-5-methyl-1H-indole-2-yl)-thiazole-4-yl]-methanol;
[2-(7-cyclopentylamino-5-methyl-1H-indole-2-yl)-thiazole-5-yl]-methanol;
cyclopentyl-(5-methyl-2-[1,3,4]oxadiazole-2-yl-1H-indole-7-yl)-amine;
cyclopentyl-(5-methyl-2-pyridine-2-yl-1H-indole-7-yl)-amine;
(5-methyl-2-pyridine-2-yl-1H-indole-7-yl)-(tetrahydro-pyran-4-yl)-amine;
cyclohexyl-(5-methyl-2-pyridine-2-yl-1H-indole-7-yl)-amine;
1-[4-(5-methyl-2-pyridine-2-yl-1H-indole-7-ylamino)-piperidine-1-yl]-ethanone;
(1-methyl-piperidine-4-yl)-(5-methyl-2-pyridine-2-yl-1H-indole-7-yl)-amine;
4-(5-methyl-2-pyridine-2-yl-1H-indole-7-ylamino)-cyclohexanone;
(1-benzyl-pyrrolidine-3-yl)-(5-methyl-2-pyridine-2-yl-1H-indole-7-yl)-amine;
cyclopentylmethyl-(5-methyl-2-pyridine-2-yl-1H-indole-7-yl)-amine;
N-(5-methyl-2-pyridine-2-yl-1H-indole-7-yl)-benzamide;
cyclopentyl-(5-methyl-2-pyrazine-2-yl-1H-indole-7-yl)-amine;
cyclopentyl-(5-ethoxy-2-pyridine-2-yl-1H-indole-7-yl)-amine;
cyclopentyl-(5-phenoxy-2-pyridine-2-yl-1H-indole-7-yl)-amine;
cyclopentyl-(3,5-dimethyl-2-phenyl-1H-indole-7-yl)-amine;
cyclopentyl-(5-methyl-2-phenyl-1H-indole-7-yl)-amine;
(2-cyclohexyl-5-methyl-1H-indole-7-yl)-cyclopentyl-amine;
cyclopentyl-[5-methyl-2-(6-methyl-pyridine-2-yl)-1H-indole-7-yl]-amine;
(5-methyl-2-phenyl-1H-indole-7-yl)-(tetrahydro-pyran-4-yl)-amine;
(5-methyl-2-phenyl-1H-indole-7-yl)-(1-methyl-piperidine-4-yl)-amine;
1-[4-(5-methyl-2-phenyl-1H-indole-7-ylamino)-piperidine-1-yl]-ethanone;
(5-methyl-2-phenyl-1H-indole-7-yl)-piperidine-4-yl-amine hydrochloride;
2-hydroxy-1-[4-(5-methyl-2-phenyl-1H-indole-7-ylamino)-piperidine-1-yl]-ethanone;
(1-methanesulfonyl-piperidine-4-yl)-(5-methyl-2-phenyl-1H-indole-7-yl)-amine;
4-(5-methyl-2-phenyl-1H-indole-7-ylamino)-cyclohexanecarboxylic acid;
4-(5-methyl-2-phenyl-1H-indole-7-ylamino)-cyclohexanecarboxylic acid (2-morpholine-4-yl-ethyl)-amide;
cyclopentylmethyl-(5-methyl-2-phenyl-1H-indole-7-yl)-amine;
(5-methyl-2-phenyl-1H-indole-7-yl)-(tetrahydro-pyran-4-ylmethyl)-amine;
(5-chloro-2-phenyl-1H-indole-7-yl)-cyclopentyl-amine;
(5-chloro-2-phenyl-1H-indole-7-yl)-(tetrahydro-pyran-4-yl)-amine;

(5-chloro-2-phenyl-1H-indole-7-yl)-(1-methyl-piperidine-4-yl)-amine;
(5-chloro-2-phenyl-1H-indole-7-yl)-cyclohexyl-amine;
(1-benzyl-pyrrolidine-3-yl)-(5-chloro-2-phenyl-1H-indole-7-yl)-amine;
4-(5-chloro-7-cyclopentylamino-1H-indole-2-yl)-benzoic acid methyl ester;
4-(5-chloro-7-cyclopentylamino-1H-indole-2-yl)-benzoic acid;
[4-(5-chloro-7-cyclopentylamino-1H-indole-2-yl)-phenyl]-methanol;
4-(7-cyclopentylamino-5-methyl-1H-indole-2-yl)-benzoic acid methyl ester;
2-(5-chloro-7-cyclopentylamino-1H-indole-2-yl)-benzoic acid methyl ester;
2-(5-chloro-7-cyclopentylamino-1H-indole-2-yl)-benzoic acid;
[2-(5-chloro-7-cyclopentylamino-1H-indole-2-yl)-phenyl]-methanol;
7-cyclopentylamino-2-phenyl-1H-indole-5-carboxylic acid ethylester;
7-cyclopentylamino-2-phenyl-1H-indole-5-carboxylic acid;
(7-cyclopentylamino-2-phenyl-1H-indole-5-yl)-methanol;
(7-cyclopentylamino-2-phenyl-1H-indole-5-yl)-acetic acid ethyl ester;
(7-cyclopentylamino-2-phenyl-1H-indole-5-yl)-acetic acid;
2-[(4S)-2-[5-methyl-7-(oxane-4-ylmethylamino)-1H-indole-2-yl]-4,5-dihydro-1,3-thiazole-4-yl]acetic acid;
2-[(4S)-2-[5-chloro-7-(oxane-4-ylmethylamino)-1H-indole-2-yl]-4,5-dihydro-1,3-thiazole-4-yl]acetic acid;
2-[(4S)-2-[7-[(4,4-difluorocyclohexyl)amino]-5-methyl-1H-indole-2-yl]-4,5-dihydro-1,3-thiazole-4-yl]acetic acid;
2-[(4S)-2-[7-(oxane-4-ylamino)-5-phenoxy-1H-indole-2-yl]-4,5-dihydro-1,3-thiazole-4-yl]acetic acid;
2-[(4R)-2-[7-(oxane-4-ylamino)-5-phenoxy-1H-indole-2-yl]-4,5-dihydro-1,3-thiazole-4-yl]acetic acid;
2-[(4R)-2-[7-(oxane-4-ylmethylamino)-5-phenoxy-1H-indole-2-yl]-4,5-dihydro-1,3-thiazole-4-yl]acetic acid;
2-[(4S)-2-[7-(cyclopentylamino)-1H-indole-2-yl]-4,5-dihydro-1,3-thiazole-4-yl]acetic acid;
2-[(4S)-2-[7-[(1-acetylpyrrolidine-3-yl)amino]-5-methyl-1H-indole-2-yl]-4,5-dihydro-1,3-thiazole-4-yl]acetic acid;
2-[(4S)-2-[7-(oxane-4-ylmethylamino)-1H-indole-2-yl]-4,5-dihydro-1,3-thiazole-4-yl]acetic acid;
2-[(4S)-2-[7-(oxane-4-ylamino)-1H-indole-2-yl]-4,5-dihydro-1,3-thiazole-4-yl]acetic acid;
2-[(4S)-2-[7-(oxane-2-ylmethylamino)-1H-indole-2-yl]-4,5-dihydro-1,3-thiazole-4-yl]acetic acid;
2-[(4S)-2-[5-methyl-7-[[1-(3,3,3-trifluoropropanoyl)piperidine-4-yl]amino]-1H-indole-2-yl]-4,5-dihydro-1,3-thiazole-4-yl]acetic acid;
2-[(4R)-2-[7-(cyclopentylamino)-5-methyl-1H-indole-2-yl]-4,5-dihydro-1,3-thiazole-4-yl]acetic acid;
2-[(4R)-2-[5-methyl-7-(oxane-4-ylmethylamino)-1H-indole-2-yl]-4,5-dihydro-1,3-thiazole-4-yl]acetic acid;
4-[2-[(4S)-2-[5-methyl-7-(oxane-4-ylmethylamino)-1H-indole-2-yl]-4,5-dihydro-1,3-thiazole-4-yl]ethyl]piperazine-2-one;
2-[(4S)-4-[2-(1,1-dioxo-1,4-thiazinane-4-ylethyl]-4,5-dihydro-1,3-thiazole-2-yl]-5-methyl-N-(oxane-4-ylmethyl)-1H-indole-7-yl-amine;
N-(4,4-difluorocyclohexyl)-5-methyl-2-[(4S)-4-(2-morpholine-4-ylethyl)-4,5-dihydro-1,3-thiazole-2-yl]-1H-indole-7-yl-amine;
4-[2-[(4S)-2-[7-[(4,4-difluorocyclohexyl)amino]-5-methyl-1H-indole-2-yl]-4,5-dihydro-1,3-thiazole-4-yl]ethyl]piperazine-2-one;
4-[2-[(4S)-2-[7-(oxane-4-ylmethylamino)-5-phenoxy-1H-indole-2-yl]-4,5-dihydro-1,3-thiazole-4-yl]ethyl]piperazine-2-one;
2-[(4S)-4-(2-morpholine-4-ylethyl)-4,5-dihydro-1,3-thiazole-2-yl]-N-(oxane-4-ylmethyl)-5-phenoxy-1H-indole-7-amine;
5-methyl-2-[(4S)-4-(2-morpholine-4-ylethyl)-4,5-dihydro-1,3-thiazole-2-yl]-N-(oxane-4-ylmethyl)-1H-indole-7-amine;
1-[2-[(4S)-2-[5-methyl-7-(oxane-4-ylmethylamino)-1H-indole-2-yl]-4,5-dihydro-1,3-thiazole-4-yl]ethyl]piperidine-4-carboxyamide;
[(2R)-1-[2-[(4S)-2-[5-methyl-7-(oxane-4-ylmethylamino)-1H-indole-2-yl]-4,5-dihydro-1,3-thiazole-4-yl]ethyl]pyrrolidine-2-yl]methanol;
(2S)-1-[2-[(4S)-2-[5-methyl-7-(oxane-4-ylmethylamino)-1H-indole-2-yl]-4,5-dihydro-1,3-thiazole-4-yl]ethyl]pyrrolidine-2-carboxyamide;
4-[2-[(4R)-2-[7-(cyclopentylamino)-5-methyl-1H-indole-2-yl]-4,5-dihydro-1,3-thiazole-4-yl]ethyl]piperazine-2-one;
2-[(4S)-2-[7-(cyclopentylamino)-5-methyl-1H-indole-2-yl]-4,5-dihydro-1,3-oxazole-4-yl]acetic acid;
{(S)-2-[5-methyl-7-(tetrahydropyran-4-ylamino)-1H-indole-2-yl]-4,5-dihydro-oxazole-4-yl}-acetic acid;
2-[(4S)-2-[5-methyl-7-(tetrahydropyran-4-ylamino)-1H-indole-2-yl]-4,5-dihydro-1,3-oxazole-4-yl]ethanol;
{5-methyl-2-[(S)-4-(2-morpholine-4-yl-ethyl)-4,5-dihydro-1,3-oxazole-2-yl]-1H-indole-7-yl}-(tetrahydro-pyran-4-yl)amine
4-[(5-chloro-2-phenyl-1H-indole-7-yl)amino]-N-ethylpiperidine-1-carboxyamide;
[4-[(5-chloro-2-phenyl-1H-indole-7-yl)amino]piperidine-1-yl]-(oxolan-3-yl)methanone;
2-[7-(oxane-4-ylamino)-2-phenyl-1H-indole-5-yl]acetic acid;
2-[7-(cyclopentylmethylamino)-2-phenyl-1H-indole-5-yl]acetic acid;
5-fluoro-N-(1-methylpiperidine-4-yl)-2-phenyl-1H-indole-7-amine;
2-[4-[(5-fluoro-2-phenyl-1H-indole-7-yl)amino]piperidine-1-yl]ethanone;
5-fluoro-N-[1-(oxane-4-yl)piperidine-4-yl]-2-phenyl-1H-indole-7-amine;
N-[1-(1,1-dioxan-4-yl)piperidine-4-yl]-5-fluoro-2-phenyl-1H-indole-7-amine;
N-(oxane-4-yl)-5-phenoxy-2-phenyl-1H-indole-7-amine;
methyl 2-[(5-fluoro-2-phenyl-1H-indole-7-yl)amino]acetate;
2-[(5-fluoro-2-phenyl-1H-indole-7-yl)amino]acetic acid;
methyl 2-[(5-chloro-2-phenyl-1H-indole-7-yl)amino]propanoate;
2-[(5-chloro-2-phenyl-1H-indole-7-yl)amino]propanoic acid;
2-[(5-phenoxy-2-phenyl-1H-indole-7-yl)amino]acetic acid;
2-[(5-phenoxy-2-phenyl-1H-indole-7-yl)amino]propanoic acid;
2-[(4S)-2-[7-(oxane-4-ylmethylamino)-2-phenyl-1H-indole-5-yl]-4,5-dihydro-1,3-thiazole-4-yl]acetic acid;

2-[(4S)-2-[7-(cyclopentylamino)-2-phenyl-1H-indole-5-yl]-4,5-dihydro-1,3-thiazole-4-yl]acetic acid;
methyl 2-[4-[5-chloro-7-(oxane-4-ylamino)-1H-indole-2-yl]phenyl]acetate;
methyl 2-[4-[5-chloro-7-(oxane-4-ylmethylamino)-1H-indole-2-yl]phenyl]acetate;
2-[4-[5-chloro-7-(oxane-4-ylamino)-1H-indole-2-yl]phenyl]acetic acid;
5-[(1,1-dioxo-1,4-thiazinane-4-yl)methyl]-N-(oxane-4-yl)-2-phenyl-1H-indole-7-amine;
5-[(1,1-dioxo-1,4-thiazinane-4-yl)methyl]-N-(oxane-4-ylmethyl)-2-phenyl-1H-indole-7-amine;
4-[[7-(oxane-4-ylamino)-2-phenyl-1H-indole-5-yl]methyl]piperazine-2-one;
5-[(1,1-dioxo-1,4-thiazinane-4-yl)methyl]-2-phenyl-N-piperidine-4-yl-1H-indole-7-amine;
[4-[[5-[(1,1-dioxo-1,4-thiazinane-4-yl)methyl]-2-phenyl-1H-indole-7-yl]amino]piperidine-1-yl]-(oxolan-3-yl)methanone;
N-[4-[5-[(1,1-dioxo-1,4-thiazinane-4-yl)methyl]-7-(oxane-4-ylamino)-1H-indole-2-yl]phenyl]acetamide;
N-[4-[7-(dicyclopentylamino)-5-[(1,1-dioxo-1,4-thiazinane-4-yl)methyl]-1H-indole-2-yl]phenyl]acetamide;
N-[4-[5-[(1,1-dioxo-1,4-thiazinane-4-yl)methyl]-7-(oxane-4-ylmethylamino)-1H-indole-2-yl]phenyl]acetamide;
N-cyclopentyl-5-[(1,1-dioxo-1,4-thiazinane-4-yl)methyl]-2-(4-methoxyphenyl)-1H-indole-7-amine;
5-[(1,1-dioxo-1,4-thiazinane-4-yl)methyl]-2-(4-methoxyphenyl)-N-(oxane-4-yl)-1H-indole-7-amine;
5-[(1,1-dioxo-1,4-thiazinane-4-yl)methyl]-N-(3-methoxybutyl)-2-phenyl-1H-indole-7-amine;
5-[(1,1-dioxo-1,4-thiazinane-4-yl)methyl]-2-(3-fluorophenyl)-N-(oxane-4-yl)-1H-indole-7-amine;
N-cyclopentyl-5-[(1,1-dioxo-1,4-thiazinane-4-yl)methyl]-2-(3-fluorophenyl)-1H-indole-7-amine;
3-bromo-5-[(1,1-dioxo-1,4-thiazinane-4-yl)methyl]-N-(oxane-4-yl)-2-phenyl-1H-indole-7-amine;
3-bromo-5-(morpholine-4-ylmethyl)-N-(oxane-4-yl)-2-phenyl-1H-indole-7-amine;
3-bromo-N-cyclopentyl-5-[(1,1-dioxo-1,4-thiazinane-4-yl)methyl]-2-phenyl-1H-indole-7-amine;
3-bromo-5-[(1,1-dioxo-1,4-thiazinane-4-yl)methyl]-N-(oxane-4-yl)-2-phenyl-1H-indole-7-amine;
5-chloro-N-(oxane-4-yl)-3-phenyl-1H-indole-7-amine;
5-chloro-N-cyclopentyl-3-phenyl-1H-indole-7-amine;
5-chloro-N-(oxane-4-ylmethyl)-3-phenyl-1H-indole-7-amine;
5-[(1,1-dioxo-1,4-thiazinane-4-yl)methyl]-N-(oxane-4-yl)-3-phenyl-2-trimethylsilyl-1H-indole-7-amine;
4-[[5-chloro-7-(cyclopentylamino)-2-phenyl-1H-indole-3-yl]methyl]piperazine-2-one;
4-[[5-chloro-7-(oxane-4-ylamino)-2-phenyl-1H-indole-3-yl]methyl]piperazine-2-one;
4-[[5-chloro-7-(oxane-4-ylmethylamino)-2-phenyl-1H-indole-3-yl]methyl]piperazine-2-one;
N-cyclopentyl-3(4-methoxyphenyl)-1H-indazol-7-amine;
3-(4-methoxyphenyl)-N-(oxane-4-yl)-1H-indazol-7-amine;
3-(4-methoxyphenyl)-N-(oxane-4-ylmethyl)-1H-indazol-7-amine; and
2-(7-cyclopentylamino-2-phenyl-1H-indole-5-yl)-ethanol.

16. The method according to claim 1, wherein the cell is animal cell isolated from tissues or organs of human or non-human animals and selected from the group consisting of liver cell, skin cell, mucous membrane cell, Langerhans islet cell, nerve cell, cartilage cell, endothelium cell, epithelial cell, bone cell and muscle cell; or sperm, egg or fertilized egg of livestock or fish.

17. The method according to claim 1, wherein the organ is selected from the group consisting of skin, cornea, kidney, heart, liver, pancreas, intestine, nerve, lung, placenta, umbilical cord and blood vessel.

18. The method according to claim 1, wherein the tissue is selected from the group consisting of skin, cornea, kidney, heart, liver, pancreas, intestine, nerve, lung, placenta, umbilical cord and blood vessel.

19. The method according to claim 1, wherein the composition is used for treating injury of organs, isolated cell systems or tissues caused by cold storage, transplant operation or post-transplantation reperfusion.

20. A method for cultivating or preserving cells, tissues or organs, in manufacturing an artificial organ using a composition comprising a compound of the following formula (1) or a pharmaceutically acceptable salt or stereoisomer thereof

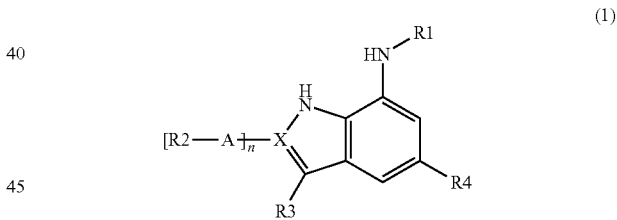

wherein X, n, A, R1, R2, R3 and R4 are the same as defined in claim 1.

* * * * *